US008580743B2

(12) United States Patent
Nishi et al.

(10) Patent No.: US 8,580,743 B2
(45) Date of Patent: *Nov. 12, 2013

(54) MODIFIED GALECTIN 9 PROTEINS AND METHODS OF TREATMENT USING THEM

(75) Inventors: Nozomu Nishi, Kagawa (JP); Mitsuomi Hirashima, Kagawa (JP); Akira Yamauchi, Kagawa (JP); Aiko Ito, Kagawa (JP)

(73) Assignee: Galpharma Co., Ltd., Kagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/591,366

(22) Filed: Aug. 22, 2012

(65) Prior Publication Data

US 2013/0017998 A1 Jan. 17, 2013

Related U.S. Application Data

(62) Division of application No. 11/547,091, filed as application No. PCT/JP2005/006580 on Mar. 29, 2005, now Pat. No. 8,268,324.

(30) Foreign Application Priority Data

Mar. 29, 2004 (JP) .................................. 2004-94401
Sep. 30, 2004 (JP) ................................ 2004-287005
Feb. 18, 2005 (JP) .................................. 2005-43156

(51) Int. Cl.
*A61K 38/00* (2006.01)
*A61K 35/02* (2006.01)
*A61K 35/04* (2006.01)
*C07K 14/00* (2006.01)
*C12P 21/00* (2006.01)

(52) U.S. Cl.
USPC ........ 514/18.7; 514/19.3; 514/19.4; 514/19.5; 514/19.6; 424/192.1; 435/69.7; 530/350

(58) Field of Classification Search
None
See application file for complete search history.

(56) References Cited

U.S. PATENT DOCUMENTS

| 5,908,761 | A | 6/1999 | Zick |
| 6,551,796 | B1 | 4/2003 | Abramson et al. |
| 2007/0042941 | A1 | 2/2007 | Hirashima et al. |

FOREIGN PATENT DOCUMENTS

| JP | 2001-501831 | 2/2001 |
| JP | 2001-522581 | 11/2001 |
| JP | 2003-189874 | 7/2003 |
| JP | 2004-346068 | 12/2004 |
| WO | 98/15624 | 4/1998 |
| WO | 99/10490 | 3/1999 |
| WO | 1 331 483 | 7/2003 |

OTHER PUBLICATIONS

T. Nakamura et al., "Tandem-repeat-gata Galectin no Linker Peptide ni Sonzai Sum Thrombin Kanjusei Bui", Seikagaku, vol. 74, No. 8, p. 843, 3P-011, 2002.
M. Sato et al., "Functional Analysis of the Carbohydrate Recognition Domains and a Linker Peptide of Galectin-9 as to Eosinophil Chemoattractant Activity", Glycobiology, vol. 12, No. 3, pp. 191-197, 2002.
U. Sahin et al., "Human Neoplasms Elicit Multiple Specific Immune Responses in the Autologous Host", Proc. Natl. Acad. Sci., vol. 92, No. 25, pp. 11810-11813, 1995.
O. Tureci et al., "Molecular Definition of a Novel Human Galectin which is Immunogenic in Patients with Hodgkin's Disease", The Journal of Biological Chemistry, vol. 272, No. 10, pp. 6416-6422, Mar. 7, 1997.
J. Wada et al., "Identification and Characterization of Galectin-9, A Novel β-Galactoside-Binding Mammalian Lectin", The Journal of Biological Chemistry, vol. 272, No. 9, pp. 6078-6086, Feb. 28, 1997.
R. Matsumoto et al., "Human Ecalectin, A Variant of Human Galectin-9, is A Novel Eosinophil Chemoattractant Produced by T Lymphocytes", The Journal of Biological Chemistry, vol. 273, No. 27, pp. 16976-16984, Jul. 3, 1998.
Matsushita et al., "Requirement of Divalent Galactoside-Binding Activity of Ecalectin/Galectin-9 for Eosinophil Chemoattraction", The Journal of Biological Chemistry, vol. 275, No. 12, pp. 8355-8360, Mar. 24, 2000.
M. A. Gitt et al., "Galectin-4 and Galectin-6 are two Closely Related Lectins Expressed in Mouse Gastrointestinal Tract", The Journal of Biological Chemistry, vol. 273, No. 5, pp. 2954-2960, Jan. 30, 1998.
N. Saita et al., "Association of Galectin-9 with Eosinophil Apoptosis", Int. Arch. Allergy Immunol., vol. 128, No. 1, pp. 42-50, 2002.
N. Nishi et al., "Development of Highly Stable Galectins: Truncation of the Linker Peptide Confers Protease-resistance on Tandem-Repeat Type Galectins", FEBS Letters, vol. 579, No. 10, pp. 2058-2064, Apr. 11, 2005.
N. Nishi et al., Production of Protease-Resistant Gelectin-9 by Modification of Linker Peptide, Seikagaku, vol. 76, No. 8, p. 1013, 4P-083, Aug. 25, 2004.
Chinese Office Action and partial English translation dated Feb. 16, 2011 issued in corresponding Chinese Application No. 200580010446.1.
Japanese Office Action issued Apr. 22, 2011, in corresponding Japanese Application No. 2006-511618 (with partial English translation).
Office Action issued Nov. 10, 2011 in corresponding Canadian Patent Application No. 2,561,696.
Japanese Office Action issued Oct. 19, 2010, in corresponding Japanese Application No. 2006-511618 (with partial English translation).
Supplementary Partial European Search Report issued May 7, 2007 in corresponding European Application No. 05 721 719.2.
European Office Action issued Sep. 26, 2007 in corresponding European Application No. 05 721 719.2.

(Continued)

*Primary Examiner* — Elly-Gerald Stoica
(74) *Attorney, Agent, or Firm* — Wenderoth, Lind & Ponack, L.L.P.

(57) ABSTRACT

A recombinant galectin 9 (rGal 9) is provided which exhibits an immune system-mediated action and a direct action on tumor cells (i.e., activity of inducing the intercellular adhesion and apoptosis of the tumor cells), thereby potent in inducing the inhibition of cancer metastasis and reduction. Moreover, the rGal 9 exerts no efficacy on non-activated lymphocytes but can induce apoptosis in activated T cells, in particular, CD4-positive T cells causing an excessive immune response.

6 Claims, 66 Drawing Sheets

(56) References Cited

OTHER PUBLICATIONS

European Office Action issued Feb. 19, 2009 in corresponding European Application No. 05 721 719.2.

European Office Action issued Oct. 6, 2010 in corresponding European Application No. 05 721 719.2.

Kashio Y et al. Rinsho Meneki (Clinical Immunity), Kagaku Hyouronsha 34[2] (2000) pp. 226 to 230.

Hirashima M. Bessatsu Igaku No Ayumi (Medical Progress, separate volume) Meneki Shikkan (Immunological Diseases) ver. 2., (2002) pp. 170-174.

Lobsanov Y et al. "*Galectin Structure*", Trends in Glycoscience and Glycotechnology, vol. 9, No. 45, Jan. 1997, pp. 145-154.

Sato et al. Glycobiology, 2002; 12(3): 191-197).

Hirashima M., Ecalectin/Galectin-9, a novel eosinophil chemoattractant: its function and production, Int. Arch. Allergy Immunol., 122 (suppl. 1), 6-9, 2000.

M: Molecular Marker

1: E. coli Lysate (Pre-Induction)

2: E. coli Lysate (Post-Induction)

3: E. coli Extract

4: Lactose-Column-Non-Adsorbed Fraction of E. coli Extract

5: Lactose-Column Eluate Fraction Purified G9NC (null)

FIG. 8

| | Positions | | | | |
|---|---|---|---|---|---|
| | 5 | 88 | 135 | 238 | 281 |
| Sequence corrected | ggt (G) | aag (K) | tcc (S) | ccc (P) | gaa (E) |
| Ecalectin | -a- (S) | — (K) | — (S) | — (P) | — (E) |
| Gal-9 | — (G) | -g- (R) | -t- (F) | -t- (L) | -g- (G) |
| EST clones (source) | | | | | |
| AA428401 (ovary tumor) | — (G) | — (K) | (S) | | |
| AA476845 (ovary tumor) | — (G) | — (K) | | | |
| AA443641 (ovary tumor) | | — (K) | — (S) | | |
| AA448365 (ovary tumor) | | | | | — (E) |
| AA477070 (ovary tumor) | | | | — (P) | |
| AA353933 (Jurkat T-cell) | — (G) | — (K) | | | |
| AA354210 (Jurkat T-cell) | — (G) | — (K) | | | |
| AA354814 (Jurkat T-cell) | | | | — (P) | |
| AA382104 (Activated T-cell) | — (G) | | | | |
| AA394654 (B-cell leukemia) | — (G) | — (K) | | | |
| AA295169 (pancreas tumor) | | (K) | — | | |
| AA295767 (pancreas tumor) | | (K) | | | |
| AA825886 (colon tumor) | | | | | — (E) |
| AA829906 (lung tumor) | | | | | — (E) |
| AA810306 (tonsil) | — (G) | — (K) | | | |
| AA484985 (tonsil) | | (K) | | | |
| AA89534 (liver and spleen) | | | | — (P) | |

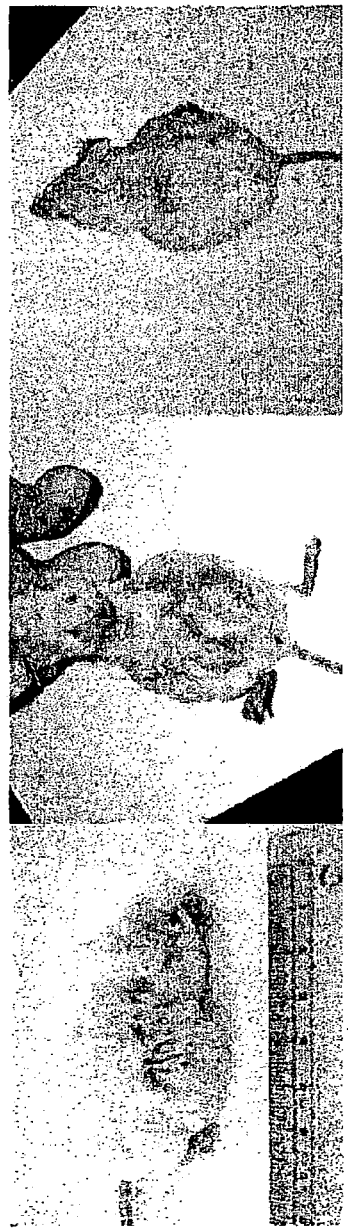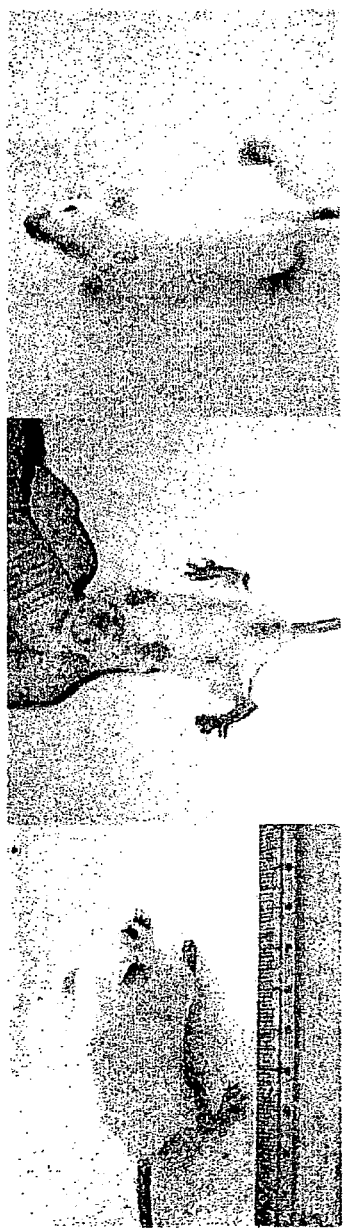
FIG. 25  A  Gal-9 Non-Administered Group : Day14    B  Gal-9 Administered Group : Day14

FIG. 31
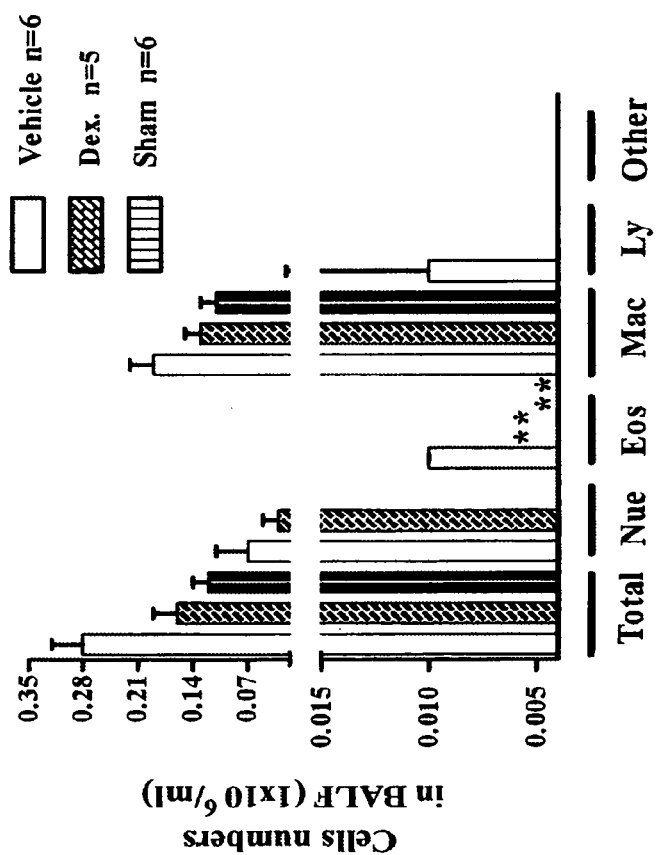
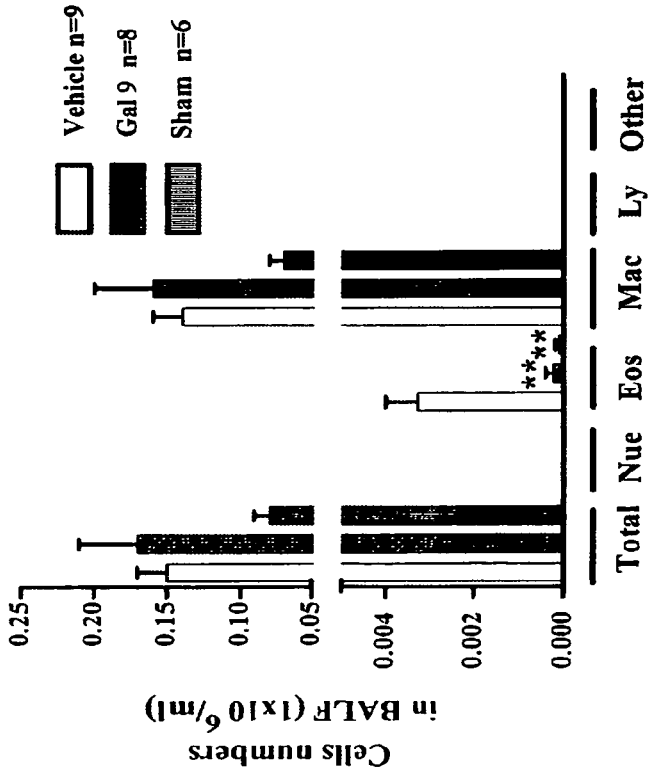

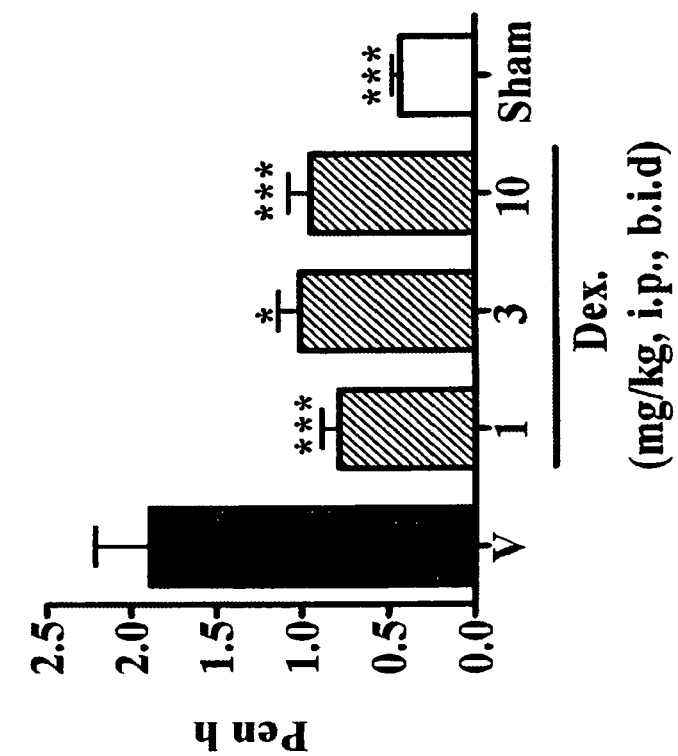
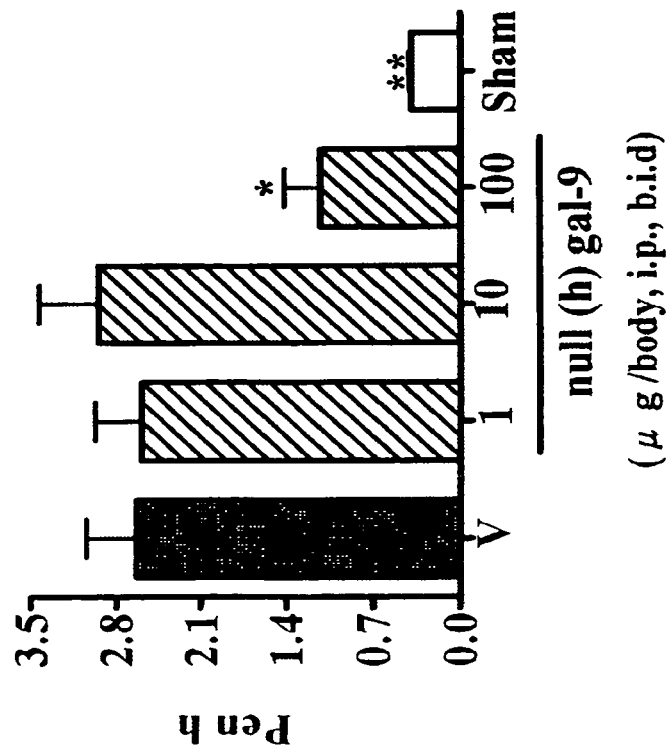
FIG. 39

FIG. 40
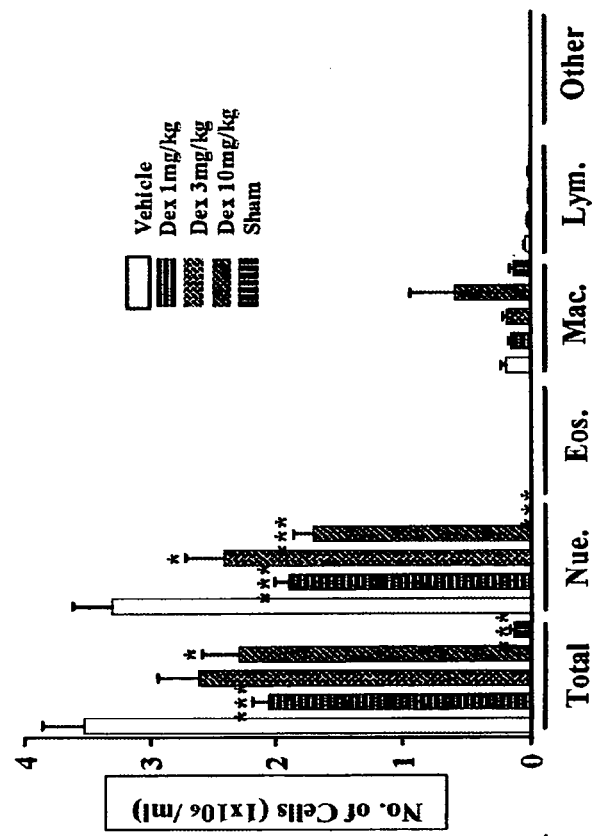
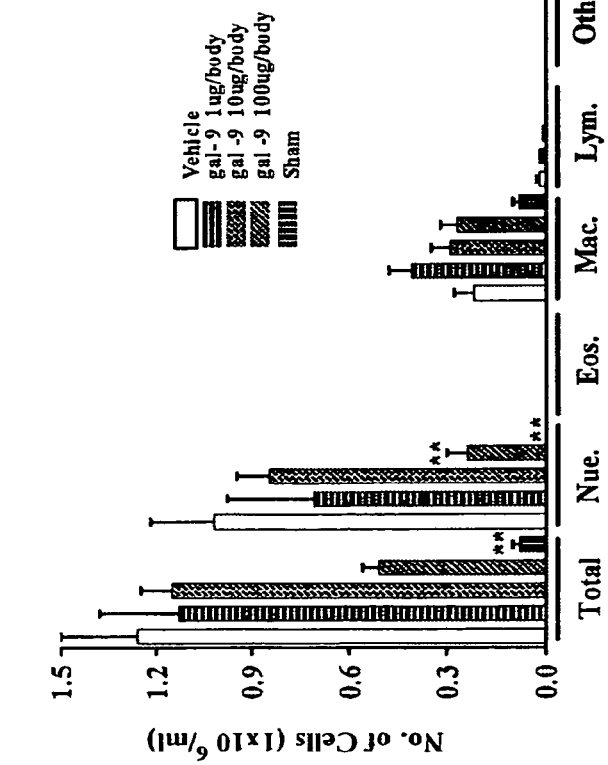

FIG. 47
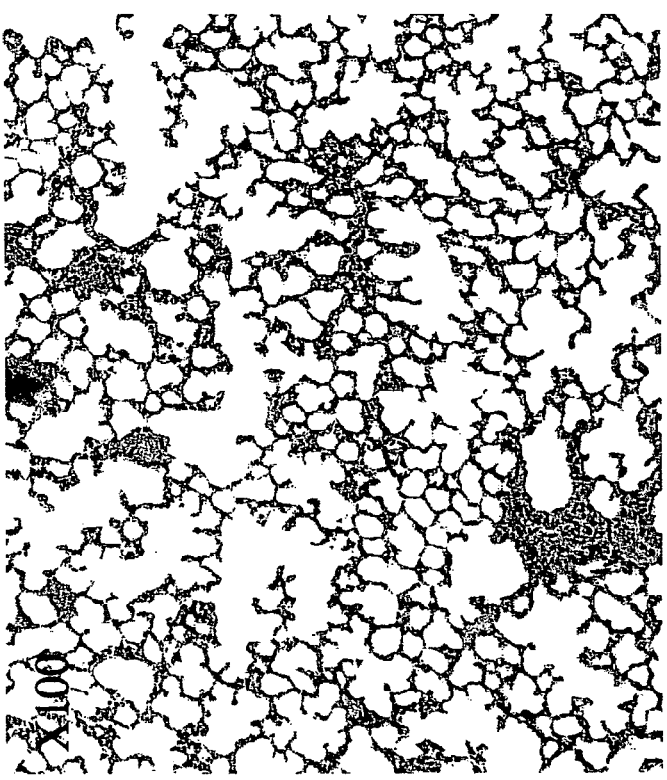
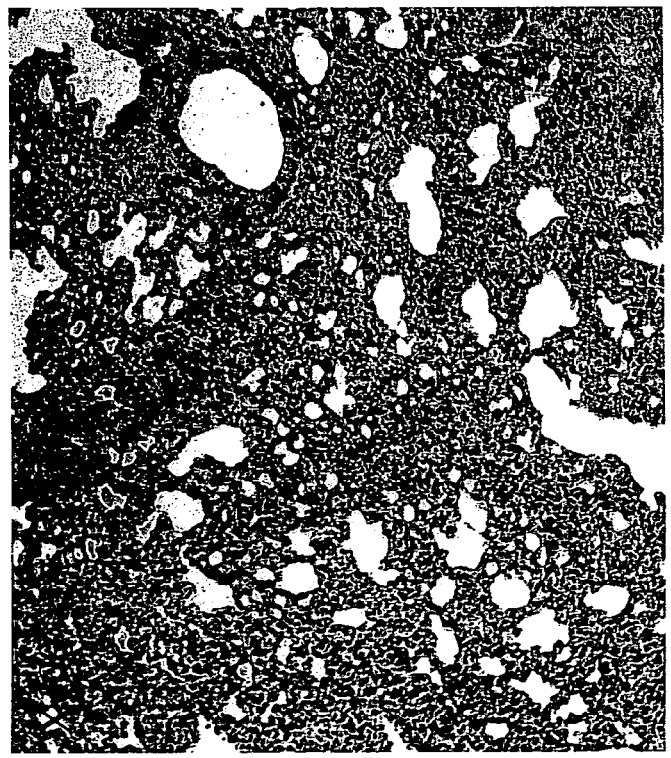

FIG. 49
Metastatic Model : B16/F10 (Melanoma)
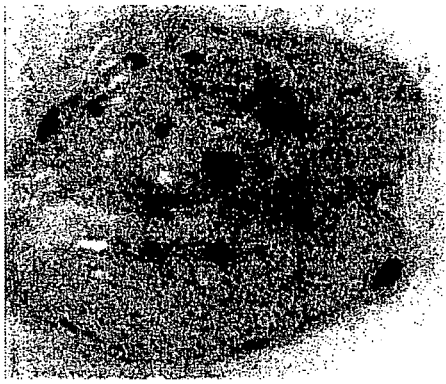
Gal-9 Group
PBS Group Metastatic Model : B16/F10 (Melanoma)

FIG. 53  Expression of Galectin-9 in RA Synovium
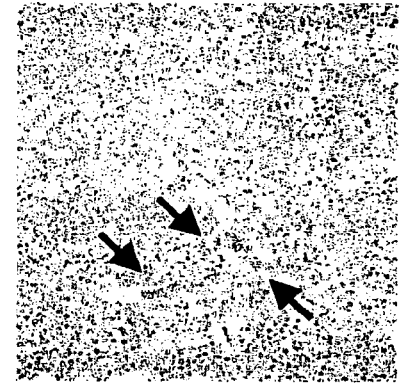
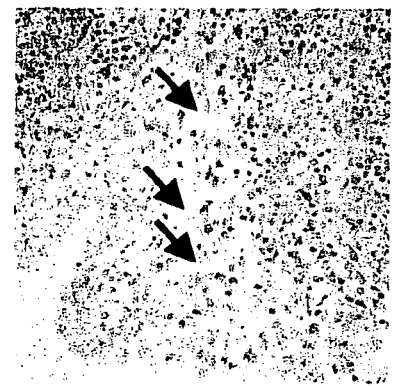
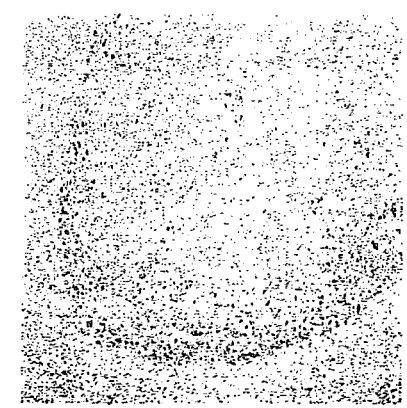
OA synovium
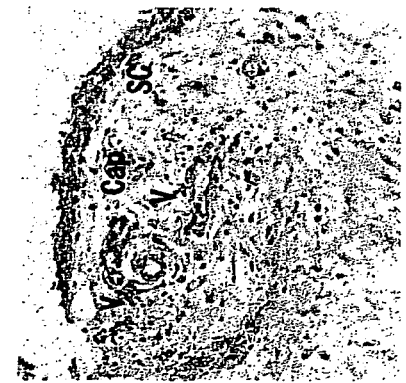
RA synovium

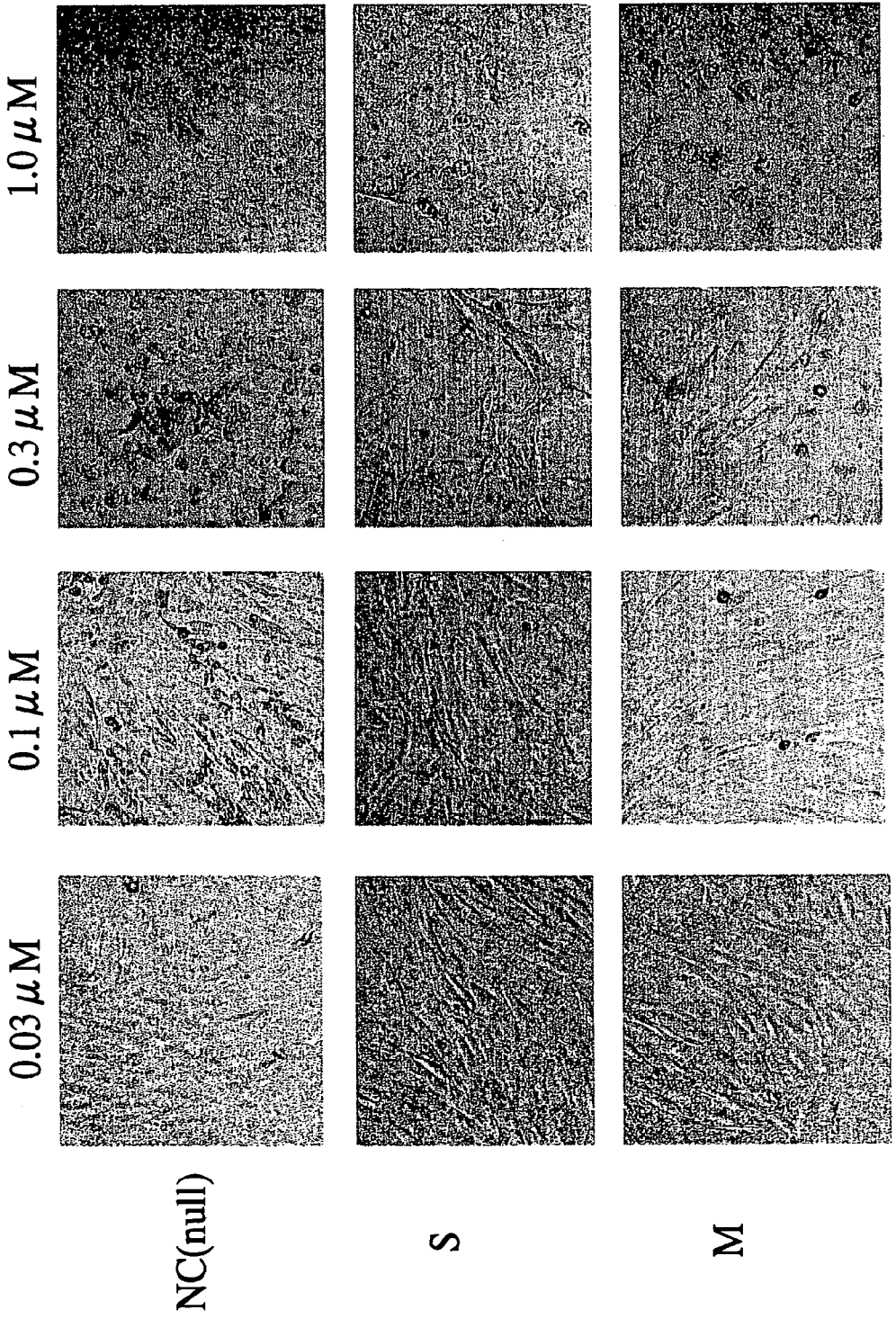
FIG. 54 Induction of Apoptotic Synovial Cell

FIG. 59
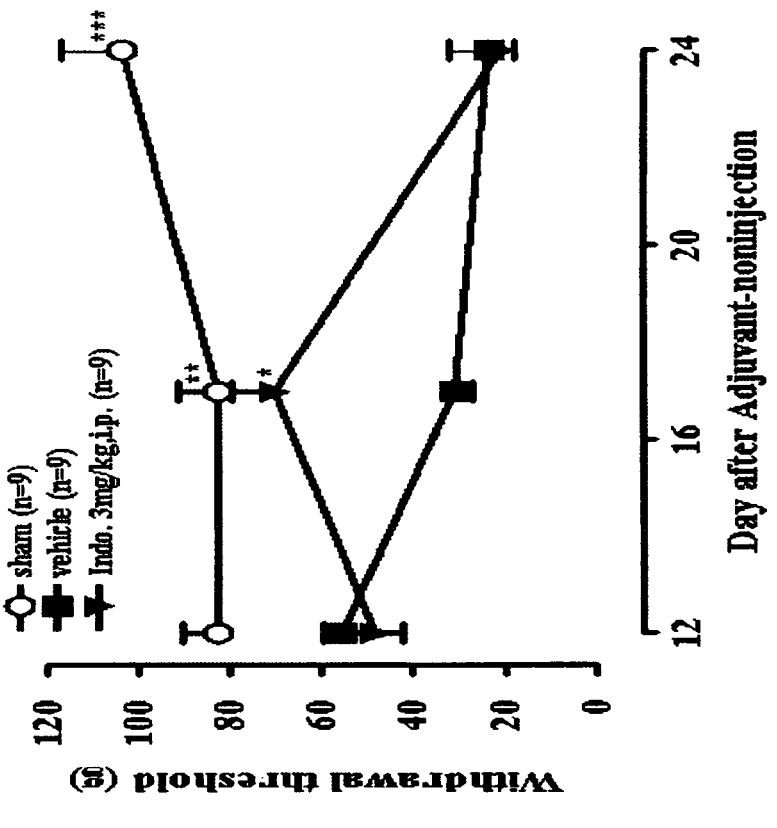
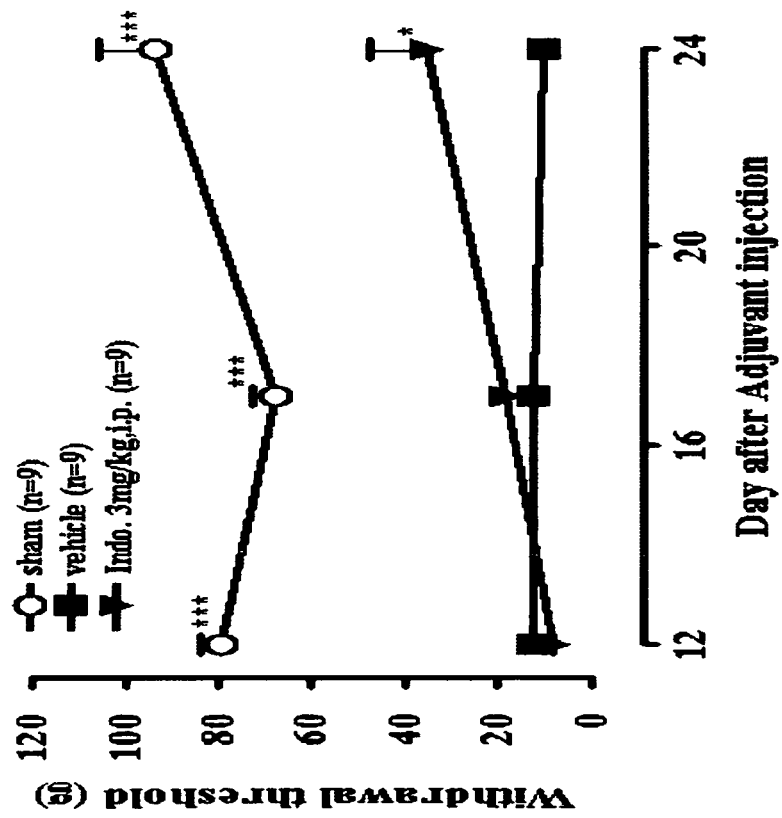

FIG. 66
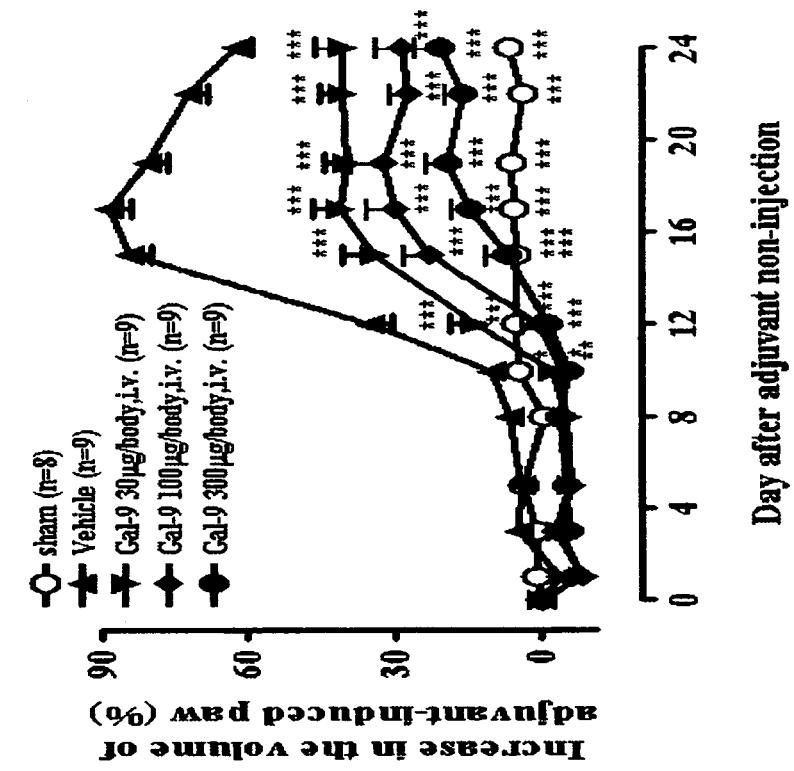
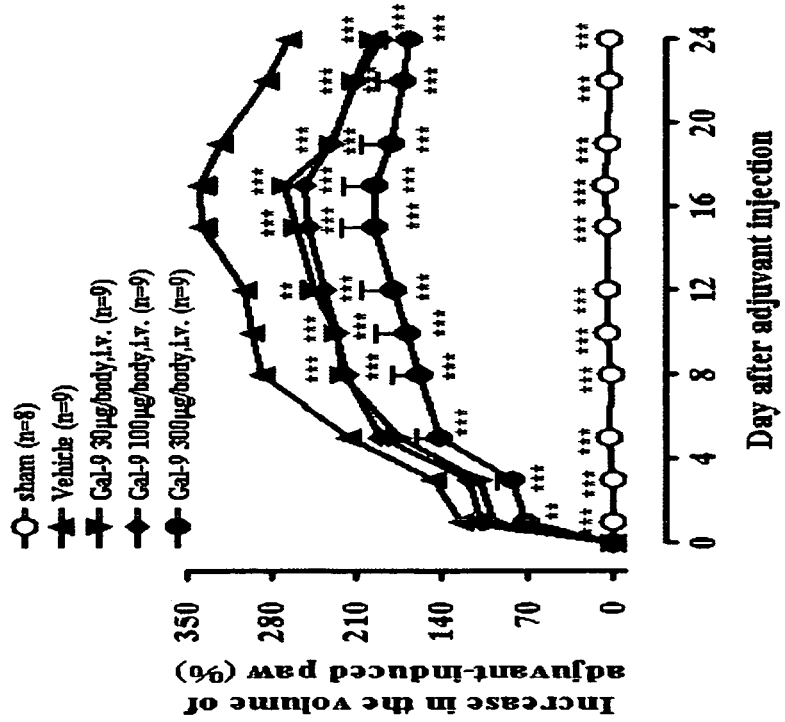

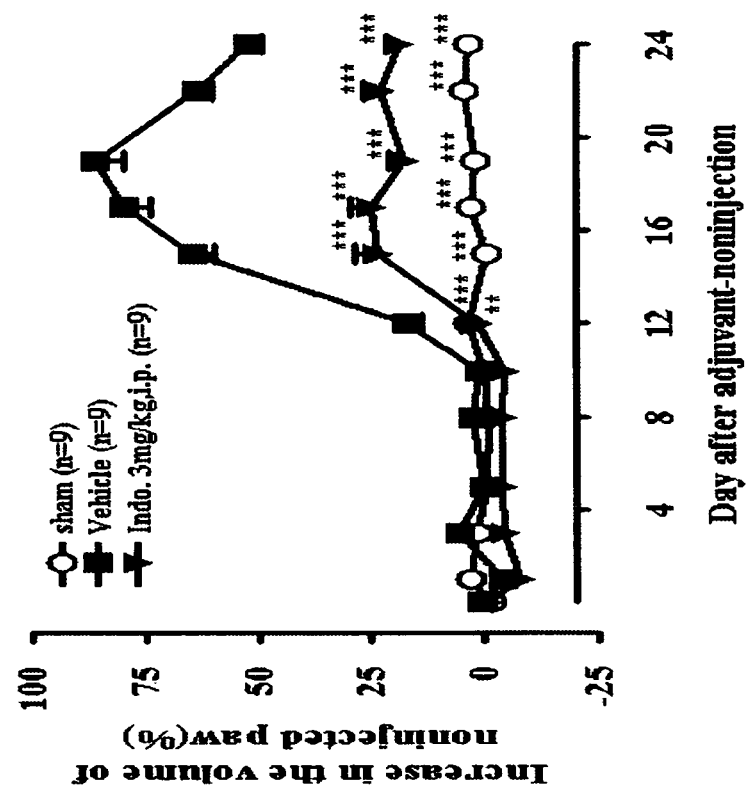
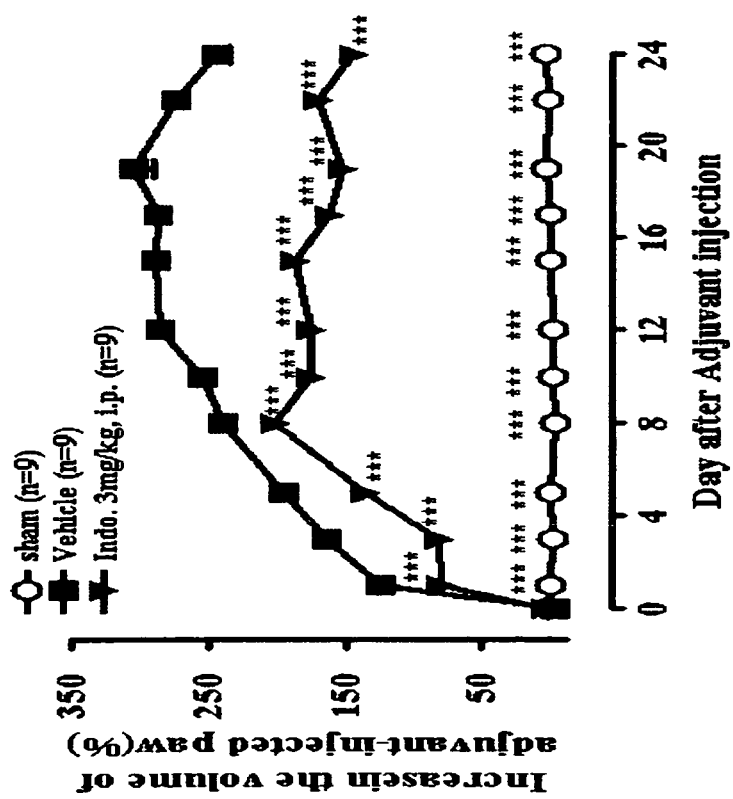
FIG. 67

SEQUENCE LISTING

```
<160> NUMBER OF SEQ ID NOS: 13

<210> SEQ ID NO 1
<211> LENGTH: 891
<212> TYPE: DNA
<213> ORGANISM: Artificial Sequence
<220> FEATURE:
<223> OTHER INFORMATION: Polynucleodide for galectin-9 mutein
<220> FEATURE:
<221> NAME/KEY: CDS
<222> LOCATION: (1)..(891)
<223> OTHER INFORMATION: G9NC(null)

<400> SEQUENCE: 1 atg gcc ttc agc ggt tcc cag gct ccc tac ctg agt cca gct gtc ccc      48
Met Ala Phe Ser Gly Ser Gln Ala Pro Tyr Leu Ser Pro Ala Val Pro
1               5                   10                  15 ttt tct ggg act att caa gga ggt ctc cag gac gga ctt cag atc act      96
Phe Ser Gly Thr Ile Gln Gly Gly Leu Gln Asp Gly Leu Gln Ile Thr
            20                  25                  30 gtc aat ggg acc gtt ctc agc tcc agt gga acc agg ttt gct gtg aac      144
Val Asn Gly Thr Val Leu Ser Ser Ser Gly Thr Arg Phe Ala Val Asn
        35                  40                  45 ttt cag act ggc ttc agt gga aat gac att gcc ttc cac ttc aac cct      192
Phe Gln Thr Gly Phe Ser Gly Asn Asp Ile Ala Phe His Phe Asn Pro
    50                  55                  60 cgg ttt gaa gat gga ggg tac gtg gtg tgc aac acg agg cag aac gga      240
Arg Phe Glu Asp Gly Gly Tyr Val Val Cys Asn Thr Arg Gln Asn Gly
65                  70                  75                  80 agc tgg ggg ccc gag gag agg aag aca cac atg cct ttc cag aag ggg      288
Ser Trp Gly Pro Glu Glu Arg Lys Thr His Met Pro Phe Gln Lys Gly
                85                  90                  95 atg ccc ttt gac ctc tgc ttc ctg gtg cag agc tca gat ttc aag gtg      336
Met Pro Phe Asp Leu Cys Phe Leu Val Gln Ser Ser Asp Phe Lys Val
            100                 105                 110 atg gtg aac ggg atc ctc ttc gtg cag tac ttc cac cgc gtg ccc ttc      384
Met Val Asn Gly Ile Leu Phe Val Gln Tyr Phe His Arg Val Pro Phe
        115                 120                 125 cac cgt gtg gac acc atc tcc gtc aat ggc tct gtg cag ctg tcc tac      432
His Arg Val Asp Thr Ile Ser Val Asn Gly Ser Val Gln Leu Ser Tyr
    130                 135                 140 atc agc ttc cag cat atg act ccc gcc atc cca cct atg atg tac ccc      480
Ile Ser Phe Gln His Met Thr Pro Ala Ile Pro Pro Met Met Tyr Pro
145                 150                 155                 160
```

| | | |
|---|---|---|
| cac ccc gcc tat ccg atg cct ttc atc acc acc att ctg gga ggg ctg<br>His Pro Ala Tyr Pro Met Pro Phe Ile Thr Thr Ile Leu Gly Gly Leu<br>               165                         170                   175 | | 528 |
| tac cca tcc aag tcc atc ctc ctg tca ggc act gtc ctg ccc agt gct<br>Tyr Pro Ser Lys Ser Ile Leu Leu Ser Gly Thr Val Leu Pro Ser Ala<br>         180                          185                       190 | | 576 |
| cag agg ttc cac atc aac ctg tgc tct ggg aac cac atc gcc ttc cac<br>Gln Arg Phe His Ile Asn Leu Cys Ser Gly Asn His Ile Ala Phe His<br>        195                         200                    205 | | 624 |
| ctg aac ccc cgt ttt gat gag aat gct gtg gtc cgc aac acc cag atc<br>Leu Asn Pro Arg Phe Asp Glu Asn Ala Val Val Arg Asn Thr Gln Ile<br>210                         215                       220 | | 672 |
| gac aac tcc tgg ggg tct gag gag cga agt ctg ccc cga aaa atg ccc<br>Asp Asn Ser Trp Gly Ser Glu Glu Arg Ser Leu Pro Arg Lys Met Pro<br>225                       230                       235                 240 | | 720 |
| ttc gtc cgt ggc cag agc ttc tca gtg tgg atc ttg tgt gaa gct cac<br>Phe Val Arg Gly Gln Ser Phe Ser Val Trp Ile Leu Cys Glu Ala His<br>                     245                       250                    255 | | 768 |
| tgc ctc aag gtg gcc gtg gat ggt cag cac ctg ttt gaa tac tac cat<br>Cys Leu Lys Val Ala Val Asp Gly Gln His Leu Phe Glu Tyr Tyr His<br>                260                       265                    270 | | 816 |
| cgc ctg agg aac ctg ccc acc atc aac aga ctg gaa gtg ggg ggc gac<br>Arg Leu Arg Asn Leu Pro Thr Ile Asn Arg Leu Glu Val Gly Gly Asp<br>275                         280                       285 | | 864 |
| atc cag ctg acc cat gtg cag aca tag<br>Ile Gln Leu Thr His Val Gln Thr<br>        290                         295 | | 891 |

<210> SEQ ID NO 2
<211> LENGTH: 296
<212> TYPE: PRT
<213> ORGANISM: Artificial Sequence
<220> FEATURE:
<223> OTHER INFORMATION: Polynucleodide for galectin-9 mutein

<400> SEQUENCE: 2

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln His Met Thr Pro Ala Ile Pro Pro Met Met Tyr Pro
145                 150                 155                 160

His Pro Ala Tyr Pro Met Pro Phe Ile Thr Thr Ile Leu Gly Gly Leu
                165                 170                 175

```
Tyr Pro Ser Lys Ser Ile Leu Ser Gly Thr Val Leu Pro Ser Ala
            180                 185                 190

Gln Arg Phe His Ile Asn Leu Cys Ser Gly Asn His Ile Ala Phe His
        195                 200                 205

Leu Asn Pro Arg Phe Asp Glu Asn Ala Val Val Arg Asn Thr Gln Ile
    210                 215                 220

Asp Asn Ser Trp Gly Ser Glu Arg Ser Leu Pro Arg Lys Met Pro
225                 230                 235                 240

Phe Val Arg Gly Gln Ser Phe Ser Val Trp Ile Leu Cys Glu Ala His
                245                 250                 255

Cys Leu Lys Val Ala Val Asp Gly Gln His Leu Phe Glu Tyr Tyr His
            260                 265                 270

Arg Leu Arg Asn Leu Pro Thr Ile Asn Arg Leu Glu Val Gly Gly Asp
        275                 280                 285

Ile Gln Leu Thr His Val Gln Thr
    290                 295

<210> SEQ ID NO 3
<211> LENGTH: 148
<212> TYPE: PRT
<213> ORGANISM: Homo sapiens

<400> SEQUENCE: 3

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Gly Thr Arg Phe Ala Val Asn
            35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln
145

<210> SEQ ID NO 4
<211> LENGTH: 146
<212> TYPE: PRT
<213> ORGANISM: Homo sapiens

<400> SEQUENCE: 4

Thr Pro Ala Ile Pro Pro Met Met Tyr Pro His Pro Ala Tyr Pro Met
1               5                   10                  15

Pro Phe Ile Thr Thr Ile Leu Gly Gly Leu Tyr Pro Ser Lys Ser Ile
                20                  25                  30

Leu Leu Ser Gly Thr Val Leu Pro Ser Ala Gln Arg Phe His Ile Asn
            35                  40                  45

Leu Cys Ser Gly Asn His Ile Ala Phe His Leu Asn Pro Arg Phe Asp
```

```
                50                    55                    60
Glu Asn Ala Val Val Arg Asn Thr Gln Ile Asp Asn Ser Trp Gly Ser
 65                  70                  75                  80

Glu Glu Arg Ser Leu Pro Arg Lys Met Pro Phe Val Arg Gly Gln Ser
                 85                  90                  95

Phe Ser Val Trp Ile Leu Cys Glu Ala His Cys Leu Lys Val Ala Val
            100                 105                 110

Asp Gly Gln His Leu Phe Glu Tyr Tyr His Arg Leu Arg Asn Leu Pro
            115                 120                 125

Thr Ile Asn Arg Leu Glu Val Gly Gly Asp Ile Gln Leu Thr His Val
130                 135                 140

Gln Thr
145

<210> SEQ ID NO 5
<211> LENGTH: 972
<212> TYPE: DNA
<213> ORGANISM: Homo sapiens
<220> FEATURE:
<221> NAME/KEY: CDS
<222> LOCATION: (1)..(972)
<223> OTHER INFORMATION: galectin-9 medium isoform

<400> SEQUENCE: 5 atg gcc ttc agc ggt tcc cag gct ccc tac ctg agt cca gct gtc ccc      48
Met Ala Phe Ser Gly Ser Gln Ala Pro Tyr Leu Ser Pro Ala Val Pro
 1               5                  10                  15 ttt tct ggg act att caa gga ggt ctc cag gac gga ctt cag atc act      96
Phe Ser Gly Thr Ile Gln Gly Gly Leu Gln Asp Gly Leu Gln Ile Thr
             20                  25                  30 gtc aat ggg acc gtt ctc agc tcc agt gga acc agg ttt gct gtg aac     144
Val Asn Gly Thr Val Leu Ser Ser Ser Gly Thr Arg Phe Ala Val Asn
         35                  40                  45 ttt cag act ggc ttc agt gga aat gac att gcc ttc cac ttc aac cct     192
Phe Gln Thr Gly Phe Ser Gly Asn Asp Ile Ala Phe His Phe Asn Pro
     50                  55                  60 cgg ttt gaa gat gga ggg tac gtg gtg tgc aac acg agg cag aac gga     240
Arg Phe Glu Asp Gly Gly Tyr Val Val Cys Asn Thr Arg Gln Asn Gly
 65                  70                  75                  80 agc tgg ggg ccc gag gag agg aag aca cac atg cct ttc cag aag ggg     288
Ser Trp Gly Pro Glu Glu Arg Lys Thr His Met Pro Phe Gln Lys Gly
                 85                  90                  95 atg ccc ttt gac ctc tgc ttc ctg gtg cag agc tca gat ttc aag gtg     336
Met Pro Phe Asp Leu Cys Phe Leu Val Gln Ser Ser Asp Phe Lys Val
            100                 105                 110 atg gtg aac ggg atc ctc ttc gtg cag tac ttc cac cgc gtg ccc ttc     384
Met Val Asn Gly Ile Leu Phe Val Gln Tyr Phe His Arg Val Pro Phe
            115                 120                 125 cac cgt gtg gac acc atc tcc gtc aat ggc tct gtg cag ctg tcc tac     432
His Arg Val Asp Thr Ile Ser Val Asn Gly Ser Val Gln Leu Ser Tyr
        130                 135                 140 atc agc ttc cag cct ccc ggc gtg tgg cct gcc aac ccg gct ccc att     480
Ile Ser Phe Gln Pro Pro Gly Val Trp Pro Ala Asn Pro Ala Pro Ile
145                 150                 155                 160 acc cag aca gtc atc cac aca gtg cag agc gcc cct gga cag atg ttc     528
Thr Gln Thr Val Ile His Thr Val Gln Ser Ala Pro Gly Gln Met Phe
                165                 170                 175 tct act ccc gcc atc cca cct atg atg tac ccc cac ccc gcc tat ccg     576
Ser Thr Pro Ala Ile Pro Pro Met Met Tyr Pro His Pro Ala Tyr Pro
            180                 185                 190
```

```
atg cct ttc atc acc acc att ctg gga ggg ctg tac cca tcc aag tcc    624
Met Pro Phe Ile Thr Thr Ile Leu Gly Gly Leu Tyr Pro Ser Lys Ser
    195             200             205 atc ctc ctg tca ggc act gtc ctg ccc agt gct cag agg ttc cac atc    672
Ile Leu Leu Ser Gly Thr Val Leu Pro Ser Ala Gln Arg Phe His Ile
210             215             220 aac ctg tgc tct ggg aac cac atc gcc ttc cac ctg aac ccc cgt ttt    720
Asn Leu Cys Ser Gly Asn His Ile Ala Phe His Leu Asn Pro Arg Phe
225             230             235             240 gat gag aat gct gtg gtc cgc aac acc cag atc gac aac tcc tgg ggg    768
Asp Glu Asn Ala Val Val Arg Asn Thr Gln Ile Asp Asn Ser Trp Gly
            245             250             255 tct gag gag cga agt ctg ccc cga aaa atg ccc ttc gtc cgt ggc cag    816
Ser Glu Glu Arg Ser Leu Pro Arg Lys Met Pro Phe Val Arg Gly Gln
            260             265             270 agc ttc tca gtg tgg atc ttg tgt gaa gct cac tgc ctc aag gtg gcc    864
Ser Phe Ser Val Trp Ile Leu Cys Glu Ala His Cys Leu Lys Val Ala
        275             280             285 gtg gat ggt cag cac ctg ttt gaa tac tac cat cgc ctg agg aac ctg    912
Val Asp Gly Gln His Leu Phe Glu Tyr Tyr His Arg Leu Arg Asn Leu
        290             295             300 ccc acc atc aac aga ctg gaa gtg ggg ggc gac atc cag ctg acc cat    960
Pro Thr Ile Asn Arg Leu Glu Val Gly Gly Asp Ile Gln Leu Thr His
305             310             315             320 gtg cag aca tag                                                    972
Val Gln Thr <210> SEQ ID NO 6
<211> LENGTH: 323
<212> TYPE: PRT
<213> ORGANISM: Homo sapiens

<400> SEQUENCE: 6

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
```

```
                    195                 200                 205
Ile Leu Leu Ser Gly Thr Val Leu Pro Ser Ala Gln Arg Phe His Ile
210                 215                 220

Asn Leu Cys Ser Gly Asn His Ile Ala Phe His Leu Asn Pro Arg Phe
225                 230                 235                 240

Asp Glu Asn Ala Val Val Arg Asn Thr Gln Ile Asp Asn Ser Trp Gly
                245                 250                 255

Ser Glu Glu Arg Ser Leu Pro Arg Lys Met Pro Phe Val Arg Gly Gln
                260                 265                 270

Ser Phe Ser Val Trp Ile Leu Cys Glu Ala His Cys Leu Lys Val Ala
                275                 280                 285

Val Asp Gly Gln His Leu Phe Glu Tyr Tyr His Arg Leu Arg Asn Leu
                290                 295                 300

Pro Thr Ile Asn Arg Leu Glu Val Gly Gly Asp Ile Gln Leu Thr His
305                 310                 315                 320

Val Gln Thr

<210> SEQ ID NO 7
<211> LENGTH: 61
<212> TYPE: PRT
<213> ORGANISM: Homo sapiens

<400> SEQUENCE: 7

Asn Pro Arg Thr Val Pro Val Gln Pro Ala Phe Ser Thr Val Pro Phe
1               5                   10                  15

Ser Gln Pro Val Cys Phe Pro Pro Arg Pro Arg Gly Arg Arg Gln Lys
                20                  25                  30

Pro Pro Gly Val Trp Pro Ala Asn Pro Ala Pro Ile Thr Gln Thr Val
            35                  40                  45

Ile His Thr Val Gln Ser Ala Pro Gly Gln Met Phe Ser
        50                  55                  60

<210> SEQ ID NO 8
<211> LENGTH: 29
<212> TYPE: PRT
<213> ORGANISM: Homo sapiens

<400> SEQUENCE: 8

Pro Pro Gly Val Trp Pro Ala Asn Pro Ala Pro Ile Thr Gln Thr Val
1               5                   10                  15

Ile His Thr Val Gln Ser Ala Pro Gly Gln Met Phe Ser
                20                  25

<210> SEQ ID NO 9
<211> LENGTH: 17
<212> TYPE: PRT
<213> ORGANISM: Homo sapiens

<400> SEQUENCE: 9

Thr Gln Thr Val Ile His Thr Val Gln Ser Ala Pro Gly Gln Met Phe
1               5                   10                  15

Ser

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide to act as a primer for PCR
```

```
<400> SEQUENCE: 10
cgtcctcata tggccttcag cggttcccag                                            30

<210> SEQ ID NO 11
<211> LENGTH: 33
<212> TYPE: DNA
<213> ORGANISM: Artificial Sequence
<220> FEATURE:
<223> OTHER INFORMATION: Oligonucleotide to act as a primer for PCR

<400> SEQUENCE: 11
cgaccgcata tgctggaagc tgatgtagga cag                                        33

<210> SEQ ID NO 12
<211> LENGTH: 33
<212> TYPE: DNA
<213> ORGANISM: Artificial Sequence
<220> FEATURE:
<223> OTHER INFORMATION: Oligonucleotide to act as a primer for PCR

<400> SEQUENCE: 12
cgtcctcata tgactcccgc catcccacct atg                                        33

<210> SEQ ID NO 13
<211> LENGTH: 33
<212> TYPE: DNA
<213> ORGANISM: Artificial Sequence
<220> FEATURE:
<223> OTHER INFORMATION: Oligonucleotide to act as a primer for PCR

<400> SEQUENCE: 13
cgaccgggat ccctatgtct gcacatgggt cag                                        33
```

MODIFIED GALECTIN 9 PROTEINS AND METHODS OF TREATMENT USING THEM

CROSS-REFERENCE TO RELATED APPLICATION

This application is a divisional of application Ser. No. 11/547,091, filed Jan. 4, 2007 now U.S. Pat. No. 8,268,324, which is the National Stage of International Application No. PCT/JP2005/006580, filed Mar. 29, 2005.

FIELD OF THE INVENTION

The present invention relates to novel modified galectin 9 proteins (galectin-9 muteins) and applications thereof. Particularly, the present invention relates to functional mutant galectin 9 proteins wherein said functional mutant galectin 9 protein has a modified link peptide region, and their practical applications in biochemistry, medical diagnostics, therapy and pharmacology.

BACKGROUND OF THE INVENTION

Evidence indicating the following fact has been found: specific saccharide chains and proteins that bind to the same play a lot of various roles and functions in physiological phenomena, events associated with development/growth, and a variety of diseases in mammal's living bodies. It has been found that there are animal lectins, in living bodies, which specifically recognize saccharide chains with β-galactoside structure. Until now at least 14 types of genes have been identified for galectins which belong to the group of such lectins. Although the galectin family is classified, based on their structure, into three subgroups, i.e., prototype, chimera, and tandem repeat groups, the in vivo functions have scarcely been disclosed. Particularly, a study on tandem repeat type galectins retaining two carbohydrate recognition domains has only a short history. Since in vivo saccharide chains (receptors) to be targeted are still not revealed, the functions are not yet clarified. From details including how galectins were found when a search was made for proteins which recognize complicated sugar chains on the surface of cells, it is forecasted that they have functions such as involvement in cell adhesion, cell-to-cell communication, cell activation, etc. Therefore, galectins attract attention. In addition, research results anticipating the following are being obtained: the galectins retain, besides such functions, a variety of other important functions.

Galectin 9, one of tandem repeat type galectins, was first identified as an autoantigen in patients with Hodgkin's disease (Non-Patent Documents 1 & 2), and surmised to play an important role on cell-to-cell interactions among immune cells. Mouse galectin 9 was cloned from the mouse kidney cDNA library by 5'-RACE PCR with degenerated primers which were designed on the basis of sequences considered to be highly conservative among the carbohydrate recognition domains of galectins (Non-Patent Document 3). It has been found that antigen-stimulated T cells produce in vivo and in vitro an eosinophil chemoattractant, i.e., ecalectin.

Further, although ecalectin is structurally different from other eosinophil chemoattractants known up to that time, it has sugar-binding affinity to β-galactoside saccharide chains, whereby it may be classified into the galectin family. Cloning of ecalectin has been a success from mRNA obtained from human T cell-derived leukemia cell lines. As a result, it has been verified that ecalectin is one of galectin 9 variants, and galectin 9 and ecalectin are identical substances (Non-Patent Document 4).

It has been reported at present that wild type galectin 9 includes L-type galectin 9 (galectin-9 long isoform or long type galectin-9: Gal-9L), M-type galectin 9 (galectin-9 medium isoform or medium type galectin-9: Gal-9M), and S-type galectin 9 (galectin-9 short isoform or short type galectin-9: Gal-9S). Any of galectin 9 members is a molecule consisting of two carbohydrate recognition domains (CRDs) and a linker peptide that is a link region between two CRDs. L-type galectin 9 is a molecule with the longest link peptide region wherein the N-terminal domain (NCRD) is linked to the C-terminal domain (CCRD) with the aid of said link peptide region while S-type galectin 9 is a molecule with the shortest link peptide region. M-type galectin 9 is a molecule with a middle-length link peptide region as compared to both, and it has been known that Gal-9M is generally found to predominantly exist in body tissue and cells in contrast with the former two. In addition, it is perceivable that there is some evidence indicating the presence of genetic polymorphism among galectin 9 genes cloned from human cells and tissue.

Wild type galectin 9 consists of two carbohydrate recognition domains (CRDs) and a link region that is a link between said CRDs. It has been suggested that recombinant galectin 9, produced in host E. coli, induces inhibition of cancer metastasis and regression of cancers by direct actions on tumor cells (activity of inducing intercellular adhesion and apoptosis of tumor cells) and actions via the immune system. It has been revealed that galectin 9 does not act on non-activated lymphocytes while it induces apoptosis of activated lymphocytes, inter alia CD4-positive T cells which will cause hyperimmune reaction. It is also disclosed that galectin 9 has a potent apoptosis-inducing property of acting on synovial cells involved in deformity of joints or other symptoms under rheumatism.

[Non-Patent Document 1] Sahin, U. et al., Proc. Natl. Acad. Sci. USA, 92, 11810-11813 (1995)

[Non-Patent Document 2] Türeci, O. et al., J. Biol. Chem., 272(10), 6416-6422 (1997)

[Non-Patent Document 3] Wada, J. et al., J. Biol. Chem., 272(9), 6078-6086 (1997)

[Non-Patent Document 4] Matsumoto, R. et al., J. Biol. Chem., 273(27), 16976-16984 (1998)

SUMMARY OF THE INVENTION

Utilization of such versatile properties possessed by galectin 9 is expected to promise therapeutic techniques for cancers, refractory autoimmune diseases (including rheumatism), allergic disorders, and others. However, recombinant galectin 9 (rGal 9) has a link area susceptible to protease wherein said link area connects two CRDs, and is therefore readily digestible with proteolytic enzymes. The proteolytic cleavage of rGal 9 will result in loss of the aforementioned activity.

The present inventors have conducted an extensive research on various molecules in order to solve the above problems. As a result, the present inventors have succeeded in producing novel molecules having a more stable molecular structure against the action of protease while the carbohydrate recognizing activity of wild type galectin 9 is retained. The present inventors have succeeded in constructing highly stabilized modified molecules without adversely affecting the aforementioned activity wherein said molecule has an altered Gal 9 link area that links two CRDs of Gal 9. Therefore, the present invention has been achieved.

The present invention provides the following:

(1) A protein, or a salt thereof, comprising a functional mutant galectin 9 protein with an amino acid sequence that differs from an amino acid sequence of wild type galectin 9 or a protein with substantially equivalent galectin 9 activity wherein said functional mutant galectin 9 protein has a modified link peptide or a modified site or region in the neighborhood of the galectin 9 link peptide.

(2) The protein, or a salt thereof, according to the above (1), wherein said functional mutant galectin 9 protein has not only a modified sequence that differs from an amino acid sequence of wild type galectin 9 or a protein with substantially equivalent galectin 9 activity by the deletion, substitution or addition of at least one or more amino acid residues at a link peptide or a site or region in the neighborhood of the galectin 9 link peptide but also altered susceptibility to degradation of said galectin 9 link peptide as compared to wild type galectin 9.

(3) The protein, or a salt thereof, according to the above (1) or (2), wherein said protein with substantially equivalent galectin 9 activity is at least 70% or more homologous to wild type galectin 9 at an amino acid level.

(4) The protein, or a salt thereof, according to any of the above (1) to (3), wherein

[1] the N-terminal carbohydrate recognition domain (NCRD) of wild type galectin 9 or a polypeptide with substantially equivalent galectin 9 NCRD activity is coupled with

[2] the C-terminal carbohydrate recognition domain (CCRD) of wild type galectin 9 or a polypeptide with substantially equivalent galectin 9 CCRD activity via

[3] a modified link peptide with an amino acid sequence that differs from an amino acid sequence of wild type galectin 9 link peptide by the deletion, substitution or addition of at least one or more amino acid residues at a galectin 9 link peptide region.

(5) The protein, or a salt thereof, according to any of the above (1) to (4), wherein

[1] a member selected from the group consisting of a polypeptide having an amino acid sequence of SEQ ID NO: 3, a polypeptide having not only substantially equivalent SEQ ID NO: 3 polypeptide activity but also an amino acid sequence at least 70% homologous to SEQ ID NO: 3, and a polypeptide having a mutant amino acid sequence that differs from an amino acid sequence of SEQ ID NO: 3 by the deletion, substitution or addition of at least 1 to 8 amino acid residues on the SEQ ID NO: 3 amino acid sequence is coupled with

[2] a member selected from the group consisting of a polypeptide having an amino acid sequence of SEQ ID NO: 4, a polypeptide having not only substantially equivalent SEQ ID NO: 4 polypeptide activity but also an amino acid sequence at least 70% homologous to SEQ ID NO: 4, and a polypeptide having a mutant amino acid sequence that differs from an amino acid sequence of SEQ ID NO: 4 by the deletion, substitution or addition of at least 1 to 21 amino acid residues on the SEQ ID NO: 4 amino acid sequence via

[3] a modified link peptide with an amino acid sequence that differs from an amino acid sequence of a member selected from the group consisting of SEQ ID NOs 7 to 9 by the deletion, substitution or addition of at least one or more amino acid residues on any amino acid sequence of SEQ ID NOs 7 to 9, provided that the deletion of residues 1 to 32 and residues 1 to 44 on SEQ ID NO: 7 and residues 1 to 12 on SEQ ID NO: 8 is excluded.

(6) A nucleic acid molecule comprising a nucleotide sequence encoding the protein according to any of the above (1) to (5).

(7) The nucleic acid molecule according to the above (6), wherein said molecule is a polynucleotide.

(8) The nucleic acid molecule according to the above (6) or (7), wherein said molecule is DNA or RNA.

(9) A recombinant vector comprising the nucleic acid molecule according to any of the above (6) to (8).

(10) The recombinant vector according to the above (9) wherein said vector comprises a nucleotide sequence coding for a protein marker and/or a peptide marker in combination with the nucleic acid molecule according to any of the above (6) to (8).

(11) A transformed or transfected cell carrying the nucleic acid molecule according to any of the above (6) to (8) or the recombinant vector according to the above (9) or (10).

(12) The transformed or transfected cell according to the above (11), wherein said host cell is procaryotic or eucaryotic.

(13) A pharmaceutical drug comprising an effective amount of at least one member selected from the group consisting of the protein according to any of the above (1) to (5), the nucleic acid molecule according to any of the above (6) to (8), the recombinant vector according to the above (9) or (10), and the transformed or transfected cell according to the above (11) or (12).

(14) The pharmaceutical drug according to the above (13) which is an immunoregulator or immunomodulator.

(15) The pharmaceutical drug according to the above (13) which is an antineoplastic or antitumor agent.

(16) The pharmaceutical drug according to the above (15) which is an antineoplastic or antitumor agent for preventing and/or treating at least one tumor selected from the group consisting of sarcomas or cancers, including brain tumors (glioblastoma multiforme, etc.), spinal tumors, maxillary sinus carcinoma, pancreatic ductal adenocarcinoma, gingival cancers, tongue cancers, lip cancers, nasopharyngeal cancers, oropharyngeal cancers, hypopharyngeal cancers, laryngeal cancers, thyroid cancers, parathyroid cancers, lung cancers, pleural tumors, carcinomatous peritonitis, carcinomatous pleurisy, esophageal cancers, stomach cancers, colon cancers, bile duct cancers, gall bladder cancers, pancreatic cancers, liver cancers, renal cancers, urinary bladder cancers, prostatic cancers, penile cancers, testicular tumors, adrenal cancers, cervical cancers, endometrial cancers, vaginal cancers, vulvar cancers, ovarian cancers, chorioepithelioma, malignant bone tumors, soft part sarcoma, breast cancers, skin cancers, malignant melanoma, basal cell tumors, leukemia, myelofibrosis associated with agnogenic myeloid metaplasia, malignant lymphoma, Hodgkin's disease, plasmacytoma, glioma and others.

(17) The pharmaceutical drug according to the above (13) which is for preventing and/or treating at least one disorder, disease or pathological condition selected from the group consisting of:

(A) a member selected from the group consisting of inflammatory diseases and disorders: a variety of acute or chronic inflammations occurring in various organs, allergic or autoimmune inflammations, and infectious diseases;

(B) a member selected from the group consisting of acute and chronic diseases and disorders: lung diseases or disorders including bronchitis, bronchopneumonia, interstitial pneumonia, pneumonitis, bronchiolitis, and acute mediastinitis; diseases or disorders of miscellaneous organs other than lung, including pericarditis, endocarditis, myocarditis, stomatitis, angular stomatitis, tonsillitis, pharyngitis, laryngitis, esophagitis, peritonitis, acute gastritis, chronic gastritis, acute enteritis, appendicitis, ischemic colitis, drug induced colitis, and proctitis; and inflammatory diseases and disorders including hepatitis A, hepatitis B, hepatitis C, fulminant hepatitis, acute or chronic hepatitis and cirrhosis, cholecystitis, acute pancreatitis, chronic pancreatitis, acute or chronic nephritis, membranous glomerulonephritis, glomerulonephritis, IgA nephritis, a variety of cystitis, encephalomyelitis, mastitis, dermatitis, superficial keratitis, xerotic keratoconjunctivitis, otitis media and rhinitis, paranasal sinusitis and nasal polyp, gingivitis, periodontitis, and other inflammatory disorders of the periodontium;

(C) a member selected from the group consisting of neurogenic inflammations, such as neurogenic gastritis and neurogenic cystitis, and pain associated with cancer and inflammation;

(D) a member selected from the group consisting of allergy associated inflammatory diseases including systemic or generalized anaphylaxis, bronchial asthma, hypersensitivity pneumonitis, pollenosis, allergic rhinitis, allergic conjunctivitis, immune complex-induced allergic diseases, and angioneurotic edema;

(E) a member selected from the group consisting of autoimmune related inflammatory diseases (autoimmune diseases): systemic diseases (chronic rheumatoid arthritis, systemic lupus erythematosis, polyarteritis nodosa, scleroderma, polymyositis/dermatomyositis, Sjögren's syndrome, Behçet's disease and others), nervous system diseases (multiple sclerosis, myasthenia gravis, HAM (HTLV-1 myelosis), amyotrophic lateral sclerosis and others), endocrine diseases (Basedow's disease, Hashimoto's thyroiditis, type 1 diabetes and others), blood diseases (idiopathic thrombocytopenic purpura, autoimmune hemolytic anemia, aplastic anemia and others), respiratory diseases (sarcoidosis, idiopathic pulmonary fibrosis and others), gastrointestinal diseases (ulcerative colitis, Crohn's disease and others), hepatic diseases (autoimmune hepatitis, primary biliary cirrhosis, primary sclerosing cholangitis, autoimmune cholangitis and others), and renal/urinary tract system diseases (anti-neutrophil cytoplasmic antibody associated nephritis, angitis, Goodpasture's syndrome, anti-glomerular basement membrane antibody disease and others);

(F) a member selected from the group consisting of infectious diseases: diseases and abnormal conditions occurring when pathogens cause damage and/or injury to cells, tissues and organs within the body, or diseases resulting from the presence or activity of the pathogen causing infection in human, wherein said pathogen is selected from the group consisting of 1) bacteria (including spirochaeta, chlamydia, and *Rickettsia*), 2) viruses, 3) fungi, 4) plants (algae), 5) protozoa, 6) parasites (Digenea (distomes or trematodes), cestodes (tapeworms), nematodes), and 7) arthropods; including bacterioses (cholera, pest, *Escherichia coli* infection, etc.), spirochetoses (leptospirosis, etc.), chlamydioses (psittacosis, etc.), rickettsial infections (*Rickettsia prowazekii*, tetanus, etc.), viral infections (herpes zoster, viral hemorrhagic fever, rabies, etc.), mycoses (candidiasis, cryptococcosis, aspergillosis, etc.), protozoal diseases (amebic dysentery, malaria, toxoplasmosis, etc.), parasitoses (distomiasis, nematodiasis, etc.), as well as mycoplasma infections (mycoplasma pneumonia, etc.), mycobacterioses (tuberculosis, atypical mycobacteriosis, etc.);

(G) a member selected from the group consisting of skin diseases and abnormal skin conditions: i) skin infections, skin inflammations including allergic inflammations and autoimmune inflammations, and skin diseases with inflammatory characteristics, such as psoriasis, hydroa, pustulosis, kerati-nization, and keratonosis, and ii) skin damages, and cosmetically disfiguring or age-related skin conditions, including dermatological diseases and cosmetically unpleasant conditions (including aging) associated with a) control of melanin metabolism (skin whitening), b) control of hair growth (trichogen), and c) control of collagen production;

(H) a member selected from the group consisting of lifestyle related diseases including hypercholesterolemia, arteriosclerosis, hypertension and diabetes.

(I) abnormal conditions with regard to the maintenance of a normal bacterial flora;

(J) a member selected from the group consisting of those including amyloidosis, Alzheimer's disease, osteoporosis, and bone fracture;

(K) inflammatory responses in brain and nervous areas: for example, inflammations occurring in response to the development of ischemic lesions, such as cerebral infarction and myocardial infarction, and schizophrenia;

(L) gout;

(M) osteoporosis; and (N) interstitial pneumonitis.

(18) An assay or test reagent comprising an effective amount of at least one member selected from the group consisting of the protein according to any of the above (1) to (5), the nucleic acid molecule according to any of the above (6) to (8), the recombinant vector according to the above (9) or (10), and the transformed or transfected cell according to the above (11) or (12).

ADVANTAGEOUS PROFILES OF THE INVENTION

Modified galectin 9 molecules, which are designed on the basis of galectin 9, are more stabilized against proteases as compared to wild type galectin 9. Therefore, the modified Gal 9 molecules can be expected to be useful in eliciting and revealing the in vivo functions of Gal 9. Said modified Gal 9 molecules are also applicable to studies on functions and actions of galectin 9 that may contribute to the regulation and control of various bioreactions including the regulation of tumorized cells, immunoregulation, and the control of allergy and inflammation. Further, said modified Gal 9 molecules and related substances thereof have bright prospects for reagents and agents in clinical, molecular biological biochemical and medical applications.

The above objects and other objects, features, advantages, and aspects of the present invention are readily apparent to those skilled in the art from the following disclosures. It should be understood, however, that the disclosures in the specification including the following best modes of carrying out the invention, examples, and others are illustrating preferred embodiments of the present invention and given for purposes of illustration only. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

BRIEF DESCRIPTION OF THE DRAWINGS

FIG. 8 is a list of amino acids at several positions in galectin-9 EST. These putative galectin-9 EST clones were identified by BLAST sequence search using the ecalectin nucleotide sequence as query. The sequence identity (homology) of these clones with the ecalectin is usually 97 to 99%. The EST clones from different sources are demonstrated without amino acids at positions 5, 88, 135, 238, and 281, respectively.

FIG. 25 shows photos showing animal states in the model of cancerous peritonitis, induced by Meth A cells, for modified galectin 9 mutein ((Gal9)-non-administered (upper) and -administered (lower) groups.

FIG. 31 shows graphs of cell numbers in BALF, assay results for actions of modified galectin 9 mutein (Gal-9) and dexamethasone (Dex.) on the model of mite antigen-induced asthma.

FIG. 39 shows graphs of assay results for actions of modified galectin 9 mutein (Gal-9) and dexamethasone (Dex.) on the model (mouse) of ARDS.

FIG. 40 shows graphs of cell numbers in BALF, assay results for actions of modified galectin 9 mutein (Gal-9) and dexamethasone (Dex.) on the model (mouse) of ARDS.

FIG. 47 shows photos showing test results for the action of modified galectin 9 mutein on the model of interstitial pneumonia. The photos exhibit lung tissue images of animals survived on Day 14 (stained with HE).

FIG. 49 shows photos showing test results for the action of modified galectin 9 mutein on the model of metastatic cancer, induced by B16/F10 cells. The photos exhibit lung images (exterior views) of model animals.

FIG. 53 shows immunohistological staining results for expression of galectin-9 in rheumatoid arthritis (RA) synovium.

FIG. 54 shows microscopic photos of RA synovial cells. The galectin-9 mediated activity of inducing apoptosis of the RA synovial cells was observed.

FIG. 59 shows graphs of assay results for the action of positive control, indomethacin, in the model of adjuvant arthritis (suppression of pain triggered by mechanical stimulation), for comparison.

FIG. 66 shows graphs of assay results for the efficacy of modified galectin 9 mutein (i.v. administration) on the model of adjuvant arthritis.

FIG. 67 shows graphs of assay results for the efficacy of positive control, indomethacin, on the model of adjuvant arthritis, for comparison.

BEST MODES OF CARRYING OUT THE INVENTION

Figure 1:
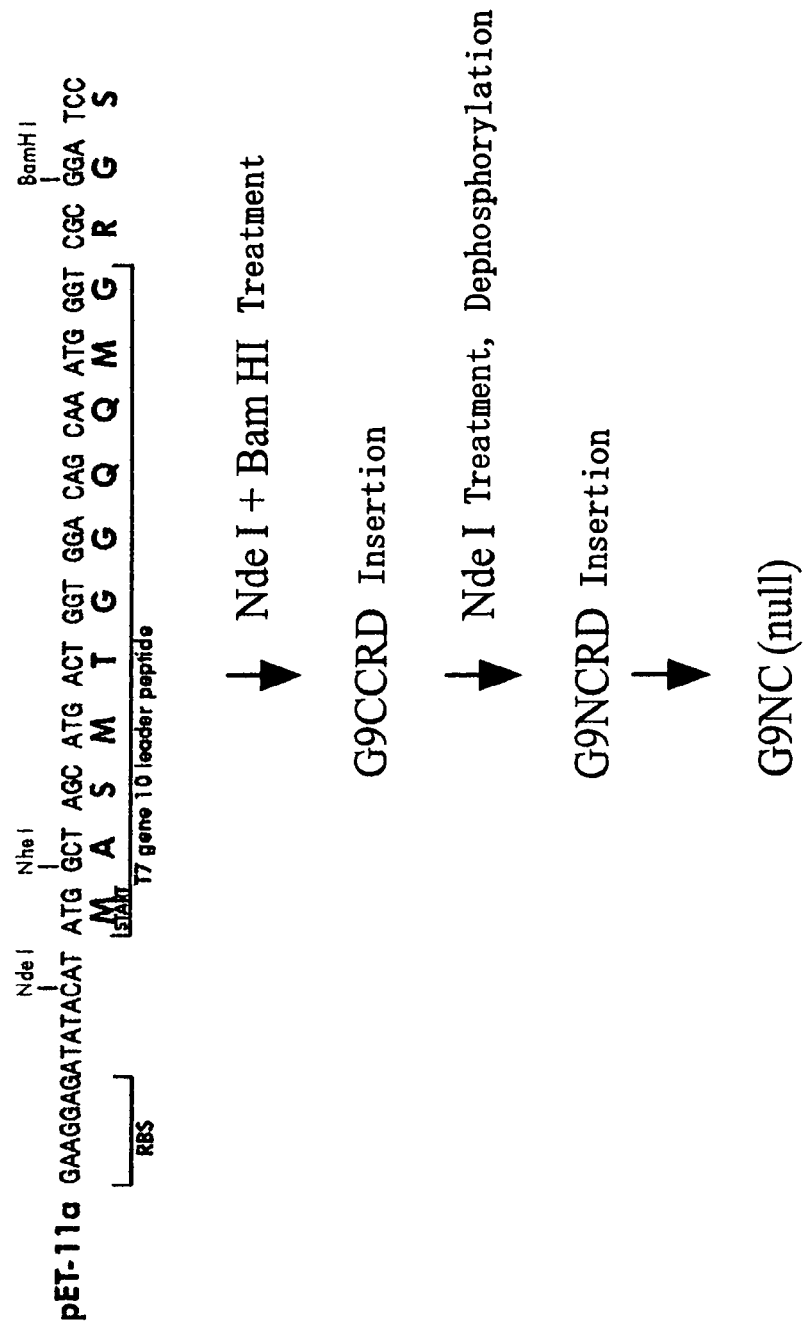
FIG. 1 is a scheme illustrating steps for construction of modified galectin 9 mutein (G9NC(null)) expression vector.

The invention described herein draws on previously published work and pending patent applications. All such published work and pending patent applications are hereby incorporated by reference in full.

The "modified galectin 9 mutein", "modified galectin 9 variant", "modified galectin 9", or "modified galectin 9 protein" refers to a substance provided with an activity to specifically bind to a specific saccharide chain wherein said activity is retained by the carbohydrate recognition domain of galectin 9, or its analogous activity (including qualitative or/and quantitative). It is noted that galectin 9 has an activity to induce apoptosis of a specific cell. The modified galectin 9 mutein may be a substance having an apoptosis-inducing activity, owned by wild type galectin 9, or an analogous activity thereof, and a substance wherein the bioactivity retained by wild type galectin 9 is altered or modified, which is preferable in some cases. The particularly preferred modified galectin 9 mutein herein is a molecule retaining a more desirable property in order to serve as a biologically active reagent in diagnostic, analytic, medical, or pharmaceutical applications than wild type galectin 9.

The modified galectin 9 mutein may be, for example, a mutant galectin 9 protein, or a salt thereof, wherein the link peptide of wild type (native) galectin 9 or a protein with substantially equivalent galectin 9 activity is modified, or the site or region in the neighborhood of said link peptide is modified; a modified galectin 9 protein, or a salt thereof, not only having a modified sequence that differs from an amino acid sequence of wild type galectin 9 or a protein with substantially equivalent galectin 9 activity by at least one deletion, substitution or addition of one or more amino acid residues at a link peptide or a site or region in the neighborhood of the galectin 9 link peptide but also altered susceptibility to degradation of said galectin 9 link peptide as compared to wild type galectin 9; a protein, or a salt thereof, not only retaining substantially equivalent galectin 9 activity but also being at least 70%, still at least 75%, yet at least 80%, also at least 85%, at least 90%, or at least 95% or higher homologous to the amino acid sequence of wild type galectin 9; a protein, or a salt thereof, having the formula:

NCRD Peptide (1)-Link Peptide (3)-CCRD Peptide (2)

in which (1) the NCRD Peptide (1) is selected from the group consisting of the N-terminal carbohydrate recognition domain (NCRD) of wild type galectin 9 and polypeptides with substantially equivalent Gal-9 NCRD activity, (2) the CCRD. Peptide (2) is selected from the group consisting of the C-terminal carbohydrate recognition domain (CCRD) of wild type galectin 9 and polypeptides with substantially equivalent Gal-9 CCRD activity, (3) the Link Peptide (3) is a modified link peptide that differs from the link peptide amino acid sequence of wild type galectin 9 by at least one deletion, substitution or addition of one or more amino acid residues in the galectin 9 link peptide amino acid sequence, and the NCRD Peptide (1) is linked to the CCRD Peptide (2) via the Link Peptide (3); etc.

By the way, it was reported in J. Biol. Chem., 272 (10): pp. 6416-6422 (1997) that a novel galectin was found in cDNA derived from the spleen of a patient with Hodgkin's disease and named "galectin 9", its sequence was reconfirmed with cDNA from normal peripheral blood in order to exclude mutations of the Hodgkin's disease tumor-derived human galectin-9 transcript, and finally the sequence of galectin 9 was determined as shown in FIG. 1 on page 6418 of said document. For galectin 9, it was further reported in J. Biol. Chem., 273 (27): pp. 16976-16984 (1998) that a novel eosinophil chemoattractant "ecalectin" was isolated from cDNA prepared from eosinophil chemoattractant-producing T-cell line STO-2, and its amino acid sequence was apparently different at amino acid residues 5, 88, 135, 238, and 281 from the amino acid sequence of the previously reported, above-described galectin 9 though it was highly homologous to the above-described galectin 9. Said ecalectin sequence is shown in FIG. 8 on page 16983 of this document wherein ecalectin is surmised to be a variant form of galectin 9.

Also, in J. Biol. Chem., 275 (12): pp. 8355-8360 (2000), galectin 9 was isolated from cDNA prepared from T-cell line Jurkat and recombinant galectin 9 proteins were produced. Since this recombinant galectin 9 exhibited eosinophil chemoattractant activity, Hirashima et al. decided to use galectin 9 with T-cell line Jurkat cell-derived sequence for their study henceforth, wherein the amino acid sequence of Jurkat cell-derived galectin 9 had Gly, Lys, Ser, Pro, and Glu at positions 5, 88, 135, 238, and 281, respectively, while it was different at amino acid residue 5 from the sequence of ecalectin reported in the aforementioned Matsumoto et al. (J. Biol. Chem., 273 (27): pp. 16976-16984 (1998)), i.e., Gly at position 5 of Jurkat cell-derived galectin 9 was replaced with Ser in the ecalectin amino acid sequence. It was disclosed that the Ser to Gly substitution at position 5 did not affect the eosinophil chemoattractant activity, and it was naturally considered in light of 17 putative galectin 9 ETS clones (including partial sequences) identified by sequence search using the galectin 9 sequence as query on the EST database that Gly, Lys, Ser, Pro, and Glu were set as the amino acids for positions 5, 88, 135, 238, and 281, respectively. Amino acid mutations in the galectin 9 sequence are also disclosed in Table II on page 8359 of said document (see FIG. 8). In FIG. 8, Gly (G), Lys (K), Ser (S), Pro (P), and Glu (E) are at positions 5, 88, 135, 238, and 281, respectively.

In J. Biol. Chem., 272 (9): pp. 6078-6086 (1997: Non-Patent Document 3), the regions for two carbohydrate recognition domains (CRDs) and a linker, 26 amino acids (for galectin 9M), between the two CRDs, were determined (see FIG. 1 in this document). In other words, when attention was given to the amino acid sequence of SEQ ID NO: 5, it was defined that the C-terminal carbohydrate recognition domain (CCRD) started from $Met^{175}$. Based on that, the CRD and link regions of human galectin 9 have been registered as Accession Number NP_033665 in the NCBI database.

Figure 2:
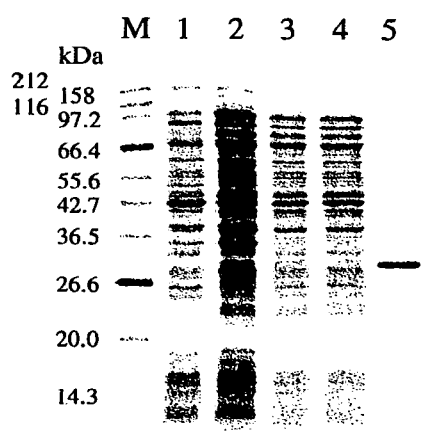
FIG. 2 is a photo showing electrophoretic patterns for an expressed modified galectin 9 mutein (G9NC(null)) product and a purified expressed G9NC(null product.

By the way, galectins 4 and 6 were reported in J. Biol. Chem., 273 (5): pp. 2954-2960 (1998), wherein definitions to the CRD and link regions thereof were given on the basis of their amino acid sequences and gene sequences, as shown in FIG. 2 on page 2956 of this document. When the configuration of galectin 9 reflects the aforementioned definitions, it is different in the link region and C-terminal CRD from the former configuration (J. Biol. Chem., 272 (9): pp. 6079-6086 (1997)), i.e., when the amino acid sequence of SEQ ID NO: 5 is based, the CCRD is defined to start from $Phe^{195}$.

The present inventor group takes into consideration the following: borders for exon splicing exist at positions closer by 3 amino acids to the C-terminal side than in the configuration set forth in Non-Patent Document 3, such as between $Gln^{148}$-$Pro^{149}$, between $Ile^{160}$-$Thr^{161}$, and between $Ser^{177}$-$Thr^{178}$. In addition, from examinations for the carbohydrate-binding property of the C-terminal CRD, i.e., on the basis of the amino acid sequence of SEQ ID NO: 5, the expression of full-length CCRD initiated from $Thr^{178}$ resulted in occurrence of its lactose-binding property, and further the deletion of 22 amino acids (CCRD fragment initiated from $Leu^{200}$) resulted in non-expression in E. coli while both the deletion of 6 amino acids (CCRD fragment initiated from $Met^{184}$) and the deletion of 12 amino acids (CCRD fragment initiated from $Ala^{190}$) did not cause a loss of lactose-binding activity, the present inventor group takes into consideration that it can be viewed that the configuration of CCRD initiated from $Phe^{195}$ is unprejudiced. Therefore, the region, $Thr^{178}$ to $Thr^{323}$, in the amino acid sequence of SEQ ID NO: 5 is defined herein as the C-terminal CRD. The N-terminal CRD (NCRD) of galectin 9 is examined on the basis of the amino acid sequence of SEQ ID NO: 5 as follows: when full-length NCRD terminated at $Gln^{148}$ was expressed, the resultant product had a lactose-binding property. Where 9 amino acids were removed (NCRD fragment of the sequence, $Met^1$ to $Ser^{139}$), however, the expression of proteins took place but the lactose-binding property was not observed. Therefore, $Met^1$ to $Gln^{148}$ in the amino acid sequence of SEQ ID NO: 5 is defined herein as the N-terminal CRD.

In preferred embodiments, the modified galectin 9 mutein include, for example, molecules wherein (1) the NCRD of galectin 9 is selected from the group consisting of the amino acid sequence of SEQ ID NO: 2, a mutant amino acid that differs from the amino acid sequence of SEQ ID NO: 2 by at least one deletion, substitution, or addition of one or more amino acid residues in the SEQ ID NO: 2 amino acid sequence, and an amino acid sequence which not only is at least 70%, still at least 75%, yet at least 80%, also at least 85%, at least 90%, or at least 95% or higher homologous to the amino acid sequence of SEQ ID NO: 2, but also retains lactose binding activity;

(2) the CCRD of galectin 9 is selected from the group consisting of the amino acid sequence of SEQ ID NO: 3, a mutant amino acid that differs from the amino acid sequence of SEQ ID NO: 3 by at least one deletion, substitution, or addition of one or more amino acid residues in the SEQ ID NO: 3 amino acid sequence, and an amino acid sequence which not only is at least 70%, still at least 75%, yet at least 80%, also at least 85%, at least 90%, or at least 95% or higher homologous to the amino acid sequence of SEQ ID NO: 3, but also retains lactose binding activity; and (3) the link region that is a link between the above (1) and (2) is selected from the group consisting of the amino acid sequence of SEQ ID NO: 9, and a mutant amino acid that differs from the amino acid sequence of SEQ ID NO: 9 by at least one deletion, substitution, or addition of one or more amino acid residues in the SEQ ID NO: 9 amino acid sequence;

preferably those which are more stabilized against proteolytic enzymes, such as matrix metalloproteinases, than native galectin 9 (wild type galectin 9). Said link peptide region (3) includes deletion analogues with at least one amino acid deletion of one or more (for example, from 1 to 2, preferably from 3 to 4, still preferably from 5 to 6, more preferably from 7 to 8, and inter alia from 1 to 9) amino acid residues in the amino acid sequence of SEQ ID NO: 9; substitution analogues where one or more (for example, from 1 to 9, preferably from 1 to 8, still preferably from 1 to 6, more preferably from 1 to 4, and inter alia from 1 to 2) amino acid residues in said amino acid sequence are substituted with other residues; and addition analogues with at least one amino acid addition (or insertion) of one or more (for example, from 1 to 60, preferably from 1 to 40, still preferably from 1 to 20, more preferably from 1 to 10, and inter alia from 1 to 5) amino acid residues, provided that residual portions derived by removing SEQ ID NO: 9 from SEQ ID NO: 7 or 8 are excluded. In representative embodiments, said link region (3) includes those having a deleted amino acid sequence that differs from the amino acid sequence of SEQ ID NO: 9 by amino acid substitution with HM, RIP, or any of sequences consisting of 2 amino acids. The substitution, deletion or insertion (addition) of amino acids may or may not cause a great alteration in physiological or chemical properties of a polypeptide. In some cases, a desirable modification will be provided. Substituents of amino acids in the amino acid sequence can be selected from other amino acids in the class to which the amino acid belongs. For instance, non-polar (hydrophobic) amino acids include alanine, phenylalanine, leucine, isoleucine, valine, proline, tryptophan, methionine and the like; polar (neutral) amino acids include glycine, serine, threonine, cysteine, tyrosine, asparagine, glutamine and the like; amino acids having a positive charge (basic amino acids) include arginine, lysine, histidine and the like; and amino acids having a negative charge (acidic amino acids) include aspartic acid, glutamic acid and the like.

Further, the link region (3) includes those having a substituted amino acid sequence that differs from the sequence of SEQ ID NO: 7 or 8 by replacement with HM, RIP, or any of sequences consisting of 2 amino acids, provided that the area corresponding to SEQ ID NO: 9 is excluded for this replacement; those having a deleted amino acid sequence that differs from the sequence of SEQ ID NO: 7 or 8 by retention of 6 amino acid residues and deletion of all the residual amino acid residues, excluding the area corresponding to SEQ ID NO: 9; and others. The link region (3) also includes deletion analogues with amino acid deletions of one or more (for example, from 1 to 5, preferably from 3 to 10, still preferably from 5 to 15, more preferably from 7 to 20, and inter alia from 1 to 32) amino acid residues in the amino acid sequence of SEQ ID NO: 7 or 8, excluding the portion corresponding to, for example, SEQ ID NO: 9, or SEQ ID NO: 8 in case of SEQ ID NO: 7; substitution analogues where one or more (for example, from 1 to 9, preferably from 1 to 8, still preferably from 1 to 6, more preferably from 1 to 4, and inter alia from 1 to 2) amino acid residues in said amino acid sequence are substituted with other residues; and addition analogues with amino acid additions (or insertions) of one or more (for example, from 1 to 60, preferably from 1 to 40, still preferably from 1 to 20, more preferably from 1 to 10, and inter alia from 1 to 5) amino acid residues, provided that residual portions derived by removing SEQ ID NO: 9 from SEQ ID NO: 7 or 8 are excluded.

The mutants as aforementioned are all included in the present invention as long as they retain the domain structure or active carbohydrate binding structure characteristic of native human galectin 9 (or wild type human galectin 9). Also, it is thought that the peptides or polypeptides of the present invention may include those having all or part of substantially equivalent primary structure conformations to those of native human galectin 9 proteins. Furthermore, it is also thought that the inventive peptides or polypeptides may include those having substantially equivalent biological activity as compared to said native human galectin 9 proteins. Moreover, they can be one derived from the mutants which naturally occur. The human-derived proteins (or peptides or polypeptides) according to the present invention include, for example, those having an amino acid sequence which is at least 60% or more, and in some cases at least 70% or more homologous to at least one sequence selected from SEQ ID NOs: 1 to 3 in the Sequence Listing of WO 02/37114 A1 at an amino acid level, and more preferably those having an 80, or 90%, or more homologous amino acid sequence to any amino acid sequence of said SEQ ID NOs: 1 to 3. The peptide fragments (partial peptides) derived from the inventive human-derived protein may be any as long as they are part of said human-derived proteins (that is, partial peptides or fragmented peptides of said proteins) and have substantially equivalent activity to the inventive galectin 9 protein. For example, the partial peptides (or peptide fragments) of the protein according to the present invention include peptides having a sequence with at least 5 or more, preferably 20 or more, still preferably 50 or more, more preferably 70 or more, still more preferably 100 or more, and, in some cases, 200 or more amino acid residues contained in the modified Gal-9 variant-constituent amino acid sequence, preferably wherein said amino acid residues are contiguous. Preferable examples thereof are those having the same homology as aforementioned, with respect to homology to the region corresponding to any amino acid sequence of SEQ ID NOs: 1 to 3 in the Sequence Listing of WO 02/37114 A1.

The term "substantially equivalent" used herein means that proteins of interest are substantially equivalent or equal one another in view of activity, for example, cytotoxic, apoptosis-inducing, anti-inflammatory, anti-allergic, immunoregulatory (or immunomodulatory), saccharide chain-binding, physiological or biological activity. Further, the meanings of that term may include a case having the substantially same quality of activity. The substantially same quality of activity can include, for example, a binding activity, a cytotoxity, an apoptosis-inducing activity, etc. The substantially same quality of activity indicates that these activities are qualitatively homogeneous; for example, they are physiologically, pharmacologically or biologically homogeneous. For instance, it is preferable that the activities such as the binding activity, the cytotoxity and the apoptosis-inducing activity are equivalent (for example, from about 0.001 to 1000 fold, preferably from about 0.01 to 100 fold, more preferably from about 0.1 to 20 fold, and still preferably from about 0.5 to 2 fold), but quantitative elements such as the extents of these activities, molecular weights of the proteins etc. may be different.

The "modified galectin 9 polypeptide", "modified Gal-9 variant polypeptide" or "modified Gal-9 mutein polypeptide" embodies modified variants, derivatives, analogues, fragments, chimeras and mutants of the native sequence of wild type galectin 9. The polypeptides are encoded by recombinantly produced polynucleotides sequences designed to encode the specific modified galectin 9 polypeptide intended for expression in a host cell. The "modified galectin 9 variant therapeutic agent" includes molecules derived from modified Gal-9 variant-coding polynucleotide (modified galectin 9 mutein polynucleotide) or modified Gal-9 polypeptide sequence, and variants, mutants, analogues, chimeras, and fragments of such modified Gal-9 polynucleotide or polypeptide. Polynucleotide modified galectin 9 mutein therapeutic agents are generally sequences encoding a modified galectin 9 polypeptide that can be recombinantly expressed in a host cell. Additionally, a modified galectin 9 mutein therapeutic agent can be a small molecule agonist of galectin 9 activity. Other modified Gal-9 mutein therapeutic agents may include substances providing a modified Gal 9 mutein, and modulators of galectin 9 activity that have modified galectin 9 mutein activity and cause a prophylactic and/or therapeutic effect on disorders, diseases, and abnormal conditions associated with the insufficiency or absence of galectin 9 activity. A modulator of galectin 9 activity can be, for example, a polynucleotide, a polypeptide, or a small molecule.

The term "diagnostic agent" as used herein refers to any agent that contributes to one or more diagnostic actions used in diagnostic applications of the invention. These diagnostic applications include methods for determining the presence of galectin 9-producing cells, or methods for determining the presence of galectin 9-binding substance presenting cells. The diagnostic agents include the following: DNA encoding a modified galectin 9 mutein, a stabilized galectin 9 variant, and cells or cell homogenates having the stabilized galectin 9 mutein.

The term "therapeutic agent" as used herein can be any agent that accomplishes or contributes to the accomplishment of one or more therapeutic actions or elements used in therapeutic applications of the invention. For example, where the therapeutic agent is a polynucleotide designed to express a modified galectin 9 mutein polypeptide, that agent is a polynucleotide that can be administered to and expressed in a cell in the mammal. Thus, the active form of the agent will initially be the expressed polypeptide. The modified galectin 9 variant therapeutic agent is a therapeutic agent with the bioactivity of galectin 9, or a therapeutic agent derived from modified galectin 9, such as a polypeptide capable of binding on a certain saccharide chain longer than native galectin 9 or a polynucleotide encoding a modified galectin 9 mutein polypeptide that is more stabilized against proteolytic enzymes such as metalloproteinase than native galectin 9. The therapeutic agent achieves a therapeutic goal, alone or in combination with other agents (for example, an agent used in other known treatments for a particular tumor or autoimmunity in conjunction with administration of modified galectin 9 mutein, or a gene delivery vehicle capable of facilitating expression of modified galectin 9 mutein in the mammal). The therapeutic agents may include for example modified galectin 9 variant-containing drugs developed for other purposes, agonists of galectin 9, and further drugs that modulate or regulate galectin 9 activity. The therapeutic agent can be, for example, a small organic molecule, a peptide, a peptoid or peptidic compound, a polynucleotide encoding a modified galectin 9 mutein polypeptide, a modified galectin 9 variant polypeptide, or a transformed or transfected cell expressing a chimera or mutant of the modified galectin 9 mutein that is stabilized toward protease more than native galectin 9 (wild type galectin 9).

The "combination therapeutic agent" is a therapeutic composition having several components or agents that produce their separate effects when administered together, and may produce a synergistic effect when administered together to treat a disease. Preferably, the separate effects of the combination therapeutic agent combine to result in a larger therapeutic effect, for example elimination or reduction of tumors, normalization of tumor cells or tissues, recovery from an autoimmune disease and long term survival. An example of separate effects resulting from administration of a combination therapeutic agent is the combination of such effects as short-term, or long-term remission, or decrease of an autoimmune response to a particular type of cell in the patient. An example of the combination therapeutic agent according to the present invention would be administration of a gene delivery vehicle including a polynucleotide encoding a modified galectin 9 mutein in combination with a polynucleotide encoding at least one member selected from the group consisting of IFNs, IL-2, and other cytokines. Alternatively, two gene delivery vectors can be used, one expressing modified galectin 9 mutein and one encoding at least one of cytokines. Also IFNs, IL-2, and others, or a gene delivery vehicle expressing at least one member selected from the group consisting of IFNs, such as IFN-γ, IL-2, and other cytokines, can be administered to upregulate modified galectin 9 mutein expression in anticipation of an administration of modified galectin 9 mutein for inducing apoptosis in target cells. The various therapeutic agents can be administered in the same pharmaceutically acceptable carrier at the same time, followed, for example, by repeated administration of one or all of the individual agents as needed to make the therapy efficacious.

The term "gene delivery vehicle" refers to a component that facilitates delivery to a cell of a coding sequence for expression of a polypeptide in the cell. The cell can be inside the mammal, as in in vivo gene therapy, or can be removed from the mammal for transfection or transformation and returned to the mammal for expression of the polypeptide as in ex vivo gene therapy. The gene delivery vehicle can be any component or vehicle capable of accomplishing the delivery of a gene to a cell, for example, a liposome, a particle, or a vector. The gene delivery vehicle includes a recombinant vehicle, such as a recombinant viral vector, a nucleic acid vector (such as plasmid), a naked nucleic acid molecule such as genes, a nucleic acid molecule complexed to a polycationic molecule capable of neutralizing the negative charge on the nucleic acid molecule and condensing the nucleic acid molecule into a compact molecule, a nucleic acid associated with a liposome (U.S. Pat. Nos. 5,166,320; 5,547,932; Wang et al., Proc. Natl. Acad. Sci. USA, 84:7851, 1987), and others. Said gene delivery vehicles include certain eukaryotic cells (e.g., a producer cell), that are capable of delivering a nucleic acid molecule biologically having one or more desirable properties to host cells. As discussed further below, the desirable properties include the ability to express a desired substance, such as, for example, a protein, enzyme, or antibody, and/or the ability to provide a biological activity, which is where the nucleic acid molecule carried by the gene delivery vehicle is itself the active agent without requiring the expression of a desired substance. One example of such biological activity is found in gene therapy where the delivered nucleic acid molecule incorporates into a specified gene so as to inactivate the gene and "turn off" the product formation directed by the gene, thereby allowing the specific expression of said delivered nucleic acid molecule. Gene delivery vehicle refers to an assembly which is capable of directing the expression of one or plural sequences or genes of interest. The gene delivery vehicle generally includes promoter elements and may include a signal that directs polyadenylation. In addition, the gene delivery vehicle includes a sequence which, when transcribed, is operably linked to one or plural sequences or genes of interest and acts as a translation initiation sequence. The gene delivery vehicle may also include a selectable marker such as Neo, $SV^2$Neo, TK, hygromycin, bleomycin (phleomycin), puromicin, histidinol, or DHFR, as well as one or more restriction sites and a translation termination sequence. Gene delivery vehicles as used within the present invention refers to recombinant vehicles, such as viral vectors (Jolly, Cancer Gen. Therapy, 1: 51-64, 1994), nucleic acid vectors, naked DNA, liposomal DNA, cosmids, bacteria, and certain eukaryotic cells (including producer cells; see U.S. Pat. No. 6,333,195).

The term "Biologically active" refers to a molecule that retains a specific activity. A biologically active modified galectin 9 polypeptide (galectin 9 mutein, or modified Gal-9 variant), for example, retains not only the ability to bind specifically a certain saccharide chain on the carbohydrate recognition domain, as possessed by the CRD of galectin 9, or a substantially equivalent property thereto, but also qualitatively or quantitatively the more stable property against digestion with proteolytic enzymes such as matrix metalloproteinase, as compared to native galectin 9 (wild type galectin 9). For example, said biologically active modified galectin 9 polypeptide has antitumor activity or the ability to activate the apoptotic pathway leading to apoptosis, as owned by native galectin 9.

The "nucleic acid molecule" or "polynucleotide," as used herein, refers to RNA or DNA molecules, or DNA:RNA hybrids that encode a specific amino acid sequence or its complementary strand. The "coding sequence" as used herein refers to any of RNA, DNA, and DNA:RNA hybrids that encode a specific amino acid sequence or its complementary strand. The polynucleotide may include, for example, an antisense oligonucleotide, or a ribozyme, and may also include such items as a 3'- or 5'-untranslated region of a gene, or an intron of a gene, or other region of a gene that does not make up the coding region of the gene. The DNA or RNA may be single stranded or double stranded. Synthetic nucleic acids or synthetic polynucleotides can be chemically synthesized nucleic acid sequences, and may also be modified with chemical moieties to render the molecule resistant to degradation. The polynucleotide can be generated, for example, by polymerase chain reaction (PCR) amplification, or recombinant expression of complementary DNA or RNA, or by chemical synthesis.

The term "expression control sequence" or "regulatory sequence" refers to a sequence that is conventionally used to effect expression of a gene that encodes a polypeptide and include one or more components, elements, or factors that affect expression, including transcription and translation signals. The expression control sequence that is appropriate for expression of the present polypeptides differs depending upon the host system in which the polypeptide is to be expressed.

The "polypeptide" of the invention is any one comprising any part of the modified galectin 9 mutein including the mature protein, as long as it includes a modified galectin 9 variant polypeptide or a fragment thereof, and may further include truncations, variants, alleles, analogs and derivatives thereof. The variants can be spliced variants expressed from the same gene as the related protein. Unless specifically mentioned otherwise, such a polypeptide possesses one or more of the bioactivities of the galectin 9 protein, including for example specific binding affinity for a specific saccharide chain or binding activity to a specific partner. This term "polypeptide" is not limited to a specific length of the product of the gene. Thus, polypeptides that are identical or contain at least 60%, preferably 70%, still preferably 80%, more preferably 90%, and most preferably 95% homology to the target protein or the mature protein with regard to the N-terminal carbohydrate recognition domain (NCRD) and C-terminal carbohydrate recognition domain (CCRD) of galectin 9, wherever derived, from human or nonhuman sources are included within this definition of the polypeptide. Also included, therefore, are alleles and variants of the product of the gene that contain amino acid substitutions, deletions, or insertions. The amino acid substitutions can be conservative amino acid substitutions or substitutions to eliminate non-essential amino acid residues, such as to alter a glycosylation site, a phosphorylation site, an acetylation site, or to alter the folding pattern by altering the position of the cysteine residue that is not necessary for function. Conservative amino acid substitutions are those that preserve the general charge, hydrophobicity/hydrophilicity and/or steric size (bulk) of the amino acid substituted, for example, substitutions between the members of the following groups are conservative substitutions: Gly/Ala, Val/Ile/Leu, Asp/Glu, Lys/Arg, Asn/Gln, Ser/Cys/Thr and Phe/Trp/Tyr.

Analogues include peptides having one or more peptide mimics, also known as peptoids, that possess the target protein-like activity. Included within the definition as set forth herein are, for example, polypeptides containing one or more analogues of an amino acid (including, for example, unnatural amino acids, etc.), polypeptides with substituted linkages, as well as other mutations/modifications known in the art, both naturally occurring and non-naturally occurring. The term "polypeptide" also does not exclude post-translational modifications of the polypeptide, for example, glycosylations, acetylations, phosphorylations, myristoylations and the like.

The term "naked DNA" as used herein refers to polynucleotide DNA for administration to a mammal for expression in the mammal. The polynucleotide can be, for example, a coding sequence, and the polynucleotide DNA can be directly or indirectly connected to an expression control sequence that can facilitate the expression of the coding sequence once the DNA is inside a cell. The indirect connection is equivalent from the perspective of facilitating the expression of the DNA in the mammalian cells, and merely allows the possibility of the inclusion of other sequences between the regulatory region and the coding sequence that may facilitate the expression further, or may merely act as a linker or spacer to facilitate connecting the two polynucleotide regions together.

The "vector" used herein refers to an assembly which is capable of directing the expression of one or more sequences of interest, or one or more genes of interest. The vector must include transcriptional promoter/enhancer or one or more locus defining elements, or other elements which control gene expression by other means, such as alternate splicing, nuclear RNA export, post-translational modification of messenger, or post-transcriptional modification of protein. In addition, the vector must include a sequence which, when transcribed, is operably linked to one or more sequences or genes of interest and acts as a translation initiation sequence. Optionally, the vector may also include a signal which directs polyadenylation, a selectable marker such as Neo, TK, hygromycin, bleomycin (phleomycin), histidinol, or DHFR, as well as one or more restriction sites and a translation termination sequence. Further, if the vector is placed into a retrovirus, the vector must include a packaging signal, long terminal repeats (LTRs), and positive and negative strand primer binding sites appropriate to the retrovirus used (if these are not already present).

The "tissue-specific promoter" refers to transcriptional promoter/enhancer or locus defining elements, or other elements which control gene expression as discussed above, which are preferentially active in a limited number of tissue types or cell types. Representative examples of such tissue-specific promoters include the PEPCK promoter, HER2/neu promoter, casein promoter, IgG promoter, chorionic embryonic antigen promoter, elastase promoter, porphobilinogen deaminase promoter, insulin promoter, growth hormone factor promoter, tyrosine hydroxylase promoter, albumin promoter, α-fetoprotein promoter, acetyl-choline receptor promoter, alcohol dehydrogenase promoter, α- or β-globin promoters, T-cell receptor promoter, or osteocalcin promoter.

The "event-specific promoter" refers to transcriptional promoter/enhancer or locus defining elements, or other elements which control gene expression as discussed above, whose transcriptional activity is altered upon response to cellular stimuli. Representative examples of such event-specific promoters include thymidine kinase or thymidilate synthase promoters, α- or β-interferon promoters, and promoters that respond to the presence of hormones (natural, synthetic or from other nonhost organisms, e.g., insect hormones).

The term "fusion protein" or "fusion polypeptide" refers to proteins or polypeptides obtainable by the recombinant expression of more than one heterologous coding sequence in a vector or contiguous connection such that expression of the polypeptide in the vector results in expression of one polypeptide that includes more than one protein or portion of more than one protein. Most optimally, the fusion protein retains the biological activity of at least one of the polypeptide units from which it is built. Preferably, the fusion protein generates a synergistic improved bioactivity by combining the portion of the separate proteins to form a single polypeptide. The produced fusion protein can also be created with a polypeptide that has function and a peptide or polypeptide that has no function when expressed, but which serves a purpose for the expression of the polypeptide with activity. Examples of fusion proteins useful for the invention include any modified galectin 9 mutein fusion polypeptide genetically engineered to some advantage for the therapy, detection or assay, and further analysis or isolation/purification.

The term "chimera" or "chimeric protein" means an equivalent to fusion protein or fusion polypeptide. The "chimeric molecule" can be a fusion polypeptide, or a polynucleotide fusion molecule encoding a fusion polypeptide. The chimera can be constructed from ligated DNA coding sequences and expressed in a cell system, or administered in a vector for expression in vivo in an animal. For example, a chimera or fusion protein including a modified galectin 9 mutein can be administered in a gene therapy protocol in vivo or ex vivo.

The "patient" can be any treatable living organism, including but not limited to an eukaryote or a prokaryote. The patient eukaryote can be, for example, a vertebrate or an invertebrate. Thus, for example, the patient can be a fish, a bird, a worm, an insect, a mammal, a reptile, an amphibian, a fungi, or a plant, preferably a mammal. The mammal can be, for example a human.

Described below is general methods of making and using a modified galectin 9 mutein therapeutic Agents and/or diagnostic agents. In one aspect, the present invention provides a technique for treating a disorder, disease, or abnormal condition occurred due to the deficiency or absence of physiological or biological activity retained by galectin 9. Said treating technique includes for example a step of providing a modified galectin 9 mutein therapeutic agent, and/or a step of administering an effective amount of the modified galectin 9 mutein therapeutic agent to a mammal bearing said disorder, etc. Modified galectin 9 muteins are cytotoxic on malignant tumor cells, active in induction of apoptosis in malignant cells, antitumor (anticancer or antineoplastic) on malignant tumor cells, active in induction of apoptosis in activated T cells (inter alia CD4-positive T cells), immunomodulatory (immunoregulatory), anti-inflammatory, and antiallergic. Therefore, modified galectin 9 muteins can be expected to serve as anti-tumor agents (anti-neoplastic agents), anti-allergy agents, immunoregulatory (immunomodulators), therapeutic agents for autoimmune diseases, anti-inflammatory agents, and alternatives to adrenocortical steroid hormones. Said treating technique includes a method for treating an autoimmune disease manifesting activated T-cells. The "autoimmune disease", "autoimmune" and "autoimmunity" all refer to a disorder characterized by autoimmunity in the mammal which is the response of an immune system against self components. An autoimmune response can develop into a condition manifesting clinical symptoms. Although strictly speaking transplantation rejection is not an autoimmune reaction, where patient condition prescribes surgery to replace or graft cells, tissue or an organ, the body receiving the allograft can react immunologically against the foreign graft. "Transplantation rejection" occurs when during an allograft of cells, tissue, or an organ, from one member of a species to another, an immune response in the recipient results, sufficient to reject the transplanted cells, tissue or organ.

The inventive methods and therapeutic agents (drugs) can be applied to "tumors". Examples of such tumors may include malignant tumors. For example, a tumor that may metastasize to several sites is a malignant neoplasm, and the term "malignant neoplasm" is generally referred to as being epithelial or non-epithelial and may be distinguished as being cancer, sarcoma, or leukemia, etc. Among the general public, when the neoplasm or tumor is simply called "cancer", it refers to a malignant neoplasm or tumor. As used herein, the term "cancer" is employed in the broadest sense and should not be interpreted as being just an epithelial malignant neoplasm. The term "cancer" used herein may cover epithelial malignant tumors and non-epithelial malignant tumors (including those that are tumorigenic and non-tumorigenic), such as skin cancers (which may include melanomas), breast cancers, ovarian cancers, uterine cancers, malignant testicular tumors, prostatic cancers, urinary bladder cancers, renal cancers, thyroid cancers, pharyngeal/larynx cancers, tongue cancers, maxillary cancers, esophageal cancers, stomach cancers, colon/rectal cancers, lung/bronchial cancers, liver cancers (including liver cell cancers and intrahepatic bile duct cancers), extrahepatic bile duct/gall bladder cancers, pancreatic cancers, leukemia, malignant lymphoma, plasmacytoma, osteosarcoma, chondrosarcoma, leiomyosarcoma, rhabdomyosarcoma, liposarcoma, fibrosarcoma, malignant hemangioma, malignant hemangioendothelioma, brain tumors (including meningioma, glyoma, astrocytoma), etc., but is not restricted to these. It should be understood that they may encompass those wherein the application of the inventive modified Gal-9 variant will give bright prospects, and further those wherein some sort of physiological or biological responses will take place in association with said modified Gal-9 variant.

Examples of "autoimmune diseases" that can be treated by the method and therapeutic agent of the invention include multiple sclerosis, Hashimoto's thyroiditis, systemic lupus erythematosus (SLE), Goodpasture's syndrome, Pemphigus, receptor autoimmunity, autoimmune hemolytic anemia, autoimmune thrombocytopenic purpura, osteoarthritis, chronic rheumatoid arthritis, scleroderma with anticollagen antibodies, mixed connective tissue disease, polymyositis, pernicious anemia, idiopathic Addison's disease, spontaneous infertility, glomerulonephritis, bullous pemphigoid, adrenergic drug resistance, chronic active hepatitis, primary biliary cirrhosis, autoimmune-based endocrine gland failure, vitiligo, vasculitis, post-myocardial infarction, cardiotomy syndrome, urticaria, atopic dermatitis, autoimmune-based asthma, autoimmune-based inflammatory reactions, granulomatous disorders, alkylizing spondylitis, poststreptococcal glomerulonephritis, autoimmune hemolytic anemia, encephalitis, autoimmune reaction secondary to lymphoma, degenerative disorders, and atrophic disorders. Autoimmune diseases manifesting receptor autoimmunity include, for example, Grave's disease, myasthenia gravis, insulin resistance and others. Autoimmune diseases of adrenergic drug resistance include, for example, asthma, cystic fibrosis, and others.

Other autoimmune diseases appropriate for the invention include, for example those for which an animal model exists, including for example, Sjögren's syndrome (autoimmune dacryodentis or immune-mediated sialadenitis), autoimmune myocarditis, primary biliary cirrhosis (PBC), inflammatory heart disease, mercury-induced renal autoimmunity, insulin dependent diabetes mellitus (type I diabetes or IDD), post-thymectomy autoimmunity, a central nervous system (CNS) demyelination disorder, CNS lupus, narcolepsy, an immune-mediated PNS disorder, osteoarthritis, rheumatoid arthritis, uveitis, medullary cystic fibrosis, autoimmune hemolytic disease, autoimmune vasculitis, ovarian autoimmune disease, human scleroderma, etc. An autoimmune disease characterized by a central nervous system (CNS) demyelination disorder can be, for example, multiple sclerosis (MS), etc. A peripheral nervous system (PNS) autoimmune disease can be, for example, Guillain-Barre syndrome (GBS).

The modified galectin 9 mutein therapeutic agent can include a polypeptide, a polynucleotide, a small organic compound, a peptide, a peptoid compound, a peptidic substance, or others. The modified galectin 9 mutein therapeutic agent can be a modified galectin 9 mutein polypeptide, a polynucleotide encoding a modified galectin 9 mutein polypeptide, a fusion polypeptide comprising a portion of the inventive modified galectin 9 mutein polypeptide, a polynucleotide encoding a fusion polypeptide comprising a portion of said modified galectin 9 mutein polypeptide, a biologically active peptide derivative of modified galectin 9 mutein polypeptide, a biologically active peptoid compound or peptidic substance derived from modified galectin 9 mutein polypeptide, or a small organic modified galectin 9 mutein mimic (including an agonist) of modified galectin 9 mutein activity. The modified galectin 9 mutein polypeptide can be a biologically active modified galectin 9 mutein polypeptide such as a modified galectin 9 mutein polypeptide variant, a modified galectin 9 mutein polypeptide derivative, a mutant polypeptide derived from the modified galectin 9 mutein polypeptide, or a truncated modified galectin 9 mutein polypeptide. The polynucleotide encoding a modified galectin 9 mutein polypeptide can be a polynucleotide sequence encoding modified galectin 9 mutein polypeptide with both full length N-terminal CRD and full length C-terminal CRD of wild type galectin 9, a sequence encoding a biologically active portion of modified galectin 9 mutein polypeptide, a sequence encoding a biologically active peptide derived from modified galectin 9 mutein polypeptide, a sequence encoding a soluble modified galectin 9 mutein polypeptide, etc. Another embodiment of the invention is a composition having a gene delivery vehicle capable of expressing a polynucleotide sequence encoding a modified galectin 9 mutein polypeptide.

In the present invention, utilization of "gene recombination techniques" allows not only construction, acquisition, isolation, and sequencing of targeted nucleic acid molecules (polynucleotides), proteins (peptides and fragments thereof), but also creation and production of recombinant constructs thereof. Gene recombination techniques (including recombinant DNA techniques) as can be used herein include those known in the art, and can be carried out by the methods described in, for example, J. Sambrook, E. F. Fritsch & T. Maniatis, "Molecular Cloning: A Laboratory Manual (2nd edition)", Cold Spring Harbor Laboratory Press, Cold Spring Harbor, N.Y. (1989); D. M. Glover et al. ed., "DNA Cloning", 2nd ed., Vol. 1 to 4, (The Practical Approach Series), IRL Press, Oxford University Press (1995); The Japanese Biochemical Society (JBS) ed., "Zoku-Seikagaku Jikken Koza 1, Idenshi Kenkyu-Hou II", Tokyo Kagaku Dozin Co. Ltd., Japan, (1986); JBS ed., "Shin-Seikagaku Jikken Koza 2, Kakusan III (Recombinant DNA technique)", Tokyo Kagaku Dozin Co. Ltd., Japan, (1992); M. J. Gait (Ed), Oligonucleotide Synthesis, IRL Press (1984); B. D. Hames and S. J. Higgins (Ed), Nucleic Acid Hybridization, A Practical Approach, IRL Press Ltd., Oxford, UK (1985); B. D. Hames and S. J. Higgins (Ed), Transcription and Translation: A Practical Approach (Practical Approach Series), IRL Press Ltd., Oxford, UK (1984); B. Perbal, A Practical Guide to Molecular Cloning (2nd Edition), John Wiley & Sons, New York (1988); J. H. Miller and M. P. Calos (Ed), Gene Transfer Vectors for Mammalian Cells, Cold Spring Harbor Laboratory, Cold Spring Harbor, N.Y. (1987); R. J. Mayer and J. H. Walker (Ed), Immunochemical Methods in Cell and Molecular Biology, Academic Press, (1987); R. K. Scopes et al. (Ed), Protein Purification: Principles and Practice (2nd Edition, 1987 & 3rd Edition, 1993), Springer-Verlag, N.Y.; D. M. Weir and C. C. Blackwell (Ed), Handbook of Experimental Immunology, Vol. 1, 2, 3 and 4, Blackwell Scientific Publications, Oxford, (1986); L. A. Herzenberg et al. (Ed), Weir's Handbook of Experimental Immunology, Vol. 1, 2, 3 and 4, Blackwell Science Ltd. (1997); R. W. Ellis (Ed), Vaccines new approaches to immunological problems, Butterworth-Heinemann, London (1992); R. Wu ed., "Methods in Enzymology", Vol. 68 (Recombinant DNA), Academic Press, New York (1980); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987); J. H. Miller ed., "Methods in Enzymology", Vol. 204, Academic Press, New York (1991); R. Wu et al. ed., "Methods in Enzymology", Vol. 218, Academic Press, New York (1993); S. Weissman (ed.), "Methods in Enzymology", Vol. 303, Academic Press, New York (1999); J. C. Glorioso et al. (ed.), "Methods in Enzymology", Vol. 306, Academic Press, New York (1999), etc., or by methods described in the references quoted therein or substantially equivalent methods thereto or modified methods thereof, the disclosures of which are incorporated herein by reference (hereinafter, all such techniques or methods shall be referred to as "gene recombination techniques").

As used herein, the term "homology" or "homologous" means the quantity (or number), in terms of identity, which can be obtained by determining that corresponding amino acid residues or corresponding nucleotide bases are matched each other between two chains in polypeptide sequences (or amino acid sequences) or polynucleotide sequences (or nucleotide sequences) when amino acid residues or nucleotide bases constituting the chain are compared one another between the two chains and it also means the level of sequence correlation in terms of similarity between two polypeptide sequences or two polynucleotide sequences. The homology can be easily calculated. Various methods for measuring the homology between two polynucleotide sequences or polypeptide sequences have been known and the term "homology" (sometimes called "identity") has been well known to the persons skilled in the art (for example, Lesk, A. M. (Ed.), Computational Molecular Biology, Oxford University Press, New York, (1988); Smith, D. W. (Ed.), Biocomputing: Informatics and Genome Projects, Academic Press, New York, (1993); Grifin, A. M. & Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991), etc.). Generic techniques for determining the homology between two strands include those disclosed in Martin, J. Bishop (Ed.), Guide to Huge Computers, Academic Press, San Diego, (1994); Carillo, H. & Lipman, D., SIAM J. Applied Math., 48: 1073 (1988), etc., but are not limited to. Preferred methods for measuring the homology include those which are designed so as to obtain the part of the highest fitting relation between the two sequences tested. An example of such methods is a technique which is constructed as a computer program. Preferred computer programming methods include a GCG program package (Devereux, J. et al., Nucleic Acids Research, 12(1): 387 (1984)), BLASTP, BLASTN, FASTA, (Atschul, S. F. et al., J. Mol. Biol., 215: 403 (1990)), etc., but are not limited to. For such methods, those known in the art may be employed.

The term "polymerase chain reaction" or "PCR" used herein usually refers to techniques described in U.S. Pat. No. 4,683,195 and other documents. For example, the PCR is an in vitro method for the enzymatic amplification of desired specific nucleotide sequences. In general, the PCR includes repetitive series of cycles wherein a primer elongation synthesis is constructed using two oligonucleotide primers capable of preferentially hybridizing with a template nucleic acid. Typically, the primers used in PCR may include those which are complementary to the internal nucleotide sequence of interest in the template. For example, preferable primer pairs as used herein may be those which are complementary to both ends of said nucleotide sequence to be amplified, or flanking regions adjacent to said nucleotide sequence. It is preferable to select a 5'-terminal primer such that at least an initiation codon is contained or the amplification can be performed including the initiation codon, and to select a 3'-terminal primer such that at least a stop codon is contained or the amplification can be performed including the stop codon. The primers include oligonucleotides made up of preferably 5 or more nucleotide bases, more preferably 10 or more nucleotide bases, and still preferably 18 to 25 nucleotide bases.

The PCR reactions can be carried out by methods known in the art or substantially equivalent methods thereto and modified methods thereof. For example, the PCR can be performed according to methods described in R. Saiki, et al., Science, 230: 1350, 1985; R. Saiki, et al., Science, 239: 487, 1988; H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995); M. A. Innis et al. ed., "PCR Protocols: a guide to methods and applications", Academic Press, New York (1990)); M. J. McPherson, P. Quirke and G. R. Taylor (Ed.), PCR: a practical approach, IRL Press, Oxford (1991); M. A. Frohman et al., Proc. Natl. Acad. Sci. USA, 85, 8998-9002 (1988) and other documents, and modified methods or variants thereof. The PCR methods can also be performed using commercially available kits suitable therefor, and can also be carried out according to protocols disclosed by manufacturers or distributors of the kits.

In a representative case, the PCR is performed for example, using a template (e.g., DNA synthesized using mRNA as a template; 1st strand DNA) and primers synthesized according to designs on said gene, in admixture with a 10× reaction buffer (contained in a Taq DNA polymerase kit), dNTPs (deoxyribonucleoside triphosphates; dATP, dGTP, dCTP and dTTP mix), Taq DNA polymerase and deionized distilled water. The mixture is subjected to 25 to 60 cycles of amplification using an automated thermal cycler such as Gene-Amp® 2400 PCR system (Perkin-Elmer/Cetus) under general PCR cycle conditions. The number of amplification cycles can be suitably set to an appropriate value depending on purposes. The PCR cycle includes, for example, denaturation at 90 to 95° C. for 5 to 100 sec, annealing at 40 to 60° C. for 5 to 150 sec and extension at 65 to 75° C. for 30 to 300 sec, and preferably denaturation at 94° C. for 15 sec, annealing at 58° C. for 15 sec and extension at 72° C. for 45 sec. For the annealing temperature and reaction time, an appropriate value is suitably selected by experimentation. For the denaturation and extension time, an appropriate value suitably varies according to the strand length of expected PCR products. In general, the annealing reaction time preferably varies depending on the Tm value of primer-template DNA hybrids. The time period of extension is usually set with the aim of getting about 1 min per 1000 bp in strand length, but it may be possible to select a shorter time period in some cases.

The term "oligonucleotide(s)" used herein refers to a relatively short single-stranded polynucleotide or double-stranded polynucleotides, or preferably polydeoxynucleotide(s). They can be chemically synthesized by known methods as described in Angew. Chem. Int. Ed. Engl., Vol. 28, pp. 716-734 (1989), including phosphotriester, phosphodiester, phosphite, phosphoramidite, phosphonate methods, and the like. It has been typically known that the synthesis can be conveniently carried out on modified solid supports. For example, the synthesis can be carried out using an automated synthesizer and such a synthesizer is commercially available. The oligonucleotide may contain one or more modified nucleotide bases. For example, it may contain a nucleotide base which does not naturally occur, such as inosine, or a tritylated nucleotide base. In some cases, they may contain one or more nucleotide bases tagged with a marker.

The target nucleic acid molecules (polynucleotides) can be identified by adaptations of hybridization techniques. The hybridization may be carried out according to methods as described in documents disclosing the aforementioned "gene recombination techniques", or substantially equivalent methods and modifications thereof. For instance, the hybridization is achieved by transferring a sample containing a nucleic acid such as DNA onto a carrier including a membrane such as a nylon filter, as required, optionally followed by denaturation, fixation, washing, etc., and then reacting the transfers on the carrier (e.g., membrane), with labeled DNA probe fragments which are, as required, optionally denatured in a hybridization buffer.

The hybridization operations can be ordinarily conducted at about 35 to about 80° C., more preferably about 50 to about 65° C., for about 15 min to about 36 hours, more preferably about 1 to about 24 hours, but optimal hybridization conditions may be suitably selected. For example, the hybridization is carried out at about 55° C. for about 18 hours. The hybridization buffers can be selected from those customarily used in the art. Examples of the hybridization buffers are Rapid hybridization buffer (Amersham), etc. The denaturation of carriers (e.g., membranes, etc.) with transfers includes techniques using an alkali denaturing solution. It is preferable to treat the carrier with a neutralizing solution and a buffer solution after the denaturation. The carrier fixation (e.g., membrane fixation) is usually achieved by baking at about 40 to about 100° C., more preferably about 70 to about 90° C., for about 15 min to about 24 hours, more preferably about 1 to about 4 hours, but desired fixation conditions may be suitably selected. For example, the fixation is carried out by baking at about 80° C. for about 2 hours. The washing of carriers (e.g., membranes) with transfers can be performed with washing solutions customarily used in the art, such as 50 mM Tris-HCl buffer, pH8.0, containing 1M NaCl, 1 mM EDTA and 0.1% sodium dodecyl sulfate (SDS). The carriers including membranes can be selected from those customarily used in the art. Examples of such carriers include nylon filters.

The alkaline denaturing solution, neutralizing solution and buffer solution can be selected from those conventionally used in the art. The alkaline denaturing solution may include, for example, solutions containing 0.5M NaOH and 1.5M NaCl, etc. The neutralizing solution may include, for example, 0.5M Tris-HCl buffers, pH8.0, containing 1.5M NaCl, etc. The buffer solution may include, for example, 2×SSPE (0.36M NaCl, 20 mM $NaH_2PO_4$ and 2 mM EDTA), etc. As required, prior to hybridization, it is desirable that carriers (e.g., membranes) with transfers are optionally prehybridized for the prevention of non-specific hybridization. For the prehybridization, the sample is dipped, for example, in a solution for prehybridization [50% formamide, 5×Denhardt's solution (0.2% bovine serum albumin and 0.2% polyvinylpyrrolidone), 5×SSPE, 0.1% SDS, and 100 µg/ml thermally denatured salmon sperm DNA] and the like, and reacted at about 35° C. to about 50° C., preferably about 42° C., for about 4 to about 24 hours, preferably about 6 to about 8 hours. These conditions can be determined by those of skill in the art with suitably repeated experiments and more preferred conditions would be selected. Labeled probe DNA fragments used in hybridization can be denatured, for example, under heating conditions at about 70 to 100° C., preferably about 100° C., for about 1 to 60 minutes, preferably about 5 minutes, etc. The hybridization is carried out by well known techniques per se in the art or according to methods analogous thereto. As used herein, the stringent conditions refer to, for example, those equivalent to hybridization in about 15 to 50 mM, preferably about 19 to 40 mM, and more preferably about 19 to 20 mM, with regard to Na ion concentration, at about 35 to 85° C., preferably about 50 to 70° C., and more preferably about 60 to 65° C. with regard to temperature.

After the hybridization is completed, the carriers (such as filters) are washed extensively to remove labeled probes other than the labeled probe DNA fragments which specifically hybridize. Thereafter, detections are done. The carrier (filter) washing process may be performed by a method suitably selected from techniques used in the art. For example, the washing is carried out in 0.5×SSC solution (×SSC=0.15M NaCl, 15 mM citric acid) containing 0.1% SDS. The hybridized nucleic acids can be detected representatively by autoradiography, but the detection may be performed by a method suitably selected from techniques used in the art. A nucleic acid band corresponding to the detected signal is suspended in a suitable buffer solution such as SM solution (50 mM Tris-HCl buffer, pH7.5, containing 100 mM NaCl and 10 mM $MgSO_4$). After the nucleic acid suspension is diluted to a suitable level, target nucleic acids can be isolated and purified. Further, the nucleic acids can be subjected to amplification.

The term "high homology" as used herein may refer to, though it depends on the sequence length of the targets, for example, 50% or higher, further 60% or higher, preferably 70% or higher, still preferably 80% or higher, in a particular case 95% or higher and most preferably 97% or higher homology. The "nucleotide sequence with the same efficacy" or "equivalently effective nucleotide sequence" includes, for example, those which hybridize with any of those containing the sequence of interest under stringent conditions. Examples of such nucleotide sequences are those which not only hybridize with a nucleotide sequence with 5 or more contiguous nucleotides, preferably 10 or more contiguous nucleotides, more preferably 15 or more contiguous nucleotides, or further preferably 20 or more contiguous nucleotides, selected from said nucleotide sequence, but also code for a substantially equivalent amino acid sequence to said polypeptide. The nucleic acid molecules may also be chemically synthesized. In such cases, fragments may be chemically synthesized and coupled together with enzymes.

Screening treatments can be repeated plural times with hybridization techniques for target nucleic acid molecules from nucleic acid samples including gene libraries, cDNA libraries, and others. Utilizable cDNA libraries are cloned human-derived ones including, for example, cDNA libraries of various human-derived tissues, cultured human cells, or human cell lines (in particular, human body parts, human tissues and cells such as kidney, brain, corpus peale, posterior pituitary gland, nerve cells, retina, retinal blood vessel cells, retinal nerve cells, thymus, blood vessel, endothelial cells, vascular smooth muscle cells, blood cells, macrophages, lymphocytes, testis, ovary, uterus, intestine, heart, liver, pancreas, small intestine, large intestine (including colon and rectum), gingiva-related cells, skin-related cells, glomerular cells, renal tubular cells, and connective tissue cells; various tumor tissues, and cancer cells; and other sources). Further, the cDNA library used as a template may be directly selected from commercially available cDNA libraries derived from a variety of tissues. Examples of the commercially available cDNA libraries are those commercially distributed or delivered by Stratagene (US), Invitrogen (US), Clontech (US), and other distributors. In typical embodiments, the utilizable products include gene libraries generated from human tissues and cells, such as human P1 artificial chromosome genomic libraries (Human Genome Mapping Resource Center, US), and human tissue cDNA libraries (e.g., available from Clontech, US). The screening with probes can be done using human genomic DNA libraries or human-derived cDNA libraries constructed from various human tissues or culture cell lines and other resources. The probe, etc. may be labeled, with a radioactive isotope, using a commercially available labeling kit, such as the Random Prime DNA Labeling Kit (Boehringer Mannheim), etc. For example, a random priming kit (Pharmacia LKB, Uppsala), etc. may be used to label the probe DNA with [α-$^{32}$P]dCTP (Amersham), etc. and thus provide a probe with radioactivity.

Phage particles, recombinant plasmids, recombinant vectors and others, containing the target nucleic acid molecules, can be isolated and purified by customary techniques used in the art. For instance, they are obtained by glycerol gradient ultracentrifugation (Molecular Cloning, a laboratory manual, ed. T. Maniatis, Cold Spring Harbor Laboratory, 2nd ed. 78, 1989), electrophoresis and other isolation/purification techniques. DNA can be isolated and purified from phage particles and the like by a member selected from customary techniques used in the art. For instance, the resulting phages are suspended in TM solution (50 mM Tris-HCl buffer, pH7.8, containing 10 mM MgSO$_4$), etc., and treated with DNase I and RNase A, etc., followed by addition of a Proteinase K mixture solution (20 mM EDTA, 50 µg/ml Proteinase K and 0.5% SDS). The resultant mixture is incubated at about 65° C. for 1 hr., subjected to phenol extraction and then to diethyl ether extraction, followed by precipitation with ethanol to form DNA pellets. Next, the resultant DNA is washed with 70% ethanol, dried and dissolved in TE solution (10 mM Tris-HCl buffer, pH8.0, containing 10 mM EDTA). A large amount of target DNA can be obtained by subcloning, etc. For example, the subcloning can be performed with plasmid vectors, etc. in host *E. coli*, etc. The DNA thus subcloned can also be isolated and purified by techniques including phenol extraction, ethanol precipitation, etc. in the same manner as aforementioned.

The resultant nucleic acid molecules (including DNA) such as PCR products are typically herein subjected to electrophoresis on 1 to 2% agarose gels. Specific bands are cut out from the gel, and DNA is extracted with a commercially available kit, e.g., Gene clean kit (Bio 101) and the like. The extracted DNA is cleaved with appropriate restriction enzymes and purified if necessary. Further, the 5'-end is, if necessary, phosphorylated with T4 polynucleotide kinase, etc. and subsequently the DNA is ligated into an appropriate plasmid vector including a pUC vector system such as pUC18, and transformed into suitable competent cells. The cloned PCR products are sequenced and analyzed. Commercially available plasmid vectors such as p-Direct (Clontech), pCR-Script® SK(+) (Stratagene), pGEM-T (Promega), and pAmp® (Gibco-BRL) are useful for cloning of the PCR products. Transformation (transfection) of host cells can be carried out by methods known in the art such as the calcium method, the rubidium/calcium method, the calcium/manganese method, the TFB high efficiency method, the FSB frozen competent cell method, the rapid colony method, electroporation and a member selected from methods known in the art and substantial equivalents thereto (D. Hanahan, J. Mol. Biol., 166: 557, 1983, etc.). Reverse transcription PCR (polymerase chain reaction coupled reverse transcription; RT-PCR) and RACE (rapid amplification of cDNA ends) can be applied to isolate the target DNA. RACE can be carried out according to the methods, for example, described in M. A. Innis et al. ed., "PCR Protocols" (M. A. Frohman, "a guide to methods and applications"), pp. 28-38, Academic Press, New York (1990), etc.

DNA of interest can be cloned depending on necessity. Suitable vectors for cloning DNA include plasmids, λ phages, cosmids, P1 phage, F element, YAC and others, and are preferably vectors derived from λ phages, such as Charon 4A, Charon 21A, λgt10, λgt11, λDASHII, λ FIXII, λEMBL3, and λZAPII® (Stratagene). The resultant DNA can be incorporated into an appropriate vector such as plasmid pEX, pMAMneo, and pKG5, as described in detail below, and can be expressed in appropriate host cells, e.g., *E. coli*, yeast, CHO cells, COS cells and others as described in detail below. The DNA fragments can be introduced into animal cells as intact molecules or appropriate control sequence-added DNA fragments or after incorporated into an appropriate vector. Thus, transgenic animals which express the given gene can be produced. The animals include mammalian animals, and include, for example, mice, rats, rabbits, guinea pigs, cattle etc. Preferably, the transgenic animal can be produced by introducing the DNA fragments into fertilized eggs of an animal such as a mouse. Targeted gene products are verified using suitable animal cells, such as 293T cells and COS-1 cells, transfected with said foreign gene.

The methods for transferring foreign genes into mammal animal cells may be practicable ones known in the art or substantially similar techniques thereto, The method may include, for example, the calcium phosphate method (e.g., F. L. Graham et al., Virology, 52: 456, 1973, etc.), the DEAE-dextran method (e.g., D. Warden et al., J. Gen. Virol., 3: 371, 1968, etc.), electroporation (e.g., E. Neumann et al., EMBO J, 1: 841, 1982, etc.), microinjection, the liposome method, virus infection, the phage particle method and others. The gene products produced in the animal cells transfected with the given gene in such ways can also be analyzed.

Any plasmid into which the target gene and others (DNA obtainable in the present invention and the like) are incorporated may be used as long as said DNA can be expressed in host cells conventionally used in genetic engineering techniques (such as prokaryotic host cells including *Escherichia coli*, *Bacillus subtilis*, etc. and eukaryotic host cells including yeast cells, CHO cells, COS cells, and insect host cells such as Sf21. It goes without saying that it is possible to use those selected from attachments and reagents in commercially available kits. In such plasmid sequences, it is possible, for example, to contain modified codons suitable for expressing the cloned DNA in selected host cells or to construct restriction enzyme sites. It is also possible to contain control sequences, enhancer sequences, and other sequences for facilitating the expression of the target gene; linkers, adaptors and others, useful for ligating the target gene; effective sequences useful in controlling resistance to antibiotics or in controlling metabolism or in selection (including those coding for hybrid proteins and fusion proteins); and the like. Preferably, suitable promoters may be used. For example, such promoters may include tryptophan promoter (trp), lactose promoter (lac), tryptophan-lactose promoter (tac), lipoprotein promoter (lpp), λ phage P$_L$ promoter, etc. in the case of plasmids where hosts are *E. coli*; SV40 late promoter, MMTV LTR promoter, RSV LTR promoter, CMV promoter, SR α promoter, etc. in the case of plasmids where hosts are animal cells; and GAL1, GAL10 promoters, etc. in the case of plasmids where hosts are yeast cells. It is also possible to use regulation systems such as CYC1, HIS3, ADH1, PGK, PHO5, GAPDH, ADC1, TRP1, URA3, LEU2, EN0, TP1, and AOX1.

An enhancer can be inserted into the vector to facilitate the transcription of DNA encoding the desired polypeptide. Such enhancers include elements of approximately 10 to 100 bp, acting on the promoter to facilitate the transcription and typically having a cis action. A great number of enhancers have been known in mammalian genes such as globin, elastase, albumin, α-fetoprotein, insulin genes and others. Preferably useful representatives of the enhancers are those obtained from eukaryotic infectious viruses, including, for example, an SV40 enhancer (100-270 bp) located at the late region of the replication origin, a cytomegalovirus enhancer for the early promoter, a polyoma enhancer located at the late region of the replication origin, an adenovirus enhancer and the like. A signal sequence fitting for the host can be added if necessary. Such signal sequences which can be used herein are well known by those skilled in the art.

The plasmids for *E. coli* hosts include, for example, pBR322, pUC18, pUC19, pUC118, pUC119, pSP64, pSP65, pTZ-18R/-18U, pTZ-19R/-19U, pGEM-3, pGEM-4, pGEM-3Z, pGEM-4Z, pGEM-5Zf(−), pBluescript KS® (Stratagene 社), etc. The plasmid vectors suitable for the expression in *E. coli* also include, for example, pAS, pKK223 (Pharmacia), pMC1403, pMC931, pKC30, pRSET-B (Invitrogen), etc. The plasmids for animal host cells include the SV40 vector, polyoma viral vector, vaccinia viral vector, retroviral vector, etc. Examples of such plasmids are pcD, pcD-SRα, CDM8, pCEV4, pME18S, pBC12BI, pSG5 (Stratagene), etc. The plasmids for yeast host cells include Yip, YEp, YRp, YCp type vectors and others. Examples of such plasmids are pGPD-2, etc. The *E. coli* host cells include those derived from the *E. coli* K12 strain or the *E. coli* B834 strain. Examples of the *E. coli* host cells are NM533, XL1-Blue, C600, DH1, DH5, DH11S, DH12S, DH5a, DH108, HB101, MC1061, JM109, STBL2, etc. for the *E. coli* K12 strain, and BL21(DE3)/pLYsS, etc. for the *E. coli* B834 strain. Examples of bacterial expression systems can be seen in the following documents: Chang et al., Nature (1978) 275: 615; Goeddel et al., Nature (1979) 281: 544; Goeddel et al., Nucleic Acid Res., (1980) 8: 4057; EP 36,776, U.S. Pat. No. 4,551,433; deBoer et al., Proc. Natl. Acad. Sci. USA (1983) 80: 21-25; Siebenlist et al., Cell (1980) 20: 269, etc. The yeast host cells include, for example, *Saccharomyces cerevisiae, Schizosaccharomyces prombe, Pichia pastoris, Kluyveromyces* cells, *Candida, Trichoderma reesia* and the other yeast cells. Examples of yeast expression systems can be seen in the following documents: Hinnen et al., Proc. Natl. Acad. Sci. USA (1978) 75: 1929; Ito et al., J. Bacteriol. (1983) 153: 163; Kurtz et al., Mol. Cell. Biol. (1986) 6: 142; Kunze et al., J. Basic Microbiol. (1985) 25: 141; Gleeson et al., J. Gen. Microbiol. (1986) 132: 3459; Roggenkamp et al., Mol. Gen. Genet (1986) 202: 302; Das et al., J. Bacteriol. (1984) 158: 1165; De Louvencourt et al., J. Bacteriol. (1983) 154: 737; Van den Berg et al., Bio/Technology (1990) 8: 135; Kunze et al., J. Basic Micr Biol. (1985) 25: 141; Cregg et al., Mol. Cell. Biol. (1985) 5: 3376; U.S. Pat. Nos. 4,837,148 & 4,929,555; Beach and Nurse, Nature (1981) 300: 706; Davidow et al., Curr. Genet. (1985) 10: 380; Gaillardin et al., Curr. Genet. (1985) 10: 49; Ballance et al., Biochem. Biophys. Res. Commun. (1983) 112: 284-289; Tilburn et al., Gene (1983) 26: 205-221; Yalton et al., Proc. Natl. Acad. Sci. USA (1984) 81: 1470-1474; Kelly and Hynes, EMBO J., (1985) 4: 475479; EP 244,234; WO 91/00357, etc.

The host cells which are animal cells include, for example, African grivet fibroblast-derived COS-7 cells, COS-1 cells, CV-1 cells, human renal cell-derived 293 cells, human epidermal cell-derived A431 cells, human colon cell-derived 205 cells, murine fibroblast-derived COP cells, MOP cells, WOP cells, Chinese hamster cell-derived CHO cells, CHO DHFR− cells, human HeLa cells, murine cell-derived C127 cells, murine cell-derived NIH 3T3 cells, murine L cells, 9BHK, HL60, U937, HaK, Jurkat cells, other transformed cell lines, normal diploid cells, cell lines induced from in vitro primary cultured tissue, etc. Techniques for expressing exogenous DNA in mammalian host cells can be seen in the following documents: Dijkema et al., EMBO J. (1985) 4: 761; Gorman et al., Proc. Natl. Acad. Sci. USA (1982b) 79: 6777; Boshart et al., Cell (1985) 41: 521; U.S. Pat. No. 4,399,216; Ham and Wallace, Methods in Enzymology (1979) 58: 44; Barnes and Sato, Anal. Biochem. (1980) 102: 255; U.S. Pat. Nos. 4,767,704; 4,657,866; 4,927,762; 4,560,655; WO 90/103430; WO 87/00195; U.S. Pat. No. RE 30,985, etc. Insect cells used include *Spodoptera frugiperda* (caterpillar), *Aedes aegypti* (mosquito), *Aedes albopictus* (mosquito), *Drosophila melanogaster* (fruitfly), silk worm larva or cultured cells (e.g., BM-N cells), in combination with vectors, silk worm (*Bombyx mori*) nuclear polyhedrosis virus, those derived therefrom or other suitable ones (for example, Luckow et al., Bio/Technology, 6, 47-55 (1988); Setlow, J. K. et al. (eds.), Genetic Engineering, Vol. 8, pp. 277-279, Plenum Publishing, 1986; Maeda et al., Nature, 315, pp. 592-594 (1985)). Methods of expressing exogenous DNA in insects can be seen in the following documents: U.S. Pat. No. 4,745,051; Friesen et al. (1986), "The Regulation of Baculovirus Gene Expression", The Molecular Biology of Baculoviruses (W. Doerfler (Ed)); EP 127,839; EP 155,476; Vlak et al., J. Gen. Virol., (1988) 69: 765-776; Miller et al., Ann. Rev. Microbiol. (1988) 42: 177; Carbonell et al., Gene (1988) 73: 409; Maeda et al., Nature, (1985) 315: 592-594; Lebacq-Verheyden et al., Mol. Cell. Biol. (1988) 8: 3129; Smith et al., Proc. Natl. Acad. Sci. USA, (1985) 82: 8404; Miyajima et al., Gene (1987) 58: 273; Martin et al., DNA (1988) 7: 99, etc. Numerous baculoviral strains and variants and corresponding permissive insect host cells from hosts are described in Luckow et al., Bio/Technology (1988) 6: 47-55; Miller et al., Generic Engineering (Setlow, J. K. et al. (Ed)) Vol. 8 (Plenum Publishing, 1986) pp. 277-279; Maeda et al., Nature (1985) 315: 592-594, etc.

With utilizing *Agrobacterium tumefaciens* etc., it is possible to use plant cells as the host cells, which have been widely known along with vectors suitable therefor in the art. In the gene engineering techniques of the present invention, it is possible to use restriction enzymes, reverse transcriptases known and widely used in the art, DNA-modifying enzymes, DNase, DNA polymerases, terminal nucleotidyltransferases, DNA ligases and the like to modify or convert DNA into a structure suitable for cloning the DNA fragment. For example, restriction enzymes include those described in, for example, R. J. Roberts, Nucleic Acids Res., 13: r165, 1985; S. Linn et al. ed. Nucleases, p. 109, Cold Spring Harbor Lab., Cold Spring Harbor, N.Y., 1982; R. J. Roberts, D. Macelis, Nucleic Acids Res., 19: Suppl. 2077, 1991, etc.

In accordance with the present invention, if necessary, appropriate selection markers are used to select host cells transformed or transfected with the expression vector containing the target polypeptide (protein)-coding polynucleotide. Cloning can be repeated to obtain stable cell clones with high expression levels. For instance, when a dhfr gene is utilized as a selection marker in the transformed or transfected animal host cells (transformants or transfectants), cell clones with higher expression levels can be obtained by culturing with a gradual increase in methotrexate (MTX) concentration to amplify the target polypeptide-coding DNA and selecting resistant cells. The transformants or transfectants can be cultured, under conditions wherein the target polypeptide-coding nucleic acid molecules are expressible, to produce and accumulate target products. The transformants (transfectants) can be cultured in a member selected from media conventionally used in the art. For example, the transformant (transfectant) in which the host is a prokaryotic cell such as *Escherichia coli* and *Bacillus subtilis*, yeast or the like can be cultivated suitably in a liquid culture medium. The culture medium may contain carbon sources, nitrogen sources, minerals, and others, necessary for growing the transformant. The carbon source may include glucose, dextrin, soluble starch, sucrose, etc. The nitrogen source may include organic or inorganic substances such as ammonium salts, nitrates, corn steep liquor, peptone, casein, meat extracts, malt extracts, bean-cakes, potato extracts, etc. Examples of the minerals may include calcium chloride, sodium dihydrogen phosphate, magnesium chloride, calcium carbonate, etc. It may also be supplemented with yeast extracts, vitamins, casamino acids, growth-promoting factors, etc. Depending on necessity, the medium may be supplemented with drugs such as 3β-indolyl acrylic acid in order to improve efficiency of the promoter. It is desirable that the pH for culture medium is from about 5 to about 8.

In the case of the *Escherichia* hosts for example, the cultivation is carried out usually at about 15 to 45° C. for about 3 to 75 hours. As required, aeration and stirring may be applied. In case of the transformants in which the hosts are animal cells, the culture medium used may include MEM medium, RPMI 1640 medium, DMEM medium, and others, which are containing, for example, fetal calf serum at about 5 to 20%. It is preferable that the pH is from about 6 to about 8. The cultivation is usually carried out at about 30 to 40° C. for about 15 to 72 hours. As required, aeration and stirring may be optionally applied. Although target gene product-expressing transformants can be used without any isolation/purification, they may be utilized in the form of cell homogenates. The target gene products may be isolated for use. To extract the products from the cultured microorganisms or cells, the microorganisms or cells are collected by known methods after the cultivation, next suspended in a suitable buffer solution, disrupted by sonication, lysozyme digestion and/or freeze-thawing, and other treatments, followed by centrifugation or filtration. Thus, crude extracts are obtained. Other conventional extraction or isolation methods can be applied. The buffer solution may contain a protein-denaturing agent such as urea or guanidine hydrochloride or a detergent such as Triton X-100 (trade name) and Tween-80 (trade name). In the case where the target products are secreted into culture media, supernatants are separated from the microorganisms or cells with widely known methods after the cultivation is finished and the resulting supernatants are collected.

The culture supernatants thus obtained and target products contained in extracts can be purified by suitable combinations of widely known per se techniques for separation, isolation and purification. Such widely known techniques are, for example, salting out such as ammonium sulfate precipitation, etc.; gel filtration on Sephadex, etc.; ion exchange chromatography using carriers having, for example, a diethylaminoethyl or carboxymethyl group, etc.; hydrophobic chromatography using carriers having, for example, a hydrophobic group such as butyl, octyl, or phenyl, etc.; dye-ligand (or chromophore-linked) gel chromatography; electrophoresis; dialysis; ultrafiltration; affinity chromatography; high performance liquid chromatography (HPLC); etc. Preferably, the target products can be isolated, separated and purified by polyacrylamide gel electrophoresis (PAGE), affinity chromatography in which ligands are immobilized. Said ligand may comprise antibodies including monoclonal antibodies, or fragments thereof, capable of recognizing specific targets, lectins, saccharides, one member of a binding pair, and others. Examples of such techniques also include immunoaffinity chromatography, gelatin-agarose affinity chromatography, heparin-agarose chromatography, etc.

In the polypeptides (proteins) of the present invention, amino acid residues contained therein can be modified by chemical techniques. Also, they can be modified and partially degraded to make derivatives thereof using enzymes such as peptidases, e.g., pepsin, chymotrypsin, papain, bromelain, endopeptidase, exopeptidase, etc. In the polypeptides of the present invention, the C-terminal end is typically a carboxyl group (—COOH) or a carboxylate (—COO$^-$), but the C-terminal end may be an amide form (—CONH$_2$) or an ester form (—COOR). For said ester, R includes $C_1$ to $C_6$ alkyl groups such as methyl, ethyl, n-propyl, isopropyl and n-butyl, $C_3$ to $C_8$ cycloalkyl groups such as cyclopentyl and cyclohexyl, $C_6$ to $C_{12}$ aryl groups such as phenyl and α-naphthyl, phenyl-$C_1$ to $C_2$ alkyl groups such as benzyl and phenethyl, $C_7$ to $C_{14}$ aralkyl groups including α-naphthyl-$C_1$ to $C_2$ alkyl groups such as α-naphthylmethyl, as well as a pivaloyloxymethyl group widely used as an oral ester. When the proteins of the present invention have a carboxyl group (or carboxylate) at a site other than the C-terminal end, amidated or esterified carboxyl groups are included in the proteins of the present invention. As the ester in this case, for example, the C-terminal ester and the like described above are used.

The polypeptides (proteins) of the present invention may be those having an N-terminal methionine residue in the above proteins, and further include those in which an amino group of the methionine residue is protected with a protecting group (for example, $C_1$ to $C_6$ acyl groups including $C_1$ to $C_5$ alkyl-carbonyl groups such as formyl and acetyl), those in which the N-terminus is cleaved in vivo and the resultant glutamyl group is pyroglutamylated, those in which substituents (for example, —OH, —COOH, amino, imidazole, indole, guanidino groups and the like) on side chains of the intramolecular amino acids are protected with appropriate protecting groups (for example, $C_1$ to $C_6$ acyl groups such as formyl and acetyl groups), or conjugated proteins (such as so-called glycoproteins) in which saccharide chains are linked.

Further, by relying on the gene nucleotide sequences associated with the present invention, equivalent polypeptides or derivatives thereof wherein each amino acid sequence of the target polypeptides is altered may be produced with conventional genetic engineering techniques. Such alterations include substitution (replacement), deletion, insertion, transfer or addition of one or more amino acid residues, etc. For example, such mutations, conversions and modifications are those described in The Japanese Biochemical Society (JBS) ed., "Zoku-Seikagaku Jikken Koza 1, Idenshi Kenkyu-Hou II", p. 105 (Susumu Hirose), Tokyo Kagaku Dozin Co. Ltd., Japan, (1986); JBS ed., "Shin-Seikagaku Jikken Koza 2, Kakusan III (Recombinant DNA technique)", p. 233 (Susumu Hirose), Tokyo Kagaku Dozin Co. Ltd., Japan, (1992); R. Wu, L. Grossman, ed., "Methods in Enzymology", Vol. 154, p. 350 & p. 367, Academic Press, New York (1987); R. Wu, L. Grossman, ed., "Methods in Enzymology", Vol. 100, p. 457 & p. 468, Academic Press, New York (1983); J. A. Wells et al., Gene, 34: 315, 1985; T. Grundstroem et al., Nucleic Acids Res., 13: 3305, 1985; J. Taylor et al., Nucleic Acids Res., 13: 8765, 1985; R. Wu ed., "Methods in Enzymology", Vol. 155, p. 568, Academic Press, New York (1987); A. R. Oliphant et al., Gene, 44: 177, 1986, etc. For example, included are methods such as the site-directed mutagenesis (site specific mutagenesis) utilizing synthetic oligonucleotides or others (Zoller et al., Nucl. Acids Res., 10: 6487, 1987; Carter et al., Nucl. Acids Res., 13: 4331, 1986), the cassette mutagenesis (Wells et al., Gene, 34: 315, 1985), restriction selection mutagenesis (Wells et al., Philos. Trans. R. Soc. London Ser A, 317: 415, 1986), the alanine scanning (Cunningham & Wells, Science, 244: 1081-1085, 1989), PCR mutagenesis, Kunkel method, dNTP[αS] method (Eckstein), the region directed mutagenesis using sulfurous acid and nitrous acid and other techniques.

The polypeptides (proteins) may be expressed as fusion polypeptides (fusion proteins) when produced by gene recombination techniques, and may be converted or processed into those having substantially equivalent biological activity as compared to those which naturally occur in vivo or in vitro. The fusion polypeptide expression system usually used in gene engineering can be applied. Such fusion polypeptides can be purified by an affinity chromatography and the like, taking advantage of their fusion moieties. Such fusion polypeptides include those fused to a histidine tag, or those fused to the amino acid sequence of β-galactosidase (β-gal), maltose-binding protein (MBP), glutathione S-transferase (GST), thioredoxin (TRX), or Cre Recombinase. Similarly, the polypeptide can be added with a tag of heterogeneous epitope, and can be isolated/purified by an immunoaffinity chromatography using an antibody specifically binding to the epitope. In more suitable embodiments, the representatives include poly histidine (poly-His) or polyhistidine-glycine (poly-His-Gly) tags, and epitope tags such as AU5, c-Myc, CruzTag 09, CruzTag 22, CruzTag 41, Glu-Glu, HA, Ha.11, KT3, FLAG (registered trademark, Sigma-Aldrich), Omni-probe, S-probe, T7, Lex A, V5, VP16, GAL4, and VSV-G (Field et al., Molecular and Cellular Biology, 8: pp. 2159-2165 (1988); Evan et al., Molecular and Cellular Biology, 5: pp. 3610-3616 (1985); Paborsky et al., Protein Engineering, 3(6): pp. 547-553 (1990); Hopp et al., BioTechnology, 6: pp. 1204-1210 (1988); Martin et al., Science, 255: pp. 192-194 (1992); Skinner et al., J. Biol. Chem., 266: pp. 15163-15166 (1991); Lutz-Freyermuth et al., Proc. Natl. Acad. Sci. USA, 87: pp. 6393-6397 (1990), etc.). Yeast two-hybrid systems are also utilizable.

Besides, the fusion polypeptides can be those tagged with a marker such that they become detectable proteins. In more suitable embodiments, the detectable markers may be Biotin-Avi Tag which is a biotin/streptavidin system, and fluorescent substances. The fluorescent substances include green fluorescent proteins (GFP) derived from luminescent jelly fish such as *Aequorea victorea* and the like, modified variants thereof (GFP variants) such as EGFP (enhanced-humanized GFP) and rsGFP (red-shift GFP), yellow fluorescent proteins (YFP), green fluorescent proteins (GFP), cyan fluorescent proteins (CFP), blue fluorescent proteins (BFP), GFP derived from *Renilla reniformis*, and the like (Atsushi Miyawaki ed., Jikken Igaku (Experimental Medicine), Besatsu (suppl.), Postgenome Jidai no Jikken Kouza 3 (GFP and Bioimaging), Yodosha Co., Ltd., 2000). Detection can be carried out using antibodies (including monoclonal antibodies and fragments thereof) which specifically recognize the above fusion tag. The expression and purification of such fusion polypeptides can be performed using commercially available kits suitable for these techniques, and can also be carried out according to protocols as instructed by manufacturers or distributors of the kits.

The resultant proteins (which may include peptides and polypeptides) can be coupled with suitable carrier or solid phases by techniques known in the enzyme immunoassay and others to form solid phased products. Solid-phased proteins and solid-phased peptides are conveniently useful in binding assays and screenings for substances.

Modifications and alterations of the polypeptide or protein structures can be performed in reference to, for example, The Japanese Biochemical Society (JBS) ed., "Shin-Seikagaku Jikken Koza 1, Protein VII, Protein Engineering" Tokyo Kagaku Dozin Co. Ltd., Japan, 1993) using the methods described therein or the methods described in the references quoted therein, and, further, substantially equivalent methods thereto. Their biological activity as described herein below may include immunological activity, for example, antigenicity. The modification and alteration may be deamination, hydroxylation, carboxylation, phosphorylation, sulfation, alkylation such as methylation, acylation such as acetylation, esterification, amidation, ring-opening, cyclization, glycosylation, alteration of contained saccharide chains to different types, increasing or decreasing the number of contained saccharide chains, lipid-binding, substitution to D-amino acid residues, etc. Those methods are known in the art (for example, T. E. Creighton, Proteins: Structure and Molecular Properties, pp. 79-86 W.H. Freeman & Co., San Francisco, USA (1983), etc.).

When modified galectin 9 proteins (modified Gal-9 variants) according to the present invention are utilized, screening can be done for compounds, or salts thereof, which promote (agonists) or inhibit (antagonists) the interesting Gal 9-mediated functions such as biological actions (e.g., cytotoxic actions, apoptosis-inducible actions, glucocorticoid-like actions, malignant cell metastasis-inhibiting actions and the like). This means that screening kits and reagents are contemplated herein. Thus, the present invention provides methods of screening for either (1) a promoting compound (agonist), or a salt thereof, which promotes the predetermined functions exerted by any of galectin 9 proteins (including human galectin 9), peptide fragments thereof, and salts thereof, etc., wherein the function may include Gal 9-mediated biological actions as identified or disclosed herein, or (2) an inhibitory compound (antagonist), or a salt thereof, which inhibits the same function, which comprises using a disclosed or identified action or activity mediated or owned by a member selected from the group consisting of said galectin 9 proteins (including human galectin 9), peptide fragments thereof, and salts thereof, in connection with a variety of substances.

For example, the screening comprises (i) contacting a modified galectin-9 protein (or modified Gal-9 variant), a peptide fragment thereof, a salt thereof, or an equivalent thereof (including a transformant or transfectant which expresses said protein; it has hereinafter the same meaning) with a suitable test sample, thereby obtaining a first assay;

(ii) incubating the protein of the present invention, a peptide fragment thereof, a salt thereof, or an equivalent thereof, without the test sample of interest, thereby obtaining a second assay; and (iii) comparing said first assay and said second assay. In an embodiment of the screening, said biological activities (e.g., activities associated with interactions between each galectin 9 protein and biological components, etc.) are measure and compared.

The screening systems may contain suitable detectable substrates for the convenience of assays. The substrates may be any as long as they are effectively utilizable in assays. For instance, they can be selected from those known to be conventional substrates and preferably include synthesized compounds and other materials. The substrate can be employed without any modification, or preferably after labeling with fluorochromes such as fluorescein, enzymes or radioactive substances.

The test samples include, for example, proteins, peptides, nonpeptidic compounds, synthetic compounds, fermented products, plant extracts, tissue extracts such as animal tissue extracts, cell extracts, etc. Examples of test compounds as used for the test samples may include preferably anti-galectin antibodies, enzyme inhibitors, cytokines, a variety of compounds having inhibitor activity, inter alia synthetic compounds, etc. These compounds can be novel or known to the public. The screening is conducted according to conventional techniques for measuring binding activities or enzyme activities, for example, by referring to known methods in the art. It can also be performed by using various labels, buffers and suitable other reagents, etc. and according to the operations, etc., as described herein for the assays. In the screening, it is possible to treat the peptides used and the like with activators, and to convert their precursors or latent forms into active forms thereof prior to the assay. The assay can usually be performed in buffer without any adverse effect on the reaction, including Tris-HCl buffer, phosphate buffer, etc., for example, at pH about 4 to 10, preferably at pH about 6 to 8. For each of these screenings, by giving technical consideration ordinarily owned by persons skilled in the art to customary conditions and operations for each method, suitable assay systems may be constructed in connection with each of the galectin 9 proteins and polypeptides or peptides having substantially equivalent activity thereto, according to the present invention. With details of those conventional techniques, a variety of reviews, reference books, etc. may be referred to (e.g., Methods in Enzymology, Academic Press, New York, USA). For apoptosis assays, it is possible to refer to Sei-ichi Tamuma (Ed.), "Saiboukagaku Bessatsu: Jikken Protocol Series, Apoptosis Jikken Protocol" (1st Edition, 2nd Print), Shujunsha Co., Ltd., Jan. 20, 1995 and others, and to use commercially available assay kits.

The compounds or salts thereof identified or obtained by the screening method or kit according to the present invention are those selected from the aforementioned test compounds, including peptides, proteins, nonpeptidic compounds, synthetic compounds, fermented products, cell extracts, plant extracts, animal tissue extracts, etc. Such compounds are those which enhance (or promote) or inhibit (or suppress) the functions of the proteins and other species according to the present invention. Salts of said compounds are, for example, pharmaceutically acceptable salts thereof, etc. Examples of such salts are those with inorganic bases, with organic bases, with inorganic acids, with organic acids, with basic or acidic amino acids, etc. Preferred examples of the inorganic base salts are alkaline metal salts such as sodium salts, and potassium salts; alkaline earth metal salts such as calcium salts and magnesium salts; aluminum salts, ammonium salts; etc. Preferred examples of the organic base salts are salts with trimethylamine, triethylamine, pyridine, picoline, 2,6-lutidine, ethanolamine, diethanolamine, triethanolamine, cyclohexylamine, dicyclohexylamine, N,N-dibenzylethylene-diamine, etc. Preferred examples of the inorganic acid salts are salts with hydrochloric acid, hydrobromic acid, sulfuric acid, phosphoric acid, etc. Preferred examples of the organic acid salts are salts with formic acid, acetic acid, propionic acid, fumaric acid, oxalic acid, tartaric acid, maleic acid, citric acid, succinic acid, malic acid, methanesulfonic acid, benzenesulfonic acid, benzoic acid, etc. Preferred examples of the basic amino acid salts are those of arginine, lysine, ornithine, etc. Preferred examples of the acidic amino acid salts are those of aspartic acid, glutamic acid, etc.

The active components of the present invention [e.g., (a) the modified Gal-9 polypeptides (modified Gal-9 variants), peptide fragments thereof, salts thereof, their related peptides, etc.; (b) the modified Gal-9 variant-coding or its related peptide-coding nucleic acid molecules (including DNA and others), etc.; (c) the compounds, or salts thereof, which control or regulate said interesting activities (or functions) exerted by Gal-9 (the compounds which promote or suppress/inhibit Gal-9 biological activities, including phenomena that they promote or suppress/inhibit Gal-9 protein-dependent cytotoxic actions, apoptosis-inducing actions, Gal-9 abilities of exerting desirable efficacies without any adverse effect on normal cells, etc. and degeneration, overproduction, or degradation of tissues or proteins); compounds, or their salts, which control or regulate said protein production; (d) the compounds identified or characterized by means of the present invention; etc.] can be employed as pharmaceutical agents. The active components can be administered alone or in the form of a pharmaceutical composition or preparation in admixture with any of various pharmaceutically acceptable aids. Preferably, it may be administered in the form of a convenient pharmaceutical composition or formulation suitable for oral, topical, parenteral application, or the like. Any of dosage forms (including those for inhalation and rectal administration) may be selected depending on purpose.

The active components of the present invention can be used in combination with any of various drugs, including antitumor drugs (antineoplastic drugs), tumor metastasis-inhibitors, inhibitors for thrombogenesis, therapeutic drugs for joint destruction, analgesics, anti-inflammatory drugs, immunoregulators (or immunomodulators) and/or immunosuppressants, which can be employed as not being restricted to particular species as long as they serve effectively or advantageously. For instance, they can be optionally selected from those known in the art.

The parenteral administration includes topical, percutaneous, intravenous, intramuscular, subcutaneous, intracutaneous, and intraperitoneal routes. It is also possible to apply the drug directly to affected sites, and, in a certain case, the direct application is suitable. Preferably mammal animals including human can receive the drug orally or parenterally (e.g., intracellularly, intra-tissularly, intravenously, intramuscularly, subcutaneously, intracutaneously, intraperitoneally, intrapleurally, intraspinally, by instillation, enterally, per rectum, by instillation into the ear, eye, or nose by swabbing or application on the teeth, skin or mucosa, etc.). Specific dosage forms of the pharmaceutical preparations and formulations include pharmaceutical solutions, pharmaceutical dispersions, semisolid preparations, particulate preparations, shaped preparations, extractives, etc. Examples of the dosage forms are tablets, coated tablets, sugar coated tablets, pills, troches, hard capsules, soft capsules, microcapsules, implants, powders, pulvis, granules, fine granules, injections, liquids and solutions, elixirs, emulsions, irrigations, syrups, mixtures, suspensions, liniments, lotions, aerosols, sprays, inhalations, nebula, ointments, plasters, patches, pastes, cataplasms, creams, oleates, suppositories (e.g., rectal suppositories), tinctures, dermatologic waters, ophthalmic solutions, collunariums, auristillae, paints, transfusions, powders for injection solutions, lyophilized preparations, conditioned gels, etc.

The pharmaceutical compositions can be formulated in accordance with conventional techniques. For example, the pharmaceutical composition or formulation may comprise at least one of said compounds (active components including proteins) of the present invention or a salt alone or in admixture with physiologically allowable carriers, pharmaceutically acceptable carriers, adjuvants, vehicles, excipients, diluents, etc. The compound (active component or protein) of the present invention or a salt thereof is usually admixed with a single member selected from the group consisting of physiologically allowable carriers, pharmaceutically acceptable carriers, adjuvants, vehicles, excipients, diluents, flavoring agents, perfuming agents, sweetening agents, expanders, antiseptics, stabilizers, binders, pH regulators, buffering agents, detergents (surfactants), bases, solvents, fillers, bulking agents, solution adjuvants, solubilizers, tonicity agents, emulsifiers, suspending agents, dispersers, viscosity-increasing agents, thickening agents, gelling agents, stiffening agents, absorbents, adhesives, elastomers, plasticizers, disintegrants, aerosol propellants, preservatives, antioxidants, opacifying agents, humectants, emollients, charge protectors, soothing agents, etc., or suitably in a combination thereof, depending on necessity, to give a unit dose form which is required for generally approved pharmaceutical practices.

Formulations suitable for parenteral routes include aseptic solutions or suspensions containing at least one active component in admixture with water or other pharmaceutically acceptable media. Examples of such parenteral formulations are injections. Preferred liquid carriers for injection generally include water, saline, dextrose solution, other related saccharide solutions, ethanol, glycols such as propylene glycol and polyethylene glycol, etc. For the preparation of injections, the active component is usually admixed with any of carriers such as distilled water, Ringer's solution, physiological saline, suitable dispersing agents, moistening agents, suspending agents, and other materials to form injectable formulations including solutions, suspensions, emulsions, etc. by known techniques in the art.

Examples of aqueous liquids for the injection are a physiological saline and isotonic solutions containing glucose and other aids (e.g. D-sorbitol, D-mannitol, sodium chloride, etc.) where they may be used in combination with a suitable pharmaceutically acceptable auxiliary solubilizer such as alcohol (e.g. ethanol, etc.), polyalcohol (e.g. propylene glycol, polyethylene glycol, etc.), nonionic surface-active agent (e.g. Polysorbate 80™, HCO-50, etc.), etc. The injectable oily liquids may include sesame oil, soybean oil, etc. where they may be used in combination with benzyl benzoate, benzyl alcohol, and other materials as auxiliary solubilizers. In addition, buffers (e.g. phosphate buffer, sodium acetate buffer, etc.) or agents for osmoregulation, analgesic agents (e.g. benzalkonium chloride, procaine hydrochloride, etc.), stabilizers (e.g. human serum albumin, polyethylene glycol, etc.), preservatives (e.g. benzyl alcohol, phenol, etc.), antioxidants such as ascorbic acid, absorbefacients, etc. may be admixed therewith too. The prepared injection solution is usually filled in suitable ampoules.

For parenteral administration, solution or suspension unit dosage forms are prepared in pharmaceutically acceptable sterile fluids such as water, ethanol, and oils, in admixture with or without detergent and other pharmaceutically acceptable aids. The oily vehicle and solvent used in the parenteral formulation may include natural, synthetic or semi-synthetic mono-, di-, or triglycerides; natural, semi-synthetic or synthetic fats and oils; and fatty acids. Examples of such oily vehicles and solvents are plant oils such as peanut oil, corn oil, soybean oil, and sesame oil. For example, this injection can usually be prepared to form unit doses each containing approximately from 0.1 to 10 parts of the compound of the present invention per 100 parts by weight of the dose composition.

The formulation suitable for topical use, such as buccal or rectal application, includes mouthwashes and gargles, dentifrices, sprays for buccal cavity, inhalants, ointments (salves), dental fillers, dental coating agents, dental pastes, suppositories, etc. The mouthwashes and other dental agents are prepared by conventional techniques, using pharmaceutically acceptable carriers. For the sprays for buccal cavity and inhalants, the compound of the present invention can be applied to teeth or other sites after dissolving alone or together with pharmaceutically acceptable inert carriers, in an aerosol or solution for nebulizers, or in the form of powders for inhalation. The ointments (salves) are prepared by conventional techniques, in admixture with conventionally employed pharmaceutical bases such as ointment bases (white petrolatum, paraffin, olive oil, macrogol 400, macrogol ointment, etc.).

The pharmaceutical drugs for topical application (including painting) to teeth and skin can be prepared in the form of a solution or suspension utilizing suitably sterilized water or non-aqueous vehicles. The additives used include buffering agents such as sodium bisulfite and disodium edetate; preservatives including antiseptic, antimicrobial and antifungal agents such as acetic acid, phenylmercuric nitrate, benzalkonium chloride and chlorhexidine; and thickeners such as hypromellose.

The suppositories can be prepared by conventional techniques utilizing carriers well known in the art, preferably suitable non-irritative excipients. Examples of the excipients are those which are solid at room temperature but liquid at rectal temperature wherein such substances melt in the rectum to deliver a drug, such as polyethylene glycols, lanolin, cacao butter, and fatty acid triglycerides. In the suppositories, the compounds of the present invention are applied in the form of compositions containing approximately from 0.1 to 95 percent (weight per volume). The compound, depending on the vehicle and concentration used, can be either suspended or dissolved in the vehicle. Adjuvants such as a local anesthetic, preservative and buffering agent can be dissolved in the vehicle. The formulations suitable for oral application include solid compositions such as tablets, pills, capsules, powders, granules, and troches; fluid compositions such as solutions, syrups, and suspensions; etc. In preparing oral formulations, pharmaceutical adjuvants known in the art are employed. The tablets and pills can be prepared further by enteric coating. When the unit dosage form is a capsule, fluid carriers such as fats and oils can be contained in addition to the aforementioned materials.

When the active components are proteins or polypeptides, conjugation to polyethylene glycol (PEG) is particularly useful, because its toxicity is extremely low in mammals. Further, the conjugation with PEG can sometimes reduce the immunogenicity and antigenicity of a heterologous compound effectively. The compound may be given after being put in a microcapsule device. A polymer such as PEG can be easily attached to an α-amino group of amino-terminal amino acids, an ε-amino group of lysine side chains, a carboxyl group of aspartic acid or glutamic acid side chains, an α-carboxyl group of carboxyl-terminal amino acids, or an activated derivative of glycosyl chains attached to certain asparagine, serine or threonine residues. Various activated forms of PEG suitable for direct reaction with proteins are known. PEG reagents useful for reaction with amino groups of a protein include active esters of carboxylic acids and carbonate derivatives, particularly those having N-hydroxysuccinimide, p-nitrophenol, imidazole, or 1-hydroxy-2-nitrobenzene-4-sulfonate as a leaving group. Similarly, PEG reagents having an aminohydrazine or hydrazide group are useful for reaction with aldehydes produced by periodate oxidation of proteins.

Practice of the invention may begin by diagnosing the mammal as is appropriate for the particular disorder/disease such as autoimmunity, tumor including malignant tumor such as cancer, allergic disease, and inflammation that they may be exhibiting. The diagnosis may also continue during treatment, as a therametric procedure, to monitor the progress of treatment, and to direct modification of such parameters as the dosage or frequency in continued treatments, for example. Additional diagnosis that might aid in determining appropriateness for administration of a modified galectin 9 mutein therapeutic agent include an analysis of expression levels of galectin 9 in the mammal, and a comparison of these levels between cells such as lymphocytes distal from the site of autoimmunity, and those proximal to the site or autoimmunity. The disorder/disease such as autoimmunity, tumor including malignant tumor such as cancer, allergic disease, and inflammation autoimmune disease in the mammal being treated can be monitored by detecting galectin 9 antigen on a cell surface. This monitoring can include contacting a sample derived from the mammal with a galectin 9-specific antibody, and detecting binding of the antibody to the sample.

Gene therapy vehicles include those for delivery of constructs including a coding sequence of a therapeutic of the invention, to be delivered to the mammal for expression in the mammal, for example, a modified galectin 9 mutein coding sequence, or also including a nucleic acid sequence of all or a portion of modified Gal-9 mutein for delivery, which can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated. Where the modified Gal-9 mutein is expressed in the mammal, it can be expressed as soluble modified Gal-9 mutein, or as a precursor form modified Gal-9 mutein, both or either including, for example, all of the modified Gal-9 mutein, or a biologically active portion, variant, derivative or fusion of modified Gal-9 mutein.

The invention includes gene delivery vehicles capable of expressing the contemplated modified Gal-9 mutein nucleic acid sequences. The gene delivery vehicle is preferably a viral vector. A more preferable gene delivery vehicle includes viral vectors such as retroviral, adenoviral, adeno-associated viral (AAV), herpes viral, or alphavirus vectors. The viral vector can also be an astrovirus, coronavirus, orthomyxovirus, papovavirus, paramyxovirus, parvovirus, picornavirus, poxvirus, togavirus viral vector. The gene delivery vehicles are disclosed generally in D. Jolly, Cancer Gene Therapy, 1(1): 51-64 (1994); O. Kimura et al., Human Gene Therapy, 5: 845-852 (1994); S. Connelly et al., Human Gene Therapy, 6: 185-193 (1995); M. G. Kaplitt et al., Nature Genetics, 8: 148-153 (1994), etc.

Retroviral vectors are well known in the art and may include any retroviral gene therapy vector employable in the invention, such as B, C and D type retroviruses, and xenotropic retroviruses (for example, NZB-X1, NZB-X2, NZB9.1: see, R. R. O'Neill, J. Virol., 53: 100-106 (1985), etc.), polytropic retroviruses (for example, MCF, MCF-MLV: see, M. Kelly, J. Virol., 45: 291-298 (1983), etc.), spumaviruses and lentiviruses and others (see, R. L. Weiss et al. (Eds.), RNA Tumor Viruses, Second Edition, Cold Spring Harbor Laboratory, Cold Spring Harbor, 1985).

Portions of the retroviral gene therapy vector may be derived from different retroviruses. For example, retrovector LTRs may be derived from a murine sarcoma virus, a tRNA binding site from a Rous sarcoma virus, a packaging signal from a murine leukemia virus, and an origin of second strand synthesis from an avian leukosis virus. These recombinant retroviral vectors may be used to generate transduction competent retroviral vector particles by introducing them into appropriate packaging cell lines (see, U.S. Pat. No. 5,591,624). Retrovirus vectors can be constructed for site-specific integration into host cell DNA by incorporation of chimeric integrase (an enzyme that enables the target DNA to be integrated into the DNA of the host cell) into the retroviral particle. It is preferable that the recombinant viral vector is a replication defective recombinant virus.

Packaging cell lines suitable for use with the aforementioned retrovirus vectors are well known in the art, are readily prepared (see, U.S. Pat. No. 6,013,517, WO 92/05266). Said packaging cell lines can be used to create producer cell lines (vector cell lines or "VCLs") for the production of recombinant vector particles. Preferably, the packaging cell lines are made from human parent cells (e.g., HT1080 cells) or mink parent cell lines, which eliminates inactivation in human serum.

Preferred retroviruses for the construction of retroviral gene therapy vectors include avian leukosis virus, bovine leukemia virus, murine leukemia virus, mink-cell focus-inducing virus, murine sarcoma virus, reticuloendotheliosis virus and Rous sarcoma virus. Particularly preferred murine leukemia viruses include for example, 4070A and 1504A (Hartley & Rowe, J. Virol., 19: 19-25 (1976)), Abelson (ATCC No. VR-999), Friend (ATCC No. VR-245), Graffi, Gross (ATCC No. VR-590), Kirsten, Harvey sarcoma virus and Rauscher (ATCC No. VR-998), and moloney murine leukemia virus (ATCC No. VR-190), etc. Such retroviruses may be obtained from depositories or collections such as the American Type Culture Collection ("ATCC") in Rockville, Md., USA or isolated from known sources using commonly available techniques.

Exemplary known retroviral gene therapy vectors employable in this invention include those described in GB 2200651, EP 0415731, EP 0345242, WO 89/02468, WO 89/05349, WO 89/09271, WO 90/02806, WO 90/07936, WO 94/03662, WO 93/25698, WO 93/25234, WO 93/11230, WO 93/10218, WO 93/10218, WO 91/02805, U.S. Pat. Nos. 5,219,740, 4,405,712, 4,861,719, 4,980,289, 4,777,127, 5,591,624, Vile, Cancer Res, 53: 3860-3864 (1993), Vile, Cancer Res, 53: 962-967 (1993), Ra, Cancer Res, 53: 83-88 (1993), Takamiya, Neurosci Res, 33: 493-503 (1992), Baba, J Neurosurg, 79: 729-735 (1993), Mann, Cell 33: 153 (1983), Cane, Proc Natl Acad Sci USA, 81: 6349 (1984), Miller, Human Gene Therapy, 1: 5-14 (1990), etc.

Human adenoviral gene therapy vectors are also known in the art and employable in this invention. Such vectors are disclosed in, for example, Berkne, Biotechniques, 6: 616 (1988); Rosenfeld, Science, 252: 431 (1991); WO 93/07283; WO 93/06223; WO 93/07282, etc. Exemplary known adenoviral gene therapy vectors employable in this invention include those described in the above referenced documents and in WO 94/12649; WO 93/03769; WO 93/19191; WO 94/28938; WO 95/11984; WO 95/00655; WO 95/27071; WO 95/29993; WO 95/34671; WO 96/05320; WO 94/08026; WO 94/11506; WO 93/06223; WO 94/24299; WO 95/14102; WO 95/24297; WO 95/02697; WO 94/28152; WO 94/24299; WO 95/09241; WO 95/25807; WO 95/05835; WO 94/18922; WO 95/09654; etc. Alternatively, administration of DNA linked to killed adenovirus as described in Curiel, Human Gene Therapy, 3: 147-154 (1992) may be employed.

The gene delivery vehicles of the invention also include adenovirus associated virus (AAV) vectors. Leading and preferred examples of such vectors for use in this invention are the AAV-2 based vectors disclosed in WO 93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, and others (Nahreini, Gene, 124: 257-262 (1993)). Another example of such an AAV vector is psub201, and others (Samulski, J. Virol., 61: 3096 (1987)). Another exemplary AAV vector is the Double-D ITR vector, etc. Methods for construction of Double-D ITR are disclosed in U.S. Pat. No. 5,478,745. Still other AAV vectors are those disclosed in U.S. Pat. Nos. 4,797, 368, 5,139,941, 5,474,935, WO 94/288157, etc. Yet a further example of an AAV vector employable in this invention is SSV9AFABTKneo, which contains the AFP enhancer and albumin promoter and directs expression predominantly in the liver. Its structure and construction are disclosed in Su, Human Gene Therapy, 7: 463-470 (1996). Additional AAV gene therapy vectors are described in U.S. Pat. Nos. 5,354, 678, 5,173,414, 5,139,941, 5,252,479, etc.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP 0176170. Additional exemplary herpes simplex virus vectors include HFEM/ICP6-LacZ disclosed in WO 95/04139, pHSVlac described in Geller, Science, 241: 1667-1669 (1988), WO 90/09441, WO 92/07945, etc., HSV Us3::pgC-lacZ described in Fink, Human Gene Therapy, 3: 11-19 (1992), HSV7134, 2RH 105 and GAL4 described in EP 0453242 A, those deposited with the ATCC as accession numbers ATCC VR-977 and ATCC VR-260, and others.

Alpha virus gene therapy vectors may be employed in this invention. Preferred alpha virus vectors are Sindbis viruses vectors, togavirus, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), those described in U.S. Pat. Nos. 5,091,309, 5,217,879, and WO 92/10578, and others. Alpha virus vectors employable herein are those disclosed in U.S. Pat. Nos. 5,091,309, 5,217,879, 5,843,723, 6,376,236, WO 94/21792, WO 92/10578, WO 95/07994 and other documents. Such alpha viruses may be obtained from depositories or collections such as the ATCC (Rockville, Md., USA), or isolated from known sources using commonly available techniques. Preferably, alphavirus vectors with reduced cytotoxicity are used (see U.S. Pat. No. 6,391,632).

DNA vector systems such as eukaryotic layered expression systems are also useful for expressing the modified galectin 9 mutein nucleic acids of the invention. Details of eukaryotic layered expression systems are disclosed in WO 95/07994. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature, 339: 385 (1989), Sabin, J. Biol. Standardization, 1: 115 (1973), etc.; rhinovirus, for example ATCC VR-1110, and those described in Arnold, J. Cell Biochem, L401-405 (1990), etc.; pox viruses such as canary pox virus or vaccinia virus, for example ATCC VR-111 and ATCC VR-2010 and those described in Fisher-Hoch, Proc Natl Acad Sci USA, 86: 317 (1989), Flexner, Ann NY Acad Sci, 569: 86 (1989), Flexner, Vaccine, 8: 17 (1990), U.S. Pat. Nos. 4,603,112 & 4,769,330, and WO 89/01973, etc.; SV40 virus, for example ATCC VR-305 and those described in Mulligan, Nature, 277: 108 (1979) and Madzak, J. Gen. Vir, 73: 1533 (1992), etc.; influenza virus (for example ATCC VR-797, etc.) and recombinant influenza viruses made employing reverse genetics techniques as described in U.S. Pat. No. 5,166,057, Enami, Proc Natl Acad Sci USA, 87: 3802-3805 (1990), Enami & Palese, J Virol, 65: 2711-2713 (1991), Luytjes, Cell, 59: 110 (1989), McMicheal., N E J Med, 309: 13 (1983), Yap, Nature, 273: 238 (1978), Nature, 277: 108 (1979), and other documents; human immunodeficiency virus as described in EP 0386882, Ruchschacher, J. Vir., 66: 2731 (1992), etc.; measles virus (for example ATCC VR-67, VR-1247) and those described in EP 0440219; Aura virus (for example ATCC VR-368, etc.); Bebaru virus (for example ATCC VR-600, ATCC VR-1240, etc.); Cabassou virus (for example ATCC VR-922, etc.); Chikungunya virus (for example ATCC VR-64, ATCC VR-1241, etc.); Fort Morgan virus (for example ATCC VR-924, etc.); Getah virus (for example ATCC VR-369, ATCC VR-1243, etc.); Kyzylagach virus (for example, ATCC VR-927, etc.); Mayaro virus (for example ATCCVR-66, etc.); Mucambo virus (for example ATCC VR-580, ATCC VR-1244, etc.); Ndumu virus (for example ATCC VR-371, etc.); Pixuna virus (for example ATCC VR-372, ATCC VR-1245, etc.); Tonate virus (for example ATCCVR-925, etc.); Triniti virus (for example ATCC VR-469, etc.); Una virus (for example ATCC VR-374, etc.); Whataroa virus (for example ATCC VR-926, etc.); Y-62-33 virus (for example ATCC VR-375, etc.); O'Nyong virus, Eastern encephalitis virus (for example ATCC VR-65, ATCC VR-1242, etc.); Western encephalitis virus (for example ATCC VR-70, ATCC VR-125L, ATCC VR-622, ATCC VR-1252, etc.); coronavirus (for example ATCC VR-740, and those described in Hamre, Proc Soc Exp Biol Med, 121: 190 (1966); etc.

Delivery of the compositions of this invention into cells is not limited to the aforementioned viral vectors. Other delivery methods and media may be employed such as, for example, nucleic acid expression vectors, polycationic condensed DNA linked or unlinked to killed adenovirus alone (for example see Curiel, Hum Gene Ther, 3: 147-154 (1992)), ligand linked DNA (for example see Wu, J Biol Chem, 64: 16985-16987 (1989)), eucaryotic cell delivery vehicles cells (see, e.g., U.S. Pat. Nos. 6,013,517, 6,015,686, etc.), deposition of photopolymerized hydrogel materials, portable gene transfer particle gun, as described in U.S. Pat. No. 5,149,655, ionizing radiation as described in WO 92/11033, nucleic charge neutralization or fusion with cell membranes. Additional approaches are described in Philip, Mol Cell Biol, 14: 2411-2418 (1994), Woffendin, Proc Natl Acad Sci USA, 91: 1581-585 (1994), etc.

Particle mediated gene transfer may be employed. The sequence can be inserted into conventional vectors that contain conventional control sequences for high level expression, and then be incubated with synthetic gene transfer molecules (for example polymeric DNA-binding cations like polylysine, protamine, and albumin, linked to cell targeting ligands such as asialoorosomucoid, as described in Wu et al., J. Biol. Chem., 262: 4429-4432 (1987), insulin as described in Hucked, Biochem Pharmacol, 40: 253-263 (1990), galactose as described in Plank, Bioconjugate Chem, 3: 533-539 (1992), lactose, or transferrin).

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO 95/13796, WO 94/23697, WO 91/144445 and EP 524,968. On non-viral delivery, the nucleic acid sequences encoding a modified galectin 9 mutein polypeptide can be inserted into conventional vectors that contain conventional control sequences for high level expression, and then be incubated with synthetic gene transfer molecules. The synthetic gene transfer molecule includes polymeric DNA-binding cations linked to cell targeting ligands such as asialoorosomucoid, insulin, galactose, lactose, or transferrin. The polymeric DNA-binding cation includes for example polylysine, protamine, albumin, etc. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al., Proc. Natl. Acad. Sci. USA, 91(24): 11581-11585 (1994).

Moreover, the coding sequence and the product of expression of such can be delivered through deposition of photopolymerized hydrogel materials. Other conventional methods for gene delivery that can be used for delivery of the coding sequence include, for example, use of portable gene transfer particle gun, as described in U.S. Pat. No. 5,149,655; use of ionizing radiation for activating transferred gene, as described in WO 92/11033.

Examples of liposome and polycationic gene delivery vehicles are those described in U.S. Pat. Nos. 5,422,120 and 4,762,915, WO 95/13796, WO 94/23697, WO 91/14445, EP 0524968, Stryer, Biochemistry, 236-240 (1975), W. H. Freeman et al., Biochem Biophys Acta, 600:1 (1980), Bayer, Biochem Biophys Acta, 550: 464 (1979), Rivnay, Meth Enzymol, 149: 119 (1987), Wang, Proc Natl Acad Sci USA, 84: 7851 (1987), Plant, Anal Biochem, 176: 420 (1989), etc.

The invention discloses a method of treating mammals afflicted with a disorder or disease selected from the group consisting of tumors including malignant ones such as cancer, allergic diseases, inflammations, conditions with immunological abnormality, and autoimmune diseases that include activated lymphocytes (inter alia, activated T-cells; may include activated B-cells), by administration of a modified galectin 9 mutein or modified galectin 9 mutein-derived therapeutic agent (for example, composition comprising, as a therapeutic agent, either a modified galectin 9 mutein polypeptide or a polynucleotide encoding a modified galectin 9 mutein polypeptide for expression in the mammal). Autoimmune diseases that can be treated by the method and compositions of the invention include any autoimmune disease, or transplantation rejection, including, but not limited to, for example, those autoimmune diseases listed herein.

Modified galectin 9 mutein can be administered, for example, as a recombinantly expressed polypeptide, or as a variant, derivative, or fusion protein of modified galectin 9 mutein polypeptide, delivered either locally or systemically to the mammal. The nucleic acid molecule (e.g., DNA, RNA, etc.) encoding modified galectin 9 mutein, or a derivative or variant of modified galectin 9 mutein, or a modified galectin 9 mutein fusion, can be administered in a gene therapy protocol, as naked plasmid DNA including regulatory regions for expression in the mammal, or in a viral vector for expression in the mammal. Delivery of modified galectin 9 mutein polypeptide for expression can be accomplished with a pharmaceutically acceptable carrier capable of facilitating the delivery. Treatment of a mammal having an autoimmune disease with a modified galectin 9 mutein-derived therapeutic agent can result in amelioration or remission or the autoimmune disease, or in absence of clinical symptoms attributable to the autoimmunity.

Although the invention is not limited to theories of how the invention as disclosed herein works, it will be posited according to activated T-cells and others that cause the self-recognition and subsequent harm in autoimmunity. By expressing modified galectin 9 mutein or causing modified galectin 9 mutein to be expressed, or by administering a modified galectin 9 mutein derived therapeutic agent, the activated lymphocytes of concern are preferentially targeted for apoptosis by receiving an action of the modified galectin 9 mutein moiety made available. The modified galectin 9 mutein polypeptide or modified galectin 9 mutein derived therapeutic agent can be administered in the region exhibiting the autoimmunity (for example, in the localized region that characterized the particular autoimmune disease being treated). This optimizes the contact between the administered modified galectin 9 mutein or other therapeutic agents and the target expressing activated T-cells, or other cells, which are specific for the targets expressed on the cells of that region. The cells of the region are thus also good candidates for expressing, by aid of a gene delivery vehicle, a polynucleotide encoding a modified galectin 9 mutein polypeptide administered to the region. Thus, in various permutations and applications of the invention, the expression of the modified galectin 9 mutein polypeptide can be recombinantly engineered to facilitate expression in cells that are under attack by the activated T-cells and other cells. Proposed in the case of transplantation rejection is a modified galectin 9 mutein polypeptide fusion with a binding portion of a molecule capable of binding a protein ubiquitously expressed on the cell surfaces of many cell types. This binding portion can be, for example, heparin, and the molecule on the cell surface to which it binds can be a glycosaminoglycan. Alternatively, the binding portion may be a single chain antibody binding domain, specific for any selected cell surface antigen.

Where the inventive agents and therapeutic techniques are applied in order to obtain cytotoxic actions on tumor cells including malignant tumor cells such as cancers, antiallergic actions, anti-inflammatory actions, normalization of immunological abnormality, and apoptosis inducing actions on activated lymphocytes (may include inter alia activated T-cells), the invention should be interpreted in the same fashion as in the aforementioned autoimmune case.

The term "administration" or "administering" as used herein refers to the process of delivering, to a mammal, a therapeutic agent, or a combination of therapeutic agents. The process of administration can be varied, depending on the therapeutic agent, or agents, and the desired effect. Administration can be accomplished by any means appropriate for the therapeutic agent, for example, by parenteral or oral delivery. The parenteral delivery can be, for example, subcutaneous, intravenous, intramuscular, intra-arterial, injection into the tissue of an organ, mucosal, pulmonary, topical, or catheter-based. Oral means is by mouth, including pills or other gastroenteric delivery means, including a drinkable liquid. Mucosal delivery can include, for example, intranasal delivery. Pulmonary delivery can include inhalation of the agent. Administration generally also includes delivery with a pharmaceutically acceptable carrier (for example, a buffer, a polypeptide, a peptide, a polysaccharide conjugate, a liposome, a lipid, etc.). A gene therapy protocol is considered to include an administration in which the therapeutic agent is a polynucleotide capable of accomplishing a therapeutic goal when expressed as a transcript or a polypeptide in the mammal, and can be applied to both parenteral and oral delivery means. Such administration means are selected as appropriate for the disease being treated. For example, where the disease is organ-based, delivery may be local, and for example, where the disease is systemic, the delivery may be systemic. The "co-administration" refers to administration of one or more therapeutic agents in course of a given treatment of a patient. The agents may be administered with the same pharmaceutical carrier, or different carriers. They may be administered by the same or different administration means. The agents may be the same type of agent or different types of agents, for example, different types can include polynucleotides, polypeptide, or small molecules. The time of administration may be exactly the same time, or one therapeutic agent may be administered before or after another agent. Thus, co-administration can be simultaneous, or consecutive. The exact protocol for a given combination of therapeutic agents is determined considering the agents and the condition being treated, among other considerations.

The term "in vivo administration" refers to administration to a patient (for example a mammal), of a polynucleotide encoding a polypeptide for expression in the mammal. In particular, direct in vivo administration involves transfecting a mammalian cell with a coding sequence without removing the cell from the mammal. Thus, direct in vivo administration may include direct injection of the DNA encoding the polypeptide of interest in the region afflicted by the autoimmune disease, resulting in expression in the patient's cells.

The term "ex vivo administration" refers to transfecting a cell (for example, a cell from a population of cells that are under autoimmune attack) after the cell is removed from the patient (for example a mammal). After transfection the cell is then replaced in the mammal. Ex vivo administration can be accomplished by removing cells from a mammal, optionally selecting for cells to be transformed (i.e., cells under attack by an autoimmune mechanism), rendering the selected cells incapable of replication, transforming the selected cells with a polynucleotide encoding a gene for expression (i.e., modified galectin 9 mutein), including also a regulatory region for facilitating the expression, and placing the transformed cells back into the patient for expression of the modified galectin 9 mutein.

The "therapeutically effective amount" is that amount that generates the desired therapeutic outcome. For example, if the therapeutic effect desired is a remission from autoimmunity, the therapeutically effective amount is that amount that facilitates the remission. The therapeutically effective amount can be an amount administered in a dosage protocol that includes days or weeks of administration, for example. Where the therapeutic effect is a reduction of the effects of an autoimmune response in the mammal, for example, during the manifestations of symptoms of an autoimmune disease, the effective amount of an agent to accomplish this in the mammal is that amount that results in reduction of the symptoms of autoimmunity.

The term "pharmaceutically acceptable carrier" refers to a carrier for administration of a therapeutic agent (for example, a polypeptide, polynucleotide, small molecule, peptoid, peptide, etc.). It refers to any pharmaceutically acceptable carrier that does not itself induce the production of antibodies harmful to the individual receiving the composition, and which may be administered without undue toxicity. Within another aspect of the invention, pharmaceutical compositions are provided, comprising a recombinant viral vector as described above, in combination with a pharmaceutically acceptable carrier or diluent. Such pharmaceutical compositions may be prepared either as a liquid solution, or as a solid form (e.g., lyophilized) which is suspended in a solution prior to administration. In addition, the composition may be prepared with suitable carriers or diluents for either surface administration, injection, oral, or rectal administration. Pharmaceutically acceptable carriers or diluents are nontoxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A particularly preferred composition comprises a vector or recombinant virus in 10 mg/ml mannitol, 1 mg/ml HSA, 20 mM Tris, pH 7.2, and 150 mM NaCl. In this case, since the recombinant vector represents approximately 1 mg of material, it may be less than 1% of high molecular weight material, and less than $1/100,000$ of the total material (including water). This composition is stable at 20° C. for at least six months.

The pharmaceutical compositions of the present invention may also additionally include factors which stimulate cell division, and hence, uptake and incorporation of a recombinant retroviral vector. Preserving recombinant viruses is described in U.S. Pat. No. 5,792,643.

All of the therapeutic agents that make up the proposed therapy of the invention can be incorporated into an appropriate pharmaceutical composition that includes a pharmaceutically acceptable carrier for the agent. The pharmaceutical carrier for the agents may be the same or different for each agent. Suitable carriers may be large, slowly metabolized macromolecules such as proteins, polysaccharides, polylactic acids, polyglycolic acids, polymeric amino acids, amino acid copolymers, and inactive viruses in particles. Such carriers are well known to those of ordinary skill in the art. Pharmaceutically acceptable salts which can be used therein, include for example inorganic acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J., USA, 1991). Pharmaceutically acceptable carriers in therapeutic compositions may contain liquids such as water, saline, glycerol and ethanol. Auxiliary substances may include wetting or emulsifying agents, etc. Additionally, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Provided are pharmaceutical compositions comprising a recombinant retrovirus or virus carrying one of the above-described vector constructs, in combination with a pharmaceutically acceptable carrier or diluent. The composition may be prepared either as a liquid solution, or as a solid form (e.g., lyophilized) which is suspended in a solution prior to administration. In addition, the composition may be prepared with suitable carriers or diluents for either surface administration, injection, oral, or rectal administration.

Pharmaceutically acceptable carriers or diluents are nontoxic to recipients at the dosages and concentrations employed. Representative examples of carriers or diluents for injectable solutions include water, isotonic saline solutions which are preferably buffered at a physiological pH (such as phosphate-buffered saline or Tris-buffered saline), mannitol, dextrose, glycerol, and ethanol, as well as polypeptides or proteins such as human serum albumin. A vector or recombinant virus can be delivered in a pharmaceutical composition in 10 mg/ml mannitol, 1 mg/ml HSA, 20 mM Tris, pH 7.2, and 150 mM NaCl. In this case, since the recombinant vector represents approximately 1 g of material, it may be less than 1% of high molecular weight material, and less than $1/100,000$ of the total material (including water). This composition is stable at 20° C. for at least six months.

The pharmaceutically acceptable carrier or diluent may be combined with the gene delivery vehicles to provide a composition either as a liquid solution, or as a solid form (e.g., lyophilized) which can be resuspended in a solution prior to administration. The two or more gene delivery vehicles are typically administered via traditional direct routes, such as buccal/sublingual, rectal, oral, nasal, topical, (such as transdermal and ophthalmic), vaginal, pulmonary, intraarterial, intramuscular, intraperitoneal, subcutaneous, intraocular, intranasal or intravenous, or indirectly.

The therapeutic drug of the present invention may include optionally, for example, polynucleotides for expression in the mammal. Said therapeutic drugs can be formulated into an enteric coated tablet or gel capsule according to known methods in the art. These are described in the following patent documents: U.S. Pat. No. 4,853,230, EP 225,189, AU 9,224, 296, AU 9,230,801, WO 92144,52, and others. Such a capsule is administered orally to be targeted to the intestinum. At 1 to 4 days following oral administration, expression of the polypeptide, or inhibition of expression by, for example a ribozyme or an antisense oligonucleotide, is measured in the plasma and blood, for example by antibodies to the expressed or non-expressed proteins.

The gene delivery vehicle can be introduced into a mammal, for example, by injection, particle gun, topical administration, parental administration, inhalation, or iontophoretic delivery, as described in U.S. Pat. Nos. 4,411,648, 5,222,936, 5,286,254, WO 94/05369, etc.

The therapeutic composition or therapeutic agent can be administered with other therapeutic agents capable of combating tumors including malignant tumors such as cancers, or ameliorating allergy, inflammation, immunological abnormality, or the autoimmune disease, or capable of enhancing the therapeutic benefits of administration of a modified galectin 9 mutein therapeutic agent. For example, administration for treatment of an allergic reaction can be by aerosol administration of modified galectin 9 mutein polynucleotide for expression in the cells present in tissue such as mucosal, nasal, bronchial or lung tissue, and may be most favorably administered in repeat administrations, for example by nasal or aerosol spray several times daily for a period of time until the allergic reaction subsides.

The gene delivery vehicle may be administered at single or multiple sites to a mammal directly, for example by direct injection, or alternatively, through the use of target cells transduced ex vivo. The present invention also provides pharmaceutical compositions (including, for example, various excipients) suitable for administering the gene delivery vehicles.

A vector construct which directs the expression of a modified galectin 9 mutein polypeptide, variant, derivative, analogue, mutant, or chimera thereof can be directly administered to a tumor site containing malignant tumor such as cancer, or a site exhibiting allergy, inflammation, immunological abnormality, or autoimmunity, for example the pancreas, kidney, liver, joints, brain, the spinal fluid, skin, or other region or organ of the body. Various methods may be used within the context of the present invention in order to directly administer the vector construct. For example, arteries which serve the region may be identified, and the vector injected into such an artery, in order to deliver the vector directly into the site. Similarly, the vector construct may be directly administered to the skin surface, for example, by application of a topical pharmaceutical composition containing the vector construct.

In a direct administration, combination therapeutic agents including a modified galectin 9 mutein therapeutic agent and other anti-autoimmune agents can be administered together. The co-administration can be simultaneous, achieved for example by placing polynucleotides encoding the agents in the same vector, or by putting the agents, whether polynucleotide, polypeptide, or other drug, in the same pharmaceutical composition, or by administering the agents in different pharmaceutical compositions injected at about the same time, and perhaps in the same location. If the co-administration is not simultaneous (for example, in the case of administration of the prodrug after administration of the prodrug activator), the second agent can be administered by direct injection as appropriate for the goals of the therapy. Thus, for example, in the case of an administration of a prodrug, the prodrug is administered at the same location as the prodrug activator. The co-administration protocol can include a combination of administrations to achieve the goal of the therapy. Further, the co-administration can include subsequent administrations as is necessary, for example, repeat in vivo direct injection administrations of a modified galectin 9 mutein.

Within the context of the present invention, it should be understood that the removed cells may be returned to the same animal, or to another allogenic animal or mammal. In such a case it is generally preferable to have histocompatibility matched animals (although not always, see, e.g., Yamamoto et al., AIDS Research and Human Retroviruses, 7: 911-922 (1991); Yamamoto et al., Journal of Virology, 67: 601-605 (1993)).

Cells may be removed from a variety of locations in the patient. In addition, within other embodiments of the invention, a vector construct may be inserted into, for example, cells from the skin (dermal fibroblasts, etc.), or from the blood (e.g., peripheral blood leukocytes, etc.). If desired particular fractions of cells such as a T cell subset or stem cells may also be specifically removed from the blood (see, for example, WO 91/16116). Vector constructs may then be contacted with the removed cells utilizing any of the above-described techniques, followed by the return of the cells to the warm-blooded animal, preferably to or within the vicinity of the region exhibiting autoimmunity.

Once the patient, for example a mammal, has been diagnosed, practice of the invention includes providing a modified galectin 9 mutein therapeutic agent, and administering it to the mammal in a manner and dose appropriate for the particular disease being treated (for example tumors, allergic or autoimmune diseases, etc.), and monitoring the mammal for determining the need for continued or modified administrations of the therapeutic agent. Practice of the invention is accomplished by identifying the disease to be treated, and determining the probable cell-type or region of the body to which a targeted gene therapy can be applied. The modified galectin 9 mutein polynucleotide is constructed, including either a plasmid with regulatory regions for expression in the mammal, or a viral vector for the expression. Some of the mammalian cells can be removed, transfected with the polynucleotide encoding modified galectin 9 mutein, and replaced into the mammal for expression of modified galectin 9 mutein. Alternatively the polynucleotide can be administered to the mammal, for example in the region where the disease is manifest, for expression in the mammalian cells in that region.

Thus, for example, in the case of malignant tumor cells, the tumor cells in diseased tissue or organ can be transfected in vivo or ex vivo with modified galectin 9 mutein. Further, for example, in the case of rheumatoid arthritis, the synovial cells can be transfected ex vivo with modified galectin 9 mutein.

For example, in treatment of multiple sclerosis, modified galectin 9 mutein can be injected into the region of the brain being effected to facilitate expression of modified galectin 9 mutein in the cells that are under attack by the activated T-cells in an autoimmune type of reaction. Also, by example, in the case of multiple sclerosis, modified galectin 9 mutein DNA can be locally injected into the mammal's brain, or cells from the spinal fluid can be removed, transfected with modified galectin 9 mutein DNA, and returned to the region of the spinal cord. Further by example, for treating a mammal having Sjögren's syndrome, the organ targeted by the disease is selected for administration of modified galectin 9 mutein polypeptide by injection. Also, by example, for mammal's suffering from Sjögren's syndrome, the affected organ can be identified, for example the kidney, and modified galectin 9 mutein DNA administered to the organ directly, or cells from the organ removed, transfected, and replaced in the body for expression of modified galectin 9 mutein in those cells in the mammal.

For example, in the case of preventing transplantation rejection, the animal to receive the transplant can receive localized or systemic administration of a modified galectin 9 mutein therapeutic agent in order to kill any activated patient cells which attacks the foreign cells, tissue or organ, or a modified galectin 9 mutein polypeptide can be expressed in cells on the external surface of the organ just prior to the transplant, in order to protect the organ once inside the patient's body. Continued administration of the modified galectin 9 mutein therapeutic agent may be necessary while the recipient's immune system adjusts to the foreign cells, tissue or organ.

The modified galectin 9 mutein therapeutic agent is expected to act analogously to native galectin 9 (wild type galectin 9). Accordingly, it will be used to cause an apoptotic reaction in the cells. Thus, stoichiometrically, the clinician would be able to be aware of the amount of modified galectin 9 mutein that needs to be expressed or otherwise administered to the mammal for achieving apoptosis. Within other aspects of the present invention, the vector constructs described herein may also direct the expression of additional non-vector derived genes. For example, a prodrug system applied in conjunction with administration of modified galectin 9 mutein can act as a safety mechanism for the gene therapy, or can act as a combination therapeutic agent.

As a safety mechanism, the prodrug activator is expressed in a vector along with the modified galectin 9 mutein. When it is determined that the system should be arrested, the prodrug is administered and the prodrug activator is activated. This allows the clinician a measure of control over the gene therapy. The prodrug activator/prodrug system may be useful for inactivating the transfected cells in the mammal, where, for example, the autoimmunity is exacerbated by the modified galectin 9 mutein expression. The prodrug activator/prodrug system can also be administered as combination therapeutic agent, in a combination therapy protocol, for achieving cell killing using the prodrug activation provided by the prodrug activator/prodrug system.

The therapy including administration of a polynucleotide encoding a modified galectin 9 mutein polypeptide, in conjunction with a prodrug activator and prodrug, can also be immunomodulatory. The "immunomodulatory" refers to use of factors which, when manufactured by one or more of the cells involved in an immune response, or, which, when added exogenously to the cells, causes the immune response to be different in quality or potency from that which would have occurred in the absence of the factor. The quality or potency of a response may be measured by a variety of assays known to one of skill in the art including, for example, in vitro assays which measure cellular proliferation (e.g., $^{3}H$ thymidine uptake), and in vitro cytotoxic assays (e.g., which measure $^{51}Cr$ release) (see, Warner et al., AIDS Res. and Human Retroviruses, 7: 645-655 (1991)). Immunomodulatory factors may be active both in vivo and ex vivo. Representative examples of such factors include cytokines, such as interleukins 2, 4, 6, 12 and 15 (among others), α-interferons, β-interferons, γ-interferons, GM-CSF, G-CSF, and tumor necrosis factors (TNFs). Other immunomodulatory factors include, for example, CD3, ICAM-1, ICAM-2, LFA-1, LFA-3, MHC class I molecules, MHC class II molecules, $\beta_2$-microglobulin, chaperones, or analogs thereof. If the gene delivery vehicle, however, does not express an immunomodulatory cofactor which is a cytokine, this cytokine may be included in the above-described compositions, or may be administered separately (concurrently or subsequently) with the above-described compositions. Briefly, within such an embodiment, the immunomodulatory cofactor is preferably administered according to standard protocols and dosages known in the art. For example, α-interferon may be administered at a dosage of 100 to 5000,000 units/day for 2 to 4 months, and IL-2 at a dosage of 10,000 to 100,000 units/kg of body weight, 1 to 3 times/day, for 2 to 12 weeks. γ-Interferon may be administered at dosages of 150,000 to 1,500,000 units 2 to 3 times/week for 2 to 12 weeks for example, for upregulating the expression of a gene concerned in activated T-cells for achieving more effective therapy with the administration of modified galectin 9 mutein.

As a combination therapeutic agent, the prodrug activator can be expressed from its own vector, or from the same vector as the modified galectin 9 mutein polypeptide. Either vector system (a single vector, or two vectors) can be administered by in vivo or ex vivo means. In an autoimmune therapy, for example, the addition of the prodrug activator facilitates further immunomodulatory effect supporting the effect achieved by modified galectin 9 mutein and in addition, addition of the prodrug can activate the killing of transfected cells.

A chaperon molecule can be administered before, contemporaneously with or after administration of the polynucleotide therapeutic, and the chaperon molecule can be, for example, a heat shock protein, such as, for example hsp70. Further, the polynucleotide being expressed in the mammal can be linked to an inducible promoter, for example a tissue specific promoter, for the purpose of, for example, ensuring expression of the polynucleotide only in the desired target cells. Additionally, for the purpose of effectively delivering the polynucleotide to a tissue, the polynucleotide can be flanked by nucleotide sequences suitable for integration into genome of the cells of that tissue.

For this and many other aspects of the invention, effectiveness of treating humans may first be tested in animal models for a given autoimmune disease. Such existing animal models include those for the following autoimmune disease: for example, Sjögren's syndrome (autoimmune dacryodentis or immune-mediated sialadenitis), autoimmune myocarditis, primary biliary cirrhosis (PBC), inflammatory heart disease, mercury-induced renal autoimmunity, insulin dependent diabetes mellitus (type I diabetes or IDD), post-thymectomy autoimmunity, a central nervous system (CNS) demyelination disorder, CNS lupus, narcolepsy, myasthenia gravis (MG), Grave's disease, a immune-mediated PNS disorder, osteoarthritis, rheumatoid arthritis, uveitis, medullary cystic fibrosis, autoimmune hemolytic disease, autoimmune vasculitis, ovarian autoimmune disease, human scleroderma, and other autoimmune-related diseases.

The multiple gene delivery vehicles may be administered to animals or plants. In preferred embodiments, the animal is a warm-blooded animal, further preferably selected from the group consisting of mice, chickens, cattle, pigs, pets such as cats and dogs, horses, and humans. For polypeptide therapeutics, for example, modified galectin 9 mutein or other cytokine, the dosage can be in the range of about 5 to 50 μg/kg of mammal body weight, also about 50 μg/kg to about 5 mg/kg, about 100 to 500 μg/kg of mammal body weight, and about 200 to about 250 μg/kg.

For polynucleotide therapeutics, for example a polynucleotide encoding a native or mutant modified galectin 9 mutein polypeptide, depending on the expression of the polynucleotide in the patient, for example a mammal, for tissue targeted administration, vectors containing expressible constructs of coding sequences, or non-coding sequences can be administered in a range of: about 100 ng to about 200 mg of DNA for local administration in a gene therapy protocol, also about 500 ng to about 50 mg, also about 1 μg to about 2 mg of DNA, about 5 μg of DNA to about 500 μg of DNA, and about 20 μg to about 100 μg during a local administration in a gene therapy protocol, and for example, a dosage of about 500 μg, per injection or administration. Where greater expression is desired, over a larger area of tissue, larger amounts of DNA or the same amounts readministered in a successive protocol of administrations, or several administrations to different adjacent or close tissue portions of for example, a tumor site, may be required to effect a positive therapeutic outcome.

For administration of small molecule therapeutics, depending on the potency of the small molecule, the dosage may vary. For a very potent inhibitor, dose levels per kilogram of mammal may be sufficient, for example, in the range of about 1 μg/kg to about 500 mg/kg of mammal weight, and about 100 μg/kg to about 5 mg/kg, and about 1 μg/kg to about 50 μg/kg, and, for example, about 10 μg/kg. For administration of peptides and peptoids the potency also affects the dosage, and may be in the range of about 1 μg/kg to about 500 mg/kg of mammal weight, and about 100 μg/kg to about 5 mg/kg, and about 1 μg/kg to about 50 μg/kg, and a usual dose might be about 10 μg/kg.

Dose levels of said active components may vary within a wide range. Specific dose levels and administration cycles for any particular patient will be employed depending upon a variety of factors including the activity of specific compounds employed, the sex, age, body weight, general health, diet, time of administration, route of administration, rate of excretion, drug combination, and the severity of the particular disease undergoing therapy.

For the manufacture of pharmaceutical compositions and preparations, the additives, other materials, preparation methods and the like can be suitably selected from those disclosed in Nippon Yakkyokuho Kaisetsusho Henshu Iinkai (Ed.), "14th Edition Nippon Yakkyokuho Kaisetsusho (Commentary on The Japanese Pharmacopoeia 14th Edition (JPXIV))", Jun. 27, 2001, Hirokawa Pub. Co., Tokyo, Japan; Hisashi Ichibagade et al. (Ed.), "Iyakuhin no Kaihatsu (Pharmaceutical Research and Development, Ikuo Suzuki, chief editor), Volume 12 (Seizai Sozai I (Pharmaceutical Necessities 1))", Oct. 15, 1990, Hirokawa Pub. Co., Tokyo, Japan; ibid., Volume 12 (Seizai Sozai II (Pharmaceutical Necessities 2)), Oct. 28, 1990, Hirokawa Pub. Co., Tokyo, Japan; etc., depending on necessity, and can be adapted by referring to the disclosures therein.

The active substances or components according to the present invention include (a) modified galectin-9 variants and polypeptides having biological activity substantially equivalent to that of said modified Gal-9 variant, (b) polynucleotides encoding modified Gal-9 variants or polypeptides having biological activity substantially equivalent to that of the modified Gal-9 variant, (c) factors discovered by applications of modified galectin-9 variant techniques, and (d) vehicles for transfer of genes coding for modified Gal-9 variants or polypeptides having biological activity substantially equivalent to that of the modified Gal-9 variant, as described herein. These substances and components are useful for utilizing the following properties of human galectin-9: exerting cytotoxicity toward tumor cells, but not toward normal cells; inducing apoptosis in tumor cells, but not in normal cells; inhibiting metastasis of malignant cells; and inducing apoptosis in activated immune cells, in particular, in activated CD4-positive T cells, but not in resting T cells, in particular, in CD4-positive T cells (helper T cells). Thus, the above-mentioned substances and components are promising to serve as drugs utilizing activities similar to those of anti-neoplastic agents, anti-allergy agents, immunoregulators (immunomodulators), therapeutic agents for autoimmune diseases, anti-inflammatory agents, and adrenocortical steroid hormones.

From biological efficacy that has been affirmed by the application of the active components of the present invention, including for example modified Gal-9 proteins (inter alia G9NC(null)), galectin 9 and modified galectin 9 proteins (inter alia G9NC(null)) are thought to be biologically active and advantageously useful in preventing or treating at least one disorder, disease or pathological condition as follows:

Inflammatory diseases and disorders include a variety of acute or chronic inflammations occurring in various organs, allergic or autoimmune inflammations, infectious diseases and others.

Acute and chronic diseases and disorders include inflammations of the lung, such as bronchitis, bronchopneumonia, interstitial pneumonia, pneumonitis, bronchiolitis and acute mediastinitis; inflammations of other miscellaneous organs, including, for example, pericarditis, endocarditis, myocarditis, stomatitis, angular stomatitis, tonsillitis, pharyngitis, laryngitis, esophagitis, peritonitis, acute gastritis, chronic gastritis, acute enteritis, appendicitis, ischemic colitis, drug induced colitis, and proctitis; various acute or chronic inflammations of the liver, such as hepatitis A, hepatitis B, hepatitis C, fulminant hepatitis, and acute hepatitis; cirrhosis; cholecystitis; acute pancreatitis, chronic pancreatitis; acute or chronic nephritis, membranous glomerulonephritis, glomerulonephritis, IgA nephritis, etc.; a variety of cystitis, encephalomyelitis, mastitis, dermatitis, superficial keratitis, xerotic keratoconjunctivitis, a variety of otitis media and rhinitis, paranasal sinusitis, nasal polyp, etc.; gingivitis, periodontitis, and other inflammatory disorders of the periodontium; other various and miscellaneous inflammations.

They are recognized to be potent and efficacious in preventing or treating neurogenic inflammations, such as neurogenic gastritis and neurogenic cystitis. For instance, it has been verified in Example 8 herein that galectin 9 potently inhibits inflammatory responses in capsaicin-induced neurogenic skin inflammation models. Capsaicin is a substance that excites afferent nerves, causing neurogenic inflammation and pain. Capsaicin stimulates the release of substance P, a neuropeptide stored by sensory C fiber endings. Substance P induces release of histamine from mast cells, thereby resulting in dilating blood vessels to form edema. Sensory nerves are stimulated by released histamine. As a result, a cascade cycle will be formed wherein substance P is released from C fiber endings and acts on surrounding mast cells, thereby resulting in more histamine release.

The galectins exert inhibitory actions on said pathogenic process.

Further, capsaicin binds to a capsaicin receptor (vanilloid receptor, a pain sensor in sensory nerve endings), causing pain. Pain is caused by activating sensory nerve endings with chemical stimuli (acid, etc), thermal stimuli (hot water, etc), and excessive mechanical stimuli (by a blow, etc.) sensory nerve endings. The capsaicin receptor is involved in pain arising from such stimuli. Therefore, it is suggested that Gal-9 inhibits capsaicin receptor-mediated activation of nerve endings. Thus, they have much promise in analgesic applications including relief of pain associated with cancer and inflammation.

Allergy associated inflammatory diseases include systemic or generalized anaphylaxis, bronchial asthma, hypersensitivity pneumonitis, pollenosis, allergic rhinitis, allergic conjunctivitis, immune complex-induced allergic diseases, angioneurotic edema, etc.

Autoimmune related inflammatory diseases (autoimmune diseases) include systemic diseases (chronic rheumatoid arthritis, systemic lupus erythematosis, polyarteritis nodosa, scleroderma, polymyositis/dermatomyositis, Sjögren's syndrome, Behçet's disease and others), nervous system diseases (multiple sclerosis, myasthenia gravis, HAM (HTLV-1 myelosis), amyotrophic lateral sclerosis and others), endocrine diseases (Basedow's disease, Hashimoto's thyroiditis, type 1 diabetes and others), blood diseases (idiopathic thrombocytopenic purpura, autoimmune hemolytic anemia, aplastic anemia and others), respiratory diseases (sarcoidosis, idiopathic pulmonary fibrosis and others), gastrointestinal diseases (ulcerative colitis, Crohn's disease and others), hepatic diseases (autoimmune hepatitis, primary biliary cirrhosis, primary sclerosing cholangitis, autoimmune cholangitis and others), and renal/urinary tract system diseases (antineutrophil cytoplasmic antibody associated nephritis, angitis, Goodpasture's syndrome, anti-glomerular basement membrane antibody disease and others), etc.

Infection is a general term for the result of invasion of the body cells, tissues and organs by pathogens. Infectious diseases are disclosed in Supervisor: Rikuo MACHINAMI, Editor: Junichi HATA & Atsuhiko SAKAMOTO, "Hyoujun Byourigaku, $2^{nd}$ Edition", Igaku-Shoin Ltd., Japan (Mar. 15, 2002; ISBN4-260-10359-8). The pathogen that causes infection in human is selected from the group consisting of 1) bacteria (including spirochaeta, chlamydia, and *Rickettsia*), 2) viruses, 3) fungi, 4) plants (algae), 5) protozoa, 6) parasites (Digenea (distomes or trematodes)), cestodes (tapeworms), nematodes), and 7) arthropods. Principle diseases resulting from the presence or activity of the pathogen include bacterioses (cholera, pest, *Escherichia coli* infection, etc.), spirochetoses (leptospirosis, etc.), chlamydioses (psittacosis, etc.), rickettsial infections (*Rickettsia prowazekii*, tetanus, etc.), viral infections (herpes zoster, viral hemorrhagic fever, rabies, etc.), mycoses (candidiasis, cryptococcosis, aspergillosis, etc.), protozoal diseases (amebic dysentery, malaria, toxoplasmosis, etc.), parasitoses (distomiasis, nematodiasis, etc.), mycoplasma infections (mycoplasma pneumonia, etc.), mycobacterioses (tuberculosis, atypical mycobacteriosis, etc.) and other infectious ones.

Sarcomas and cancers include brain tumors (glioblastoma multiforme, etc.), spinal tumors, maxillary sinus carcinoma, pancreatic ductal adenocarcinoma, gingival cancers, tongue cancers, lip cancers, nasopharyngeal cancers, oropharyngeal cancers, hypopharyngeal cancers, laryngeal cancers, thyroid cancers, parathyroid cancers, lung cancers, pleural tumors, carcinomatous peritonitis, carcinomatous pleurisy, esophageal cancers, stomach cancers, colon cancers, bile duct cancers, gall bladder cancers, pancreatic cancers, liver cancers, renal cancers, urinary bladder cancers, prostatic cancers, penile cancers, testicular tumors, adrenal cancers, cervical cancers, endometrial cancers, vaginal cancers, vulvar cancers, ovarian cancers, chorioepithelioma, malignant bone tumors, soft part sarcoma, breast cancers, skin cancers, malignant melanoma, basal cell tumors, leukemia, myelofibrosis associated with agnogenic myeloid metaplasia, malignant lymphoma, Hodgkin's disease, plasmacytoma, glioma and others.

The active components of the present invention are useful in dermatological applications. For example, 1) skin diseases and abnormal skin conditions include skin infections, skin inflammations including allergic inflammations and autoimmune inflammations; and skin diseases with inflammatory characteristics, such as psoriasis, hydroa, pustulosis, keratinization, and keratonosis, etc. Further, cosmetic and skin care applications include:

a) Control of Melanin Metabolism (Skin Whitening)
  Galectin 9 gene-transferred melanoma cells turned white from black tones. Galectin 9-positive cells are present in the skin's basal cell layer.
  b) Control of Hair Growth (Trichogen)
  Galectin 9 is expressed at the hair root site in a time-dependent manner. Hairs are grown extremely well in a galectin 9 gene-transferred mouse as compared to a mutant galectin 9 gene-transferred mouse.
  c) Control of Collagen Production, Etc.
  Fibroblasts express galectin 9 in response to a variety of stimuli. Galectin 9-positive portions are present in fibrous connective tissues.

Life-style related diseases include hypercholesterolemia, arteriosclerosis, hypertension, diabetes, etc. It has been clarified that gal9-positive and gal9-negative cells are present in foam cells, involved in formation of life-style related disease arteriosclerosis. From that, it is suggested that gal9 participates in the pathologic condition of arteriosclerosis. Thus, it cannot be denied to allow the prevention and therapy of the disease via its control.

For hypertension, where the onset of hypertension occurs in experimental animal models, the expression of galectin 9 will be enhanced in the uriniferous tubules and glomerulus. Therefore, the regulation of galectin 9 expression and administration of galectin 9 may allow therapeutic merits.

The active components of the present invention are also applicable to the maintenance of a normal bacterial flora. For example, gal9 is intensely expressed in intestinal epithelium even under normal conditions. When the bad bacterial flora is administered, the expression of galectin 9 is enhanced in the intestinal epithelium and inflammatory cells such as macrophage. From that, it is clearly suggested that galectin 9 will participate in the maintenance of the normal bacterial flora at digestive ducts.

The active components of the present invention can be applied to amyloidosis. For example, there are galectin 9-expressing macrophages among those at a site where amyloidosis is perceivable. Therefore, it may be possible to control the deposition of amyloids with galectin 9.

The active components of the present invention are useful in preventing or treating Alzheimer's disease, osteoporosis, bone fracture, etc. For example, in the brain of a patient with Alzheimer's disease, degenerative nerve cells give galectin 9-positive appearance. Therefore, it may be possible to use it for therapy and diagnosis. For osteoporosis, it can be viewed that galectin 9 may prevent bone absorption and facilitate bone formation. It is thought that such actions are suitable for ideal drugs in consideration of bone metabolism.

The active components of the present invention are useful in brain and nervous areas. For instance, the development of ischemic lesions, such as cerebral infarction and myocardial infarction, accompanies infiltration of inflammatory cells, leads to occurrence of superoxide production, etc. and comes to a deterioration. It can be expected that galectin 9 and modified galectin 9 mutein may regulate said inflammation.

The demyelinating disease that is caused by inflammation and alteration of the immune system includes, for example, multiple sclerosis, etc. The degenerative disease also includes amyotrophic lateral sclerosis, Parkinson's disease, etc. It is said that schizophrenia may be caused by inflammatory alteration. That is, EPA (eicosapentaenoic acid) is used to control inflammatory reaction in brain and form nerve cell membranes. There are study examples revealing that EPA and other essential fatty acids in cell membranes are exhausted in Schizophrenia patients. It can be anticipated that galectin 9 and modified galectin 9 mutein may be effective in gout. It can be expected that galectin 9 and modified galectin 9 mutein may be effective in controlling acute inflammation with a severe pain, due to tissue deposition of uric acid crystals.

Asthma is a disease of the respiratory system in which reversible airway obstruction (asthmatic attack) occurs. The disorder is a condition in which the airways develop increased responsiveness to antigen-specific or non-specific stimuli (allergen, infection, cold air, etc.). In recent years, it is demonstrated that there are inflammations in which eosinophils, T lymphocytes, and mast cells predominate even during a stable stage free of an attack in asthma airways. It is now thought that the main part of asthma is chronic bronchitis. Most of pediatric asthma diseases are closely related to a cause of atopy (IgE production), e.g., atopic asthma, and cases where the involvement of IgE in adult asthma is non-provable are recognized to be about half (non-atopic asthma). Guidelines on the prophylaxis and management of asthma (1998 Ministry of Health and Welfare (MHW), Research Committee, Japan) have been prepared, wherein asthma treatments are classified into two techniques, one for acute attacks and the other for chronic airway inflammatory disease. The therapeutics for asthma attacks include bronchodilators ($\beta_2$-agonists, aminophylline, etc.), which are first-line drugs. However, these drugs are insufficient to medicate moderate or severe attacks, for which high-dose steroid drugs are applied by systemic administration. The steroid drugs have powerful side effects, including especially serious peptic ulcer, hypertension, hyperglycemia, psychogenic symptoms and others. When the steroids are applied for a long time, infectious diseases, depressed functioning of the adrenal gland, osteoporosis and other symptoms will become problems. In addition, when the disorder is associated with complications, the use of steroids is accompanying risk. It is demanded to develop drugs with efficacy equivalent to the steroid and less adverse reaction. The core of long-term medications for chronic inflammatory airway disease is an anti-inflammatory drug. The use of inhaled steroid drugs inter alia is recommended. When the steroid drugs are applied for a long term at high-dose levels, there is no denying that it is potential to produce harmful side effects such as depressed functioning of the adrenal gland, osteoporosis, and airway infection. Further, inhaled drugs require exact inhaling techniques and are poor in view of compliance as compared to oral drugs. In addition to medications with inhaled steroid drugs, moderate or severe asthma is recommended to be treated with a combination of inhaled $\beta_2$-agonists, leukotriene modifiers (leukotriene antagonists) or sustained release theophylline drugs. Systemic steroid administration is unavoidable in severe asthma patients. It is demanded to develop alternative drugs for such drugs. It is known that the infiltration of T lymphocytes and eosinophils into lung tissue and airways plays an important role in the formation of asthma disease. Galectin 9 functions in inducing apoptosis of cells, and induces apoptosis of activated T cells and eosinophils. In view of studies wherein modified galectin 9 muteins and other materials are employed in the present invention based on these, it has been clarified that galectin 9 and modified galectin 9 mutein are active in ameliorating (inhibiting) inflammatory airway symptoms associated with asthma.

Further, galectin 9 and modified galectin 9 mutein have activity of enhancing the growth and differentiation of osteoblasts and inhibiting the differentiation of osteoclasts, and are thought to be useful in prophylactic and/or therapeutic treatment of osteoporosis, and bone growth inhibition, one of side effects which become problems when steroids are administered for a long time. Galectin 9 and modified galectin 9 mutein act in activated lymphocyte-specific inhibition, differently from steroids, with regard to actions on lymphocytes, and can be expected to be less adverse, for example, less immunodepressant, as compared to steroids. In addition, they have inhibitory actions on functions of adhesive molecules and neurogenic inflammation while steroids do not, and are promising therapeutic drugs for asthma, e.g., therapeutic drugs for asthma attacks. In our opinion, it may be possible to relieve steroidal side reaction.

EXAMPLES

Details of the present invention are described by the following examples but such examples are provided only for illustrative purposes, and for referential embodiments of the present invention. These examples have been described herein for the purpose of illustrating specific embodiments of the present invention but should not be construed as in any sense limiting the scope of the invention disclosed herein. It should be understood in the present invention that various embodiments can be made or executed within the spirit, scope and concept disclosed herein. All the examples were carried out or can be carried out, unless otherwise disclosed herein specifically, by standard techniques which are well known and conventional to those skilled in the art.

Specific molecular biological operations, treatment conditions, etc. in examples as described herein below are conducted or selected according to customary techniques disclosed in standard experimental manuals: for DNA cloning, J. Sambrook, E. F. Fritsch & T. Maniatis, "Molecular Cloning", 2nd ed., Cold Spring Harbor Laboratory, Cold Spring Harbor, N.Y. (1989), and D. M. Glover et al. ed., "DNA Cloning", 2nd ed., Vol. 1 to 4, (The Practical Approach Series), IRL Press, Oxford University Press (1995); when PCR techniques are applied, H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995), and M. A. Innis et al. ed., "PCR Protocols", Academic Press, New York (1990) and others. When commercially available reagents and kits are used, protocols, agents, drugs, and the like attached thereto are employed herein.

Example 1

(A) Construction of Expression Vector for Modified Galectin 9 Mutein

The expression vectors were constructed with the following:

(1) cDNA, prepared from a Jurkat cell poly(A)$^+$RNA fraction
(2) pET-11a vector (STRATAGENE)
(3) primers for PCR:

```
G9NCRD1:
                                       SEQ ID NO: 10
CGTCCTCATATGGCCTTCAGCGGTTCCCAG

G9NCRD6:
                                       SEQ ID NO: 11
CGACCGCATATGCTGGAAGCTGATGTAGGACAG

G9CCRD5:
                                       SEQ ID NO: 12
CGTCCTCATATGACTCCCGCCATCCCACCTATG

G9CCRD6:
                                       SEQ ID NO: 13
CGACCGGGATCCCTATGTCTGCACATGGGTCAG
```

Jurkat cells (T cell-derived cell line) were obtained from American Type Culture Collection (ATCC). The cell line was maintained in FCS (10%)-added RPMI-1640 (Sigma, St. Louis, USA) at 37° C. under 5% $CO_2$/air.

Total RNA extraction from Jurkat cells was conducted as follows: Briefly, Jurkat cells were cultured in RPMI-1640 containing 10% FBS, and then collected with a centrifuge. The resultant cells were washed twice with 10 ml of PBS. To the washed cell pellets was added ISOGEN (Trade Name: NIPPON GENE Co., Ltd., Japan) at 15 ml per $2 \times 10^8$ cells, and total RNA was extracted according to the kit manual (NIPPON GENE Co., Ltd., Japan). Poly(A) $^+$RNA purification from total RNA and cDNA synthesis were conducted as follows: Briefly, Jurkat cell derived total RNA was dissolved in DEPC-treated water to make the concentration 1 mg/ml. The purification of poly(A) $^+$RNA from total RNA was carried out with PolyATtract® mRNA Isolation System (Trade Name: Promega) according to the kit manual. The purified poly(A) $^+$RNA was dissolved in DEPC-treated water to make the concentration 5 µg/20 µl.

The synthesis of cDNA from poly(A) $^+$RNA (5 µg) was performed with First-Strand cDNA Synthesis Kit (Trade Name: Amersham Biosciences) according to the kit manual, wherein Not I-d(T)$_{18}$ was used as a primer.

Next, into the NdeI-BamHI site of vector pET-11a was inserted the N-terminal carbohydrate recognition domain (NCRD) and C-terminal carbohydrate recognition domain (CCRD) of galectin 9 according to steps as shown in FIG. 1 to generate an expression vector for modified galectin 9 (G9NC (null)) wherein the linker peptide lacked. First, (1) cDNA corresponding to the C-terminal CRD of human galectin 9 and (2) cDNA corresponding to the N-terminal CRD of human galectin 9, respectively, were obtained from galectin 9 cDNA. Briefly, cDNA corresponding to the C-terminal CRD of human galectin 9 (G9CCRD) was amplified from galectin 9 cDNA with PCR primers: G9CCRD5+G9CCRD6. G9CCRD was digested with restriction enzymes (NdeI+BamHI), and inserted into vector pET-11a treated with the same restriction enzymes to create pET-G9CCRD. The PCR was performed with KOD DNA polymerase kit (TOYOBO Code No. KOD-101). A PCR Reaction mixture (dNTP mix, 25 mM $MgCl_2$, 10× Buffer, KOD DNA polymerase (0.05 u), primers and template cDNA) was reacted under the following PCR cycle conditions: After treatment at 94° C. for 2 min, a cycle consisting of 98° C. for 15 sec, then 65° C. for 2 sec, and next 74° C. for 30 treatments was repeated 25 times, and finally the reaction was terminated at 4° C. The insertion of the PCR-amplified fragment into the vector was carried out with Ligation high kit (TOYOBO Code No. LGK-101). For reaction, the PCR-amplified fragment was mixed with the vector at a molar ratio of insert:vector=about 5:1, and then admixed with the reagent "Ligation high" at a ratio of reagent/total total DNA solution=1/2 (volume/volume). The insertion was done by O/N reaction at 16° C. for 16 hr.

Secondly, cDNA corresponding to the N-terminal CRD of human galectin 9 (G9NCRD) was amplified from galectin 9 cDNA with PCR primers: G9NCRD1+G9NCRD6. G9NCRD was digested with restriction enzyme NdeI, and the resultant fragment was inserted into a site derived from pET-G9CCRD by digestion with the same restriction enzyme (NdeI) followed by dephosphorylation to create pET-G9NC (null). The PCR amplification and incorporation into the vector were carried out in the same manner as aforementioned. In pET-G9NC(null) is encoded a polypeptide having a mutant amino acid sequence that differs from the amino acid sequence of human M-type galectin 9 (hGal-9M) by the amino acid replacement of a region ranging from $Pro^{149}$ to $Ser^{177}$ (29 amino acids) with the sequence: His-Met. That is, the construct has a nucleotide sequence of SEQ ID NO: 1, which codes for a polypeptide with the amino acid sequence of SEQ ID NO: 2.

(B) Expression and Purification of Recombinant Modified Galectin 9 Mutein (Recombinant Protein)

The expression plasmid vector pET-G9NC(null) obtained in the aforementioned step (A) was introduced into *E. coli* (BL21(DE3)). The introduction was done by electroporation (or electropermeabilization). Briefly, a mixture of competent BL21(DE3) and an aqueous plasmid vector solution was subjected to electroporation at a voltage of 1.8 kV for transfection. The expression of recombinant proteins were conducted as follows: *E. coli* was cultured in 2×YT medium containing 2% (w/v) glucose and 100 µg/ml ampicillin, and admixed with 0.1 M isopropyl-β-D-thiogalactopyranoside for induction of recombinant proteins at a point where an optical density at 600 nm reached 0.7 (final concentration, 0.1 mM). After cultivation at 20° C. for 18 hr, the cells were collected with a centrifuge, and then suspended in 10 mM Tris-HCl (pH 7.5), containing 0.5 M NaCl, 1 mM DTT, and 1 mM PMSF. The resultant suspension was sonicated for 10 min, then admixed with 10% (w/v) Triton X-100 (final concentration, 1%), and stirred at 4° C. for 30 min. The mixture was centrifuged at 15,000×g for 30 min, and the resulting supernatant was subjected to affinity chromatography on lactose agarose gels to isolate purified recombinant proteins.

Figure 3:
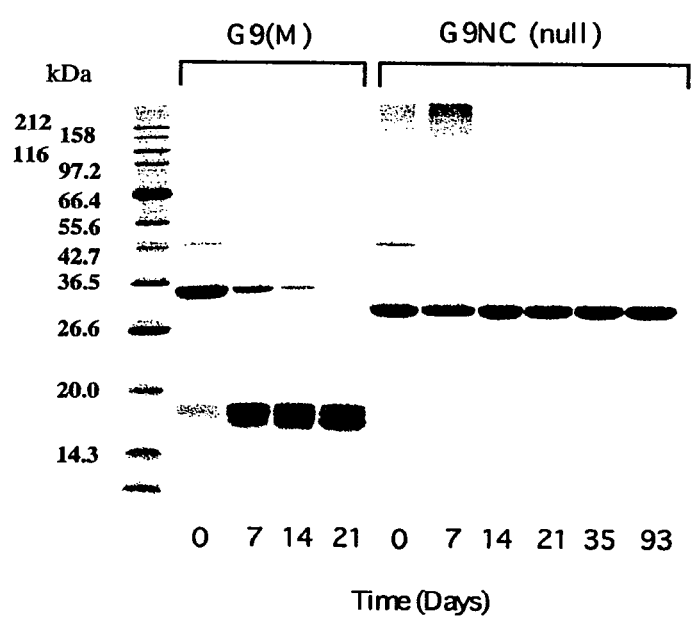
FIG. 3 is a photo showing electrophoretic patterns resulting from comparison for resistance against proteases between wild type galectin 9 (G9(M)) and modified galectin 9 mutein (G9NC(null)). Purified samples were tested for resistance against contaminated E. coli proteases.

As a result, recombinant protein samples with high purity were obtained in comparatively good yields. The resultant electrophoretic patterns of recombinant protein products are shown in FIG. 2. SDS-PAGE conditions were as follows: Gel, Acrylamide-BIS (12% gel), buffer for electrophoresis, 25 mM Tris-192 mM glycine-0.1% SDS, electrical conditions, 180V, 45 min.; staining, CBB, 60° C./30 min. Samples for electrophoresis were adsorbed on Strata Clean™ Resin (Stratagene), treated with 1× sample buffer (62.5 mM Tris-HCl, Ph6.8, 2% (w/v) SDS, 5% (W/V) 2-ME, Glycerol) to make the mixture 0.2 mg/ml, thermally treated at 98° C./3 min, and then subjected to electrophoresis at about 2 µg (protein) per lane. The purified modified galectin 9 mutein, G9NC(null), were stably preservable at 4° C. for at least 90 days while most of wild type galectin 9 (M-type, G9(M)) was decomposed within 2 weeks under the same storage conditions (see FIG. 3). This decomposition is thought to be caused by an action of *E. coli*-derived proteases contained in the purified galectin sample.

Example 2

Figure 4:
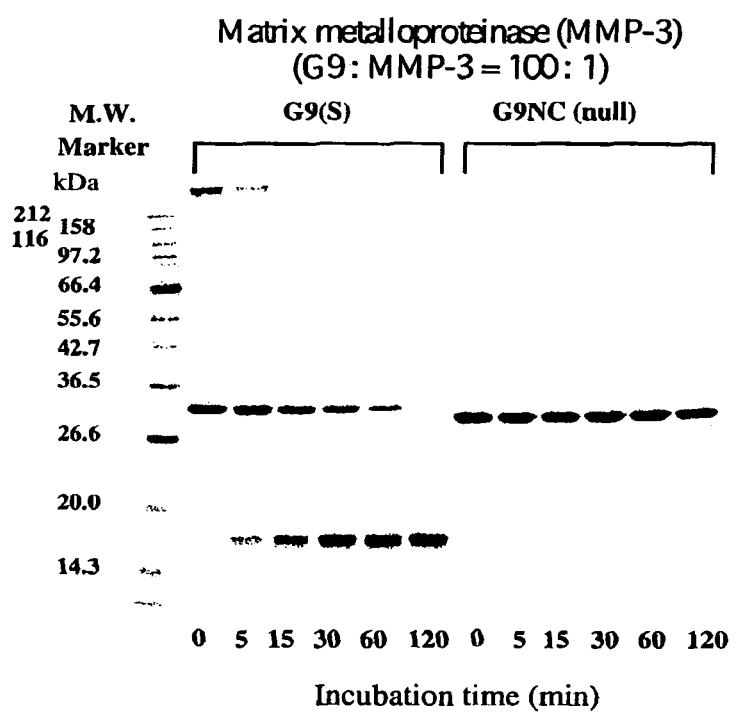
FIG. 4 is a photo showing electrophoretic patterns resulting from comparison for resistance against proteases between wild type galectin 9 (G9(S)) and modified galectin 9 mutein (G9NC(null)). Purified samples were tested for resistance against matrix metalloproteinase-3 (MMP-3).
Figure 5:
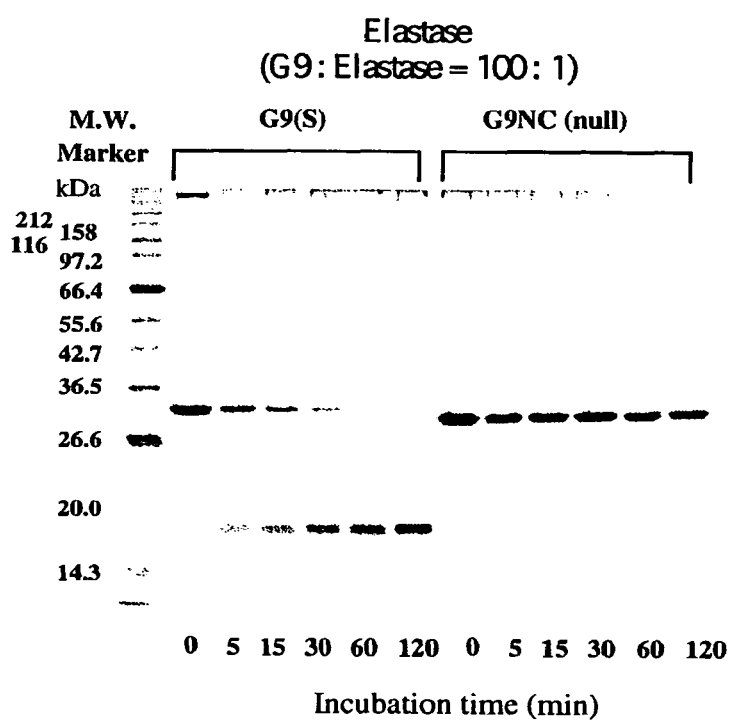
FIG. 5 is a photo showing electrophoretic patterns resulting from comparison for resistance against proteases between wild type galectin 9 (G9(S)) and modified galectin 9 mutein (G9NC(null)). Purified samples were tested for resistance against elastase.

The susceptibility to proteases existing in human tissue was examined between wild type galectin 9 (S-type, G9(S):

isoform with the shortest linker peptide) and G9NC(null) for comparison. To the galectins dissolved in PBS was added matrix metalloproteinase-3 (MMP-3) or elastase at 1/100 (weight ratio), and the mixture was incubated at 37° C. Most of G9(S) was decomposed within 1 to 2 hr in either case while G9NC(null) was not degraded at all even after the passage of 2 hr (see FIGS. 4 and 5).

Example 3

In order to examine how incorporation of the mutation into wild type galectin 9 affects galectin 9 bioactivity, assays were done for activity of inducing apoptosis of MOLT-4 cells (human T cell leukemia derived cell line) and eosinophil chemoattractant activity (ECA activity) for peripheral blood eosinophils.

(a) Cell Culture

MOLT-4 (T cell) was obtained from American Type Culture Collection (ATCC). The cell line was maintained in an RPMI-1640 medium (Sigma, St. Louis, US) supplemented with 10% FCS in 5% $CO_2$ at 37° C. Lactose (30 mM) was added to the culture medium to inhibit Gal-9 activity. The same concentration of sucrose was used as a control.

(b) Apoptosis Assay (1) Cell Cycle (Apoptosis) Analysis with PI (PI Method)

Cells that underwent apoptosis induction were centrifuged at 4° C. for 5 min at 1,000 rpm, and the cell pellet was resuspended in PBS (300 µL), and adjusted to a final concentration of 70% by gradually adding 100% cold ethanol (700 µL) to the suspended cells with vortexing. The cells were fixed by incubation at 4° C. for 30 min. After addition of PBS (1 mL), the cells were centrifuged at 4° C. for 5 min at 1,000 rpm and the cell pellet was resuspended in PBS (440 µL). The cells were incubated with 2.5 mg/ml ribonuclease A (10 µL; the final concentration 50 µg/mL, Sigma, St. Louis, Mo., US) at 37° C. for 30 min, and then with 2.5 mg/mL propidium iodide (PI, 4 µL; the final concentration, 20 µg/mL; Sigma) at 4° C. for 10 min in the dark. After removal of aggregated cells through a nylon mesh followed by increasing the cell volume with PBS, stained cells were analyzed by flow cytometry (Sandstrom, K. et al., J Immunol Methods, 240: 55 (2000) and Zhang L. et al., Cancer Lett, 142: 129 (1999)).

(2) TUNEL (TdT-Mediated Label dUTP Nick End Labeling) Assay

DNA fragmentation within the cell nucleus, a distinctive feature of apoptosis, was detected by incorporating labeled nucleotides (dUTP-biotin or FITC-dUTP, etc.) into the ends generated by DNA fragmentation with an enzyme that adds nucleotides at DNA ends (TdT; Terminal deoxynucleotidyl transferase). MEBSTAIN Apoptosis Kit Direct (MBL, Nagoya, Japan) was used in the experiment. Experiments were carried out according to the manufacturer's instruction as described below. Briefly, cells that underwent apoptosis induction (approx. $2\times10^5$ cells/sample) were washed with PBS containing 0.2% FSA. After adding 4% paraformaldehyde (in 0.1 M $NaH_2PO_4$, pH 7.4), the cells were fixed at 4° C. for 30 min, and washed with PBS containing 0.2% FSA. After adding 70% cold ethanol to increase the permeability, the cell pellet was incubated at −20° C. for 30 min. After washing with PBS containing 0.2% FSA, TdT reaction mixture (TdT, FITC-dUTP and TdT buffer mix) was added to the washed cell pellet, the mixture was stirred, and incubated at 37° C. for 1 hr. Stained cells were washed with PBS containing 0.2% FSA, then resuspended in PBS containing 0.2% FSA and analyzed by flow cytometry.

(c) T Cell Analysis

To prepare a well plate coated with anti-CD3 Ab, a 24 well palate was incubated with TBS solution (pH8.0) containing 3 µg/mL anti-CD3 Ab (Immunotech, Marseille, France) per well at 4° C. overnight, and each well was washed with PBS after removing anti-CD3 Ab solution.

Mononuclear leukocyte fractions were isolated from heparinized blood using HISTOPAQUE (Registered trademark, SIGMA). Next, CD4-Positive Isolation Kit (DYNAL, Oslo, Norway) was used for isolation of $CD4^+$ T cells and Dynabeads M-450 CD8 (Registered trademark, DYNAL, Oslo, Norway) for isolation of $CD8^+$ T cells, respectively, according to the manufacturer's instructions. To activate T cells, $CD4^+$ or $CD8^+$ T cells at $1\times10^6$ cells/mL in an RPMI-1640 medium containing 10% FCS were incubated on the plate coated with anti-CD3 Ab for 20 to 24 hr at 37° C. in a 5% $CO_2$ incubator, and then incubated with recombinant galectin 9 (wild type G9(S)) or modified galectin 9 mutein, G9NC (null)), at 37° C. in a 5% $CO_2$ incubator. Next, apoptosis assay was conducted as described in (b). That is, cells were incubated with 50 µg/mL PI (SIGMA) at 37° C. for 10 min in the dark. Stained cells were analyzed by flow cytometry (Sandstrom, K. et al., J Immunol Methods, 240: 55 (2000) and Zhang L. et al., Cancer Lett, 142: 129 (1999)).

After incubation with recombinant galectin 9 (wild type G9(S)) or modified galectin 9 mutein, G9NC(null)), at 37° C. in a 5% $CO_2$ incubator, apoptosis assay was also conducted for non-activated (resting) T cells in the same manner as described above.

(d) Results

Figure 6:
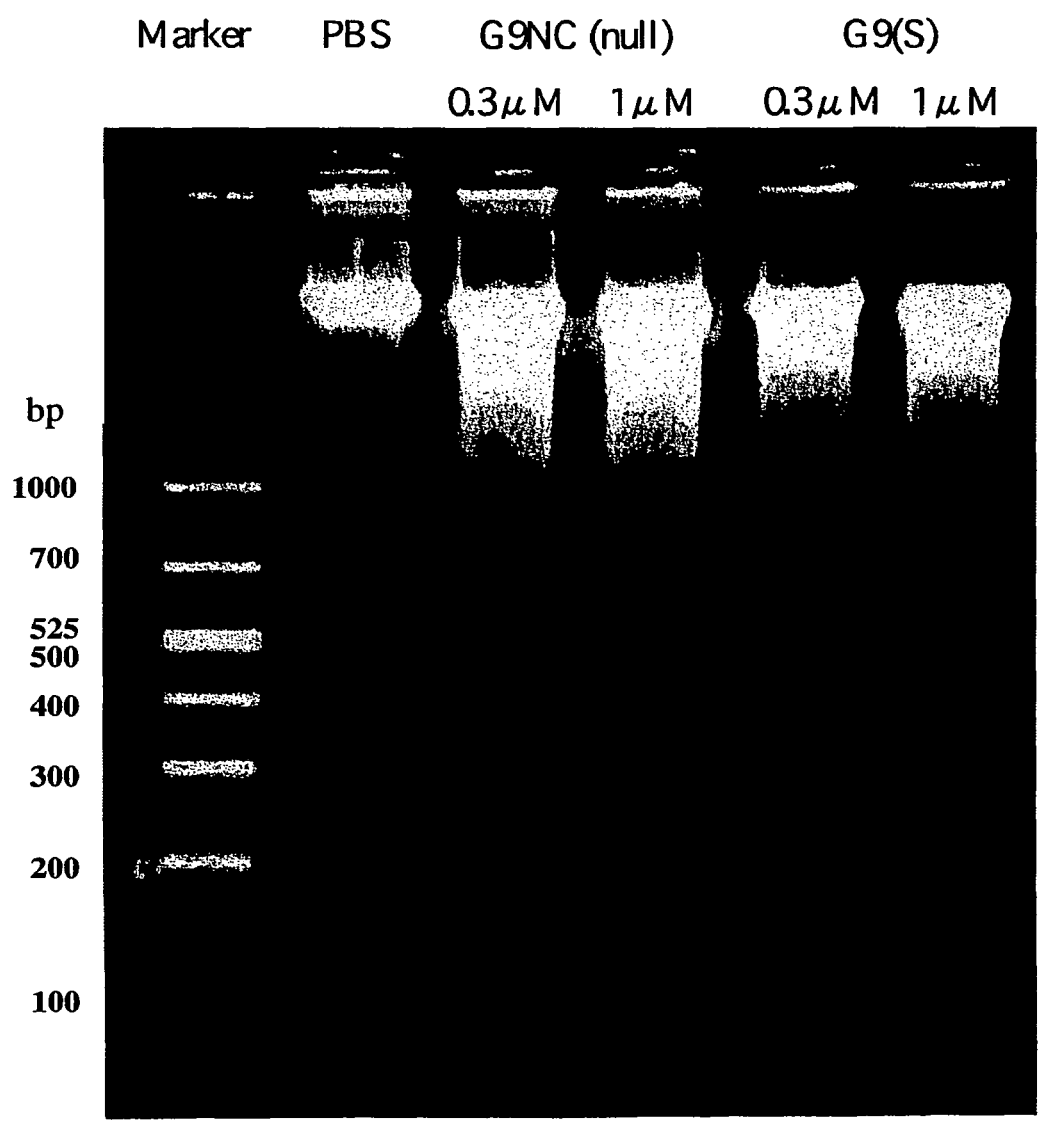
FIG. 6 is a photo showing electrophoretic patterns resulting from comparison for bioactivity between wild type galectin 9 (G9(S)) and modified galectin 9 mutein (G9NC(null)). The activity of inducing apoptosis of MOLT-4 cells (DNA laddering) was assayed.
Figure 7:
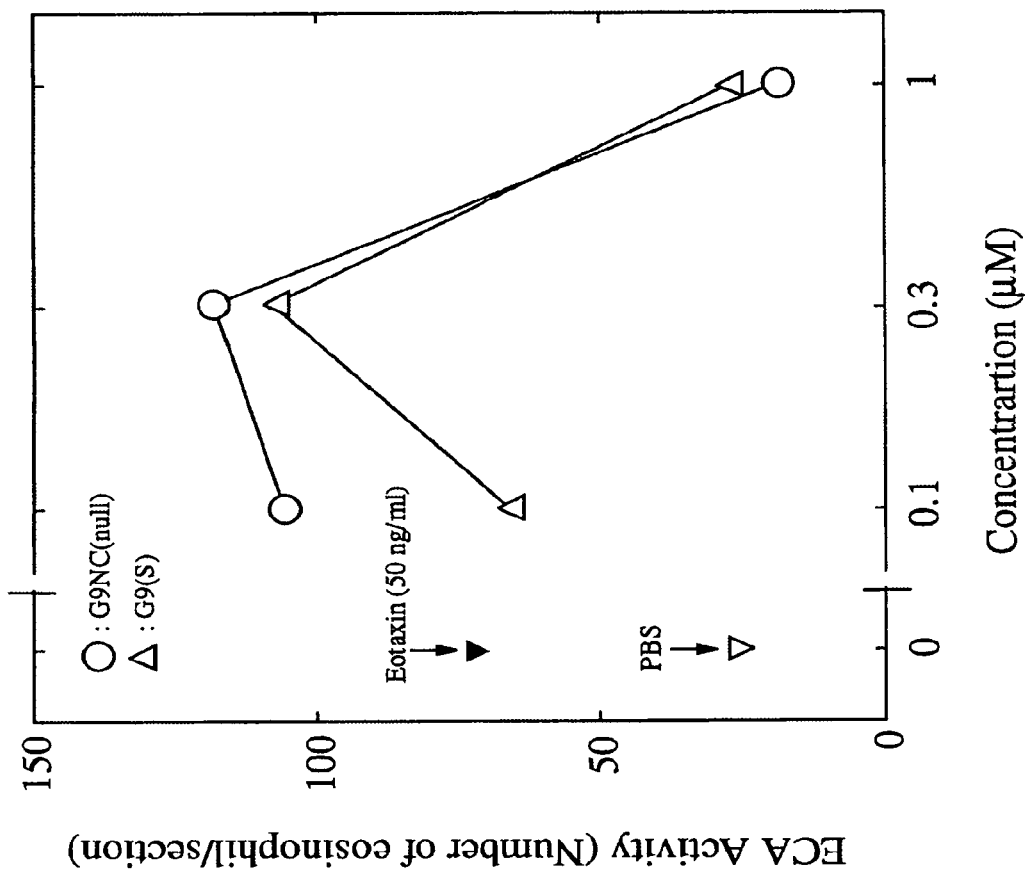
FIG. 7 is a graph showing comparison results for bioactivity between wild type galectin 9 (G9(S)) and modified galectin 9 mutein (G9NC(null)). ECA activity on peripheral blood eosinophils was assayed.

As a result of examining DNA fragmentation associated with apoptosis by agarose gel electrophoresis and FACS, it has been revealed that the apoptosis inducing activity retained by G9NC(null) is equivalent to or higher than that by G9(S) even when either assay method is applied (FIG. 6 & Table 1). As a result of assaying for ECA activity according to the chamber technique, G9NC(null) exhibited higher activity than G9(S) (FIG. 7).

TABLE 1

| | Apoptotic MOLT-4 Cell Rate (%) | | | | |
| --- | --- | --- | --- | --- | --- |
| | control | 0.1 µM | 0.3 µM | 0.5 µM | 1 µM |
| G9(M) | 4.2 | 5.5 | 13.8 | 28.9 | 58.8 |
| G9(S) | 4.5 | 8.7 | 23.6 | 44.7 | 64.0 |
| G9NC (null) | 5.1 | 11.5 | 33.9 | 57.8 | 72.1 |

Table 1 shows comparison results between wild type galectin 9 (G9(S)) and modified galectin 9 mutein (G9NC(null)) for their bioactivities, wherein each activity of inducing apoptosis of MOLT-4 cells was examined (FACS analysis).

Example 4

1. Expression of Galectin-9 in Rheumatoid Arthritis (RA) Synovium

[Method]

Patient tissue materials used were synovium tissue samples from RA patients complied with American College of Rheumatology (ACR), classification criteria. Immunohistological staining of patient tissue samples was performed according to the following steps: Preparation of section samples was done as follows:

(1) De-paraffinization: xylene 3 times (10 min each), 100% alcohol-90% alcohol-75% alcohol (2 min each).

(2) Microwave (MW) treatment: 10 mM citric acid buffer (pH6.0) was prepared upon use. Each section sample was dipped in the buffer pre-boiled by MW irradiation, and then subjected to MW irradiation (5 min×3 times, total 15 min for 500 W electric microwave oven). The treated sections were allowed to stand at room temperature for 20 min while gradually cooling.

(3) Inactivation of endogenic peroxidase: 0.3% peroxide-methanol was prepared upon use and the section sample was dipped thereinto for 30 min. Washing with PBS 5 min×3 times. An aliquot (4 drops) of 5% BSA was dropped onto the section for blocking. Next, the section was placed in a wet box at room temperature for 1 hr.

Onto the section sample were applied 6 drops of a primary antibody or a control antibody with a Pasteur pipette. The sample was allowed to stand in a wet box at 4° C. overnight, and washed with PBS (5 min×3 times) on the next day. An aliquot (6 drops) of second antibody, horseradish peroxidase (HRP)-labeled Ab (DACO Envision$^+$), was applied onto the tissue sample. After placing the tissue sample in a wet box at room temperature for 1 hr, the tissue sample was washed with PBS (5 min×3 times). Visualization with a DAB (3,3'-diaminobenzidine-tetrahydrochloride) reagent (the DAB reagent was prepared upon use). The coloring process was carried out for 3 min after dipping the section sample. Immediately, the coloring reaction was stopped by washing with tap water. Nuclear staining was performed with Mayer's hematoxylin (20 sec). Immediately, the sample was washed with running water for 15 min. Dehydration, penetration, and sealing; 75% alcohol-90% alcohol-100% alcohol (2 min each), xylene 3 times (3 min each).

[Results]

The results are shown in FIG. 53. Galectin-9 was observed to be expressed selectively in synovial cells and lymph parafollicular cell groups, as well as in endothelial cells of dendriform blood vessels inside the lymphatic follicle. Galectin 9-positive cells were scarcely observed in OA (osteoarthritis) (see FIG. 53). Galectin 9 is a molecule that is inducible at high levels in synovial cells and lymphatic cells which are essential for growth of RA synovium, and further in new blood vessels, while galectin-1 is detectable in synovial cells and pericytes and galectin-3 in the whole constituent cells of RA synovium.

2. Galectin-9 Mediated Activity of Inducing Apoptosis of Synovial Cells

[Method]

The efficacy of galectin 9 was tested on synovial cells which will cause the destruction of joints. For synovium, the synovium tissue of a rheumatoid arthritis (RA) patient was harvested aseptically, and subjected to separation to isolate cells which were cultured. After 1 to 2 cell culture passages, the resultant cells were used in experiments. The tested tissue was obtained from the right knee RA of 67-old woman. The synovial cells were seeded, and then cultured overnight. After cell adhesion was affirmed, rhGal-9 (each of hG9NC(null), rhGal-9S, and rhGal-9M) was added to make the final concentration 0, 0.03, 0.1, 0.3, and 1.0 µM, respectively. After cultivation for 72 hr, cells were observed with an optical microscope. Next, the cells were collected, and assayed for apoptosis-inducing activity with PI technique. Apoptosis-inducing activity assay was done in the same fashion as in Example 3.

[Results]

Figure 55:
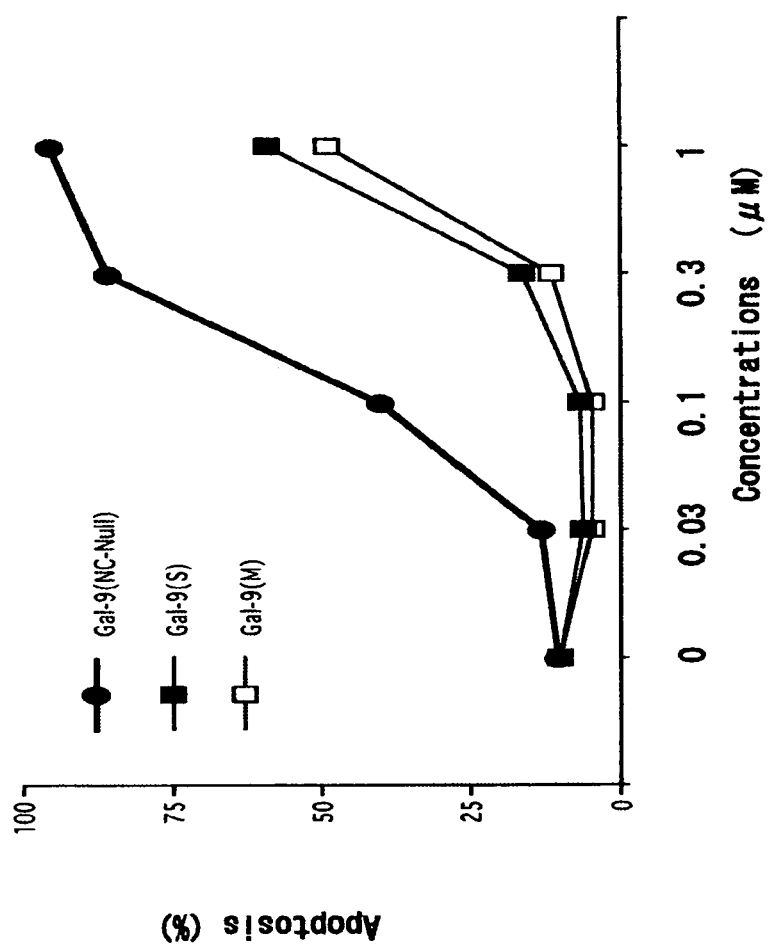
FIG. 55 is a graph showing PI assay results for galectin-9 mediated activity of inducing apoptosis of RA synovial cells.

The results from observation with an optical microscope are shown in FIG. 54. The PI assay results for apoptosis-inducing activity are shown in FIG. 55.

The apoptosis-inducing activity of modified galectin-9 mutein (Gal-9(NC-Null)) was more intense than those of native (wild type) galectin-9 (Gal-9(M), and Gal-9(S)). It was observed that all recombinants had the apoptosis-inducing activity in a dose-dependent manner. Lactose (30 mM) inhibited the apoptosis-inducing actions but sucrose (30 mM) did not affect.

3. Comparison between Galectin-Mediated Apoptosis-Inducing Activity in and Growth-Inhibitory Activity Against Synovial Cells

[Method]

The actions of human galectins (Gal-1, Gal-3, Gal-8(M), and Gal-9NC(null)) on synovial cells were examined.

The synovium tissue of a RA patient was collected aseptically, and subjected to separation to isolate synovial cells which were then cultured. After 1 to 2 cell culture passages, the synovial cells were seeded, and then cultured overnight. After cell adhesion was affirmed, each human galectin (each of Gal-1, Gal-3, Gal-8(M), and Gal-9NC(null)) was added to make the final concentration 0, 0.01, 0.03, 0.1, 0.3, and 1.0 µM, respectively. After cultivation for 24 hr, cells were collected and assayed for apoptosis-inducing activity by the PI method. For inhibitory efficacy on synovial cells, each human galectin was added to each well of a 96 well plate to make the final concentration 0, 0.03, 0.1, 0.3, and 1.0 µM, respectively, followed by cultivation for 48 hr. After the cultivation, the plate was washed with PBS, and cells emitting intense fluorescent light (λex=490 nm, λem=515 nm) where cell counting kit-F (Dojindo Laboratories, Japan, cat. no. 343-07743) was used were counted with a fluorescent plate reader.

[Results]

Figure 56:
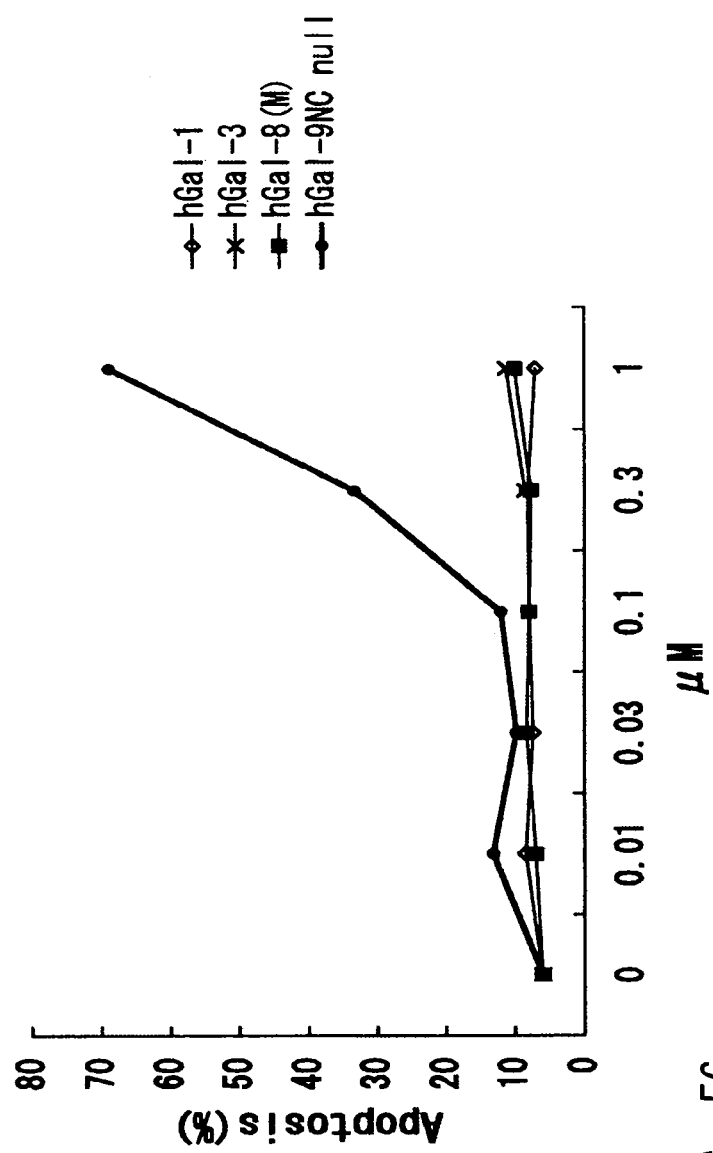
FIG. 56 is a graph showing assay results for galectin mediated activity of inducing apoptosis of RA synovial cells.
Figure 57:
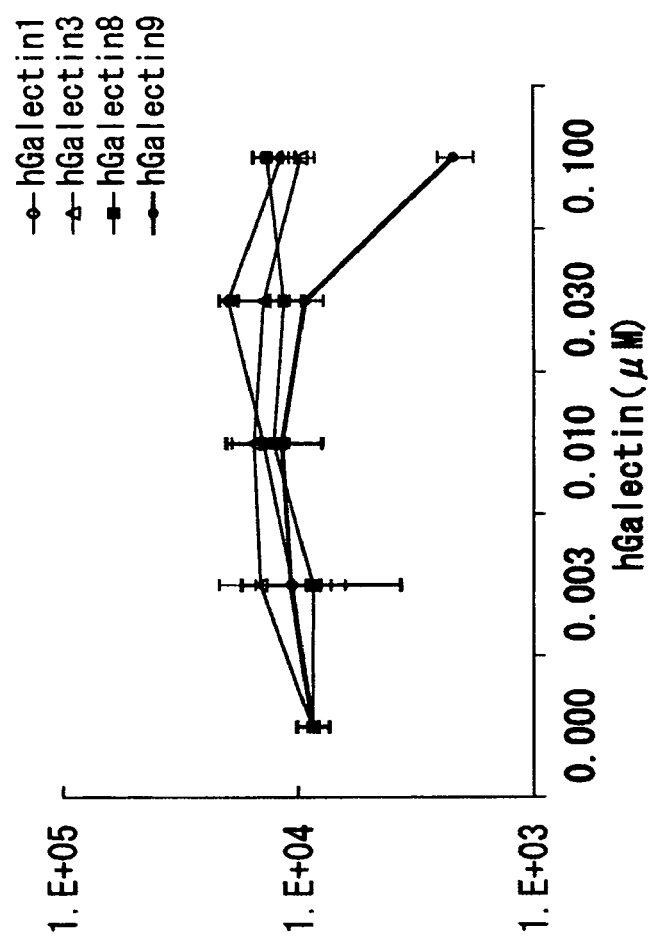
FIG. 57 is a graph showing assay results for galectin mediated activity of inhibiting the growth of RA synovial cells.

Apoptosis-inducing activity assay results are shown in FIG. 56, and results from assays for inhibitory activity in the growth of synovial cells are shown in FIG. 57. In the drawings, hGalectin 1 is recombinant human galectin 1; hGalectin 3, recombinant human galectin 3; hGalectin 8(M), recombinant human galectin 8M; and hGalectin 9, hGal-9NC null. It is very important to inhibit the growth of synovial cells in view of rheumatoid arthritis therapy. Modified galectin-9 mutein (hGal-9NC null) induced apoptosis of proliferated synovial cells, and inhibited the growth of synovial cells. Therefore, modified galectin-9 mutein (hGal-9NC null) is useful as an anti-rheumatoid arthritis drug. No such actions were observed among other galectins.

The efficacy of modified galectin-9 mutein, h-G9NC(null), was examined in a variety of inflammatory diseases, i.e., acute/chronic allergy, immune system disease mouse models.

From these results, it is suggested that modified galectin 9 mutein has an inhibitory or increasing action on a variety of inflammations and also a regulatory action in the production of various cytokines whereby modified galectin 9 mutein is useful in control of inflammatory reaction. Described below are examples illustrating these efficacious advantages.

In the following examples (Examples 5 to 12), G9NC(null) (gal9NC(null), h-gal9NC(null), hG9NC(null) or h-G9NC (null) (human null galectin-9)) is available from Galpharma Co., Ltd., Kagawa, Japan). Dexamethasone (dexamethasone 21-phosphate disodium salt, Sigma-Aldrich, MO, USA) was obtained from the supplier indicated

Example 5

Zymosan-Induced Pleurisy Model

First, mice received a pleural injection of each of G9NC (null) [100 μg/mouse, h-gal9NC(null)], zymosan (100 μg/mouse, Sigma-Aldrich, MO, USA), and dexamethasone (30 mg/kg/mouse, Sigma-Aldrich, MO, USA), or a mixture thereof under anesthetization with diethyl ether (Wako Pure Chemical Industries, Ltd., Japan). PBS was used as a control. Four hours after injection, mice received an intraperitoneal injection of 0.2 to 0.3 ml of a diluted pentobarbital injection with a dilution ratio of Injectable NEMBUTAL® (Trade Name: pentobarbital, Dainippon Pharmaceutical Co., Ltd., Japan):PBS=1:10 for anesthetization, and blood samples were collected from abdominal aorta after laparotomy. Thereafter, mice were euthanized by bleeding, and pleural fluid samples were collected by washing the pleural cavity twice with PBS (1 ml).

Figure 9:
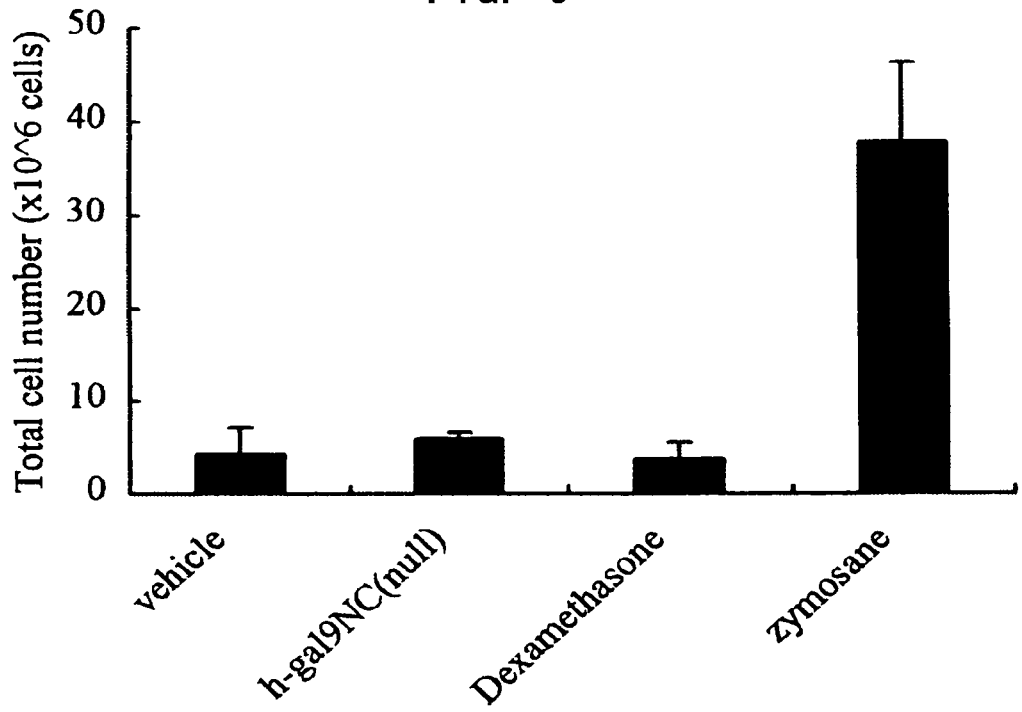
FIG. 9 is a graph showing that zymosan induces pleurisy while modified galectin 9 mutein (h-gal9NC(null)) alone does not.
Figure 10:
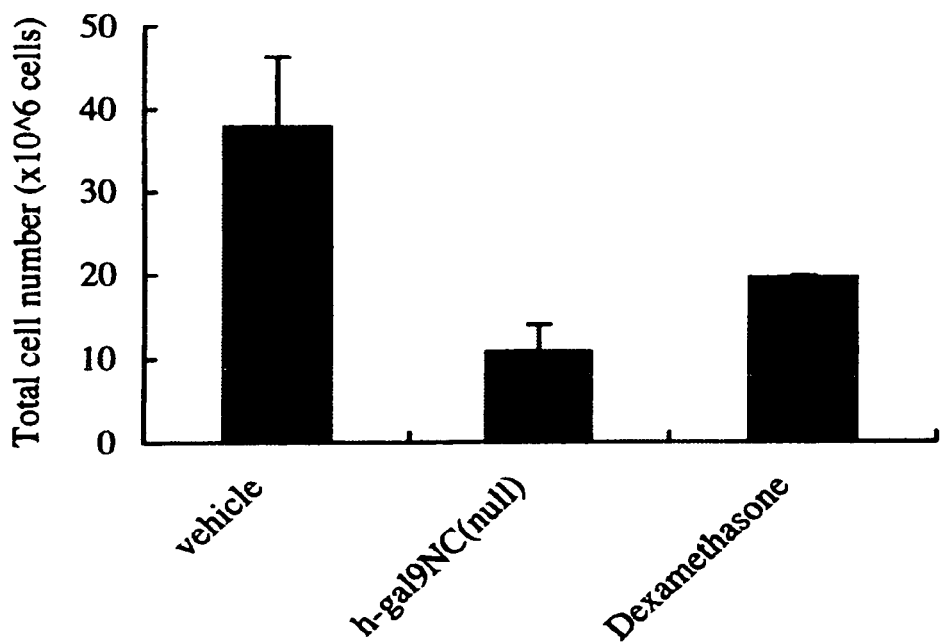
FIG. 10 is a graph showing assay results for the efficacy of galectin 9 mutein (h-gal9NC(null)) on the model of zymosan-induced pleurisy.

The blood samples were allowed to stand at ambient temperature, then centrifuged at 5000 rpm for 10 min, supernatants were collected as serum samples, and freeze-preserved. The pleural fluid samples were subjected to total cell number counting with Turk's solution. After counting, part of the samples were subjected to the Cytospin, air-dried, stained with Diff-Quik (International Reagents Co., Ltd., Japan) or May-Grünwald's solution (Muto Pure Chemical Co., Ltd) and Giemsa solution (Merck Japan Ltd.), and examined microscopically. Each number of neutrophils, eosinophils, macrophages, lymphocytes, mast cells and others was checked for the total cell count of 200 cells. The results are shown in FIGS. 9 and 10.

Example 6

PMA-Induced Dermatitis Model

Phorbol 12-myristate 13-acetate (PMA, Sigma-Aldrich, MO, USA) was obtained from the supplier indicated. For administration to animals, compounds were suspended in PBS(−), which was used as the vehicle in all experiments (this is hereinafter applied in Examples disclosed below).

Balb/c mice (7-week-old) were purchased from SLC (Shizuoka, Japan). Animals were kept under standard conditions in a 12 h day/night rhythm with free access to food and water ad libitum. All animals received humane care in accordance with international guidelines and national law (this is hereinafter applied in Examples disclosed below).

Induction of ear edema in mice was conducted as follows: A solution of phorbol 12-myristate 13-acetate (PMA, 15 mg) dissolved in acetone (30 ml) was applied to the inner and outer surface of the right ear of each mouse (BALB/c, ♀, 7 to 8 weeks old, SPF, SLC Inc.). Acetone was applied to the left ear as a control.

Mice received an i.p. administration of G9NC(null), dexamethasone, or vehicle at a dose of 0.345 ml/head 30 min prior to PMA application. After PMA application, ear thickness was measured at 0, 3, 6, 8 and 24 hours with a calibrated thickness gauge (Mitsutoyo, Tokyo, Japan) under anesthetization with ether. Ear edema was expressed as $(R-L)-(R_0-L_0)$, where $R_0$ and $L_0$ represent the thickness of the right and left ear, respectively, at the beginning of the experiment (0 h), and R and L stand for the thickness values obtained at each given time point.

Figure 11:
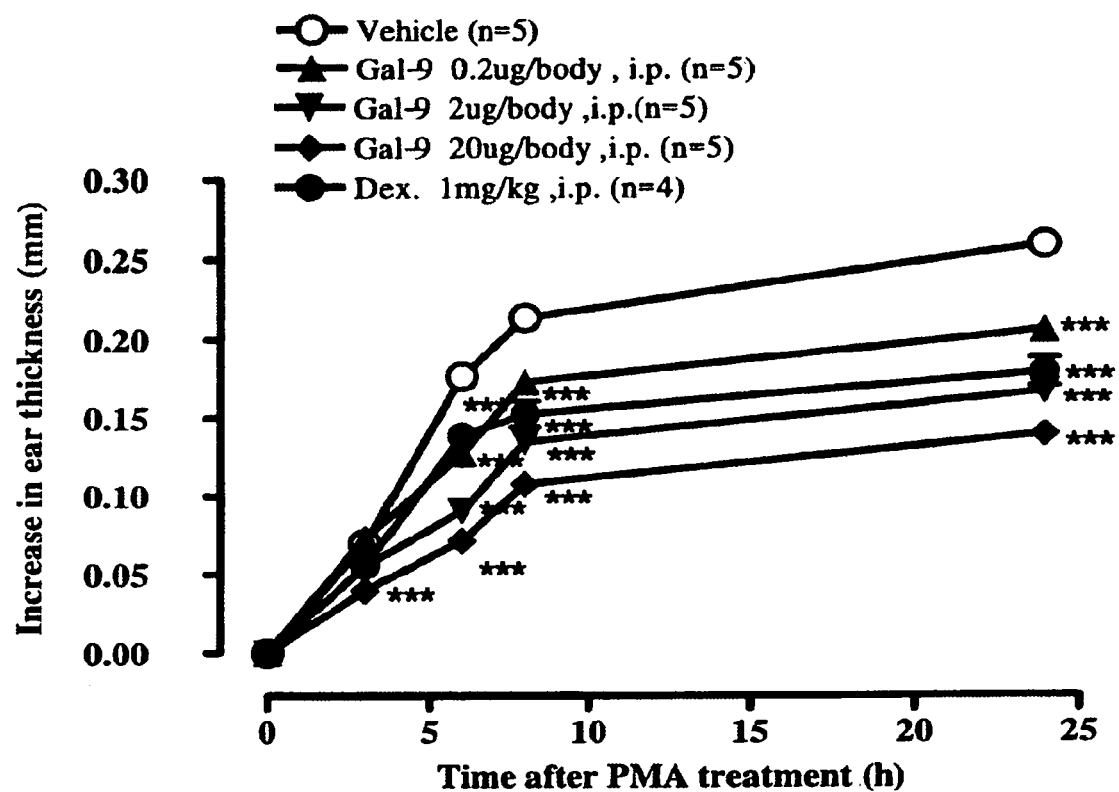
FIG. 11 is a graph showing assay results for the efficacy of galectin 9 mutein (Gal-9=G9NC(null)) on the model of PMA-induced dermatitis (model susceptible to steroid).

Statistical analysis was conducted as follows: Unless otherwise stated, data are expressed as mean values±SEM. Statistical differences of data sets were analyzed using two-way ANOVA, and differences between groups were assessed by Bonferroni post-test using commercially available statistics software (GraphPad Software, Inc., San Diego, USA). P values <0.05 were considered statistically significant. Details are given in each drawing (this is hereinafter applied in Examples disclosed below). The results are shown in FIG. 11.

Example 7

AA-Induced Dermatitis Model

Arachidonic acid (AA, Sigma-Aldrich, MO, USA) was obtained from the supplier indicated. The rest was the same as in Example 6.

Induction of ear edema in mice was conducted as follows: A solution of arachidonic acid (AA, 750 mg) dissolved in acetone (30 ml) was applied to the inner and outer surface of the right ear of each mouse (BALB/c, ♀, 7 to 8 weeks old, SPF, SLC Inc.). Acetone was applied to the left ear as a control.

Figure 12:
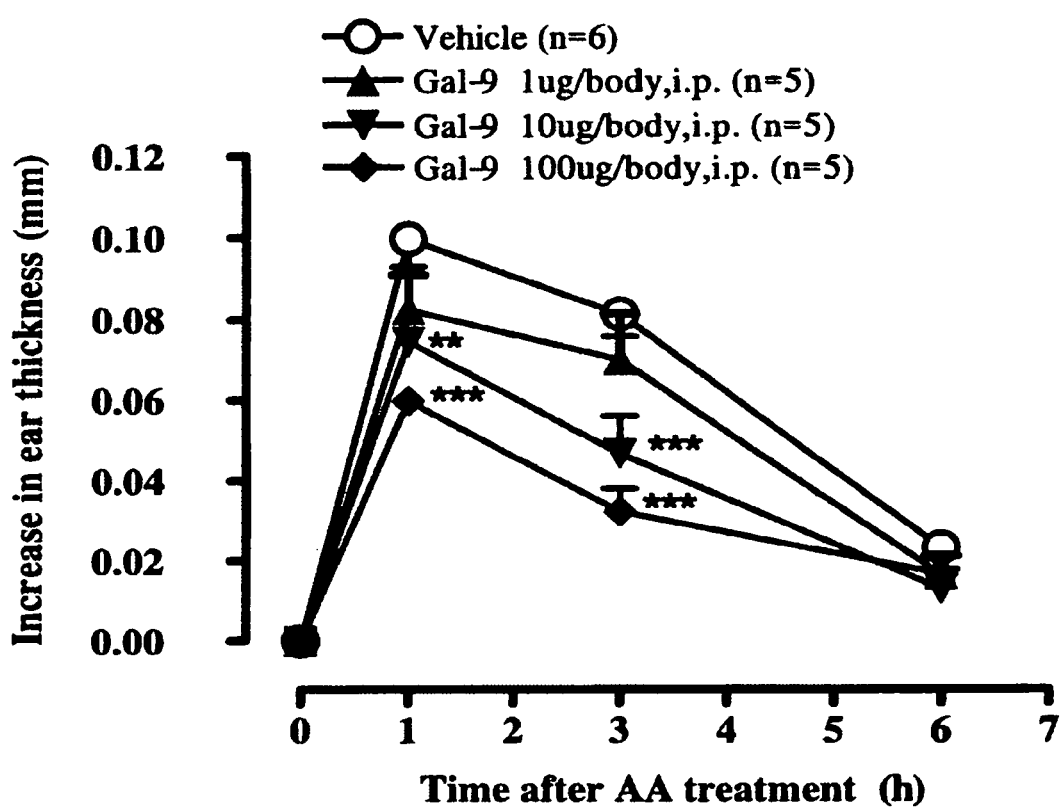
FIG. 12 is a graph showing assay results for the efficacy of galectin 9 mutein (Gal-9=G9NC(null)) on the model of AA-induced dermatitis (model non-susceptible to steroid).

Animals received an i.p. administration of G9NC(null), dexamethasone, or vehicle at a dose of 0.345 ml/head 30 min prior to AA application. After AA application, ear thickness was measured at 0, 1, 3 and 6 hours with a calibrated thickness gauge (Mitsutoyo, Tokyo, Japan) under anesthetization with ether. Ear edema was expressed as $(R-L)-(R_0-L_0)$, where $R_0$ and $L_0$ represent the thickness of the right and left ear, respectively, at the beginning of the experiment (0 h), and R and L stand for the thickness values obtained at each given time point. Statistical analysis was conducted in the same manner as in Example 6. The results are shown in FIG. 12.

Example 8

Capsaicin-Induced Dermatitis Model

Cyproheptadine (Sigma-Aldrich, MO, USA) and capsaicin (Nakarai, Tokyo, Japan) were obtained from each supplier indicated. The rest was the same as in Example 6.

Induction of ear edema in mice was conducted as follows: A solution of capsaicin (500 mg) dissolved in 30 ml of acetone/olive oil (volume/volume=4/1) was applied to the inner and outer surface of the right ear of each mouse (BALB/c, ♀, 7 to 8 weeks old, SPF, SLC Inc.). The vehicle, acetone/olive oil, was applied to the left ear as a control.

Figure 13:
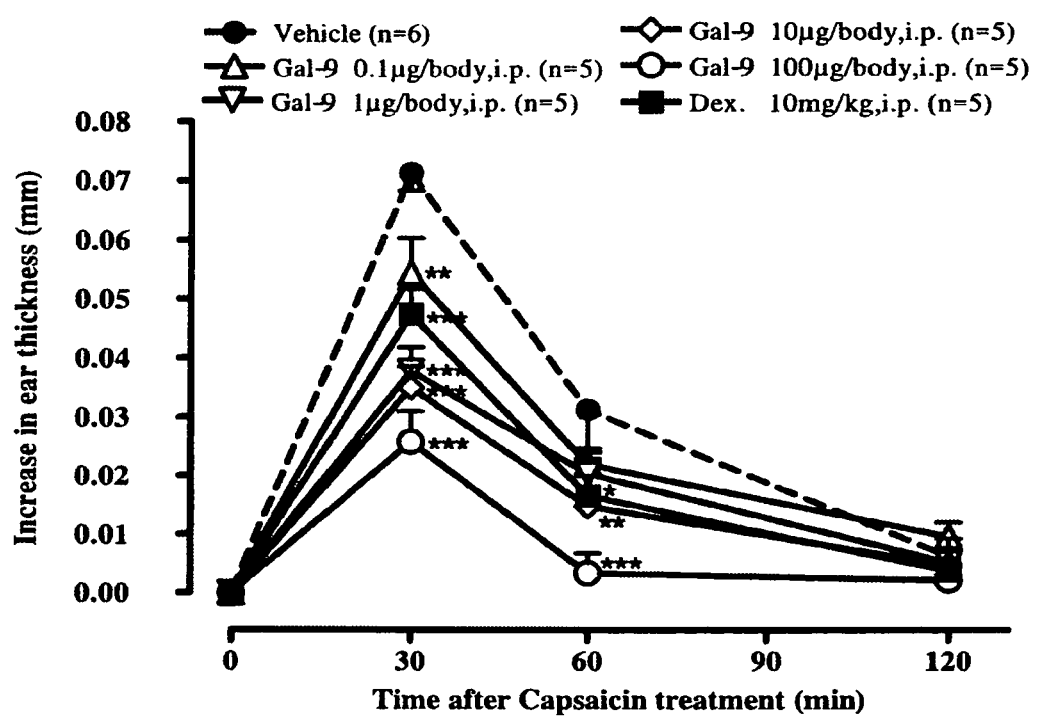
FIG. 13 is a graph showing assay results for the efficacy of galectin 9 mutein (Gal-9=G9NC(null)) on the model of capsaicin-induced dermatitis.

Animals received an i.p. administration of G9NC(null), dexamethasone, cyproheptadine, or vehicle at a dose of 0.345 ml/head 30 min prior to capsaicin application. After capsaicin application, ear thickness was measured at 0, 0.5, 1 and 2 hours with a calibrated thickness gauge (Mitsutoyo, Tokyo, Japan) under anesthetization with ether. Ear edema was expressed as $(R-L)-(R_0-L_0)$, where $R_0$ and $L_0$ represent the thickness of the right and left ear, respectively, at the beginning of the experiment (0 h), and R and L stand for the thickness values obtained at each given time point. Statistical analysis was conducted in the same manner as in Example 6. The results are shown in FIG. 13.

Example 9

DNFB-Induced Contact Dermatitis Model

Dinitro-fluoro-benzene (DNFB, Sigma-Aldrich, MO, USA) was obtained from the supplier indicated. The rest was the same as in Example 6.

Induction of ear edema in mice was conducted as follows: In the model of delayed-type hypersensitivity (DTH)-induced edema, mice were sensitized on days −7 and −6 by applying a solution (30 ml) of 0.5% dinitro-fluorobenzene (DNFB) in acetone/olive oil (volume/volume=4/1) to their shaved abdomen. On day 0, challenge reactions were elicited with 30 ml of 0.3% DNFB in acetone/olive oil (volume/volume=4/1) applied topically to the inner and outer surface of the right ear of each mouse. The vehicle, acetone/olive oil, was applied to the left ear as a control.

Figure 14:
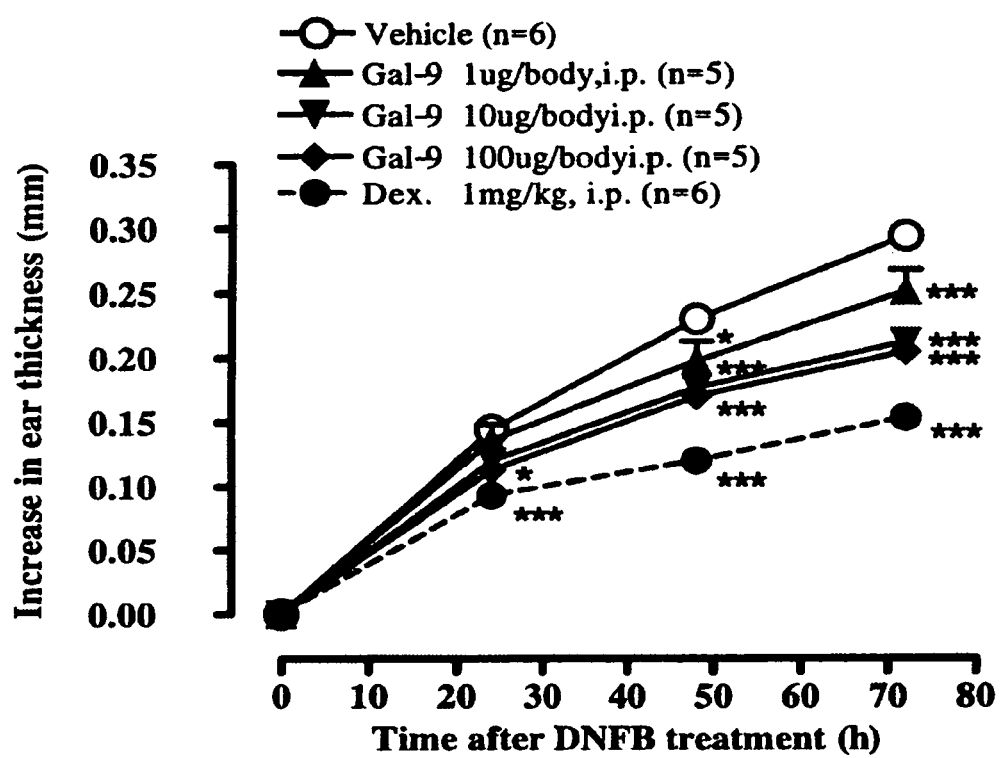
FIG. 14 is a graph showing assay results for the efficacy of galectin 9 mutein (Gal-9=G9NC(null)) on the model of DNFB-induced contact dermatitis.
Figure 15:
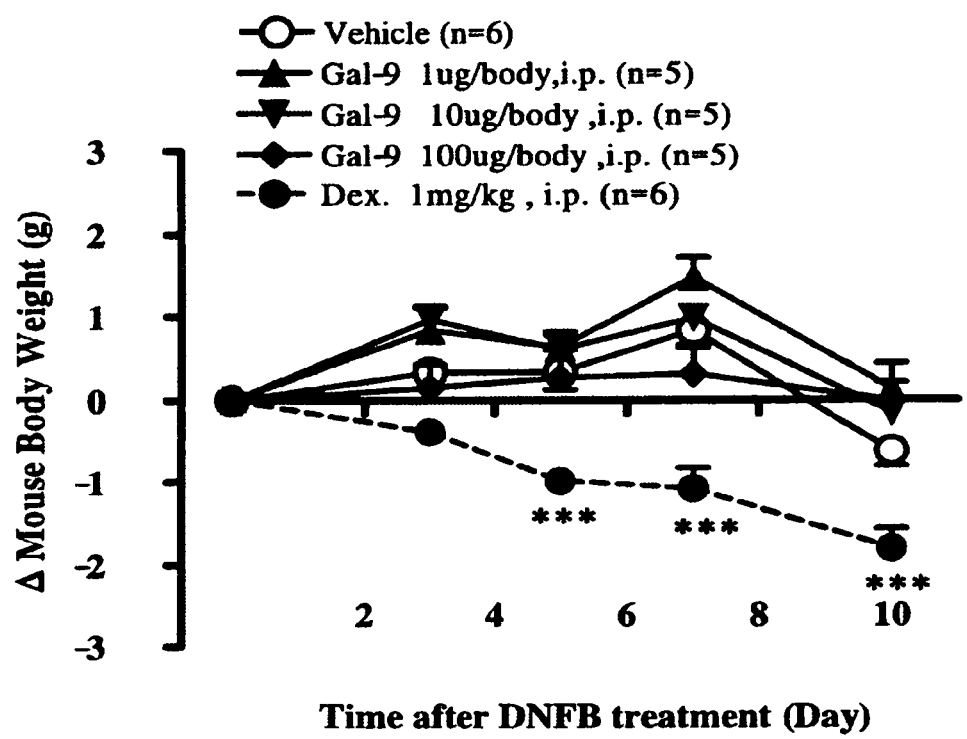
FIG. 15 is a graph showing assay results for the efficacy of galectin 9 mutein (Gal-9=G9NC(null)) on the model of DNFB-induced contact dermatitis.

Mice received i.p. administrations of G9NC(null), dexamethasone, or vehicle at a dose of 0.345 ml/head on days −7 to 0 prior to DNFB challenge, 24 and 48 hours after DNFB challenge. After DNFB challenge, ear thickness was measured at 0, 24, 48 and 72 hours with a calibrated thickness gauge (Mitsutoyo, Tokyo, Japan) under anesthetization with ether. Ear edema was expressed as $(R-L)-(R_0-L_0)$, where $R_0$ and $L_0$ represent the thickness of the right and left ear, respectively, at the beginning of the experiment (0 h), and R and L stand for the thickness values obtained at each given time point. Statistical analysis was conducted in the same manner as in Example 6. The results are shown in FIGS. 14 and 15.

Example 10

FITC-Induced Atopic Dermatitis Model

Fluorescein isothiocyanate (FITC, Sigma-Aldrich, MO, USA) was obtained from the supplier indicated. The rest was the same as in Example 6.

Induction of ear edema in mice was conducted as follows: In the model of FITC-induced edema, mice were sensitized on days −7 and −6 by applying a solution (400 ml) of 0.5% fluorescein isothiocyanate (FITC) in acetone/dibutyl phthalate (volume/volume=1/1) to their shaved abdomen. On day 0, challenge reactions were elicited with 30 ml of 0.5% FITC in acetone/dibutyl phthalate (volume/volume-1/1) applied topically to the inner and outer surface of the right ear of each mouse. The vehicle, acetone/dibutyl phthalate, was applied to the left ear as a control.

Figure 16:
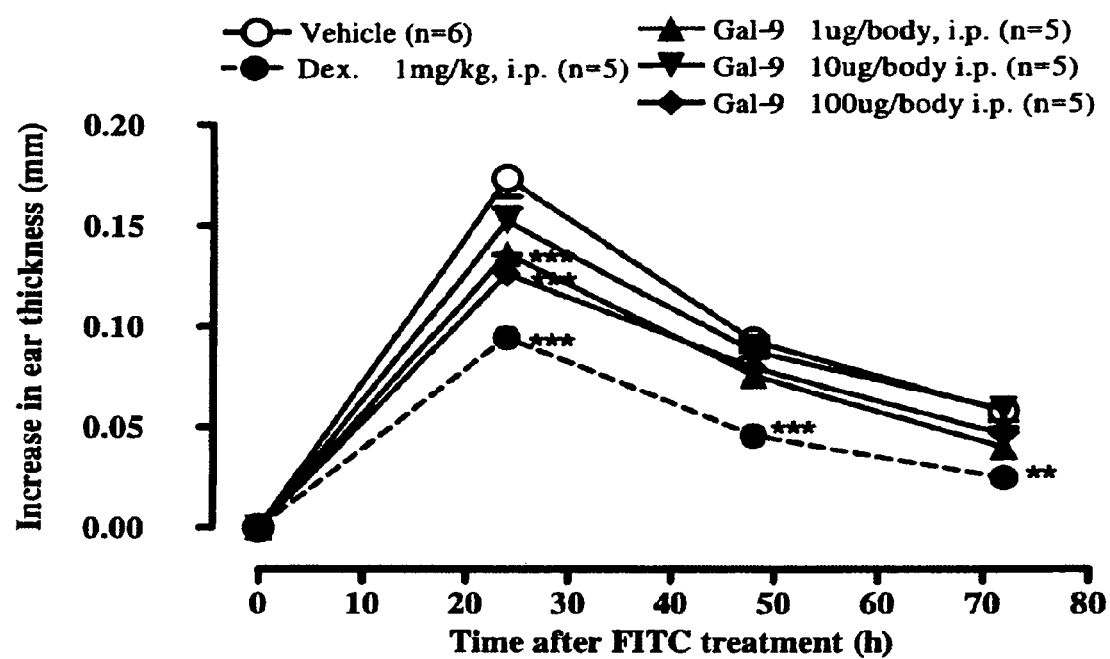
FIG. 16 is a graph showing assay results for the efficacy of galectin 9 mutein (Gal-9=G9NC(null)) on the model of FITC-induced atopic dermatitis.

Mice received i.p. administrations of G9NC(null), dexamethasone, or vehicle at a dose of 0.41 ml/head 30 minutes prior to FITC challenge, 24 and 48 hours after FITC challenge. After FITC challenge, ear thickness was measured at 0, 24, 48 and 72 hours with a calibrated thickness gauge (Mitsutoyo, Tokyo, Japan) under anesthetization with ether. Ear edema was expressed as $(R-L)-(R_0-L_0)$, where $R_0$ and $L_0$ represent the thickness of the right and left ear, respectively, at the beginning of the experiment (0 h), and R and L stand for the thickness values obtained at each given time point. Statistical analysis was conducted in the same manner as in Example 6. The results are shown in FIG. 16.

Example 11

Urticaria Model

Anti-DNP IgE (SPE7, Sigma-Aldrich, MO, USA) and dinitro-fluorobenzene (DNFB, Sigma-Aldrich, MO, USA) were obtained from the supplier indicated. The rest was the same as in Example 6.

Induction of ear edema in mice was conducted as follows: In the model of biphasic cutaneous reaction model, mice were sensitized on day −1 by i.v. injection of anti-DNP IgE (5 mg/mouse) in PBS(−). On day 0, challenge reactions were elicited with 30 ml of 0.15% DNFB in acetone/olive oil (volume/volume=4/1) applied topically to the inner and outer surface of the right ear of each mouse. The vehicle, acetone/olive oil, was applied to the left ear as a control.

Figure 17:
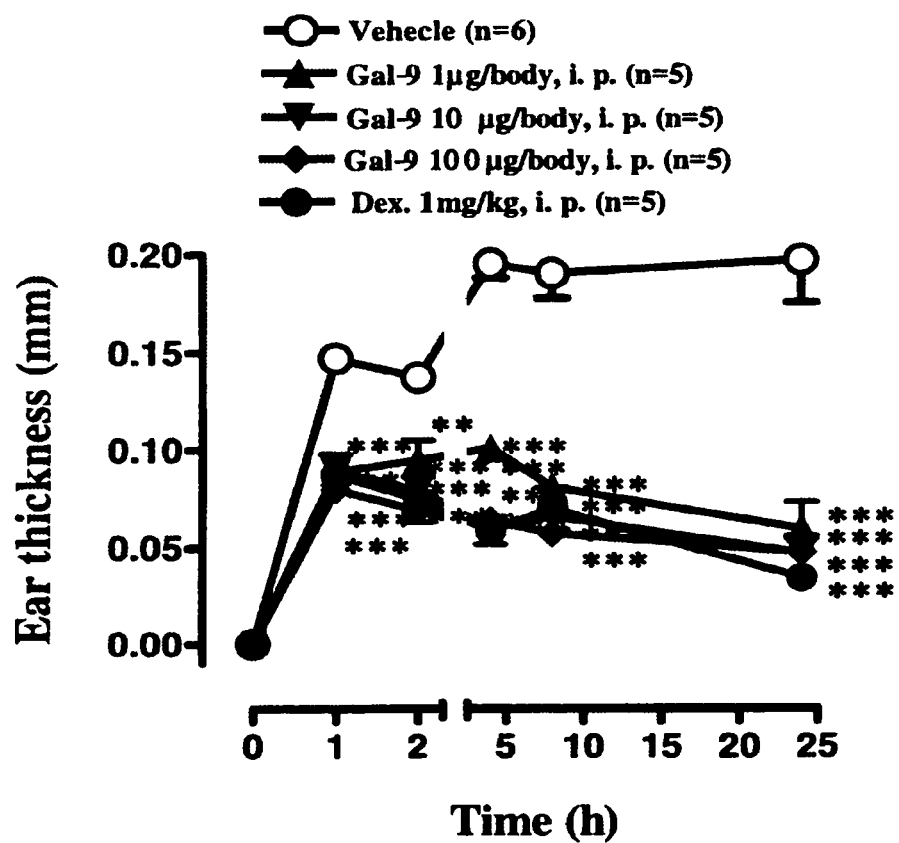
FIG. 17 is a graph showing assay results for the efficacy of galectin 9 mutein (Gal-9=G9NC(null)) on the model of urticaria.
Figure 18:
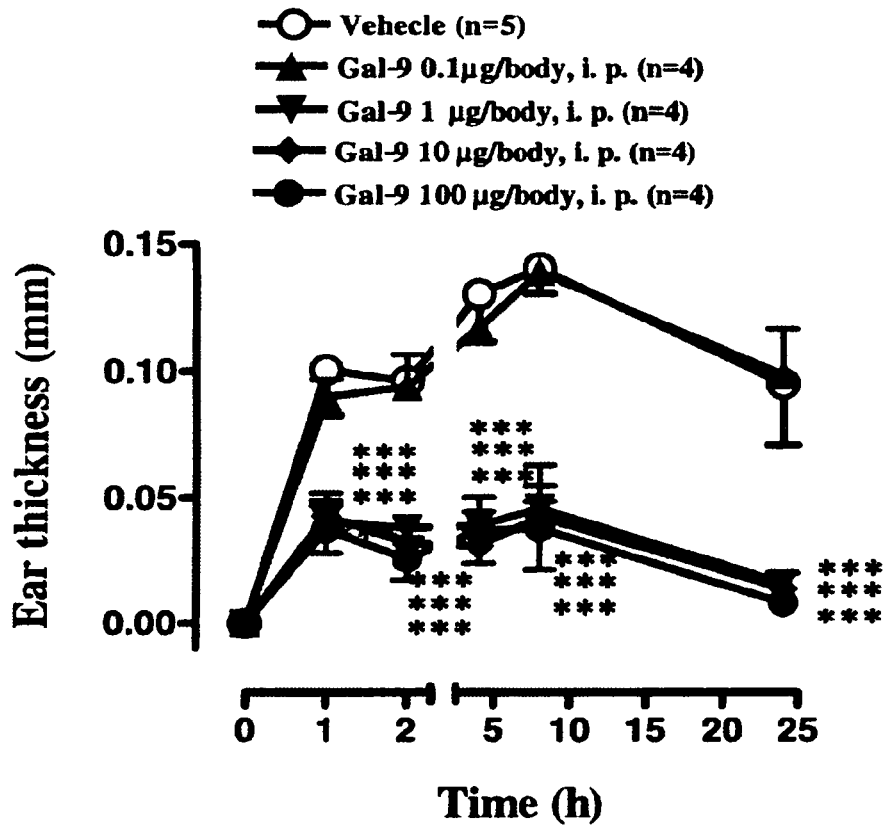
FIG. 18 is a graph showing assay results for the efficacy of galectin 9 mutein (Gal-9=G9NC(null)) on the model of urticaria.

Mice received an i.p. administration of G9NC(null), dexamethasone, or vehicle at a dose of 0.345 ml/head 30 minutes prior to DNFB challenge. After DNFB challenge, ear thickness was measured at 0, 1, 2, 4, 8 and 24 hours with a calibrated thickness gauge (Mitsutoyo, Tokyo, Japan) under anesthetization with ether. Ear edema was expressed as $(R-L)-(R_0-L_0)$, where $R_0$ and $L_0$ represent the thickness of the right and left ear, respectively, at the beginning of the experiment (0 h), and R and L stand for the thickness values obtained at each given time point. Statistical analysis was conducted in the same manner as in Example 6. The results are shown in FIG. 17.

Example 12

Arthritis Model

Figure 19:
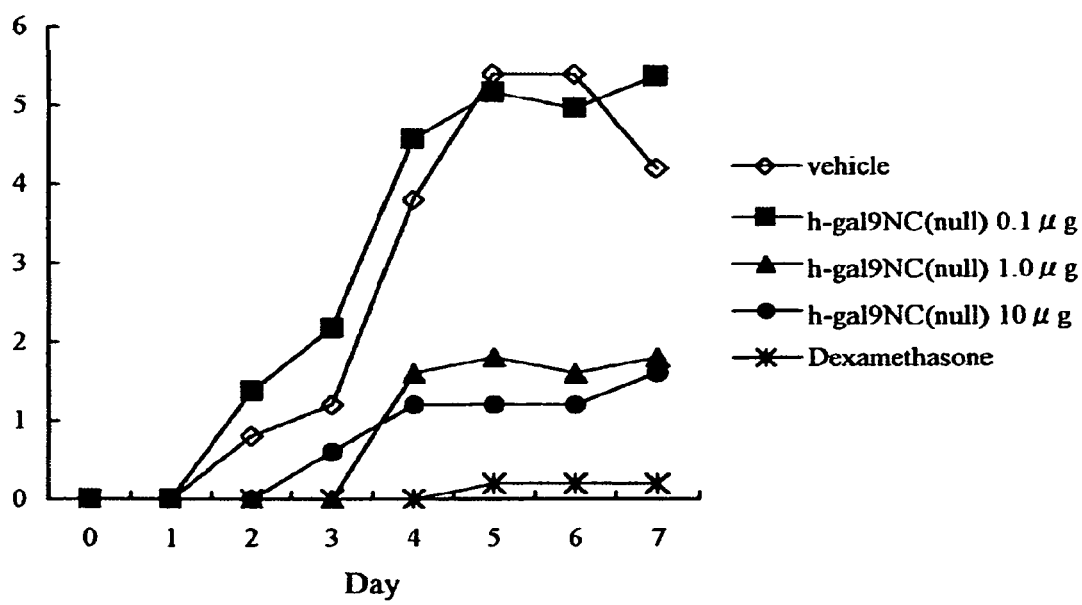
FIG. 19 is a graph showing assay results for the efficacy of galectin 9 mutein (Gal-9=G9NC(null)) on the model of arthritis.

DBA/1J female mice (7-week-old) were used. An arthritis-inducing monoclonal antibody cocktail (Chondrex, WA, USA; No. 62100) was intravenously administered to the tail of each animal at 2 mg/0.5 ml/body. Three days later, the animals received an i.p. application of a sample mix (100 μL) wherein 5 μg of LPS (SIGMA, L6511) was premixed with h-Gal9NC (null) at each given dose. After sample administration, the swelling degree of each limb joint (of right and left, fore and hind limbs) was measured once a day and severity of arthritis was scored. The results are shown in FIG. 19.

The efficacy of h-G9NC(null) was examined in acute inflammation models, represented by zymosan-induced pleurisy models (Example 5) and LPS-induced peritonitis models. As a result, it was observed that the i.p. administration of h-G9NC(null) at a dose of 100 μg led to inhibition of pleurisy in the zymosan-induced pleurisy model. It was noted that h-G9NC(null) alone had almost no influence on the mice. In addition, h-G9NC(null) affected conditions in carrageenan- and fMLP-induced pleurisy models.

Also, in the model of LPS-induced peritonitis, it was observed that h-G9NC(null) induced changes in production of serum cytokines (IFN-γ, IL-4, IL-12, IL-10, etc.) induced upon inflammation. For instance, when blood was collected from the orbit of a mouse 6, 12, and 24 hours after contemporaneous i.p. administration of LPS and h-G9NC, and the level of serum IFN-γ was assayed, the level of IFN-γ induced upon inflammation was observed to be elevated transiently in the group receiving the administration of LPS alone while the elevation (induction) of IFN-γ was inhibited in the group receiving the contemporaneous administration of LPS and h-G9NC(null) in an h-G9NC(null)-dose dependent fashion. In view of these, it has been suggested that h-G9NC(null) can regulate the production of cytokines whereby inflammation can be controlled.

Further, it has been observed that h-G9NC(null) has inhibitory actions in models of inflammation, susceptible to steroid (PMA-induced) and non-susceptible to steroid (arachidonic acid-induced) (Examples 6 & 7), as well as in the model of capsaicin-induced inflammation (Example 8).

The efficacy of h-G9NC(null) on allergic inflammation was examined wherein said allergic inflammation included the models of DNFB-induced contact dermatitis, FITC-induced atopic dermatitis, anti-DNP monoclonal IgE Ab-sensitized urticaria. For example, in the model of DNFB-induced contact dermatitis (Example 9), h-G9NC(null) was i.p. administered and its efficacy was evaluated by using ear edema as an index to skin response. As a result, the medications with h-G9NC(null) at 1, 10, and 100 μg, respectively, were observed to exert inhibitory actions while h-G9NC(null)

was not observed to lead to significant body weight reduction, induced by the administration of dexamethasone. In the model of FITC-induced atopic dermatitis (Example 10), the efficacy of h-G9NC(null) in the elicited phase was found when h-G9NC(null) was i.p. administered. In addition, when h-G9NC(null) was administered i.p. to the model mice of anti-DNP monoclonal IgE Ab-sensitized urticaria (Example 11) at 1, 10, and 100 μg, respectively, biphasic cutaneous reaction due to antigen (DNFB) painting was inhibited.

Embodiments disclosed herein demonstrate the efficacy of h-G9NC(null) on antibody cocktail-induced arthritis, one of autoimmune disease models. H-G9NC(null) affects conditions in models of adjuvant arthritis, collagen arthritis and others. For instance, even 1 μg of h-G9NC(null) has been observed to have an inhibitory action in Example 12.

Example 13

Modified Galectin 9 Mutein-Mediated Induction of Apoptosis (Cytotoxicity) in Tumor Cells

[Protocol]

Each cell was suspended in RPMI (SIGMA) containing 10% FBS (JRH), placed into a 96 well plate (FALCON) at $3\times10^3$ cells/90 μL, and cultured for 24 hr (37° C., 5% $CO_2$). After the cultivation, modified galectin 9 mutein, h-G9NC (null), was added to make the final concentration 0.03 to 1 μM (10 μl), followed by incubation for 24 hr. After the incubation, 10 μL of reagent WST-1 (Roche, 1 644 807) was added to each well, and incubated at 37° C. in a 5% $CO_2$ incubator for 2 to 4 hr. Thereafter, the absorbance (O.D.) at 450 nm was measured with a plate reader. The efficacy of inducing apoptosis (cytotoxicity) in each tumor cell was evaluated as follows:

Viability (%)=[(Sample O.D.−Blank)]/(Negative Control O.D.−Blank)]×100

Tumor cells used are shown in Table 2.

TABLE 2

Modified Galectin 9 Mutein's Efficacy of Inducing Apoptosis (Cytotoxicity) in Tumor Cells: Data

| Cell name | Animal | 1 μM killing | IC50 (μM) | Tissue |
|---|---|---|---|---|
| L1210 | Mouse (BDF1) | 99 | 0.026 | Spleen Lymph node, leukemia |
| EL-4 | Mouse (C57BL/6) | 50 | 1.038 | Spleen |
| P388 D1 | Mouse (DBA/2) | 78 | 0.626 | Lymphoma, macrophage, monocyte |
| NS-1 | Mouse (BALB/c) | 92 | 0.062 | Bcell (myeloma), derived from MOPC-21 |
| Meth A | Mouse (BALB/c) | 92 | 0.198 | Fibrosarcoma, subcutaneous |
| MH134 | Mouse (C3H/He) | 91 | 0.262 | Liver, ascites hepatoma |
| B16/BL6 | Mouse (C57BL/6) | 0 | | Melanoma |
| B16/F10 | Mouse (C57BL/6) | 0 | | Melanoma |
| B16/F1 | Mouse (C57BL/6) | 45 | 1.286 | Melanoma |
| MM-RU | Human | 58 | 0.899 | Melanoma |
| MM-BP | Human | 53 | 0.937 | Melanoma |
| PK-1 | Human | 66 | 0.184 | Pancreas |
| PK-9 | Human | 59 | 0.624 | Pancreas |
| PANC-1 | Human | 58 | 0.866 | Pancreatic carcinoma of ductal origin |
| KLM-1 | Human | 55 | 0.883 | Pancreas |
| Wi-Dr-Tc | Human | 32 | | Colon adenocarcinoma |
| COLO205 | Human | 0 | | Colon adenocarcinoma |
| Colon26 | Mouse (BALB/c) | 30 | | Rectum carcinoma |
| Hu09N2 | Human | 26 | | Bone |
| HMC-1 | Human | 19 | | Human mast cell |
| MCF-7 K10 | Human | 17 | | Breast adenocarcinoma |
| SK-Br-3 | Human | 0 | | Breast |
| HT17 | Human | 70 | 0.214 | Liver, low differentiated |
| Hull-7 | Human | 0 | | Liver, high differentiated |
| KATOIII | Human | 89 | 0.210 | Stomach |

In Table 2, "Cell name" indicates each cell name; "Animal", each animal origin from which the indicated tumor cell is derived; "1 μM killing", killing (%) when 1 μM of modified galectin 9 mutein is added; and "Tissue", each tissue/organ site from which the indicated tumor cell is derived.

[Results]

Table 2 shows results from modified galectin 9 mutein h-G9NC(null) mediated apoptosis (cytotoxicity)-inducing assays in cultured cells. As a result, it has been determined that modified galectin 9 muteins are:
1) effective in blood cell tumors
2) also effective in non-epithelial neoplasms such as malignant melanoma and fibrosarcoma
3) effective in epithelial neoplasms such as stomach cancers, pancreas cancers, and lung cancers, too.

Example 14

Anti-Tumor (Antineoplastic) Efficacy of Modified Galectin 9 Mutein in Model of Subcutaneously Transplanted Tumor

[Protocol]

The target tumor cells used were LLC cells. The cultured cells ($1\times10^6$ cells/100 μL) were incubated with modified galectin 9 mutein, h-G9NC(null), at 100 μg/100 μL, or physiological saline at 100 μL at 37° C. for 1 hr, and then injected subcutaneously into the back of each C57BL6 mouse. Tumor size (longitude, latitude) was measured.

Five weeks after transplantation, the administered skin portion (tumor) was cut out to give histopathological test samples which were fixed with a 10% neutral buffered formaldehyde solution. The paraffin-embedded tissue was sliced to give sections which were stained with HE (hematoxylin-eosin) reagent.

[Results]

Figure 20:
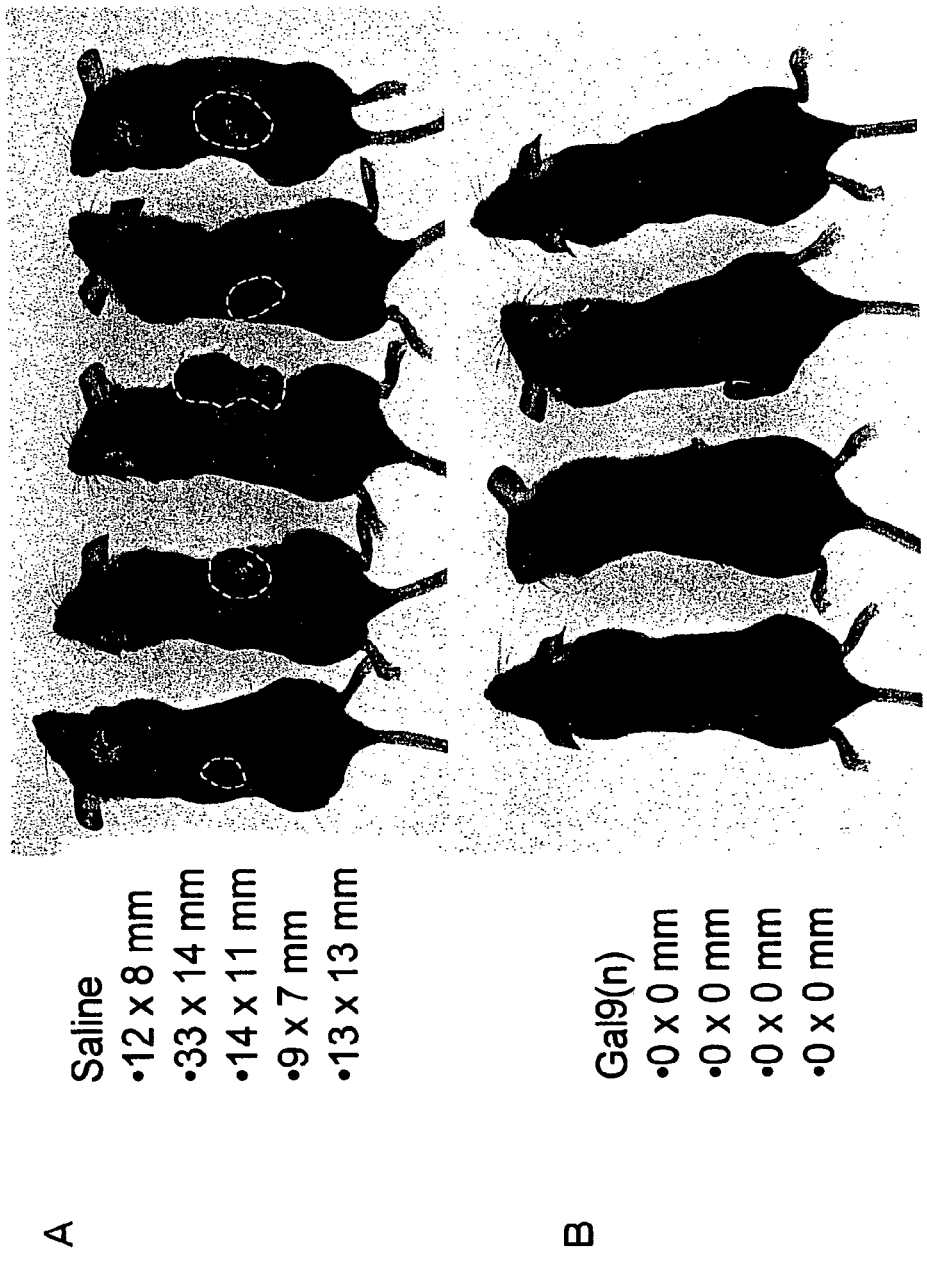
FIG. 20 shows assay results from examinations of modified galectin 9 mutein's efficacy of inhibiting the growth of tumor cells, i.e., anti-tumor activity (anti-neoplastic) in the model of subcutaneously transplanted tumor. Upper: control group Lower: modified Gal-9 mutein-administered group (no tumor was observed for 5 weeks so far).
Figure 21:
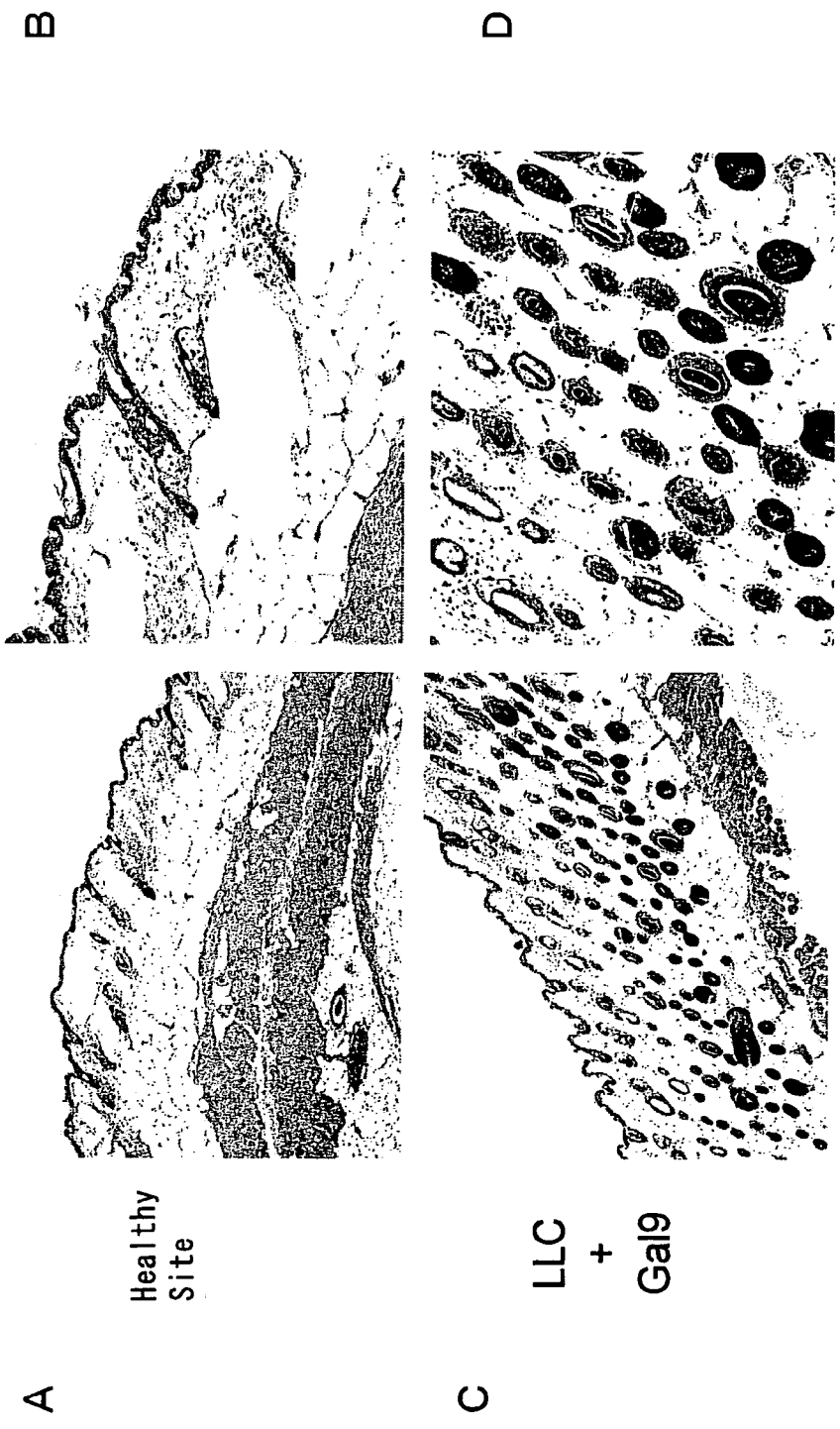
FIG. 21 shows histopathological tissue photos from assays for modified galectin 9 mutein's efficacy of inhibiting the growth of tumor cells, i.e., anti-tumor activity (anti-neoplastic) in the model of subcutaneously transplanted tumor, wherein the 5-week skin states are shown when LLC+Modified Gal-9 Mutein (Gal9) were administered (lower photos): macroscopically white tone.

In the model of subcutaneously transplanted tumor, modified galectin 9 mutein's efficacy of inhibiting the growth of tumor cells, i.e., anti-tumor activity (anti-neoplastic) is shown in FIG. 20. The results from histopathological examinations for anti-tumor activity (anti-neoplastic) are also shown in FIG. 21. In the drawings, Gal9(n) and Gal9 indicate modified galectin 9 mutein, h-G9NC(null), and 5 W does 5 weeks.

Where LLC was cultured in the presence of modified galectin 9 mutein, h-G9NC(null), the apparent transformation of cancer cells was observed in a phase-contrast microscope. At this stage, modified galectin 9 mutein reduced dose-dependently the number of viable LLC cells (MTT assay), and induced the loss of ability to synthesize DNA ($^3$H-thymidine intake property) and an increase in released LDH levels in culture supernatants. These anti-tumor effects mediated by modified galectin 9 mutein were also observed for human lung cancer cell lines H226 (squamous cell carcinoma), A549 (adenocarcinoma), and H69 (small cell carcinoma). However, the level of expressed Annexin V in LLC significantly increased in the presence of modified galectin 9 mutein.

In contrast, when LLC was inoculated subcutaneously into isogenic C57BL6 mice in the coexistence of modified galectin 9 mutein, tumors were not successfully engrafted, clear differences from the control group were observed 5 weeks after the inoculation. The survival proportion of mice was significantly improved in the presence of modified galectin 9 mutein. It has been revealed that modified galectin 9 mutein induces apoptosin in cancer cells and exerts anti-tumor actions.

In experimental models of human small cell lung carcinoma cell line H69 cells injected intravenously into nude mice, which mimic multiple organ micrometastases of human lung cancers, it was observed that metastasis-inhibitory efficacy was attained with the i.p. application of modified galectin 9 mutein.

Example 15

Modified Galectin 9 Mutein-Mediated Induction of Apoptosis (Cytotoxicity) in Cultured Tumor Cells

Figure 22:
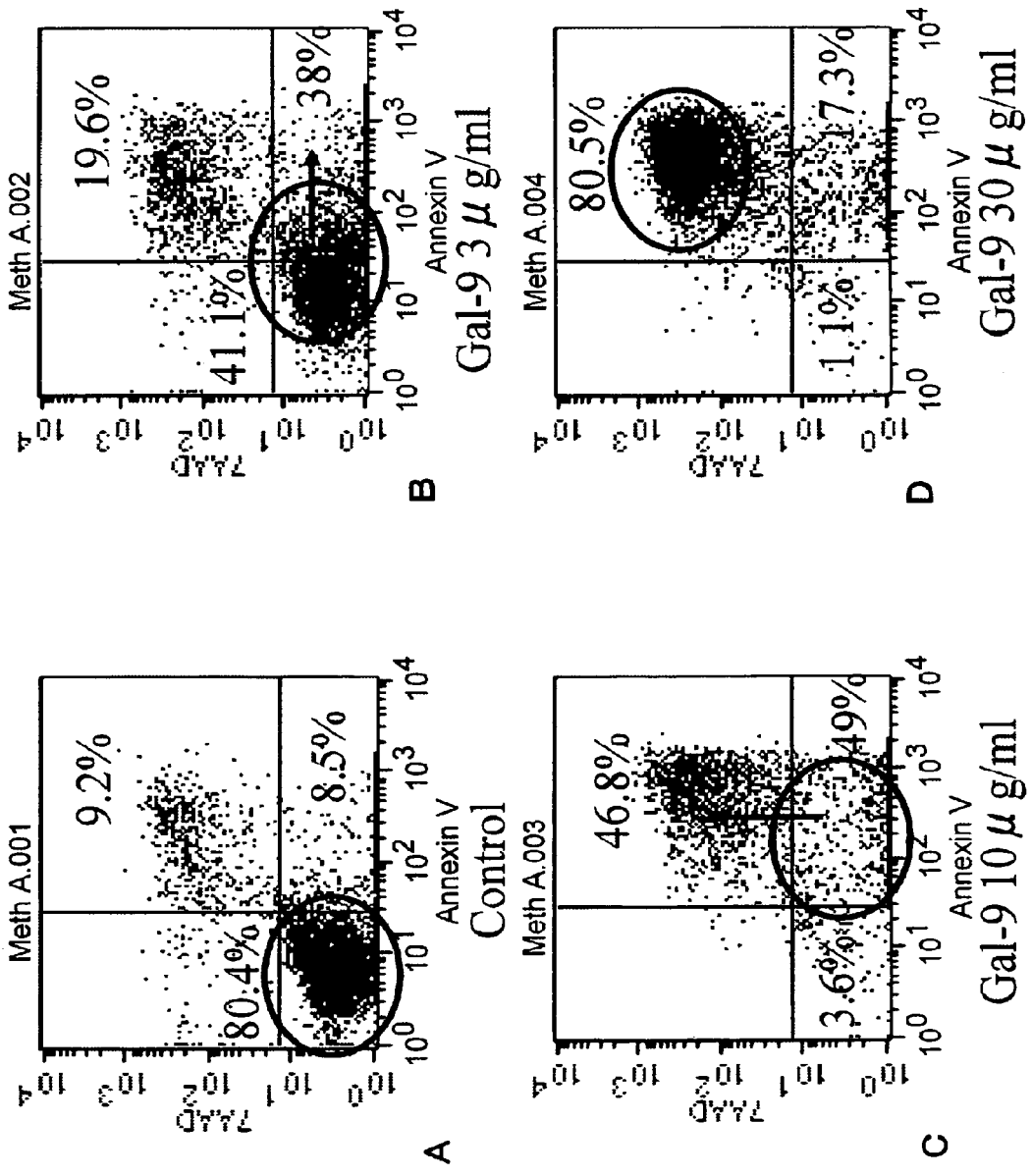
FIG. 22 shows assay results for modified galectin 9 mutein-mediated induction of apoptosis (cytotoxicity) in cultured tumor cells (Meth A cells, 24 h).
Figure 23:
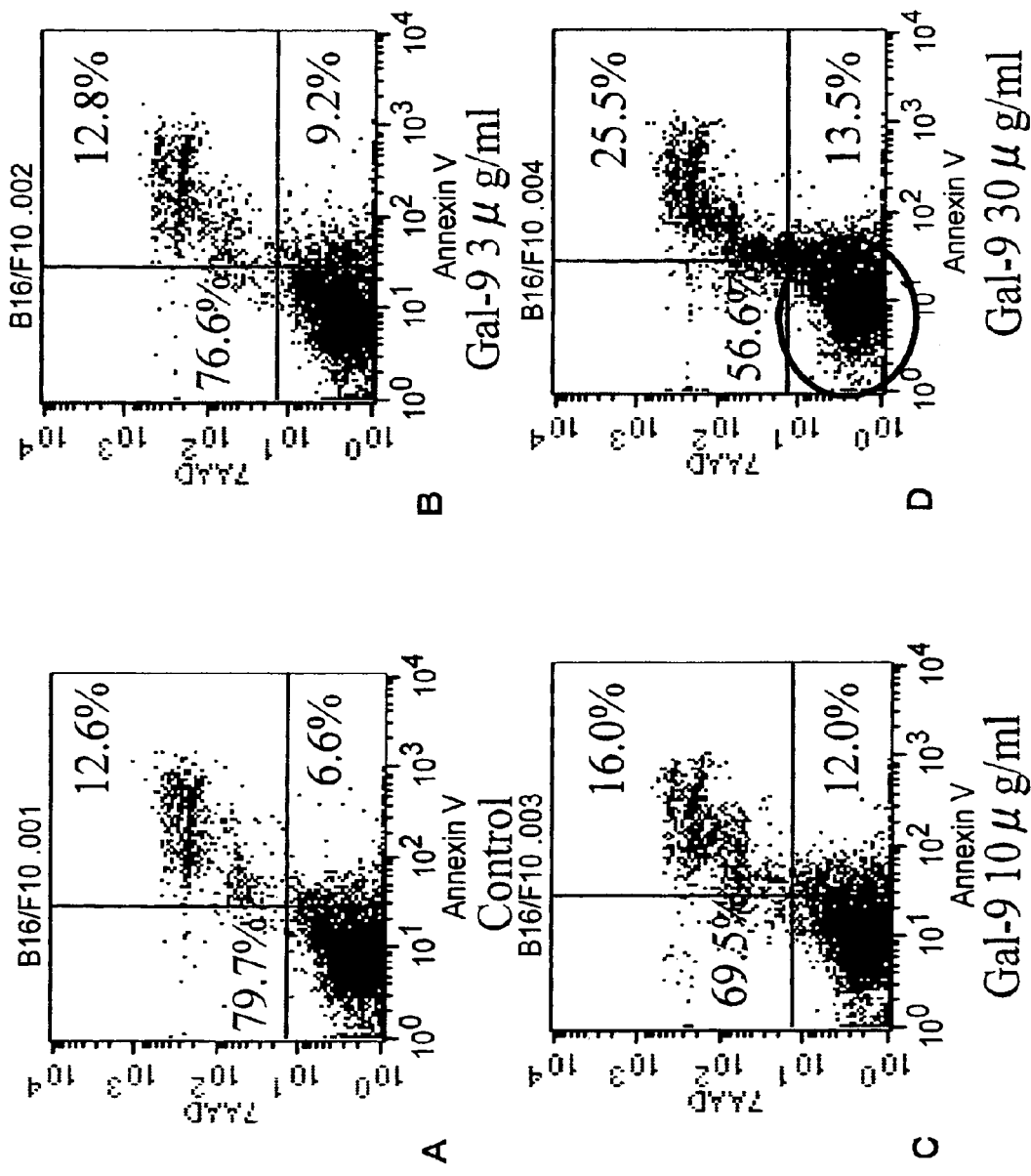
FIG. 23 shows assay results for modified galectin 9 mutein-mediated induction of apoptosis (cytotoxicity) in cultured tumor cells (B16/F10 cells, 24 h).

[Protocol]
(1) Apoptosis of Meth A Cell
A suspension of Meth A in RPMI (SIGMA) containing 10% FBS (JRH) was placed into a 96-well plate (FALCON) at $4\times10^4$ cells/90 µl, contemporaneously followed by addition of modified galectin 9 mutein, h-G9NC(null), at a dose of 1 to 30 µg/ml (10 µl). The cells were then incubated for 24 hr (37° C., 5% $CO_2$). Twenty four hours later, the cells were washed once with 200 µl of PBS(−), suspended in Annexin v Binding Buffer (BD PharMingen), admixed with Annexin V-PE (BD PharMingen) and 7-amino-actinomycin D, incubated at room temperature for 15 min in the dark, and then subjected to analysis with FACS calibur (Becton, Dickinson).
(2) Apoptosis of B16/F10 Cell
A suspension of B16/F10 in RPMI (SIGMA) containing 10% FBS (JRH) was placed into a 96-well plate (FALCON) at $4\times10^4$ cells/90 µl, and then incubated for 24 hr (37° C., 5% $CO_2$). Thereafter, modified galectin 9 mutein, h-G9NC(null), was added to make the final concentration 1 to 30 µg/ml, and the cells were incubated for 24 hr. After the incubation for 24 hr, the cells were washed once with 200 µl of PBS (−), treated with 0.05% Trypsin EDTA (GIBCO), then washed once with a culture medium, followed by washing with PBS(−). Thereafter, the cells were suspended in Annexin V Binding Buffer (BD PharMingen), admixed with Annexin V-PE (BD PharMingen) and 7-amino-actinomycin, incubated at room temperature for 15 min in the dark, and then subjected to analysis with FACS calibur (Becton, Dickinson).
[Results]
The results are shown in FIGS. 22 and 23. FIG. 22 shows analysis results for modified galectin 9 mutein (h-G9NC (null))-mediated induction of apoptosis in Meth A cells. FIG. 23 shows analysis results for modified galectin 9 mutein (h-G9NC(null))-mediated induction of apoptosis in B16/F10 cells.

Example 16

Anti-Tumor (Antineoplastic) Efficacy of Modified Galectin 9 Mutein in Model of Cancerous Peritonitis

[Protocol]
(1) Meth A Cell: A cell suspension ($5\times10^5$ cells/100 µL) of Meth A cells in PBS(−) was inoculated into BALB/c mice (SLC, 6-week-old female, n=3) intraperitoneally (i.p.).

Figure 24:
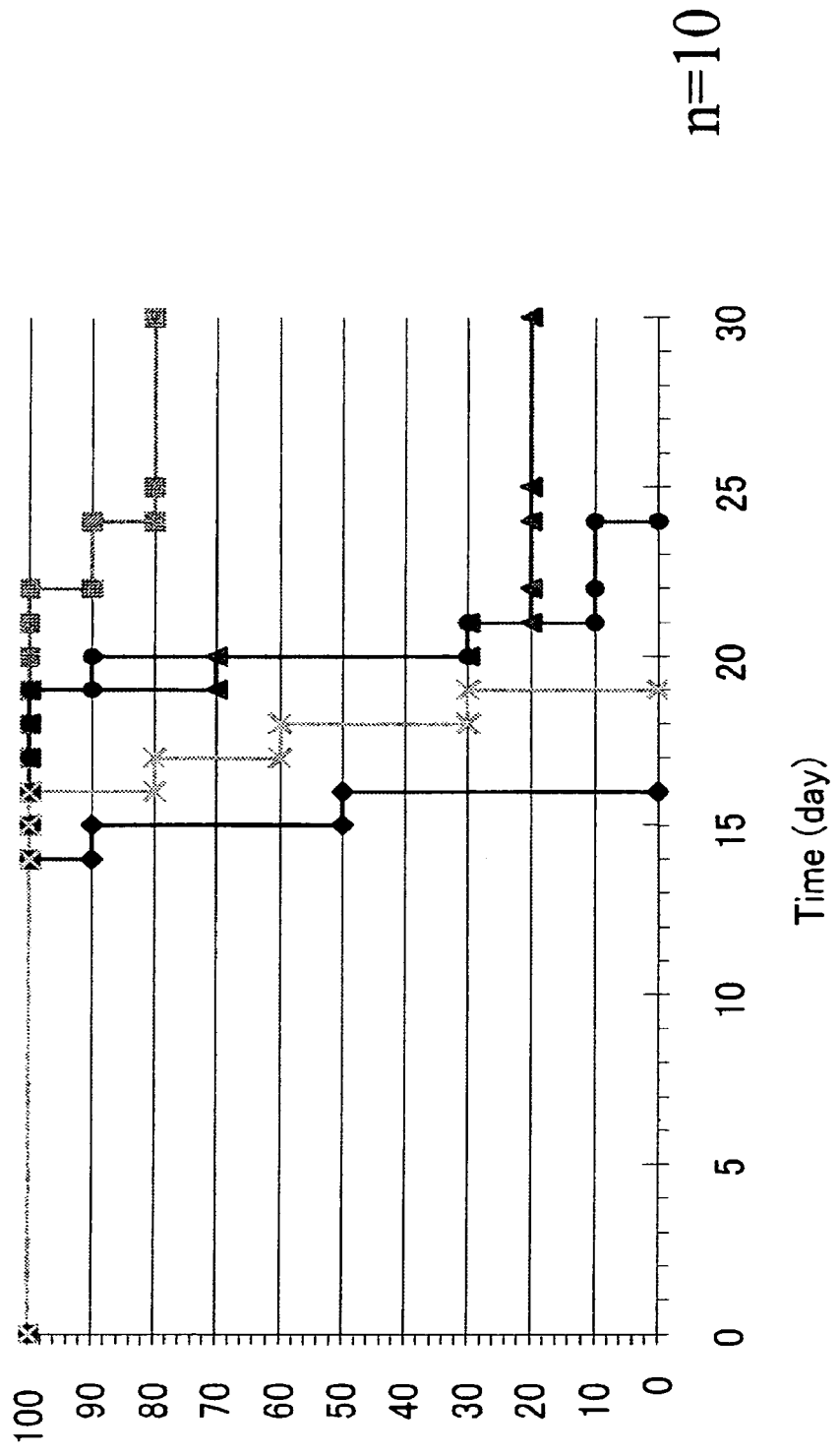
FIG. 24 is a graph of animal survival curves showing that modified galectin 9 mutein has anti-tumor efficacy in the model of cancerous peritonitis, induced by Meth A cells.
Figure 26:
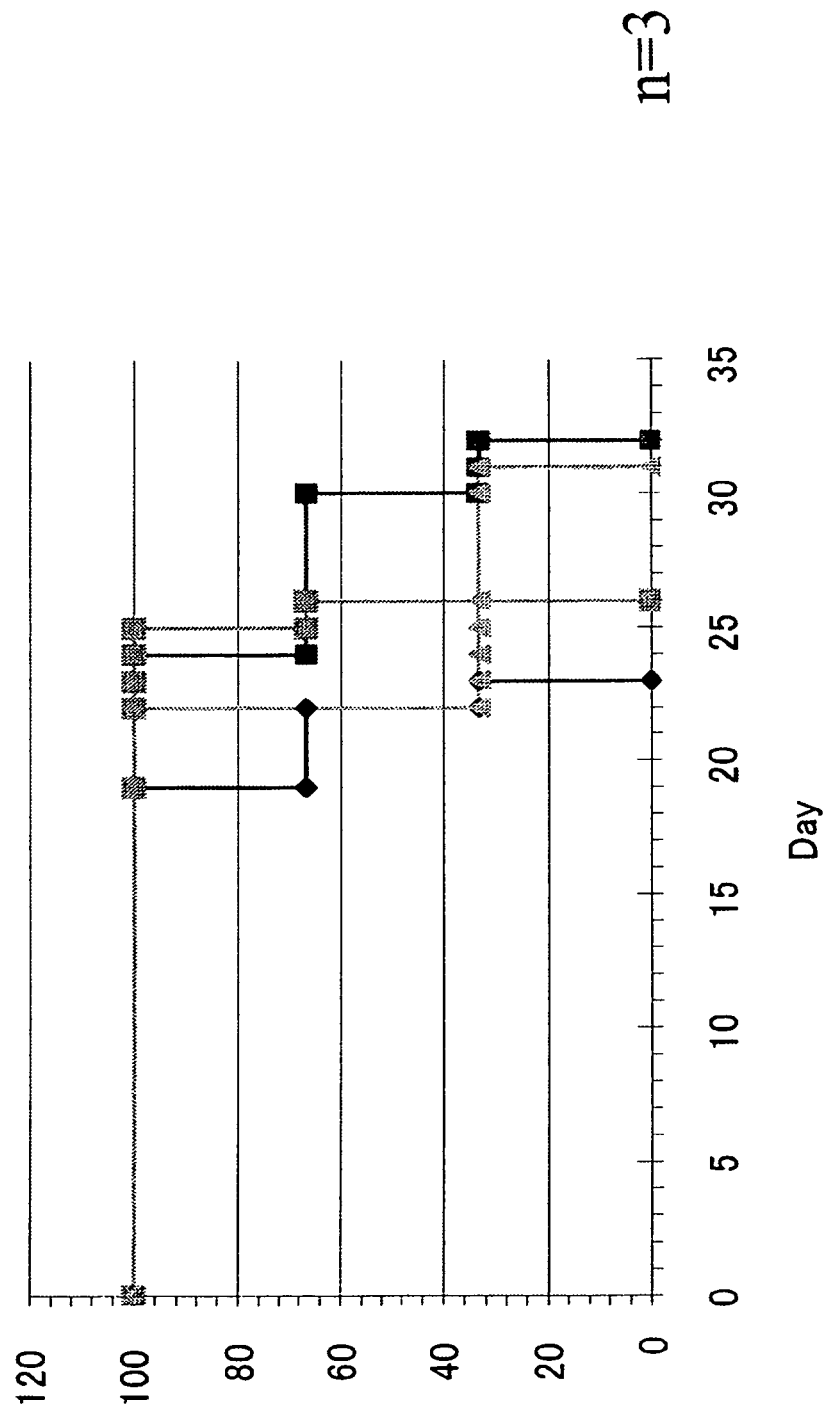
FIG. 26 is a graph of animal survival curves showing that modified galectin 9 mutein has anti-tumor efficacy in the model of cancerous peritonitis, induced by B16/F10 cells.
Figure 27:
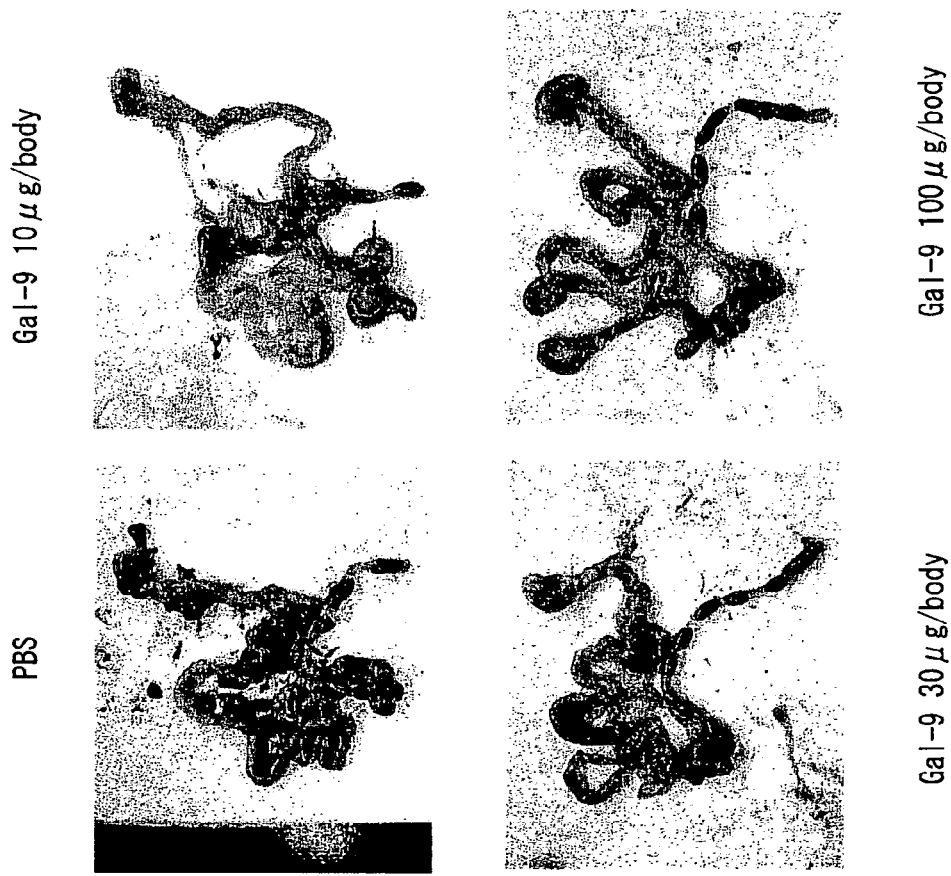
FIG. 27 shows internal organ tissue (Day 14) photos wherein the animal states of modified galectin 9 mutein (Gal-9)-administered groups are compared to those of non-administered groups in the model of cancerous peritonitis, induced by B16/F10 cells (melanoma).
Figure 48:
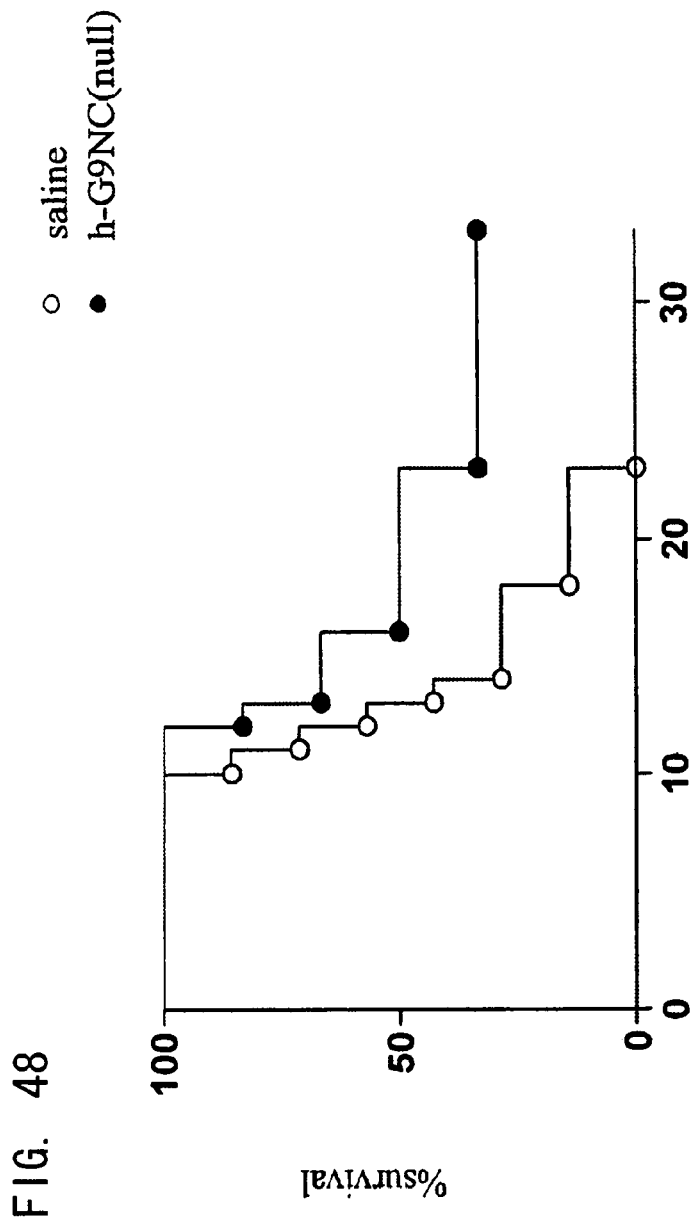
FIG. 48 is a graph showing animal survival curves. It is revealed that modified galectin 9 muteins have anti-tumor efficacy on the model of cancerous peritonitis, induced by LLC cells (apoptosis (+)).

Modified galectin 9 mutein (h-G9NC(null), 100 µg/300 µL) was administered i.p. every day through Day 18 after cell inoculation. Animals were divided into four groups (n=10), depending on initiation time of administration, i.e., 1) immediately, 2) on Day 3, 3) on Day 7, and 4) on Day 10 after Meth A cell inoculation, and survival proportions compared.
(2) B16/F10 Cell: Cells ($5\times10^5$ cells/100 µL) were inoculated i.p. into C57/BL6 mice (SLC, 6-week-old female). Immediately after inoculation, each concentration of modified galectin 9 mutein (h-G9NC(null); 10, 30, and 100 µg/300 µL) was administered i.p. every day for 14 days. Survival rates were compared. On Day 14 after inoculation, organs were examined.
[Results]
The results are shown in FIGS. 24 to 27 and 48. FIG. 24 shows survival curves indicating that modified galectin 9 mutein has antitumor activity against the model of cancerous peritonitis, induced by Meth A cells. FIG. 25: photos showing each state of mice, modified galectin 9 mutein (Gal9) non-administered group (upper) and Gal9 administered group (lower). FIG. 26 shows survival curves indicating that modified galectin 9 mutein has antitumor activity against the model of cancerous peritonitis, induced by B16/F10 cells. FIG. 27: photos showing each internal organ tissue state of model mice with cancerous peritonitis, induced by B16/F10 cells as compared between modified galectin 9 mutein (Gal-9)-administered and non-administered groups. FIG. 48 is a graph for survival curves when mice inoculated i.p. with LLC cells ($1\times10^6$ cells) received modified galectin 9 mutein (h-G9NC(null), 100 µg/mouse), or vehicle, i.p. every day (administered every day from Day 0, each group consisting of 7 mice). In the mouse model of cancerous peritonitis (Meth A, B16/F10 cell, LLC cell), the efficacy of keeping animals alive is found when G9NC(null) is administered i.p. (administered contemporaneously with and after cancer cell inoculation). Meth A and LLC cells are cells wherein apoptosis can be induced by modified galectin 9 mutein. However, apoptosis in B16/F10 cells is non-inducible with modified galectin 9 mutein. For B16/F10 cells, it is clarified that modified galectin 9 mutein inhibits the binding of cancer cells with extracellular matrices in a dose-dependent fashion. Further, in the model of cancerous peritonitis, induced by B16/F10 cells, the number of peritoneal fluid NK and NKT cells was increased in G9NC(null)-administered groups as compared to control groups. Although B16/F10 melanoma cells are resistant to stabilized galectin 9-mediated apoptosis, survival proportion relief and inhibition of melanoma cell adhesion on the abdominal wall can be observed. It has been suggested that the modified galectin 9 mutein-mediated anti-tumor efficacy in the model of cancerous peritonitis may be associated with inhibition of tumor cell adhesion on an extracellular matrix, i.e., the efficacy of inhibiting inflammatory cell infiltration, and immune-cells including NK, NKT cells, and others.

Example 17

Infiltrated Intra-Abdominal B16/F10 Cell Analysis

[Protocol]
A suspension ($5\times10^5$ cells/200 µl) of B16/F10 cells in PBS(−) was inoculated into the abdominal cavity of each C57/BL6 mouse (SCL), together with an i.p. contemporaneous administration of modified galectin 9 mutein (h-G9NC (null)) at a dose of 30 µg/300 µl. Twenty four hours later, peritoneal cells were collected, and suspended in PBS(−). The cell suspension was incubated with purified anti-mouse CD16/CD32 (2.4G2; BD PharMingen) at 4° C. for 5 min, and then with an antibody selected from PE anti-mouse CD122 (TM-(3-1; BD PharMingen), FITC anti-mouse TCR β-chain (H57-597; BD PharMingen), PE anti-mouse CD11b (M1/70; BD PharMingen), APC-labeled anti-mouse CD11c (HL3; BD PharMingen), APC anti-mouse CD8a (BD PharMingen), FITC anti-mouse CD4 (BD PharMingen), at 4° C. for 30 min, and analyzed with an FACS calibur (Becton, Dickinson).

[Results]

Figure 28:
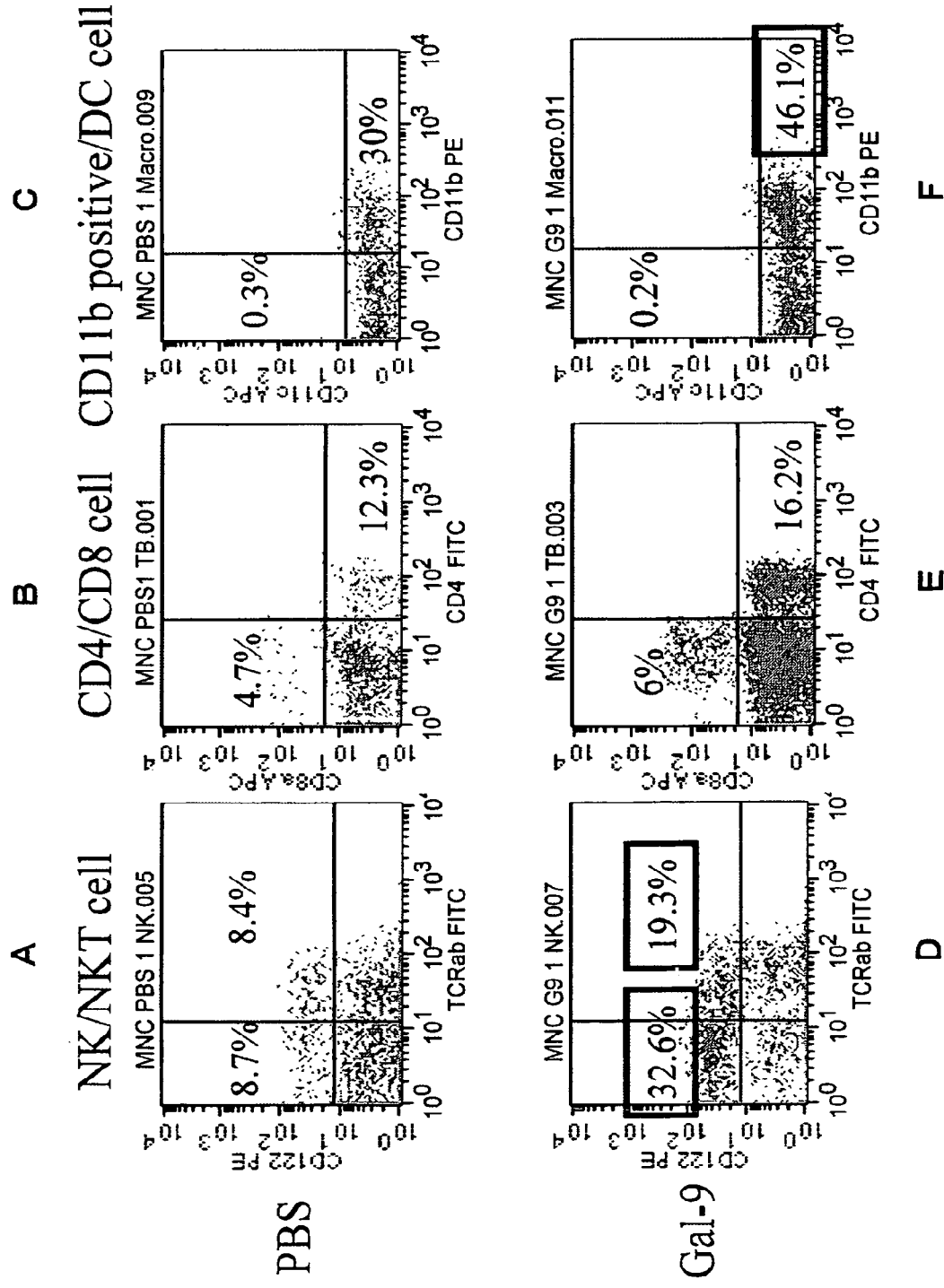
FIG. 28 shows infiltrated intra-abdominal B16/F10 cell analysis results from examinations of modified galectin 9 mutein (Gal-9)-mediated actions in immune cells.

The results are shown in FIG. 28. As compared to PBS-administered groups, immune-related cells such as NK/NKT cells are recognized to be mobilized into an abdominal lavage fluid among modified galectin 9 mutein-administered groups (30 μg).

Example 18

Modified Galectin 9 Mutein Mediated Activity of Inhibiting B16/F10 Cell Adhesion

[Protocol]

To a 96 well plate (CHEMICON) coated with collagen type I, IV, laminin, fibronectin, and vitronectin, respectively, was dispensed modified galectin 9 mutein, h-G9NC(null), at 10 μl to make the final concentration 1 to 30 μg/ml. On the plate was seeded a cell suspension of B16/F10 cells in RPMI (SIGMA) containing 0.02% BSA (Wako) at $4 \times 10^4$ cells/well (90 μl), and incubated for 1 hr (37° C., 5% $CO_2$). One hour later, a supernatant was removed. Then, each well was washed with 200 μl of PBS(-) twice, admixed with 90 μl of RPMI containing 0.02% BSA and 10 μl of WST-1 (Roche), and incubated for 2 to 3 hr. Lastly, each absorbance (OD) at 450 to 600 was measured with a plate reader. Adherence (%) is calculated:

Adherence (%)=[(Test Sample OD−Blank/(Negative Control OD−Blank))×100

[Results]

Figure 29:
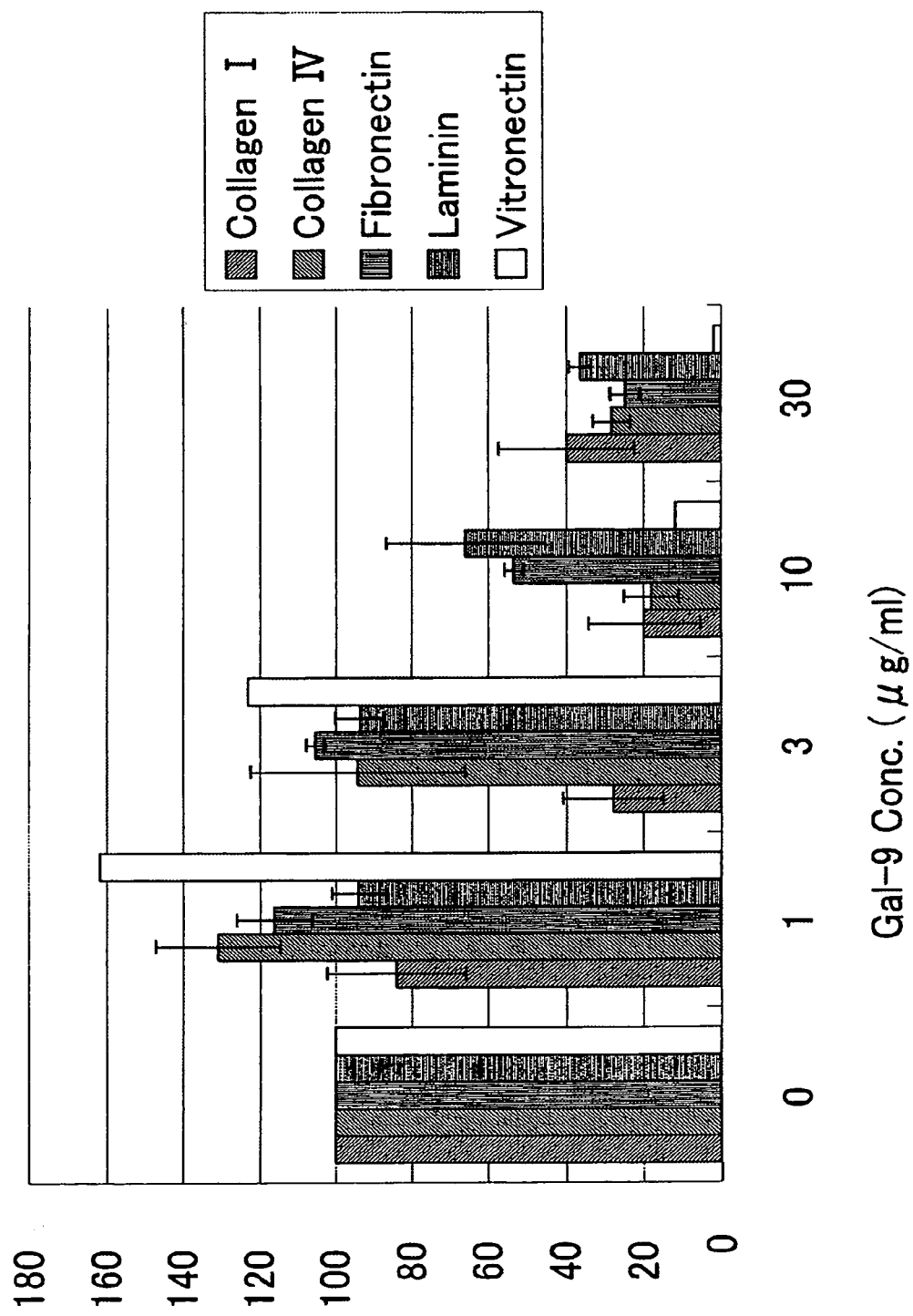
FIG. 29 shows assay results for modified galectin 9 mutein (Gal-9)-mediated inhibition of cell adhesion (B16/F10 cell, 1 h). In the drawing, Collagen I indicates collagen type I; Collagen IV, collagen type IV; Laminin, laminin; Fibronectin, fibronectin; and Vitronectin, vitronectin.

The results are shown in FIG. 29. The binding of B16/F10 cells with each extracellular matrix (collagen type I, collagen type IV, laminin, fibronectin, and vitronectin) was inhibited by modified galectin 9 mutein (in the drawing, written as Gal-9). The inhibitory action was observed to be modified galectin 9 mutein dose-dependent.

Next, modified galectin 9 mutein's bioactivity on inflammation was examined. The inflammation used herein in order to examine modified galectin 9 mutein's bioactivity includes bronchial asthma, classified into an inflammatory disease form of I type; autoimmune hemolytic anemia, classified into an inflammatory disease form of II type; Arthus reaction (angiitis), classified into an inflammatory disease form of III type.

Example 19

Allergen (Der f)-Induced AHR Model

[Protocol]

Dexamethasone (dexamethasone 21-phosphate disodium salt, Sigma, Mo., USA), methacholine (MCh, Sigma, Mo., USA) and Allergenic Extract mixed Insects MITE (*D. Farinae*; Der f)) were obtained from each supplier indicated. For administration to animals, compounds were suspended in PBS(-), which was used as the vehicle in all experiments.

Balb/c mice (7-week-old) were purchased from SLC (Shizuoka, Japan). Animals were kept under standard conditions in a 12 h day/night rhythm with free access to food and water ad libitum. All animals received humane care in accordance with international guidelines and national law.

Induction of asthmatic hypersensitive response (AHR) in mice was conducted as follows: In order to induce airway hypersensitivity to methacholine and eosinophil infiltration into murine airway tissue, male mice were sensitized and later challenged with the above-described mite antigen (Der f) as the allergen. Mice were immunized by intranasal (i.n.) administrations of 0.05 ml of Der f (0.5 mg/ml) on days 0, 7 and 20, and then challenged with 1% aerosolized Der f for 30 min using a nebulizer. The control group received i.n. administrations of normal PBS (0.05 ml) on days 0, 7 and 20, and then challenged with PBS for 30 min using a nebulizer.

To study the effect of modified galectin 9 mutein, h-G9NC (null), and dexamethasone, mice received i.p. injections of modified galectin 9 mutein, h-G9NC(null) (100 μg/410 μl (in PBS)/body), or dexamethasone (3 mg/200 μl (in PBS)/kg (body weight)) before and after Der f challenge.

Bronchioalveolar lavage (BAL) fluid samples were collected from each animal. The total pulmonary airflow in unrestrained conscious mice was estimated with an unrestrained whole body plethysmograph (PULMOS-I; M.I.P.S, Osaka, Japan). Pressure differences between a chamber containing the mice and a reference chamber were used to extrapolate minute volume, tidal volume, breathing frequency, and specific airway resistance (sRAW). Specific airway resistance is a dimensionless parameter that is a function of total pulmonary airflow in mice during the respiratory cycle. Mice were challenged with aerosolized PBS (for the baseline measurement) or MCh (6 to 25 mg/ml) for 2 min. Readings were taken and averaged for 100 times of breaths after each nebulization. Suspension cells were stained with Turk's solution, and counted with a hemocytometer to determine each cell number (cells/ml). Next, cytospin preparations were made to determine cell differentials with Giemsa-May-Grünwald solution via identification of morphological characterization. On each slide, 200 to 500 leukocytes were counted.

[Results]

Figure 30:
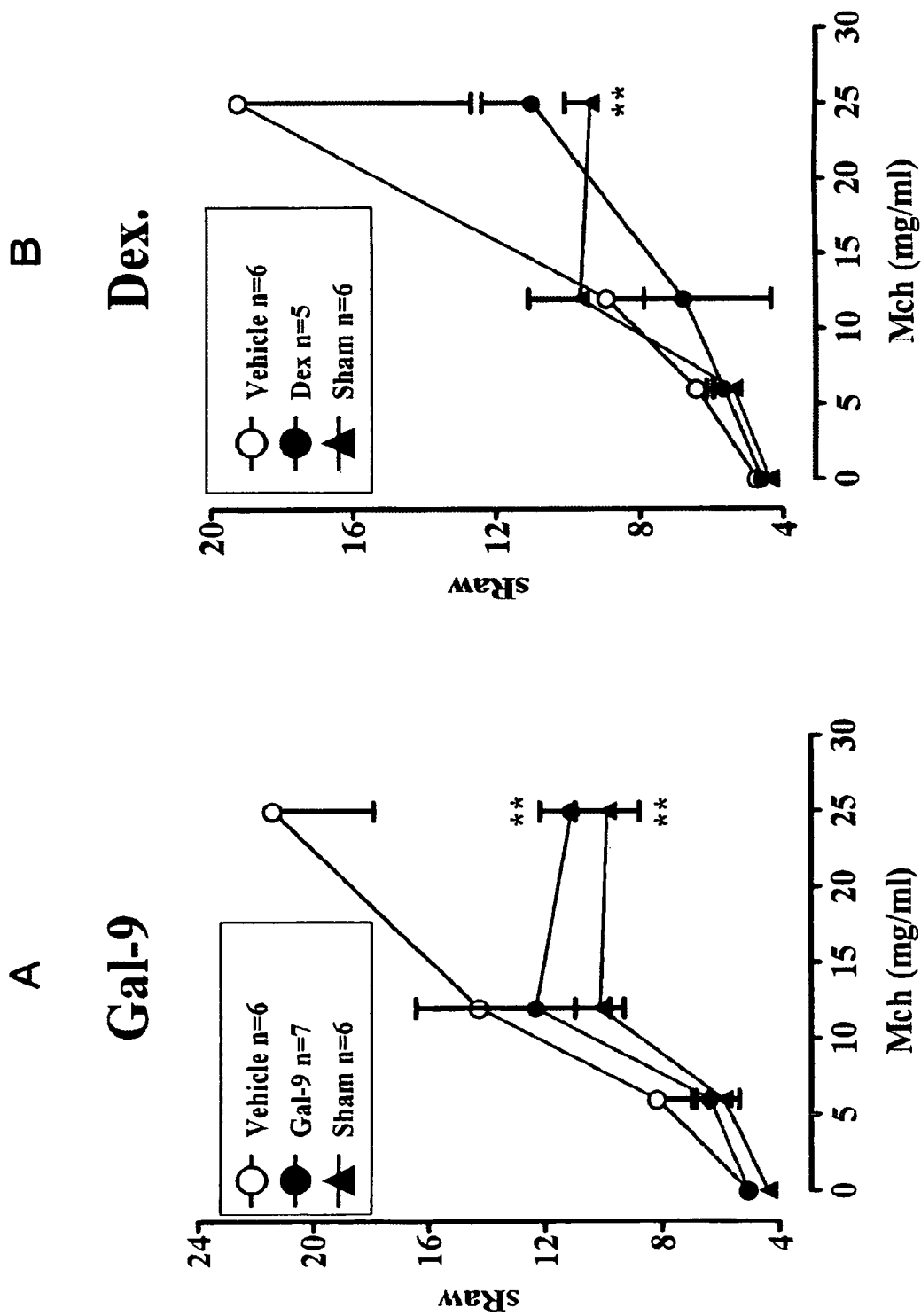
FIG. 30 shows graphs of assay results for actions of modified galectin 9 mutein (Gal-9) and dexamethasone (Dex.) on the model of mite antigen-induced asthma.
Figure 32:
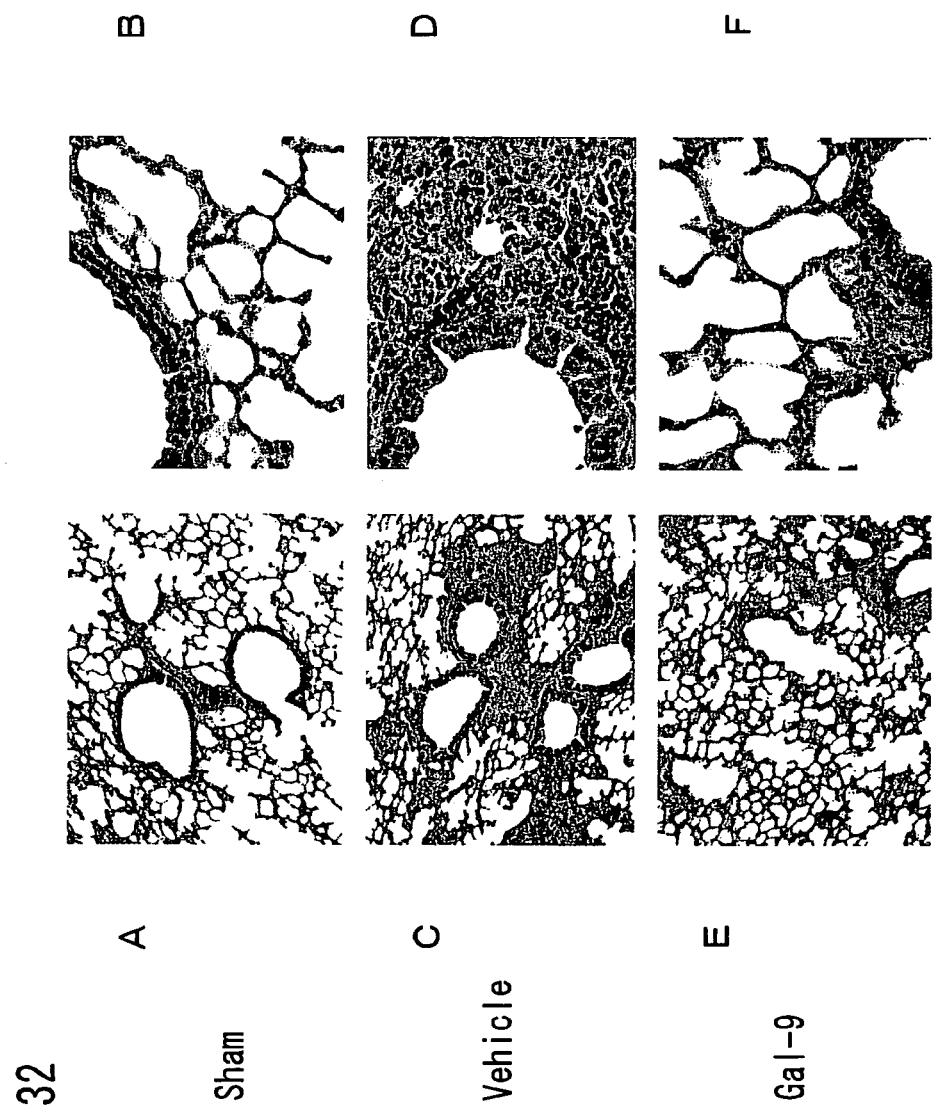
FIG. 32 shows bronchial tube surrounding tissue photos for assay results for actions of modified galectin 9 mutein (Gal-9) on the model of mite antigen-induced asthma.

The results are shown in FIGS. 30, 31 and 32. In the drawings, each value represents the mean±S.E. of 7 animals. Statistical differences were analyzed using one-way ANOVA, and differences between groups were assessed using Dunnett's Multiple Comparison Test (*p<0.05, p<0.01, *p<0.001). From FIG. 30, it is revealed that the administration of h-G9NC(null) [Gal-9] leads to relief for enhanced airway hyperresponsiveness. From FIG. 31, it is apparent that eosinophil infiltration in BALF is inhibited when h-G9NC (null) [Gal-9] is administered. From FIG. 32, it is clear that h-G9NC(null) [Gal-9] administration inhibits the infiltration of inflammatory cells into surroundings of bronchial tubes. Thus, it is suggested that galectin 9 inhibits infiltration of inflammatory cells into airways whereby airway hypersensitivity will be ameliorated.

Example 20

OVA-Induced AHR Model)

[Protocol]

The animals used were mice and guinea pigs. Ovalbumin (OVA, Sigma, Mo., USA), metopyrone (Sigma, Mo., USA), and mepyramine (Sigma, Mo., USA) were obtained from the supplier indicated. The rest of compounds was obtained in the same manner as in Example 19. For administration to animals, compounds were suspended in PBS(-), which was used as the vehicle in all experiments. Balb/c mice (7-week-old) were purchased from SLC (Shizuoka, Japan), and guinea pigs (5-week-old) from Kudou Co. Ltd (Kumamoto, Japan). Animals were kept in the same manner as in Example 19. Induction of AHR in mice was conducted as follows:

In order to induce airway hypersensitivity to methacholine and eosinophil infiltration into murine airway tissue, male mice were sensitized and later challenged with the above-described OVA as the allergen. Mice were immunized by i.p. administrations of 0.2 ml of aluminum potassium sulfate-complexed OVA (0.5 mg/ml) on days 0 and 14. On days 14, 18 and 22, mice were anesthetized with 0.2 to 0.3 ml of pentobarbital dilution (5.0 mg/ml) in normal saline. All the OVA-sensitized groups received i.n. 0.05 ml of 2.0 mg/ml OVA in normal saline on days 14, 18 and 22. The control group of animals received i.p. normal PBS in admixture with aluminum potassium sulfate on days 0 and 14, and next i.n. 0.05 ml of normal PBS on days 14, 18 and 22.

To study the effect of modified galectin 9 mutein, h-G9NC (null), and dexamethasone, mice received i.p. injections of modified galectin 9 mutein, h-G9NC(null) (100 μg/410 μl (in PBS)/body), or dexamethasone (3 mg/200 μl (in PBS)/kg (body weight)), on days 0, 7, 14, 15, 16, 17, 18, 19, 20, 21, and 22 before and after OVA challenge.

BAL fluid samples were collected from each animal. The total pulmonary airflow in unrestrained conscious mice was estimated with a whole body barometric plethysmograph (Buxco Electronics, Inc., Sharon, Conn.). The apparatus yields a measure of changes in respiratory pattern known as enhanced Pause (Penh), which correlates with and can be used to monitor airway resistance. Mice were challenged with aerosolized PBS (for the baseline measurement) or MCh (3 to 50 mg/ml) for 2 min. Readings were taken and averaged for 100 times of breaths after each nebulization of MCh. Suspension cells were stained with Turk's solution, and counted with a hemocytometer to determine each cell number (cells/ml). Next, cytospin preparations were made to determine cell differentials with Giemsa-May-Grünwald solution via identification of morphological characterization. On each slide, 200 to 500 leukocytes were counted.

Induction of AHR in guinea pigs was conducted as follows:

In order to induce immediate asthmatic response (IAR) and late asthmatic response (LAR) to antigen and eosinophil infiltration into airway tissue, male guinea pigs were sensitized and later challenged with the above-described OVA as the allergen. Guinea pigs were sensitized for 10 min with an aerosol of 1% OVA in saline using an Omron NE-U17 nebulizer (Tateishi Electric Co., Tokyo, Japan) on days 0 to 7. Thirty minutes prior to the sensitization and the challenge, mepyramine (10 mg/kg) was administered to all animals in order to avoid the anaphylaxis shock.

To study the effect of modified galectin 9 mutein, h-G9NC (null), guinea pigs received an i.p. injection of modified galectin 9 mutein, h-G9NC(null), at 1 μg/4 ml (in PBS)/body before and after OVA challenge.

BAL fluid samples were collected from each animal. On day 3 after the primary sensitization, the animals were placed in a whole-body plethysmograph chamber equipped with a mouth-nose mask isolated from a body chamber (PULMOS-I; M.I.P.S, Osaka, Japan). Specific airways conductance (SGaw) was measured according to Agrawal's methods. The relationship between airflow and box volume change, which is calculated from change of box pressure, can be determined as slope in an x-y plot of box volume change and airflow. The average of slopes in five respiratory cycles was used for the calculation of SGaw. Guinea pigs received an i.p. injection of 10 mg/kg metopyrone before OVA challenge, and were challenged for 5 min with an aerosol of 2% OVA in saline at a flow rate of 3 l/min using an Omron NE-U17 nebulizer (Tateishi Electric Co., Tokyo, Japan). Then, changes in SGaw were monitored 1 min prior to and 2, 4, 5, 6, 7, 8 and 23 hours after the antigen challenge. Readings were taken and averaged for 100 times of breaths after each point. Each SGaw value was compared with that obtained before the immunochallenge, which was defined as percent change in SGaw. Suspension cells were stained with Turk's solution, and counted with a hemocytometer to determine each cell number (cells/ml). Next, cytospin preparations were made to determine cell differentials with Giemsa-May-Grünwald solution via identification of morphological characterization. On each slide, 500 leukocytes were counted.

[Results]

Figure 33:
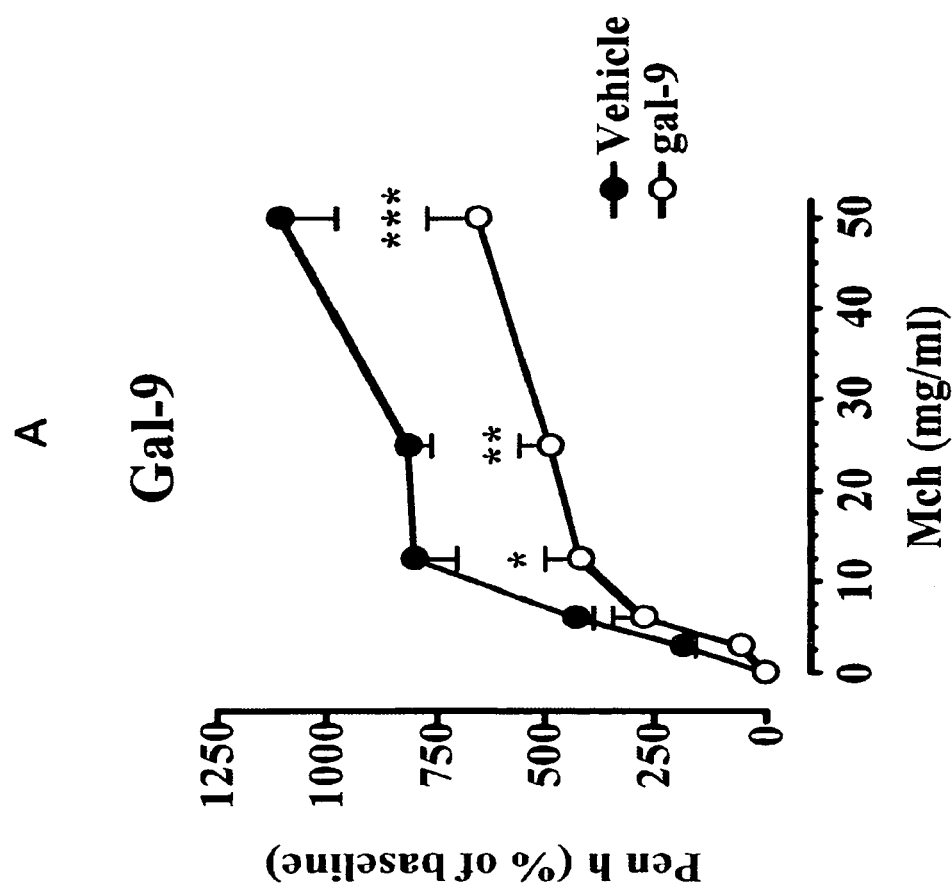
FIG. 33 shows graphs of assay results for actions of modified galectin 9 mutein (Gal-9) and dexamethasone (Dex.) on the model (mouse) of OVA-induced asthma.
Figure 34:
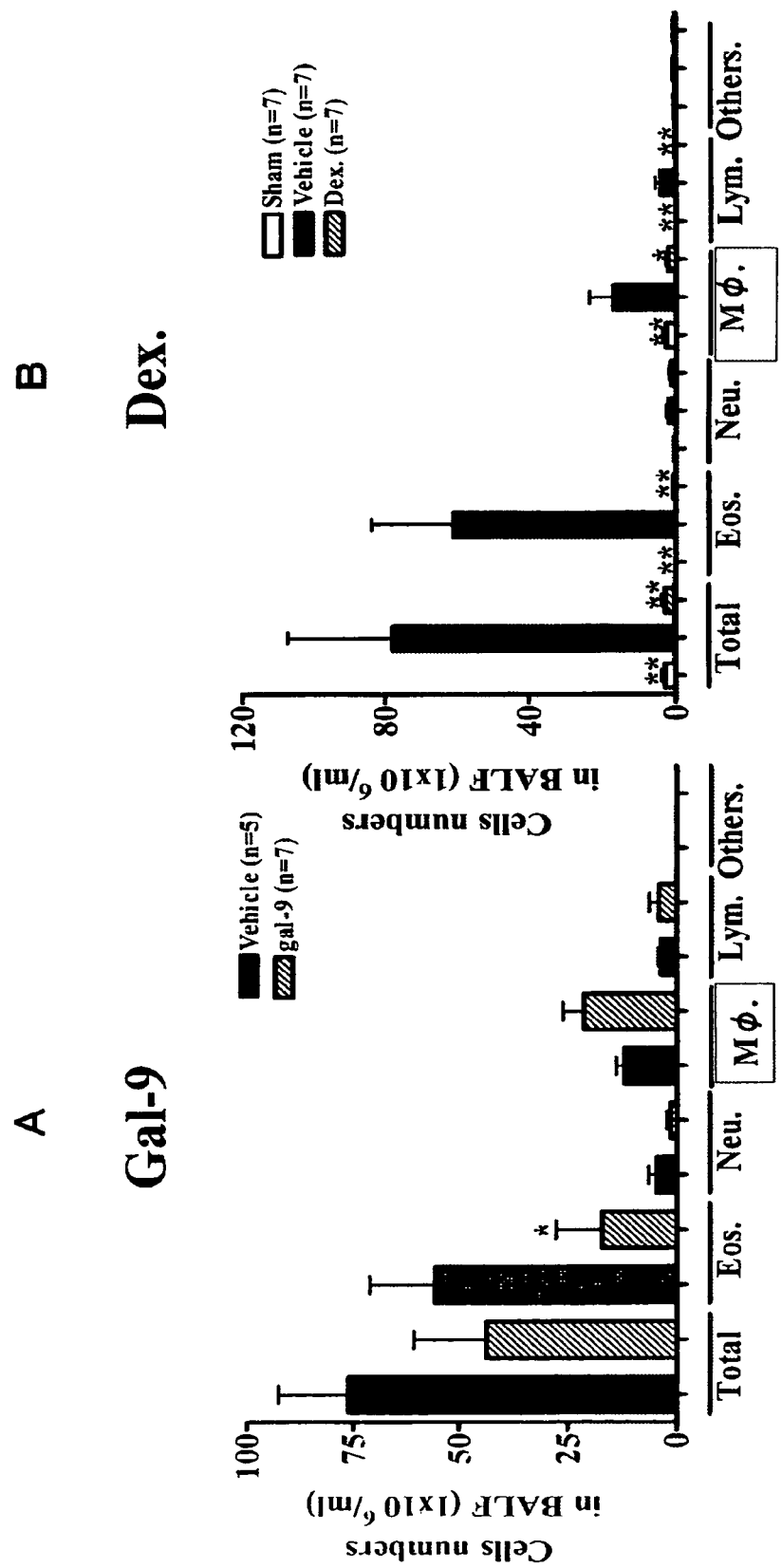
FIG. 34 shows graphs of cell numbers in BALF, assay results for actions of modified galectin 9 mutein (Gal-9) and dexamethasone (Dex.) on the model (mouse) of OVA-induced asthma.
Figure 35:
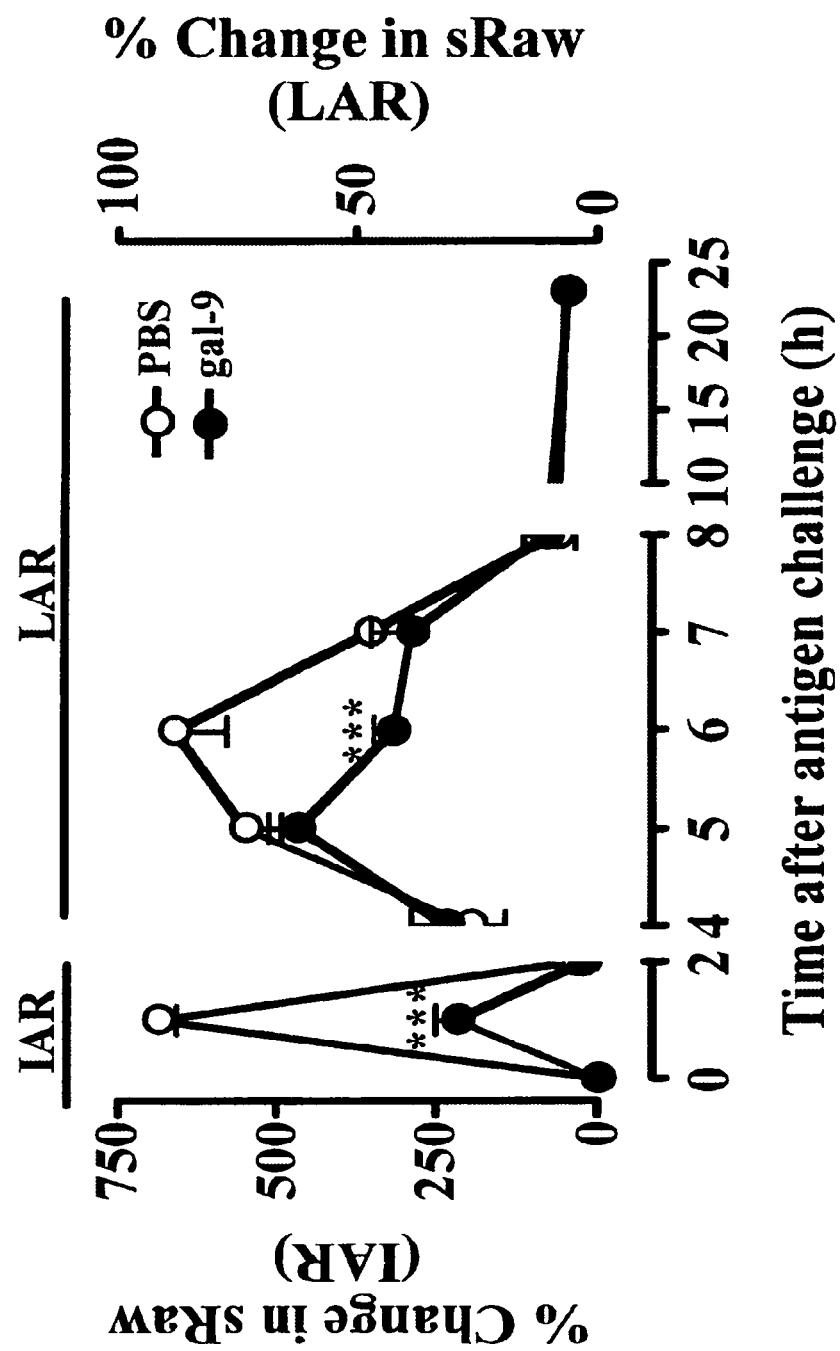
FIG. 35 is a graph showing actions of modified galectin 9 mutein (gal-9) on IAR/LAR in the model (mouse) of OVA-induced asthma.
Figure 36:
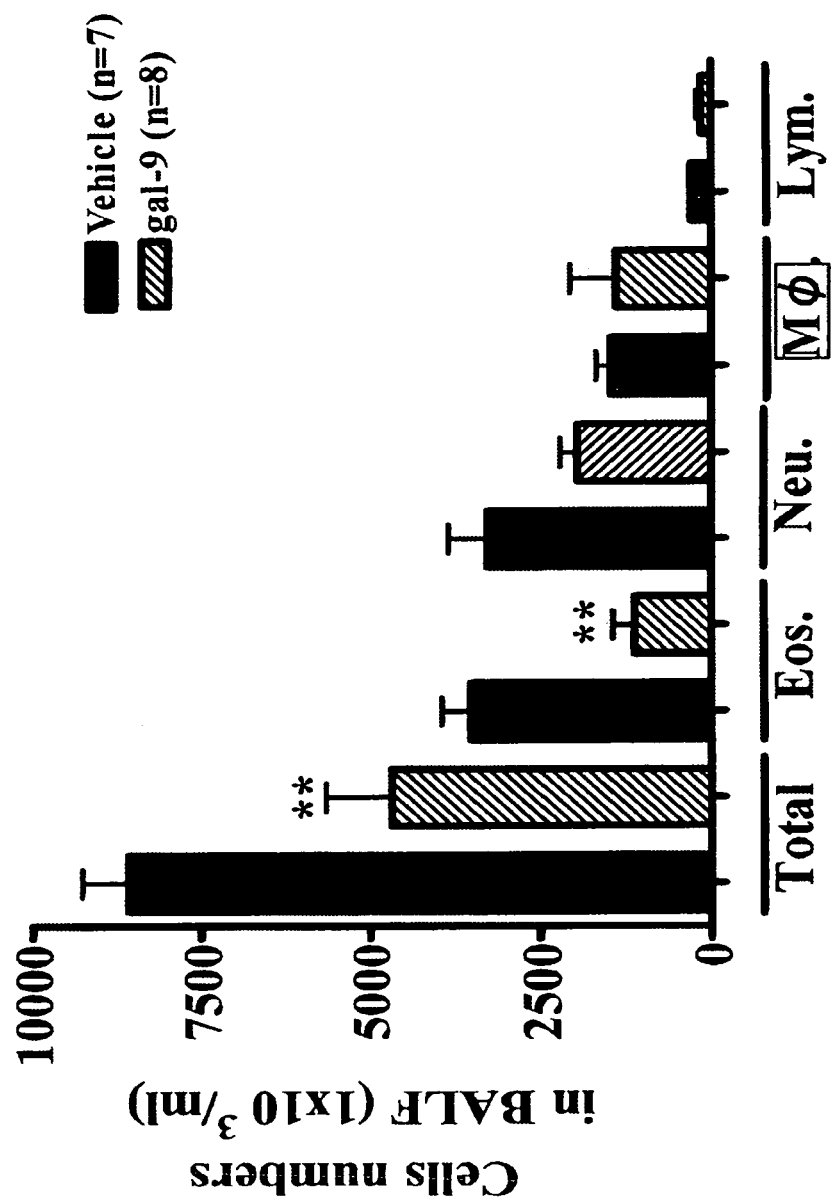
FIG. 36 is a graph showing cell numbers in BALF, assay results for actions of modified galectin 9 mutein (gal-9) on the model (mouse) of OVA-induced asthma.

The results for mice are shown in FIGS. 33 and 34. The results for mice are shown in FIGS. 35 and 36. In the drawings, each value represents the mean±S.E. of 7 animals (FIG. 33), 5 to 7 animals (FIG. 34), and 7 or 8 animals (FIGS. 35 and 36), respectively. Statistical differences were analyzed using one-way ANOVA, and differences between groups were assessed using Dunnett's Multiple Comparison Test (*p<0.05, p<0.01, *p<0.001).

FIG. 33 indicates that modified galectin 9 mutein, h-G9NC (null), relieves airway hypersensitivity. FIG. 34 indicates that modified galectin 9 mutein, h-G9NC(null), inhibits eosinophil infiltration in BALF.

FIG. 35 shows the efficacy of modified galectin 9 mutein, h-G9NC(null) on IAR/LAR. As a result, among the modified galectin 9 mutein-administered groups, a significant difference is recognized in both IAR and LAR, as compared to the control groups, that is, the inhibitory efficacy is perceivable.

FIG. 36 shows the efficacy of modified galectin 9 mutein, h-G9NC(null), on infiltration of inflammatory cells into airways. As a result, among the modified galectin 9 mutein groups, a significant difference in total cell numbers and eosinophils is found, as compared to the control groups. A tendency to inhibit the infiltration of other cells is also found.

It is suggested that it will be potential to inhibit antigen-induced immediate and late asthmatic responses and infiltration of cells into airways among actively sensitized guinea pigs when modified galectin 9 mutein is administered i.p. at a dose of 1 mg/body prior to antigen sensitization and challenge.

Example 21

Autoimmune Hemolytic Anemia (RαMRC Ab-Induced AIHA Model)

[Protocol]

Cyclophosphamide (CY, Sigma, Mo., USA), azathioprine (AZ, Sigma, Mo., USA), methotrexate (MTX, Sigma, Mo., USA), and rabbit anti-mouse red blood cell antibody (RαMRC Ab) were obtained from the supplier indicated. The rest of compounds was obtained in the same manner as in Example 19. For administration to animals, compounds were suspended in PBS(−), which was used as the vehicle (V) in all experiments. Balb/c mice (7-week-old) were purchased from SLC (Shizuoka, Japan). Animals were kept in the same manner as in Example 19.

Induction of autoimmune hemolytic anemia (AIHA) in mice was conducted as follows:

Hemolytic anemia was induced by an i.v. injection of rabbit αMRBC autoantibody in mice. Animals received an i.p. injection of modified galectin 9 mutein (h-G9NC(null)), dexamethasone, other drugs, or vehicle, at 0.345 ml/head 30 minutes before and Days 1 to 4 after rabbit αMRBC autoantibody injection.

Blood samples were collected into heparinized microhematocrit capillary tubes and centrifuged for 5 min at 12,000 rpm in a microfuge. Hematocrits measured by the percentage of packed PBCs were directly determined after centrifugation.

Statistical analysis was conducted as follows:

Unless otherwise stated, data are expressed as mean values±SEM. Statistical differences of data sets were analyzed using one-way ANOVA, and differences between groups were assessed by Dunnett's Multiple Comparison Test using commercially available statistics software (GraphPad Software, Inc., San Diego, USA). P values <0.05 were considered statistically significant.

[Results]

Figure 37:
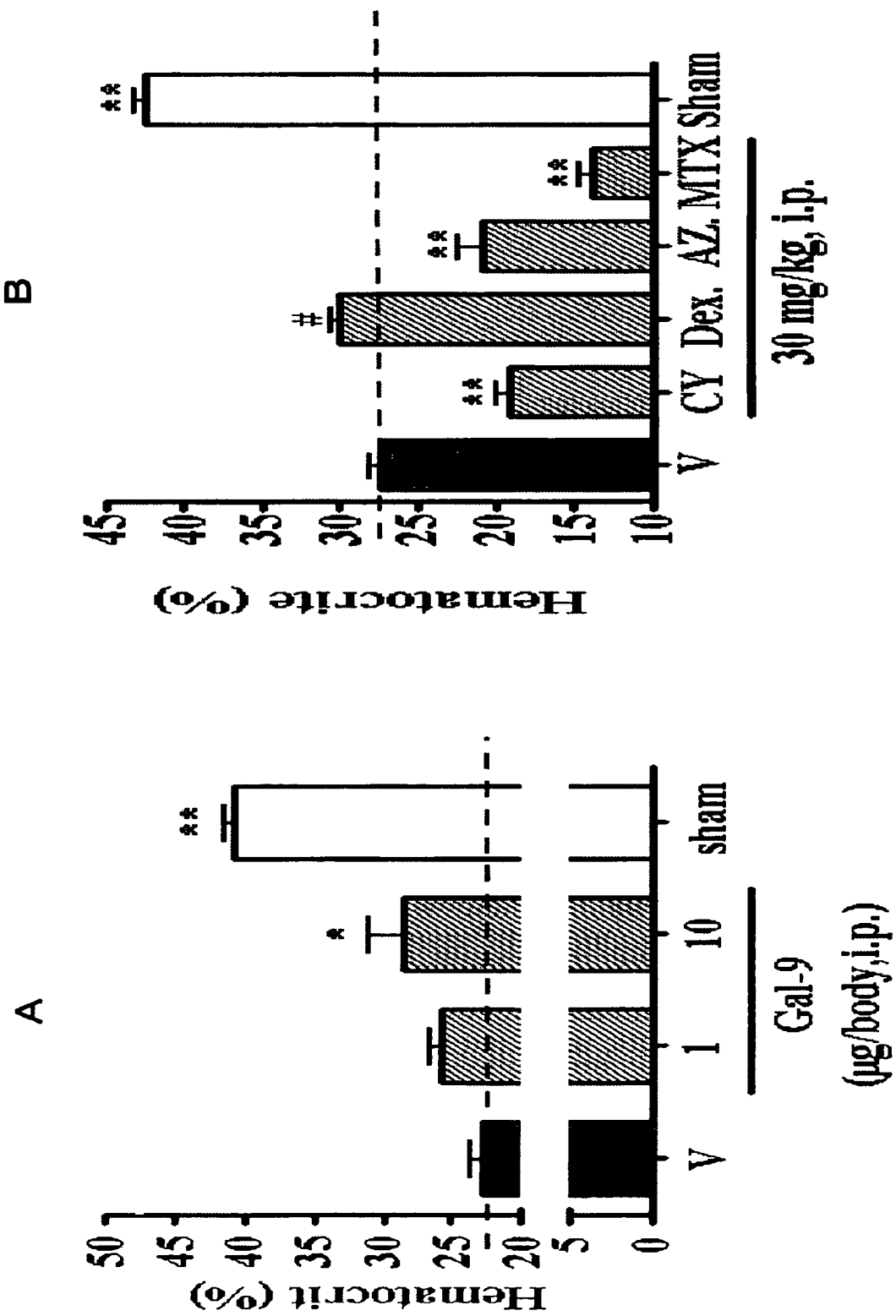
FIG. 37 shows graphs of hematocrit values (%), as assay results for actions of modified galectin 9 mutein (Gal-9) on the model (mouse) of autoimmune hemolytic anemia.

The results are shown in FIG. 37. In the modified galectin 9 mutein-administered groups, a tendency to inhibit the occurrence of diseased conditions was observed. In the drawing, each value represents the mean±SEM of 5 to 6 animals (*p<0.05, **p<0.01).

Example 22

Arthus Reaction (Angiitis)

[Protocol]

The efficacy of modified galectin 9 mutein on biphasic cutaneous reaction induced by immune complexes (Arthus reaction) was examined.

Anti-OVA IgG was obtained from the supplier indicated. The rest of compounds was obtained in the same manner as in Example 20. For administration to animals, compounds were suspended in PBS(−), which was used as the vehicle in all experiments. Balb/c mice (7-week-old) were purchased from SLC (Shizuoka, Japan). Animals were kept in the same manner as in Example 19.

Induction of ear edema in mice was conducted as follows:

In the model of biphasic cutaneous reaction, mice were sensitized by i.d. injection of anti-OVA IgG (50 µg/mouse) into each right ear, and immediately challenged by i.v. injection of 200 µl of 1% OVA in PBS. Animals received i.v. injections of modified galectin 9 mutein (h-G9NC(null)), dexamethasone, or vehicle, at 0.345 ml/head 30 minutes prior to and 5 hours after OVA injection. After OVA injection, ear thickness was measured at 0, 2, 4, 8 and 24 hours with a calibrated thickness gauge (Mitsutoyo, Tokyo, Japan) under anesthetization with ether.

Ear edema was expressed as $(R-L)-(R_0-L_0)$, where $R_0$ and $L_0$ represent the thickness of the right and left ear, respectively, at the beginning of the experiment (0 h), and R and L stand for the thickness values obtained at each given time point.

Statistical analysis was conducted as follows:

Unless otherwise stated, data are expressed as mean values±SEM. Statistical differences of data sets were analyzed using one-way ANOVA, and differences between groups were assessed by Bonferroni Post-Test using commercially available statistics software (GraphPad Software, Inc., San Diego, USA). P values <0.05 were considered statistically significant.

[Results]

Figure 38:
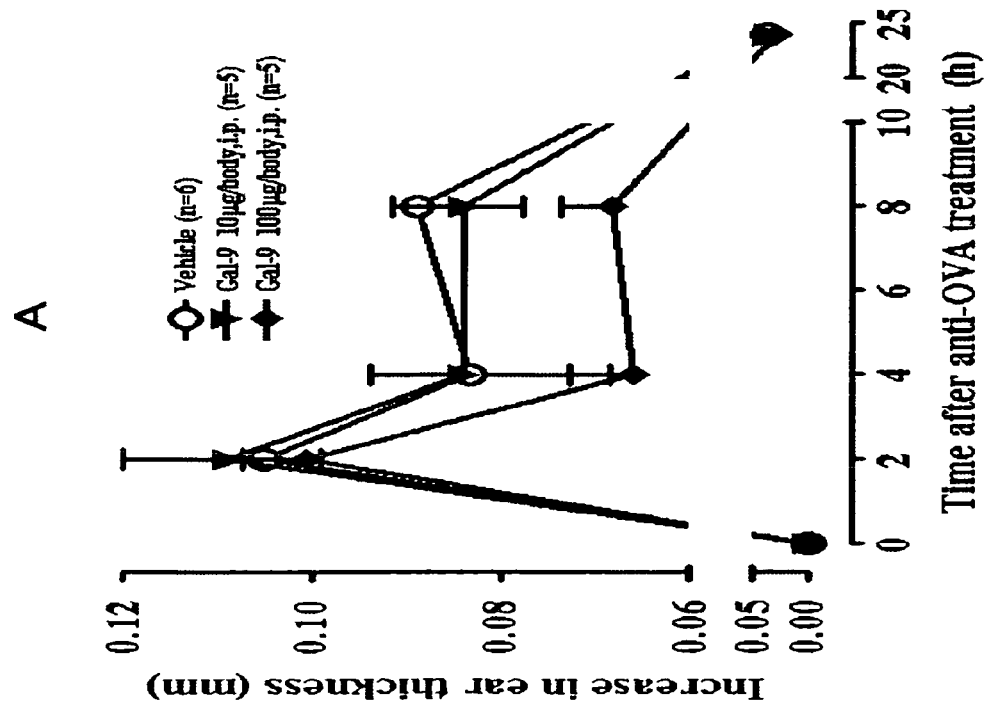
FIG. 38 shows graphs of assay results for actions of modified galectin 9 mutein (Gal-9) and dexamethasone (Dex.) on the model (mouse) of Arthus reaction (angiitis).

The results are shown in FIG. 38. In the modified galectin 9 mutein-administered groups, a tendency to inhibit the occurrence of diseased conditions was observed. In the drawing, each value represents the mean'SEM of 5 to 6 animals (*p<0.05, **p<0.01).

Example 23

ARDS Model (LPS-Induced ARDS Model)

[Protocol]

Lipopolysaccharide (LPS, Sigma, Mo., USA) was obtained from the supplier indicated. The rest of compounds was obtained in the same manner as in Example 19. For administration to animals, compounds were suspended in PBS(−), which was used as the vehicle in all experiments. Balb/c mice (7-week-old) were purchased from SLC (Shizuoka, Japan). Animals were kept in the same manner as in Example 19.

Induction of ARDS in mice was conducted as follows:

In order to induce dyspnea and neutrophil infiltration into murine airway tissue, male mice were challenged with LPS as lung injury model. Mice were received an i.n. injection of LPS (0.6 mg/ml, 0.05-ml volume). The control group received an administration of normal PBS (0.05 ml) by the same route.

To study the effect of modified galectin 9 mutein, h-G9NC (null), and dexamethasone, mice received i.p. injections of modified galectin 9 mutein, h-G9NC(null) (100 µg/410 µl (in PBS)/body), or dexamethasone (1 to 10 mg/200 µl (in PBS)/kg(body weight)) 30 minutes before and 6 hours after LPS challenge.

Mouse lung function ((Penh value and tidal volume) was analyzed by whole body barometric plethysmography (Buxco Electronics, Inc., Sharon, Conn.) and unrestrained whole body plethysmograph (PULMOS-I; M.I.P.S, Osaka, Japan) one hour prior to and 12 hours after LPS challenge.

After analysis of lung function, BAL fluid samples were collected from each animal.

The total pulmonary airflow in unrestrained conscious mice was estimated with an unrestrained whole body plethysmograph.

Pressure differences between a chamber containing the mice and a reference chamber were used to extrapolate minute volume, tidal volume, breathing frequency, Penh value, and specific airway resistance (sRAW). Specific airway resistance is a dimensionless parameter that is a function of total pulmonary airflow in mice during the respiratory cycle.

Suspension cells were stained with Turk's solution, and counted with a hemocytometer to determine each cell number (cells/ml). Next, cytospin preparations were made to determine cell differentials with Giemsa-May-Grünwald solution via identification of morphological characterization. On each slide, 200 to 500 leukocytes were counted.

Statistical analysis was conducted as follows:

Unless otherwise stated, data are expressed as mean values±SEM. Statistical differences of data sets were analyzed using one-way ANOVA or two-way ANOVA, and differences between groups were assessed by Dunnett's Multiple Comparison Test or Bonferroni Post-Test using commercially available statistics software (GraphPad Software, Inc., San Diego, USA). P values <0.05 were considered statistically significant.

[Results]

The results are shown in FIGS. 39 and 40. In the drawing, each value represents the mean±SEM of 5 to 6 animals. Statistical differences were analyzed using one-way ANOVA. Differences between groups were assessed by Dunnett's Multiple Comparison Test (*p<0.05, p<0.01, *p<0.001). FIG. 39 shows the efficacy of modified galectin 9 mutein (h-G9NC(null)) on airway hyperresponsivity where relief is observed. FIG. 40 indicates that modified galectin 9 mutein (h-G9NC(null)) inhibits neutrophil infiltration in BALF.

Example 24

Capsaicin-Induced Inflammatory Disease Model

[Protocol]

Cyproheptadine (Sigma, Mo., USA) and capsaicin (Nakarai, Tokyo, Japan) were obtained from each supplier indicated. The rest of compounds was obtained in the same manner as in Example 19. For administration to animals, compounds were suspended in PBS(−), which was used as the vehicle in all experiments. Balb/c mice (7-week-old) were purchased from SLC (Shizuoka, Japan). Animals were kept in the same manner as in Example 19.

Induction of ear edema in mice was conducted as follows:

A solution of capsaicin (500 µg) in acetone/olive oil (4/1, 30 µl) was applied to the inner and outer surface of the right ear of each mouse (BALB/c, 7 to 8 weeks old, SPF, SLC Inc.). The vehicle, acetone/olive oil, was applied to the left ear as a control.

Animals received injections of modified galectin 9 mutein (h-G9NC(null)), dexamethasone, cyproheptadine, or vehicle, (i.p., 0.345 ml/head) 30 minutes, and i.v. 10 minutes prior to capsaicin administration. After capsaicin administration, ear thickness was measured at 0, 0.5, 1 and 2 hours with a calibrated thickness gauge (Mitsutoyo, Tokyo, Japan) under anesthetization with ether.

Ear edema was expressed as $(R-L)-(R_0-L_0)$, where $R_0$ and $L_0$ represent the thickness of the right and left ear, respectively, at the beginning of the experiment (0 h), and R and L stand for the thickness values obtained at each given time point.

Statistical analysis was conducted as follows:

Unless otherwise stated, data are expressed as mean values±SEM. Statistical differences of data sets were analyzed using one-way ANOVA, and differences between groups were assessed by Bonferroni Post-Test using commercially available statistics software (GraphPad Software, Inc., San Diego, USA). P values <0.05 were considered statistically significant.

Figure 41:
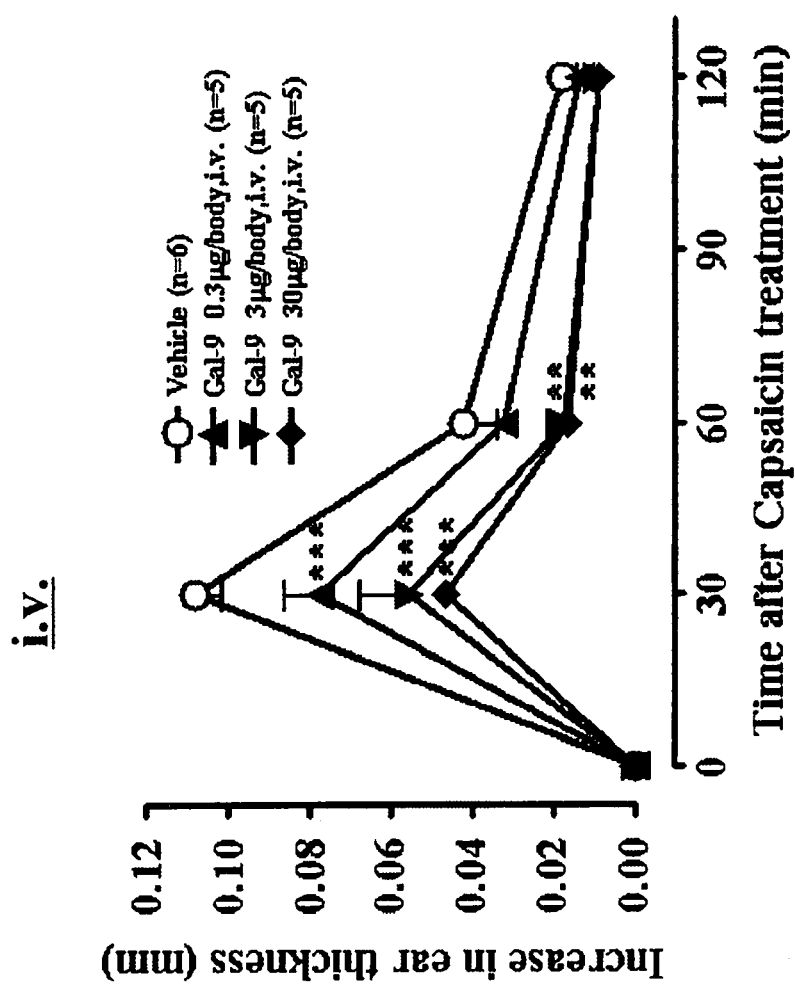
FIG. 41 is a graph showing assay results for actions of modified galectin 9 mutein (Gal-9, i.v.) on the model (mouse) of capsaicin-induced inflammation.

The results are shown in FIG. 41. Inhibition of disease occurrence is found in the modified galectin 9 mutein-administered groups (i.v. injection). In the drawing, each value represents the mean±SEM of 5 to 6 animals. Statistical differences were analyzed using two-way ANOVA. Differences between groups were assessed by Dunnett's Multiple Comparison Test (*p<0.05, p<0.01, *p<0.001). Modified galectin 9 muteins are expected to serve as inhibitors for neurogenic, inflammatory pain (including pain due to inflammation).

Example 25

Modified Galectin 9 Mutein's Action on Bone Absorption and Bone Formation

[Protocol]
1. Bone Absorption
(Osteoclast Formation)

Peripheral blood mononuclear cells (PBMC, $1\times10^5$ cells) were cultured in the presence of RANKL (50 ng/ml) and M-CSF (50 ng/ml) for 9 days. The number of TRAP-positive multinucleated cells (osteoclasts) in modified galectin 9 mutein (h-G9NC(null))-added groups (0.1 to 10 nM) was compared with that in non-added groups. H-G9NC(null) inhibited concentration-dependently the formation of TRAP-positive multinucleated cells (osteoclasts). The term "h-G9NC(null)" is also sometimes herein abbreviated to "gal-9".

Figure 42:
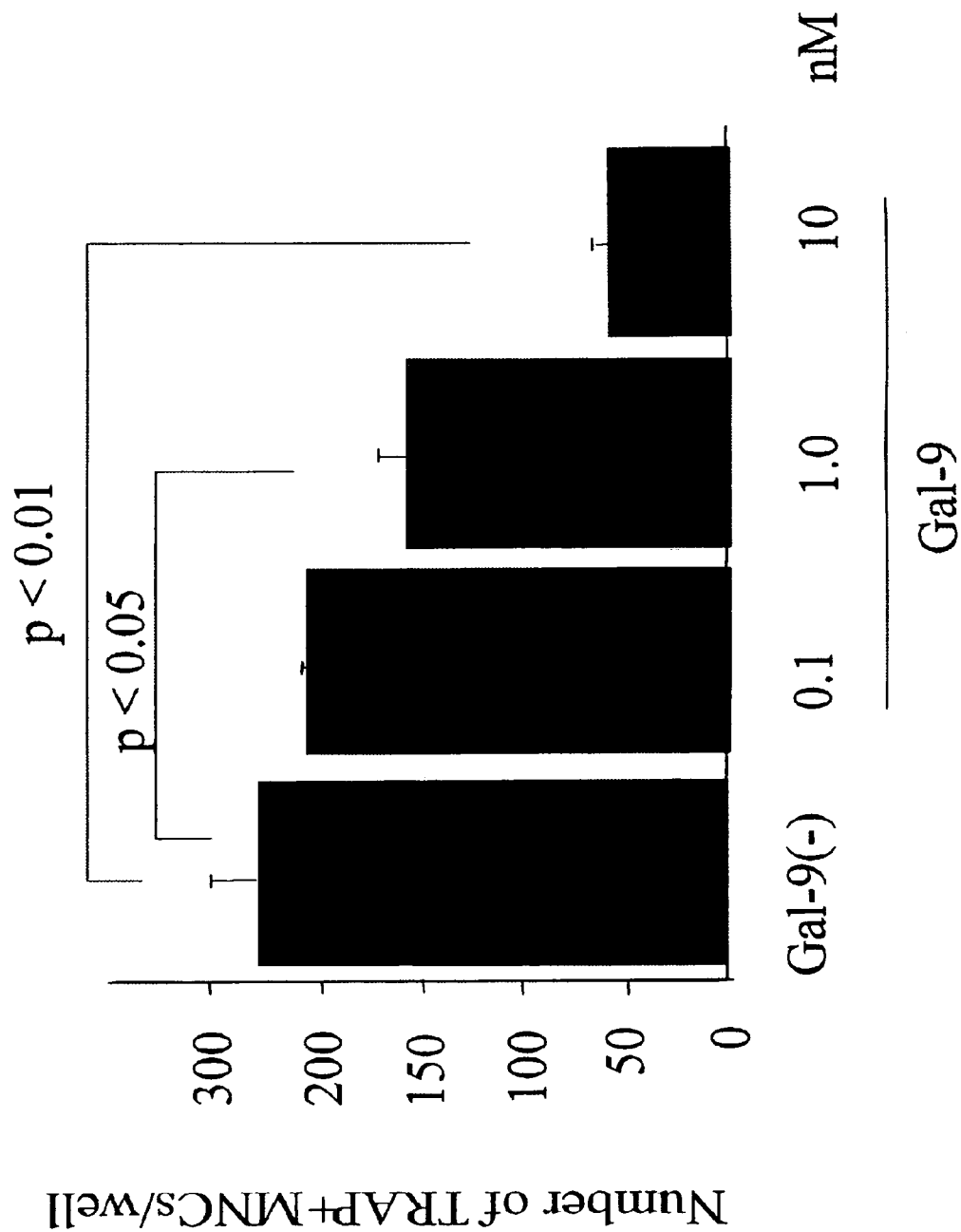
FIG. 42 is a graph showing assay results for the efficacy of modified galectin 9 mutein (Gal-9) on osteoclast formation. It is apparent that Gal-9 exerts inhibitory efficacy.
Figure 43:
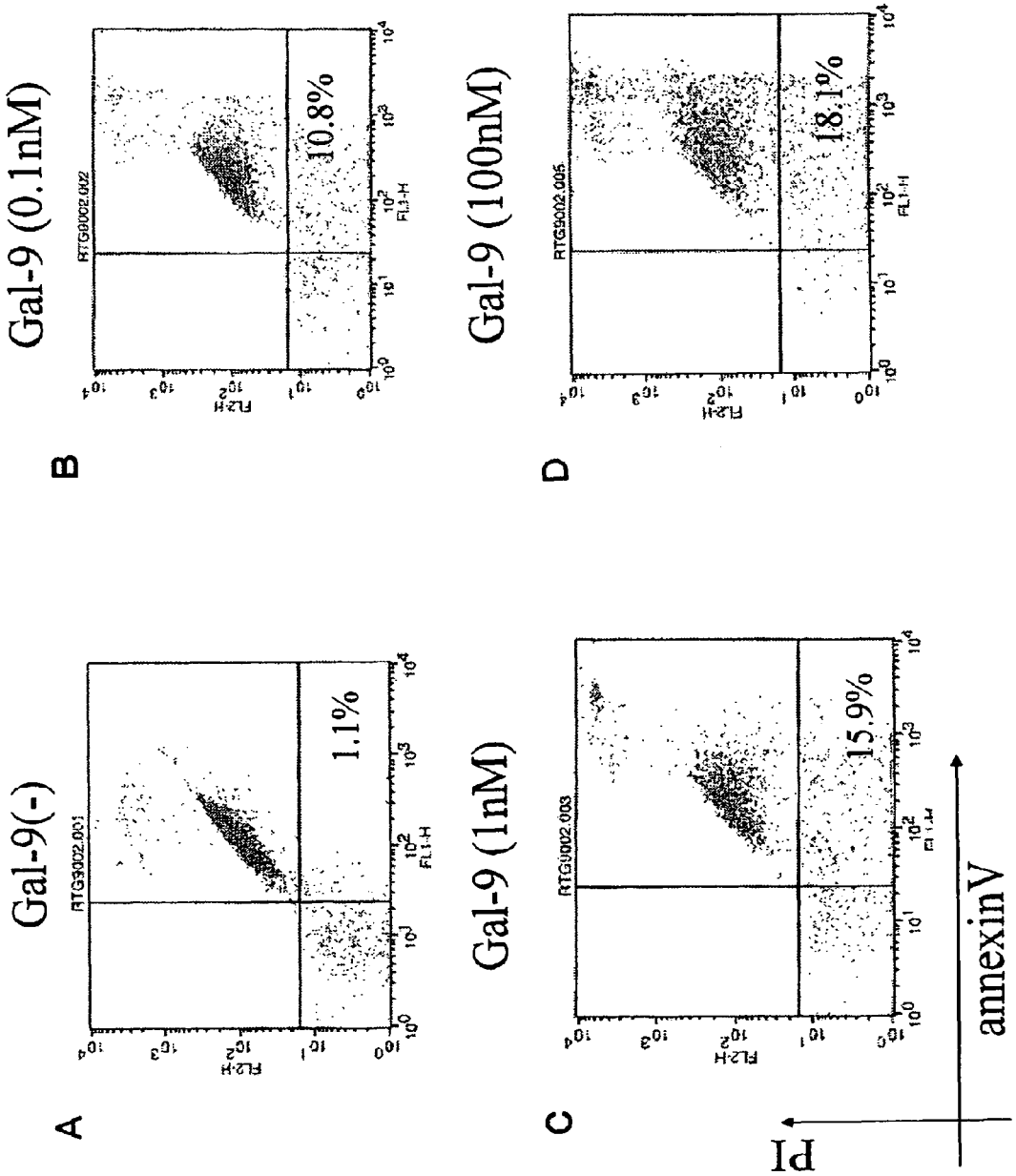
FIG. 43 shows assay results for apoptosis-induction (in the presence of CSF) of mononuclear cells by modified galectin 9 mutein (Gal-9) stimulation.

The results are shown in FIG. 42. Control group (cont.): 500±13.2 cells/well Modified Gal-9 mutein-administered groups
(h-G9NC(null), 0.1 nM): 451±7.6 cells/well,
(h-G9NC(null), 1.0 nM): 151±12.5 cells/well, and
(h-G9NC(null), 10 nM): 29±14.0 cells/well.
2. Bone Formation
(Osteoblast Proliferation)

To examine the influence of h-G9NC(null) (0.1 to 100 nM) on the proliferation of human osteoblasts, cells were seeded on a 96 well plate at $2\times10^3$ cells/well, incubated overnight, then stimulated with h-G9NC(null), and observed at 0, 24, and 48 hr. Cell proliferation was evaluated based on absorbance (OD) readings by the Tetra color-1 assay.

Figure 44:
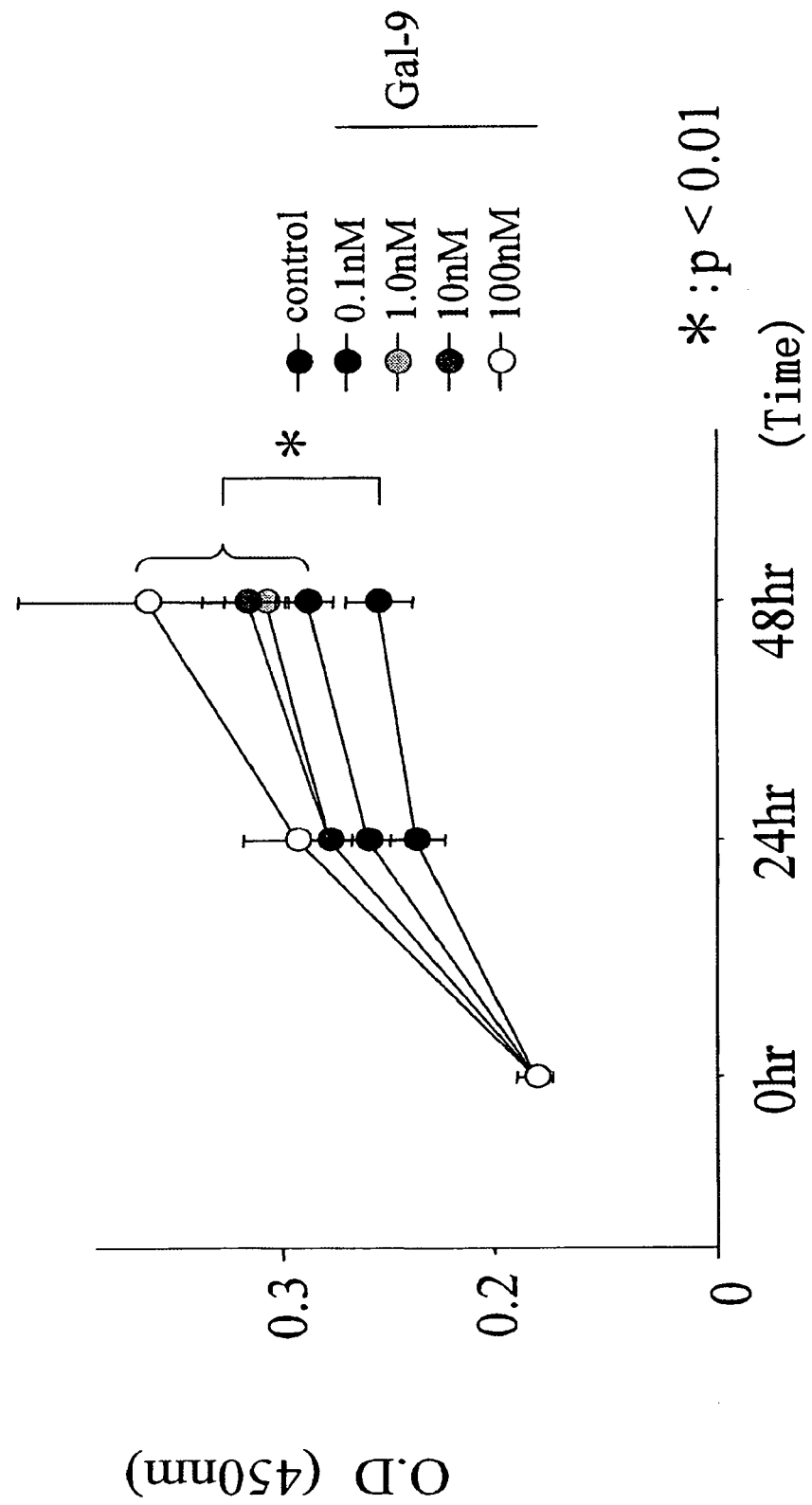
FIG. 44 is a graph showing assay results for the efficacy of modified galectin 9 mutein (Gal-9) on osteoblast proliferation.

The results are shown in FIG. 44. Modified galectin 9 muteins induced concentration-dependently osteoblast proliferation, where said induction was inhibited by lactose. Modified galectin 9 muteins induced the proliferation of osteoblasts concentration-dependently and said Gal-9 mutein-mediated induction was inhibited by lactose (30 mM).

Absorbance readings: control, 0.21±0.01; h-G9NC(null) (0.1 nM), 0.22±0.01; h-G9NC(null) (1.0 nM), 0.24±0.01; h-G9NC(null) (10 nM), 0.25±0.01; and h-G9NC(null) (100 nM), 0.26±0.02 at 24 hr;

48 hr later, control, 0.22±0.01; h-G9NC(null) (0.1 nM), 0.23±0.01; h-G9NC(null) (1.0 nM), 0.26±0.01; h-G9NC (null) (10 nM), 0.27±0.01; and h-G9NC(null) (100 nM), 0.31±0.04.

(Osteoblast Differentiation)

To examine the influence of modified galectin 9 mutein (h-G9NC(null)) (100 nM) on the differentiation of human osteoblasts, a suspension of cells in 10% FCS/DMEM was seeded on a 6 well plate at $1\times10^5$ cells/well, incubated for 24 hr, then subjected to starvation in 1% FCS/DMEM overnight, stimulated with gal-9, and observed 8 hr later. Cell differentiation was evaluated based on intracellular ALP and osteocalcin values measured using a flow cytometer.

Figure 45:
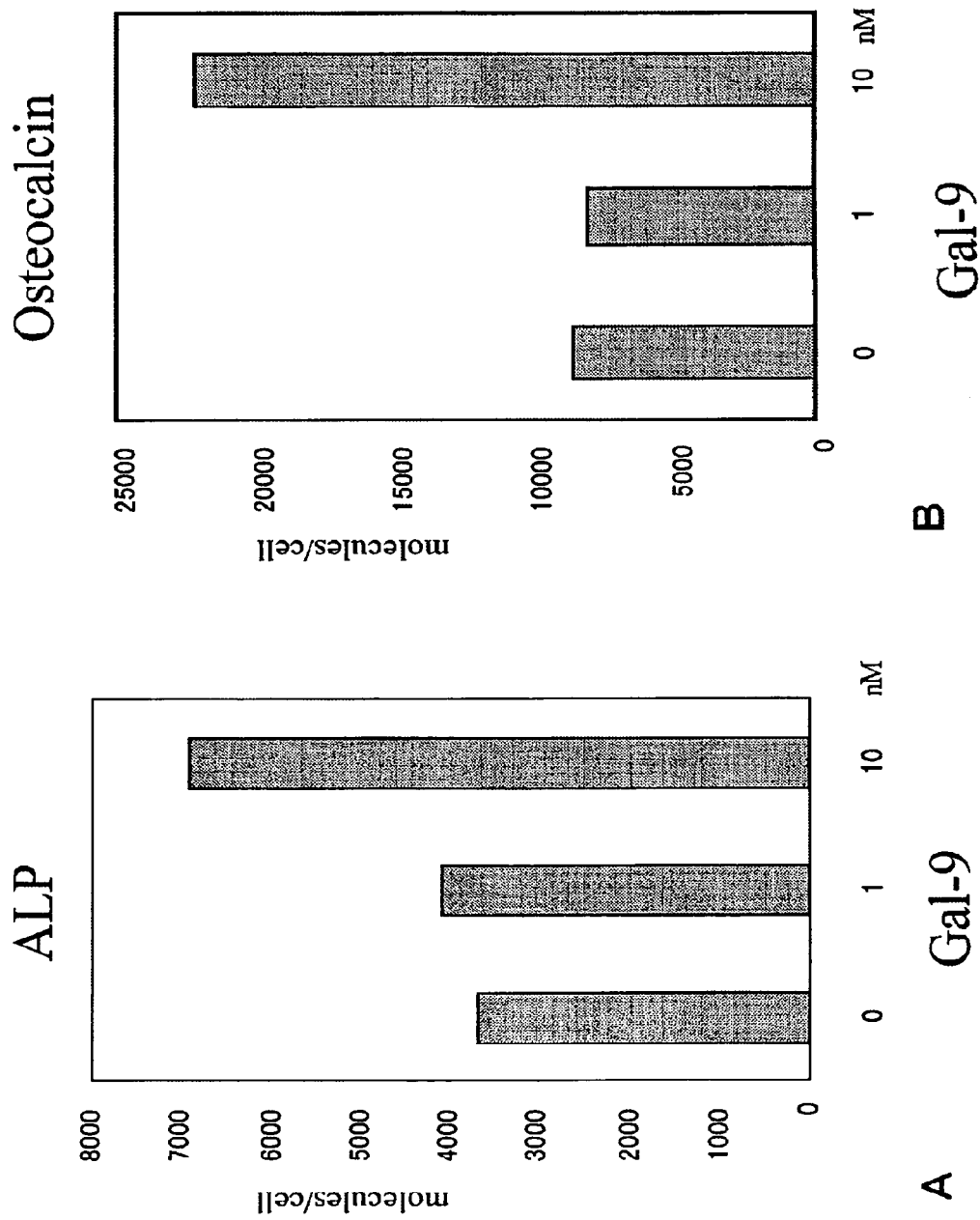
FIG. 45 shows graphs of assay results for the efficacy of modified galectin 9 mutein (Galectin-9) stimulation (8 hr) on the expression of human osteoblast proliferation markers.

The results are shown in FIG. 45. Modified galectin 9 muteins induced the expression of ALP and osteocalcin, the markers of new bone formation in osteoblasts. ALP increased by 400 molecules/cell in comparison with non-stimulated groups, and osteocalcin did by 800 molecules/cell in comparison with non-stimulated groups. In addition, when osteoblasts were admixed with h-G9NC(null) (10 nM) and cultured for 28 days, ALP staining as well as von Kossa staining was promoted as compared with non-added groups.

From the foregoing tests, the aggregation of mononuclear cells took place within 6 hours after addition of modified galectin 9 mutein. Modified galectin 9 muteins inhibited the formation of TRAP-positive multinuclear cells concentration-dependently. Modified galectin 9 muteins induced the proliferation of osteoblasts concentration-dependently. Modified galectin 9 muteins induce the expression of ALP and osteocalcin in osteoblasts.

In view of the above described results, it is suggested that modified galectin 9 muteins and native galectin 9 proteins may act on bone absorption suppressively and on bone formation acceleratingly. Therefore, it will be considered that they may serve as bone formation-accelerating drugs for therapeutic applications to postmenopausal osteoporosis.

Example 26

Modified Galectin 9 Mutein's Action on Interstitial Pneumonia Model

[Protocol]

Mice are used for interstitial pneumonia model animals. C57BL/6 mice (4,6-week-old, 7 to 8 weeks old when used, 20 animals) were treated according to reference documents: Blood 2002, 99: 1289-98 and Am J Respir Crit. Care Med 2003, 168: 1075-83 to raise interstitial pneumonia. Compounds, rhIL-2 (PeproTech, 5 μg×10 animals×2 groups×14 days=1400 μg=1.4 mg) and rmIL-18 (MBL, 0.2 μg×10 animals×2 groups×14 days=56 μg), were used.

Sample groups consist of control groups and modified galectin 9 mutein (Gal-9)-administered groups prepared.
(1) Control Group (10 Mice)

Mice received intraperitoneal (i.p.) injections of IL-2 (5 μg/mouse/day)+IL-18 (0.2 μg/mouse/day) on Days 0 to 13 every day. Control mice received i.p. injections of PBS (200 μl/mouse/day) on Days 0 to 13 every day.
(2) Gal-9-Administered Group (10 Mice)

Mice received i.p. injections of IL-2 (5 μg/mouse/day)+IL-18 (0.2 μg/mouse/day) on Day 0 to 13 every day. A solution of modified galectin 9 mutein, h-G9NC(null), in PBS was injected to animals at 100 μg/300 μl PBS/mouse from Days 0 to 13 every day. Both the groups received an i.p. injection of NEMBUTAL® for anesthetization.

Each mice survival proportion was taken as the first indicator of efficacy evaluation. Animals that survived to Day 14 were subjected to examination of their lung tissue.

Mouse sampling was conducted as follows:

Mice that died during the test were dissected on their death to provide lung tissue samples.

Mice that survived to day 14 were treated as follows: ether anesthetization→collection of blood from the orbit→dislocation of the cervical vertebrae→thoracotomy→collection of lung tissue.

The effect of rhGal-9null i.p. administration in this model was examined. The respective survival proportions on Day 14 of rhGal-9null-administered and non-administered groups were taken as efficacy evaluation standards, and further their tissue images on Day 14 were compared.

Figure 46:
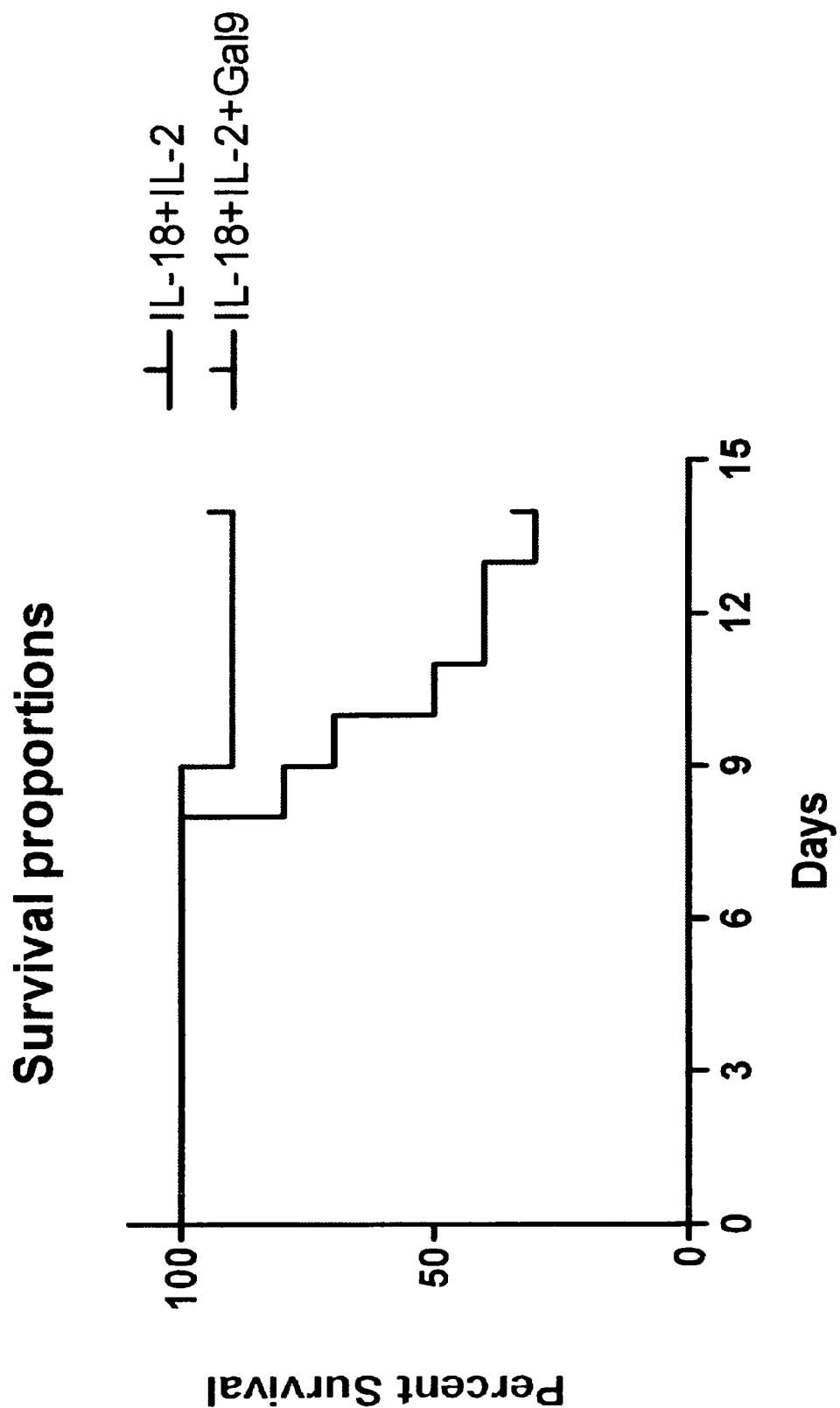
FIG. 46 is a graph showing survival proportions. Modified galectin 9 mutein's actions on the model of interstitial pneumonia were assayed.

The results are shown in FIGS. 46 and 47. FIG. 46 shows survival proportions. For the survival proportions on Day 14, the non-administered group gave 30% (3 animals survived among 10) while the h-G9NC(null) (Gal-9)-administered group did 90% (9 animals survived among 10). Thus, an improvement in the survival proportion was attained through administration of modified galectin 9 mutein (h-G9NC(null): Gal-9).

FIG. 47 shows lung tissue images (stained with HE, photograph) from survived mice on Day 14. In the non-administered group, even survived mice gave thickening at the lung interstices, accompanying the widespread, intensive invasion of cells. In the modified galectin 9 mutein (h-G9NC(null): Gal-9)-administered group, both interstice thickening and cell invasion were slight, and a lot of normal tissue residuals were found. Therefore, it has been revealed that galectin 9 (Gal-9) is effective in the suppression of disease occurrence in this model. Although changes in body weight took place in this test, no significant change in body weight was observed for both dead and survived mice in the non-administered group.

Example 27

Activity Against Cancer Metastasis Model

[Protocol]

To examine the action of modified galectin 9 muteins on the model of cancer metastasis, B16/F10 cells were used.

Cells ($5 \times 10^5$ cells/200 μL) were inoculated intravenously (i.v.) into the tail of each C57/BL6 mouse (SLC, 6-week-old female). Immediately after the inoculation, modified galectin 9 mutein (h-G9NC(null), abbreviated to "Gal-9"; 100 μg/300 μL) or PBS (N=15 each) was administered i.v. into the tail every day for 11 days (12 injections). Twelve days after the administration, animals were dissected, and the number of colonies was counted.

Figure 50:
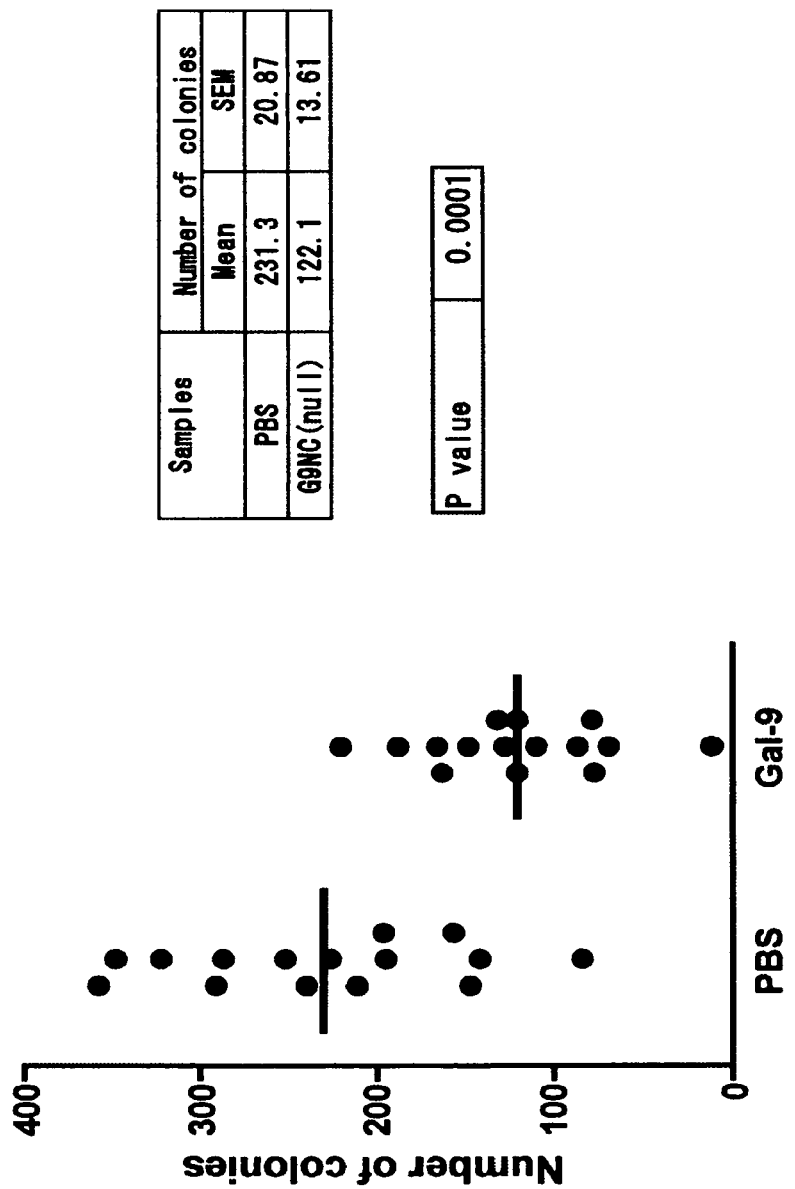
FIG. 50 shows assay results for the action of modified galectin 9 mutein (G9NC(null)) on the model of metastatic cancer, induced by B16/F10 cells. The number of colonies in each lung was counted.

FIG. 49 shows test results (each exterior view of model animal's lungs). The counting results of the lung colony number are shown in FIG. 50. As a result of comparing the modified galectin 9 mutein-administered group (Gal-9 group) with the PBS-administered group (PBS group), the metastasis-inhibiting efficacy of modified galectin 9 muteins was found. In the comparison of lung colony numbers, mean colony numbers are: modified galectin 9 mutein-administered group (Gal-9), 231.3±20.87; and PBS-administered group (PBS), 122.1±13.61. P values <0.0001 were considered significant. Thus, it has been verified that modified galectin 9 muteins are effective in inhibition of cancer metastasis.

Example 28

Carrageenan-Induced Inflammatory Disease Model

Carrageenan-Induced Rat Paw Edema

Carrageenan (Izushi kagaku, Japan) was obtained from the supplier indicated. For administration to animals, compounds were suspended in PBS(−), which was used as the vehicle in all experiments. Female Lewis rats (5-week-old) were purchased from SLC (Shizuoka, Japan). Animals were kept in the same manner as in Example 19. To examine the effect of modified galectin 9 muteins, rats received an i.v. injection of modified galectin 9 mutein (h-G9NC(null), abbreviated to "gal-9"; 30 to 300 μg/body (in PBS)) 10 min prior to carrageenan injection. Positive control groups received dexamethasone (Dex.) at a dose of 3 mg/kg, or 7 mg/kg.

[Carrageenan-Induced Paw Edema]

To examine the anti-inflammatory activity of modified galectin 9 mutein (human null galectin-9, h-G9NC(null)), carrageenan-induced paw edema tests in rats were performed according to Sugishita et al. (1981) methods. Rats received an i.v. injection of a drug compound (30, 100 and 300 μg/body) or vehicle (PBS) 10 minutes prior to injection of carrageenan (0.15 ml; 1% w/v in saline) into the footpad of the right hind paw. The volume of the paw was measured by mercury displacement plethysmography (Muromachi, Tokyo, Japan). The paw volume measurements were repeated for the carrageenan-injected paw and the contra-lateral paw (saline was injected into the right hind paw) at −1, 2, 4, 6, 24, 48 and 72 h after edema induction. Changes in paw volume were calculated as the differences between the −1 h reading and each given time point reading. Carrageenan-induced edema was expressed as the difference between the carrageenan-injected paw and the contra-lateral paw for each animal.

Statistical analysis was conducted as follows:

Unless otherwise stated, data are expressed as mean values±SEM. Statistical differences of data sets were analyzed using one-way ANOVA or two-way ANOVA, and differences between groups were assessed by Dunnett's Multiple Comparison Test or Bonferroni Post-Test using commercially available statistics software (GraphPad Software, Inc., San Diego, USA). P values <0.05 were considered statistically significant.

[Results]

Figure 51:
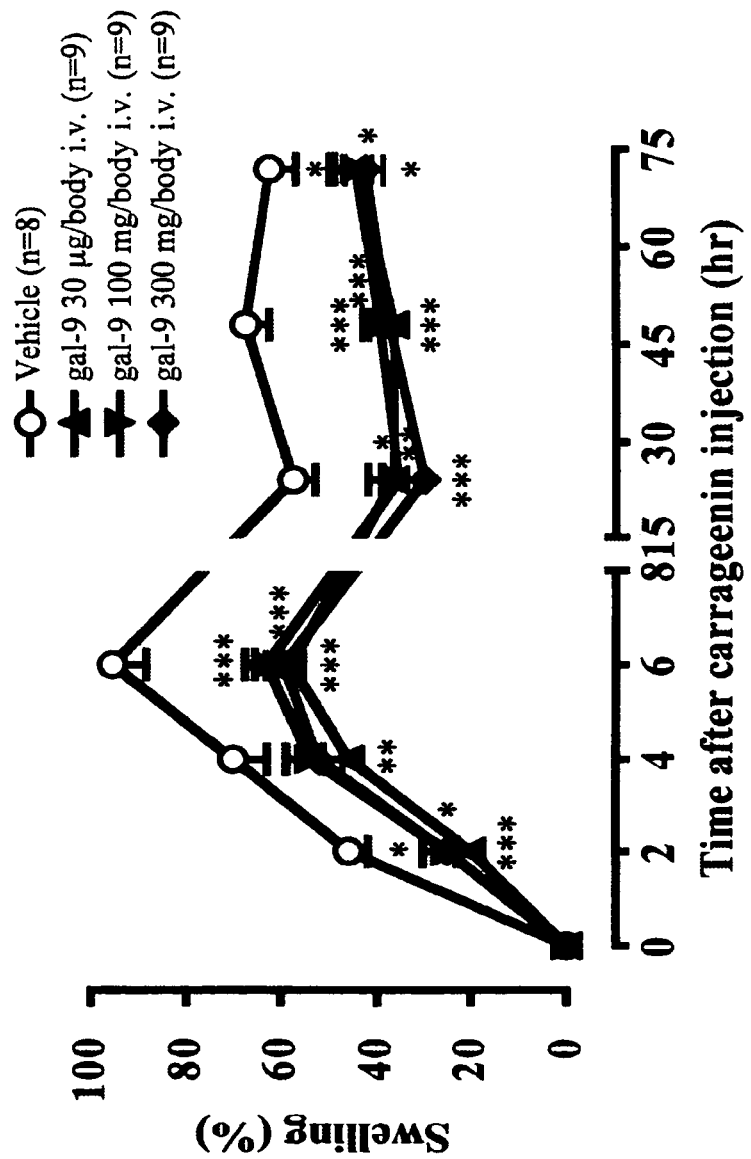
FIG. 51 is a graph showing assay results for the efficacy of modified galectin 9 mutein (gal-9) (i.v. administration) on the model of carrageenan-induced inflammatory disease.
Figure 52:
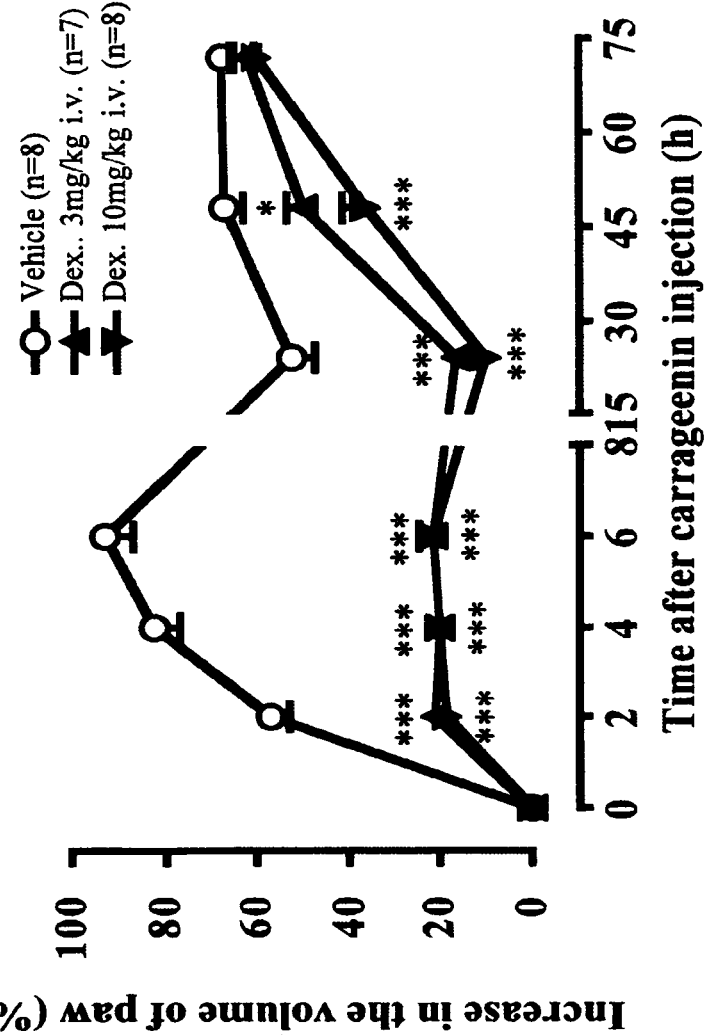
FIG. 52 is a graph showing assay results for the efficacy of positive control, dexamethasone (Dex.), on the model of carrageenan-induced inflammatory disease, for comparison.

The results are shown in FIG. 51 (modified galectin 9 mutein) and FIG. 52 (dexamethasone). Modified galectin 9 muteins have been observed to be active in inhibition of the disease occurrence even at a dose level of 30 μg/mouse.

Example 29

1. Modified Galectin 9 Mutein's Analgesic Action in Adjuvant Arthritis Model

[Protocol]
[Pain Triggered by Mechanical Stimuli (Randall-Selitto Test=Vertical Pressure Measurement of Pain Threshold)]

*Mycobacterium butyricum* (Difco, Detroit, Mich., USA) was obtained from the supplier indicated. For administration to animals, compounds were suspended in PBS(−), which was used as the vehicle in all experiments. Female Lewis rats (5-week-old) were purchased from SLC (Shizuoka, Japan). Animals were kept in the same manner as in Example 19. To examine the effect of modified galectin 9 muteins, rats received i.v. injections of modified galectin 9 mutein, h-G9NC(null) (abbreviated to "Gal-9") at a dose of 30 to 300 μg/body (in PBS) on Days 0 to 22 before and after adjuvant injection. The positive control group received indomethacin (Indo) at a dose of 3 mg/kg.

[Adjuvant Arthritis]

Female Lewis rats (5-week-old) were weighed, and each rat tail was marked. Animals were then divided into groups wherein each group consisted of 9 animals. The body weight of each rat and the footpad volume of both hind paws were recorded prior to adjuvant injection (Day 0). Next, adjuvant was injected into the right hind paw of each rat. Adjuvant-uninjected groups were taken as normal age-matched controls (sham). The body weight and paw volume of rats in each group were recorded prior to rat sacrifice on each given day after adjuvant injection.

[Protocol for Adjuvant]

*Mycobacterium butyricum* was ground down in a mortar to give an adjuvant which was admixed with an oil to make the final concentration 10 mg/ml. An aliquot (0.2 ml) of the adjuvant mixture was injected into the footpad of the right hind rat paw with a 27-gauge, 0.5-inch needle.

[Analysis of Pain Triggered by Mechanical Stimulation]

The intensity of hyperalgesia was assessed using the method of Randall-Selitto with some modifications in order to study whether or not modified galectin 9 mutein, human null galectin-9 (h-G9NC(null)), had analgesic activity such as activity of relieving peripheral hyperalgesia in response to external pressure in acute inflamed and uninflamed tissue. Briefly, an aliquot of Complete Freund's Adjuvant was injected s.c. into the right hind paw of each female Lewis rat (5-week-old) to induce acute and chronic inflammatory disease. The intensity of hyperalgesia in response to external pressure was measured by the Randall-Selitto test, in acute inflamed and uninflamed tissue 2 days prior to adjuvant injection and 5 days after adjuvant injection, and monitoring was continued to Day 25 (1 time/week). External pressure was then gradually applied to both the inflamed and contra-lateral uninflamed paws (0 to 200 g) with a Digital Force Measurement Gauge (Imada, Aichi, Japan) under the control of an observer. The "pain threshold" was defined as the pressure when the animal first showed evidence of the sensation of pain, indicated by the extension of digits and/or the initial signs of paw withdrawal and/or vocalization.

Statistical analysis was conducted in the same fashion as in Example 28. Briefly, unless otherwise stated, data are expressed as mean values±SEM. Statistical differences of data sets were analyzed using one-way ANOVA or two-way ANOVA, and differences between groups were assessed by Dunnett's Multiple Comparison Test or Bonferroni Post-Test using commercially available statistics software (GraphPad Software, Inc., San Diego, USA). P values <0.05 were considered statistically significant.

[Results]

Figure 58:
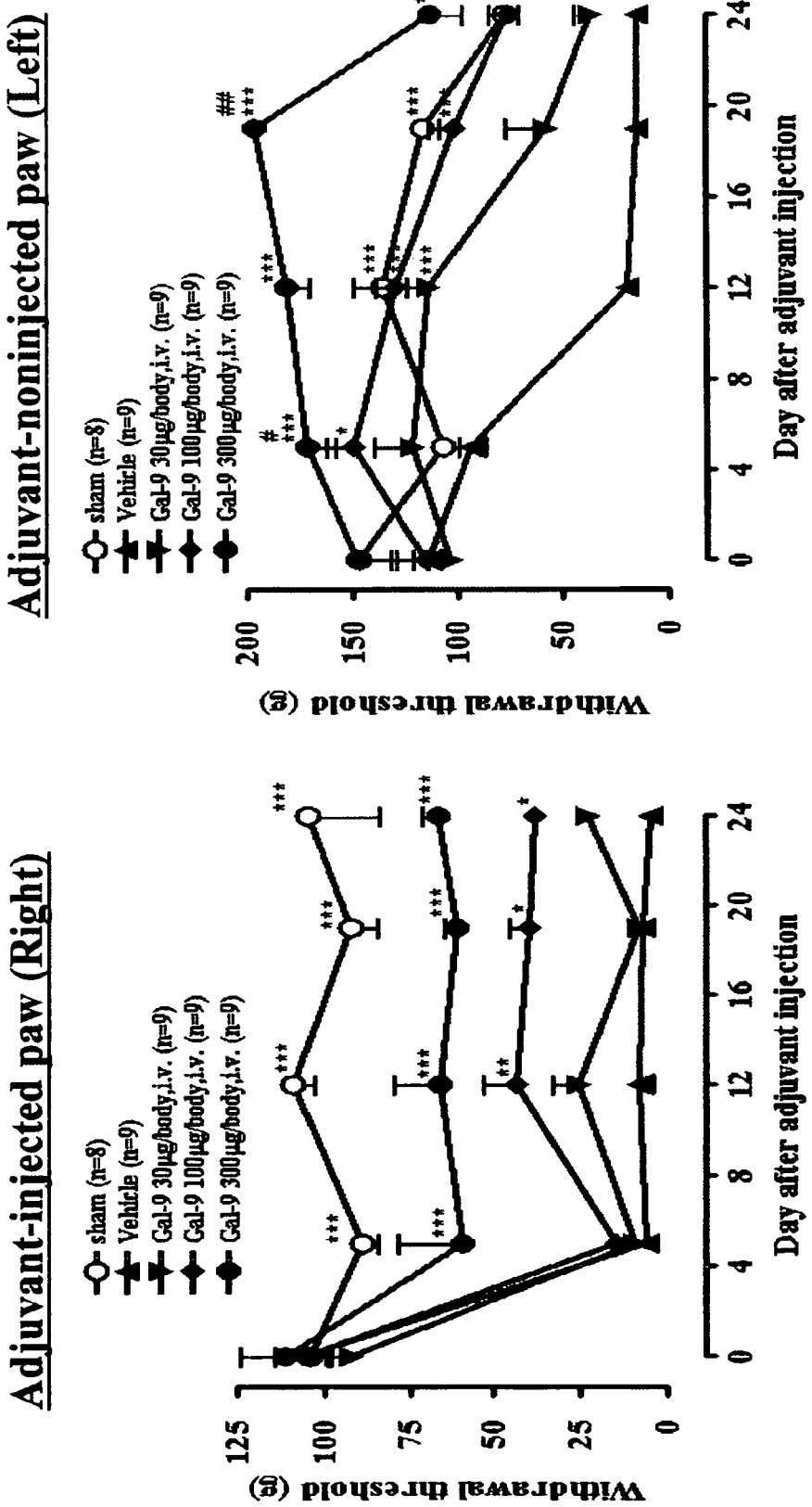
FIG. 58 shows graphs of assay results for modified galectin 9 mutein's action in the model of adjuvant arthritis (suppression of pain triggered by mechanical stimulation).

The results are shown in FIG. 58 (modified galectin 9 mutein, Gal-9) and FIG. 59 (indomethacin). In the drawings, each value represents the mean±SEM of 8 to 9 animals (n=8 to 9, FIG. 58) and of 9 animals (n=9, FIG. 59) at each given point. Statistical differences were analyzed using two-way ANOVA, and differences between groups were assessed using Bonferroni Post-Test (*p<0.05, p<0.01, *p<0.001). When modified galectin 9 muteins were administered, the pain threshold in response to external stimulation increased concentration-dependently for not only uninflamed sites but also inflamed sites (see FIG. 66 left). That is, modified galectin 9 muteins elevate systemically pain thresholds.

2. Carrageenan-Induced Acute Inflammatory Disease Model

Carrageenan-Induced Paw Edema in Rats

[Protocol]

Carrageenan (Izushi kagaku, Japan) was obtained from the supplier indicated. For administration to animals, compounds were suspended in PBS(−), which was used as the vehicle in all experiments. Female Lewis rats (5-week-old) were purchased from SLC (Shizuoka, Japan). Animals were kept in the same manner as in Example 19. To examine the effect of modified galectin 9 muteins, rats received an i.v. injection of modified galectin 9 mutein, h-G9NC(null) (abbreviated to "Gal-9"), at a dose of 30 to 300 μg/body (in PBS) 10 minutes prior to injection of carrageenan. The positive control group received dexamethasone (Dex) at a dose of 3 mg/kg or 7 mg/kg.

[Analysis of Pain Triggered by Mechanical Stimulation]

The intensity of hyperalgesia was assessed using the method of Randall-Selitto with some modifications in order to study whether or not modified galectin 9 mutein, human null galectin-9 (h-G9NC(null)), had analgesic activity such as activity of relieving peripheral hyperalgesia in response to external pressure in acute inflamed and uninflamed tissue. Briefly, carrageenan was injected s.c. into the right hind paw of each female Lewis rat (5-week-old) to induce acute and chronic inflammatory disease. The intensity of hyperalgesia in response to external pressure was measured by the Randall-Selitto test, in acute inflamed and uninflamed tissue 1 day prior to carrageenan injection and at 6 hours after carrageenan injection, and monitoring was continued to 75 h (1 time/day). External pressure was then gradually applied to both the inflamed and contra-lateral uninflamed paws (0 to 200 g) with a Digital Force Measurement Gauge (Imada, Aichi, Japan) under the control of an observer. The "pain threshold" was defined as the pressure when the animal first showed evidence of the sensation of pain, indicated by the extension of digits and/or the initial signs of paw withdrawal and/or vocalization.

Statistical analysis was conducted in the same fashion as in Example 28. Briefly, unless otherwise stated, data are expressed as mean values±SEM. Statistical differences of data sets were analyzed using one-way ANOVA or two-way ANOVA, and differences between groups were assessed by Dunnett's Multiple Comparison Test or Bonferroni Post-Test using commercially available statistics software (GraphPad Software, Inc., San Diego, USA). P values <0.05 were considered statistically significant.

[Results]

Figure 60:
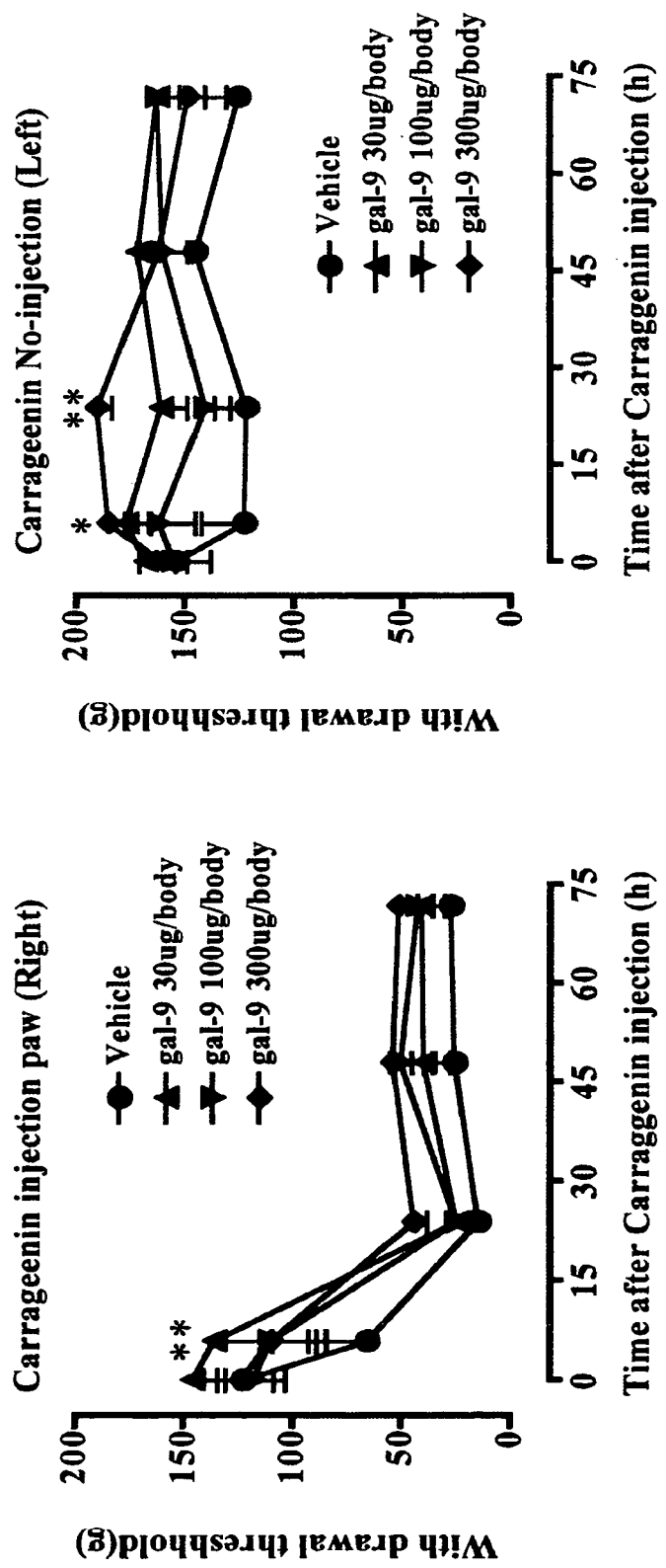
FIG. 60 shows graphs of assay results for modified galectin 9 mutein's action in the model of carrageenan-induced acute inflammatory disease (suppression of pain triggered by mechanical stimulation).
Figure 61:
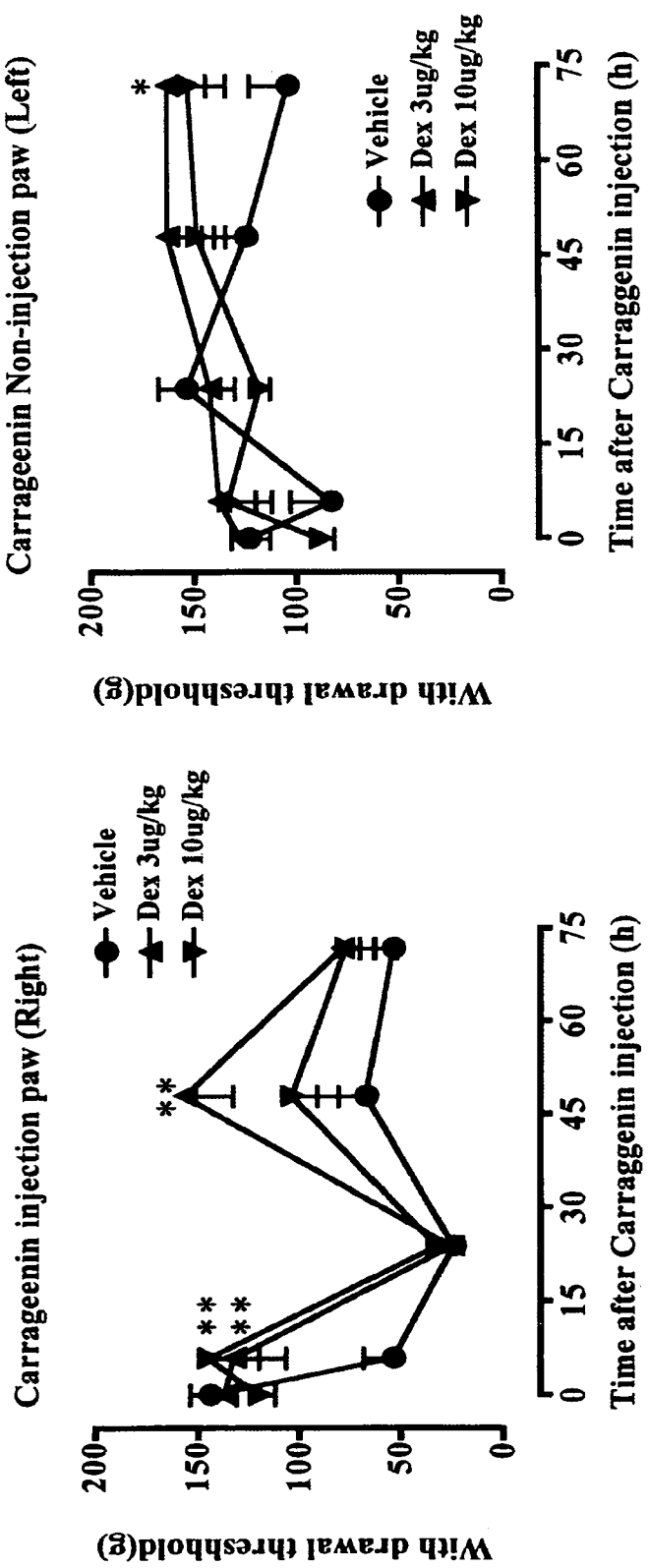
FIG. 61 shows graphs of assay results for the action of positive control, dexamethasone, in the model of carrageenan-induced acute inflammatory disease (suppression of pain triggered by mechanical stimulation), for comparison.

The results are shown in FIG. 60 (modified galectin 9 mutein, gal-9) and FIG. 61 (dexamethasone). In the drawings, each value represents the mean±SEM of 9 animals (n=9) at each given point. Statistical differences were analyzed using two-way ANOVA, and differences between groups were assessed using Bonferroni Post-Test (*p<0.05, p<0.01, *p<0.001). When modified galectin 9 muteins are administered, the pain threshold in response to external stimulation increases concentration-dependently for not only uninflamed sites but also inflamed sites. That is, modified galectin 9 muteins-elevate systemically pain thresholds.

Example 30

Stability of Modified Galectin 9 Mutein in Human Synovial Fluid

| Reaction Condition | |
| --- | --- |
| Human rheumatoid arthritis synovial fluid sample | 160 μL |
| G9NC(null) or G9(S) (5 μL in PBS) | 40 μL |

Galectin 9 was incubated in 80% synovial fluid at 37° C. for 24 hr or 96 hr (sampling at 6, 24, 48, and 72 hr during the incubation).

| SDS treatment and Western blot | |
| --- | --- |
| Sample | 4.5 μL |
| H$_2$O | 40.5 μL |
| Sample buffer (4x, +2-ME) | 15 μL |
| SDS-PAGE: 12.5% (10 μL/lane). | |

Figure 62:
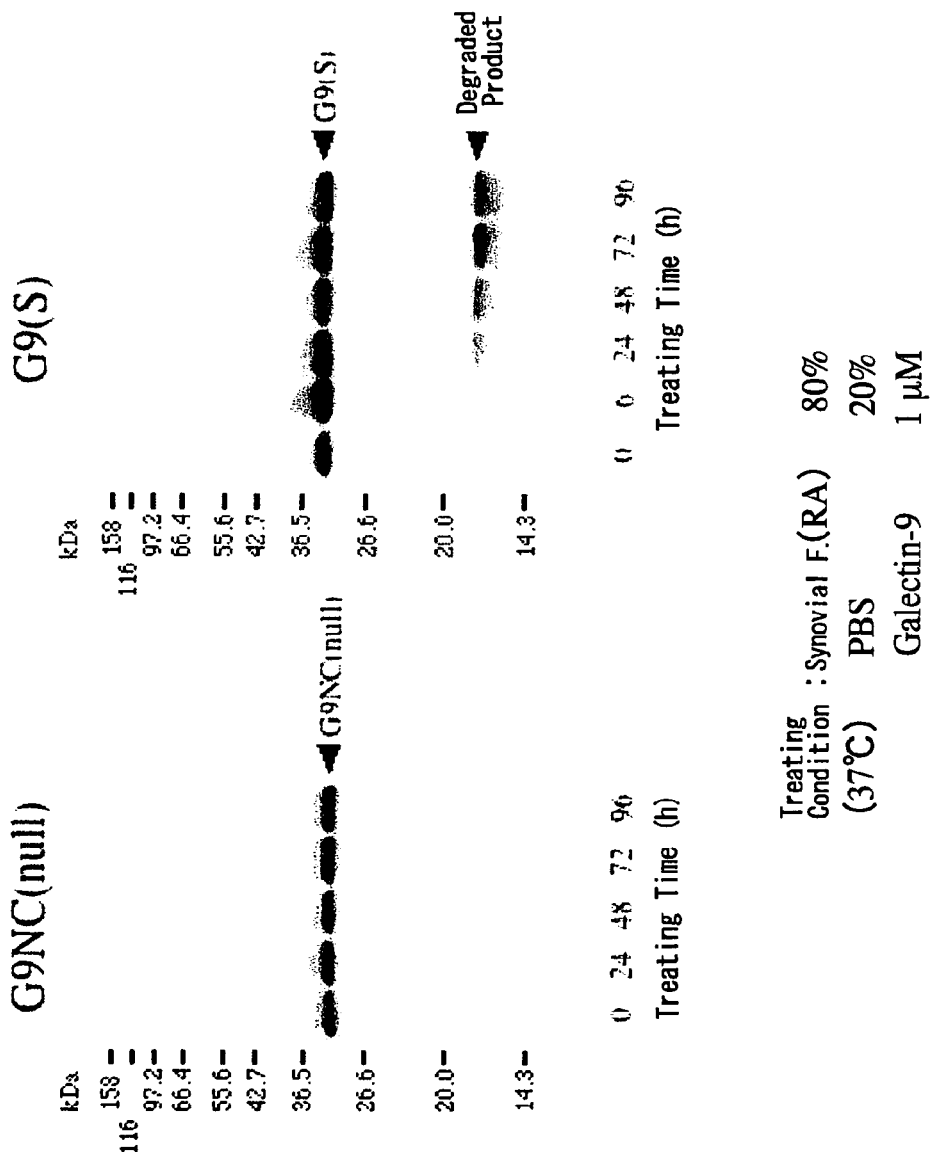
FIG. 62 shows SDS-PAGE results from examination of modified galectin 9 mutein stability in human synovial fluid.

The results are shown in FIG. 62. It has been clarified that modified galectin 9 mutein, G9NC(null), is more stable even in synovial fluid with high protease activity than galectin-9S (G9(S)).

Example 31

Arthritis Model

1. Ab Cocktail-Induced Model: Modified Galectin 9 Mutein (i.v. Administration)

[Protocol]

DBA/1J female mice (7 to 8 weeks old) were used. An arthritogenic monoclonal antibody cocktail (Chondrex, WA, USA; No. 62100) was intravenously (i.v.) administered to the tail of each animal at 2 mg/0.5 ml/body. Three days later, the animals received an i.p. injection of LPS (SIGMA, L6511) at 50 μg/0.2 mL. Further, a solution of modified galectin 9 mutein, h-Gal9NC(null) (abbreviated to "Gal-9"), was injected i.v. into the tail of each animal at 30 μg/200 μL. Test groups consist of 3 groups; PBS-administered group, and h-Gal9NC(null)-administered groups consisting of singly administered group (administered once on Day 0, i.e., LPS administration date) and daily administered group (administered every day to Day 10, 10 administrations). Each group was measured for the swelling degree of each limb joint (of right and left, fore and hind limbs) once a day and severity of arthritis was scored.

[Results]

Figure 63:
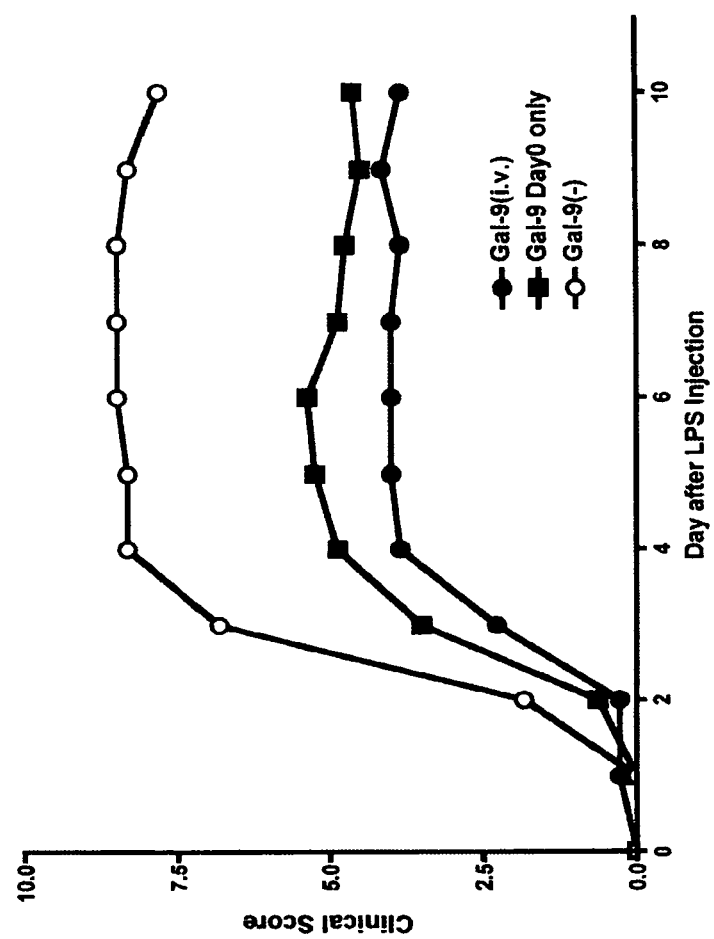
FIG. 63 is a graph showing assay results for the efficacy of modified galectin 9 mutein (stabilized galectin 9) (i.v. administration) on the model of arthritis (Ab cocktail-induced arthritis).

The results are shown in FIG. 63. After Ab cocktail administration, arthritis was induced with LPS. When modified galectin 9 muteins were i.v. applied, arthritis was inhibited, too. It has been observed that even the single administration leads to inhibitory effect on the occurrence of the disease.

2-1. CIA (Collagen-Induced Arthritis) Model: Modified Galectin 9 Mutein (i.p. Administration)

[Protocol]

Bovine collagen type II (BCII: Chondrex Inc., cat no 2002-1) was dissolved in complete adjuvant (CFA: Difco cat no 263810) to form an emulsion which was injected subcutaneously (s.c.) into the base of each mouse tail (DBA/1J mouse, 7- to 8-week-old, female) at a dose of 100 μL (BCII 0.1 mg/100 μL/mouse). On day 21 post-immunization, the booster injection of collagen emulsion was given, and severity of arthritis was scored three times a week for 4 limbs. Immediately after booster injection, modified galectin 9 mutein (abbreviated to "Gal-9"; 30 μg/mouse) or PBS was i.p. given. Thereafter, the drug injection was repeated every day. Mice were monitored by plural observers and each limb was given a clinical score (arthritic observations). Each limb was graded, and a total score per animal was obtained by adding up each individual score, resulting in a maximal clinical score of 16 per animal. Finally, each mean score was calculated.

① one digit swollen: 1
② two digits swollen: 2
③ swelling to the dorsum of paw: 3
④ severe swelling, deformities: 4

[Results]

Figure 64:
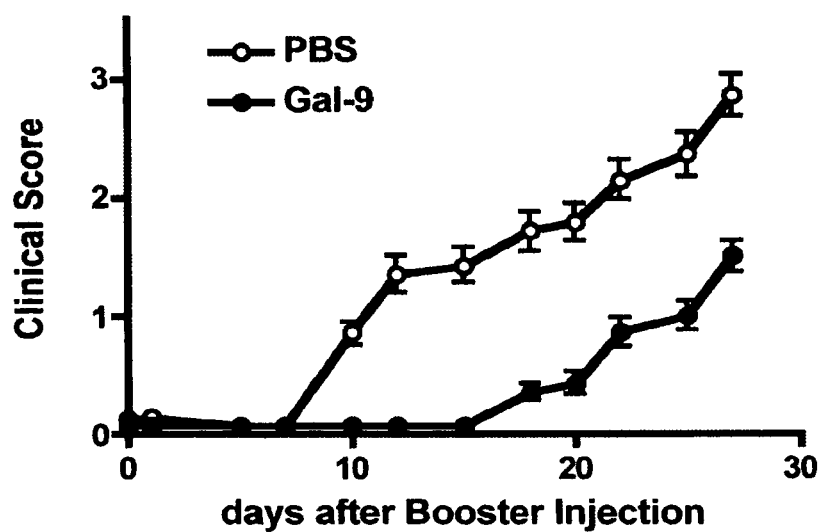
FIG. 64 is a graph showing assay results for the efficacy of modified galectin 9 mutein (stabilized galectin 9) (i.p. administration) on the model of arthritis (collagen-induced arthritis).

The results are shown in FIG. 64. It has been verified that modified galectin 9 muteins are inhibitory against the occurrence of the disease.

2-2. CIA (Collagen-Induced Arthritis) Model: Modified Galectin 9 Mutein (i.v. Administration)

[Protocol]

Bovine Collagen type II (BCII: Chondrex Inc., cat no 2002-1) was dissolved in incomplete Freund's Adjuvant (IFA: Difco) premixed with *Mycobacterium Tuberculosis* H37 Ra, desiccated (H37 Ra: Difco) to form an emulsion which was injected s.c. into the base of each mouse tail (DBA/1J mouse, 7- to 8-week-old, female) at a dose of 100 μL (BCII 0.2 mg/H37 Ra 0.2 mg/100 μL/mouse). On day 21 post-immunization, the booster injection of collagen emulsion was given, and severity of arthritis was scored three times a week for 4 limbs. Mice were monitored by plural observers and each limb was given a clinical score (arthritic observations). Each limb was graded, and the cumulative score for all four limbs of each animal was calculated (maximum of 16 per animal). Finally, each mean score was calculated.

Immediately after booster injection, modified galectin 9 mutein (abbreviated to "Gal-9"; 30 μg/mouse: N=15) or PBS (N=10) was i.p. given. Thereafter, the drug injection was repeated every day.

Reference Document: "Enhancement of collagen-induced arthritis in mice genetically deficient in extracellular superoxide dismutase", Ross A D, Banda N K, Muggli M, Arend W P. Arthritis Rheum. 2004 November; 50(11):3702-11.

[Results]

Figure 65:
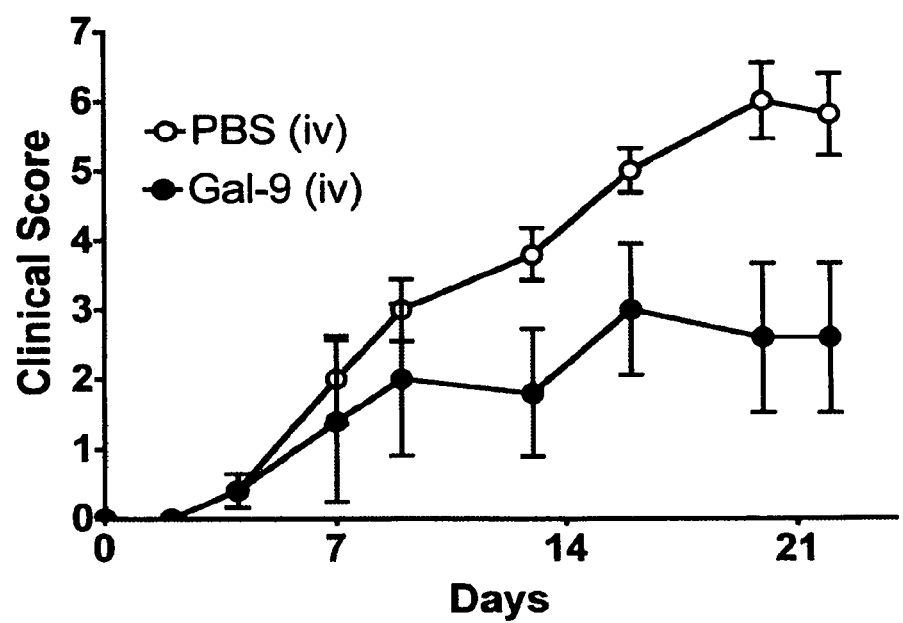
FIG. 65 is a graph showing assay results for the efficacy of modified galectin 9 mutein (stabilized galectin 9) (i.v. administration) on the model of arthritis (collagen-induced arthritis).

The results are shown in FIG. 65. It has been verified that modified galectin 9 muteins are inhibitory against the occurrence of the disease.

3. Adjuvant-Induced Arthritis (AIA) Model: Modified Galectin 9 Mutein (i.v. Administration)

[Protocol]

*Mycobacterium butyricum* (Difco, Detroit, Mich., USA) was obtained from the supplier indicated. For administration to animals, compounds were suspended in PBS(-), which was used as the vehicle in all experiments. Female Lewis rats (5-week-old) were purchased from SLC (Shizuoka, Japan). Animals were kept in the same manner as in Example 19. To examine the effect of modified galectin 9 muteins, rats received i.v. injections of modified galectin 9 mutein, h-G9NC(null) (abbreviated to "Gal-9"; 30-300 μg/body (in PBS)), on Days 0 to 22 before and after adjuvant injection.

[Adjuvant Arthritis]

Female Lewis rats (5-week-old) were weighed, and each tail was marked. Animals were divided into groups wherein each group consisted of 9 animals. The body weight of each rat and the footpad volume of both hind paws were recorded prior to adjuvant injection (Day 0). Next, adjuvant was injected into the right hind paw of each rat. Adjuvant-uninjected groups were taken as normal age-matched controls (sham). The body weight and paw volume of rats in each group were recorded prior to rat sacrifice on each given day after adjuvant injection.

[Paw Volume]

The volume of the paw was measured by mercury displacement plethysmography (Muromachi, Tokyo, Japan). Changes in paw volume were calculated as the differences between the Day 0 reading and each given date point reading.

[Clinical Evaluation]

The severity of arthritis was assessed for each limb as follows: Each of fore and hind limbs were graded for 1. interphalangeal joints and digits, 2. dorsum or palm, and 3. ankle joint or wrist, using a scale of 0 to 3: 0, no erythema and swelling; 1, slight erythema or swelling; 2, moderate erythema or swelling in ankle joint or wrist; and 3, severe erythema or swelling.

The severity of the disease was scored for each rat group. The daily cumulative arthritis score per rat was obtained by adding up each individual graded paw arthritis score.

[Protocol for Adjuvant]

*Mycobacterium butyricum* was ground down in a mortar to give an adjuvant which was admixed with an oil to make the final concentration 10 mg/ml. An aliquot (0.2 ml) of the adjuvant mixture was injected into the footpad of the right hind rat paw with a 27-gauge, 0.5-inch needle.

Statistical analysis was conducted in the same fashion as in Example 28. Briefly, unless otherwise stated, data are expressed as mean values±SEM. Statistical differences of data sets were analyzed using one-way ANOVA or two-way ANOVA, and differences between groups were assessed by Dunnett's Multiple Comparison Test or Bonferroni Post-Test using commercially available statistics software (GraphPad Software, Inc., San Diego, USA). P values <0.05 were considered statistically significant.

[Results]

The results are shown in FIG. 66 (modified galectin 9 mutein, Gal-9) and FIG. 67 (indomethacin, Indo). Adjuvant arthritis is inflammation occurring due to acquired immunity mainly associated with innate immunity and T cells. Although modified galectin-9 muteins inhibit both inflammations, they primarily inhibit intensely inflammation due to acquired immunity. It is noted that the modified galectin-9 mutein-administered group tended to work for a gain or loss in body weight in the same fashion as the indomethacin-administered group.

Example 32

Rat CIA (Collagen-Induced Arthritis) Model

Modified Galectin 9 Mutein (i.v. Administration)

[Protocol]

Bovine collagen type II (Collagen Gijutsu Kenkyukai, Tokyo, Japan) was dissolved in incomplete Freund's adjuvant (IFA: Difco) to form an emulsion which was injected s.c. into the back of each rat (DA/Slc, 11-week-old: Japan SLC, Inc., Japan) at a dose of 500 μL (collagen 50 μg/500 μL/mouse) for primary sensitization. One week later, an aliquot of the same collagen emulsion (collagen, 50 μg/500 μL/mouse) was injected into the base of each animal tail for secondary sensitization. Each limb was scored three times a week. Immediately after booster injection, animals received an i.v. injection of modified galectin 9 mutein (null human galectin-9=h-G9NC(null); 3, 10, and 30 μg/1 mL/mouse), or negative reference material, PBS (1 mL/mouse), or an oral application of positive reference material, prednisolone (3 mg/10 mL/kg: SIGMA), once a day for 32 days to Day 38.

The paw volume of each limb (including right and left, fore and hind limbs) was measured on Day 0 (date of collagen primary sensitization), Days 7, 15, 18, 22, 26, 30, and 39 after the primary sensitization and each percent swelling (%) was calculated according to the following formula:

Percent swelling (%)=[postchallenge paw volume (mL)−prechallenge paw volume (mL)]/[prechallenge paw volume (mL)]×100

Figure 68:
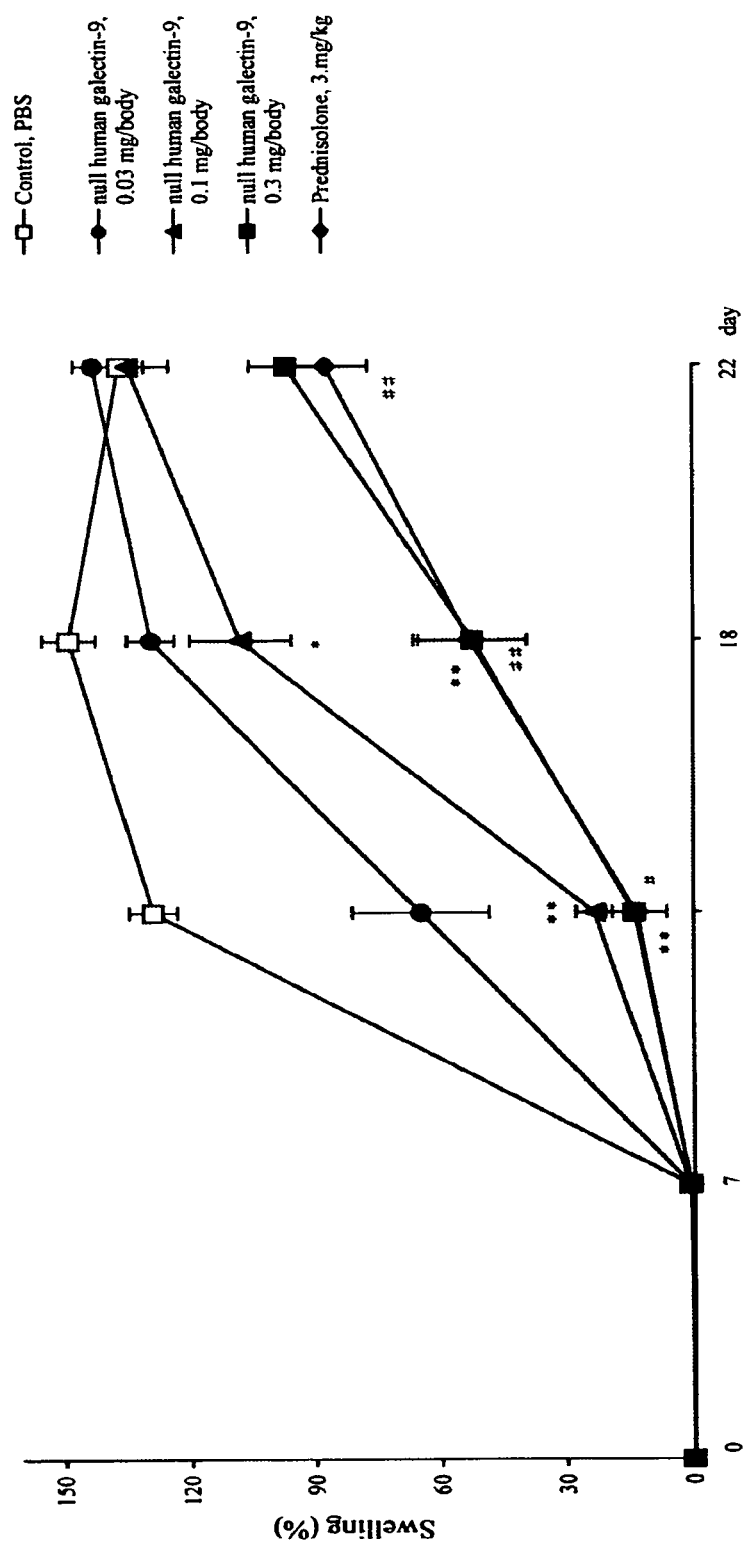
FIG. 68 is a graph showing assay results for the efficacy of modified galectin 9 mutein (i.v. administration) on the rat model of collagen-induced arthritis (CIA).

Statistical analysis was conducted as follows:

The cumulative value for right and left hind paw values was taken as the individual value for each animal. Results were expressed as the mean value of percent swelling (%) and a standard error. The equality of variances between the PBS group and the prednisolone-administered group was examined by F test. Comparison of data between the PBS group and the prednisolone-administered group was performed using Student's t test for equal variances but using Aspin-Wech's t test for unequal variances. Next, the equality of variances between the PBS group and the modified galectin-9 mutein-administered group was examined by Bartlet's test. Comparison of data between the PBS group and the modified galectin-9 mutein-administered group was performed using parametric Dunnett's test for equal variances but using nonparametric Dunnett's test for unequal variances. The significance level was set at less than 5% (P values <0.05 were considered significant). Values less than 5% were expressed separate from values less than 1% (p<0.01). The results are shown in FIG. 68 and Table 3. In Table 3, each value represents the mean±SEM. ##: significantly different from control (Days 15, 18, and 22: Student's t test, *p<0.05, **p<0.01: significantly different from control (Days 18 and 22: parametric Dunnett's test; Day 15: nonparametric Dunnett's test). It has been found that modified galectin-9 muteins are inhibitory against onset of the disease.

TABLE 3

| Group | Dose | Route | N | Swelling (%) on day 7 | 15 | 18 | 22 |
|---|---|---|---|---|---|---|---|
| Control, PBS | — | i.v. | 8 | 0.8 ± 0.2 | 129.1 ± 5.8 | 149.0 ± 6.3 | 137.0 ± 5.9 |
| null human galectin-9 | 0.03 mg/body | i.v. | 8 | 0.7 ± 0.2 | 65.0 ± 16.3 ** | 129.5 ± 5.7 * | 143.2 ± 4.7 |
|  | 0.1 mg/body | i.v. | 8 | 0.8 ± 0.2 | 23.5 ± 4.3 ** | 108.0 ± 12.3 ** | 135.0 ± 9.9 ** |
|  | 0.3 mg/body | i.v. | 8 | 0.7 ± 0.1 | 13.9 ± 2.3 ## | 52.5 ± 13.0 ## | 96.9 ± 8.9 ## |
| Prednisolone | 3 mg/kg | p.o. | 8 | 0.7 ± 0.2 | 13.5 ± 7.2 | 53.1 ± 13.5 | 87.4 ± 10.1 |

The modified galectin 9 muteins (stabilized galectin 9, for example h-G9NC(null), etc.) exert anti-tumor efficacy, expectable from the following bioactivity:

| | |
|---|---|
| tumor cell aggregation | aggregating efficacy on a variety of tumor cells |
| inhibition of adhesion | efficacy of inhibiting adhesion to extracellular matrices |
| apoptosis, cytotoxicity | efficacy of inducing apoptosis in a variety of tumor cells |
| activation of dendritic cell (DC) | efficacy of inducing the differentiation of DC |
| NK, NKT activation | efficacy of accelerating recruitment |
| pain suppression | suppression of pain triggered by capsaicin. |

The present inventor and associate group has verified that through the study on the expression of galectin 9 in breast cancer tissue the frequency of distant metastasis is lower in galectin 9-positive samples. Based on this, diagnostic kits for predicting metastasis are now being developed (Clin Cancer Res, 2005 in press, Galectin-9 as a prognostic factor with anti-metastatic potential in breast cancer). It has also been verified that galectin 9 gene-transferred human breast cancer cell lines exhibit in vitro highly aggregative property, and exert the similar aggregativity in nude mouse bodies. Further, it has been observed to be cytotoxic against various cell lines including hematologic malignant tumor cells. It has been verified that most of such actions are attributed to induction of apoptosis (Int J Cancer. 2002 20; 99(6):809-816, Possible role of galectin-9 in cell aggregation and apoptosis of human melanoma cell lines and its clinical significance; J immunol. 2003 1; 170(7d):3631-3636, Galectin-9 induces apoptosis through the carcium-calpain-caspase-1 pathway). In addition, when galectin 9 is topically applied, recruitment of NK/NKT cells, Mφ cell lines and others is observable, thereby suggesting that it may be possible to induce the mechanism of cell-mediated immunity (cellular immunity) against cancer.

In view of the foregoing, the stabilized galectin 9 molecules (or stable galectin 9 molecules, i.e., modified galectin 9 muteins, for example, h-G9NC(null) and related materials) exert cytotoxic efficacy against hematologic malignancy such as leukemia, and liberated cancer cells in post-surgical patients; metastasis-suppressing efficacy, ascribable to inhibition of cancer cell aggregation/cancer cell adhesion to the blood vessel wall and cancer cell infiltration into other tissue; efficacy of suppressing onset of cancerous peritonitis; and further actions including elevation of antitumor immune responsiveness due to recruitment of effector cells to the surroundings of tumor. Thus, they can be expected to have more preferable actions and effects. Therefore, they are expected to serve as novel anti-cancer materials with less side effects.

Targets of biological drugs (such as monoclonal antibody) that are now being developed are immune cell surface molecules, intracellularly functional molecules and inflammatory cytokines. That is, such drugs physiologically and pharmacologically act with their inhibitory efficacy. In contrast, the stabilized galectin 9 molecule drugs exert efficacy of inducing apoptosis of synovial cells and activated T cells and of suppressing bone destruction, thereby providing an expectation of innate immunoregulation, anti-inflammation and bone/cartilage tissue regeneration. Accordingly, the inventive materials provide a novel development approach conceptually entirely different from anti-cytokine therapy, etc. Pain is a mainly observed sign in rheumatoid arthritis, and capsaicin used in the above-described examples is an important mediator that induces inflammatory pain in neurogenic inflammatory disease. Stabilized galectin 9 inhibits ear edema induced by capsaicin painting. In other words, stabilized galectin 9 is expected to serve as a novel less side-effect therapeutic agent for systemic autoimmune diseases. The stabilized galectin 9 molecules have novel functions, thereby promising to potentially serve as anti-rheumatoid arthritis agents that exhibit less side-effects. The stabilized galectin 9 molecules have clinically effective characteristics, including inhibition of inflammation, repair of articular tissue, and suppression of pain whereby they can be expected to provide mechanisms such as (1) induction of apoptosis in activated T cells, (2) apoptosis of synovial cells, (3) arachidonic acid cascade, and (4) suppression of bone destruction. Therefore, the stabilized galectin 9 molecules will be promising to be act as therapeutic agents for rheumatoid arthritis. In practice, it has been verified that they inhibit the onset of arthritis in the model of CIA (Ab cocktail).

INDUSTRIAL APPLICABILITY

Modified galectin 9 muteins are more resistant against enzymes than wild type Gal-9 proteins. Therefore, the modified galectin 9 muteins are quite useful in effectively utilizing and applying versatile actions and functions owned by wild type galectin 9. It is suggested that wild type galectin 9 induces metastasis inhibition and regression of cancer by direct actions on tumor (activity of inducing cell-to-cell adhesion and apoptosis of tumor cells), and/or actions via immune system. Accordingly, the modified galectin 9 muteins can be expected to act as advantageous active materials having equivalent galectin 9 activity, for example, anti-tumor drugs. Wild type galectin 9 does not act on non-activated lymphocytes but induces apoptosis in activated T cells, including inter alia CD4-positive T cells causing hyperimmune responses. Therefore, the modified galectin 9 muteins can be expected to act as advantageous active materials having equivalent galectin 9 activity, for example, anti-inflammatory drugs, anti-allergic drugs, and/or osteoporosis drugs. Since it is apparent that wild type galectin 9 has a potent apoptosis-inducing property against synovial cells involved in the deformity of joints and others in rheumatoid arthritis, the modified galectin 9 muteins can be expected to act as advantageously active materials having equivalent galectin 9 activity. Thus, the present invention is utilizable as a tool for not only the development of therapeutic drugs for cancers, refractory autoimmune diseases (including rheumatoid arthritis), allergic diseases, inflammatory diseases, disorders related to bone metabolism but also the revelation, research & development of galectin 9 functions.

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

SEQUENCE LISTING FREE TEXT

SEQ ID NO: 1, Description of Artificial Sequence: Polynucleotide for galectin-9 mutein, G9NC(null)
SEQ ID NO: 2, Description of Artificial Sequence: Polynucleotide for galectin-9 mutein
SEQ ID NO: 5, galectin-9 medium isoform
SEQ ID NO: 10, Description of Artificial Sequence: Oligonucleotide to act as a primer for PCR
SEQ ID NO: 11, Description of Artificial Sequence: Oligonucleotide to act as a primer for PCR
SEQ ID NO: 12, Description of Artificial Sequence: Oligonucleotide to act as a primer for PCR
SEQ ID NO: 13, Description of Artificial Sequence: Oligonucleotide to act as a primer for PCR

What is claimed is:

1. A pharmaceutical drug comprising:
an effective amount of a protein, or a salt thereof,
wherein the protein, or a salt thereof, comprises a mutant galectin 9 protein having β-galactoside binding activity and having the structure (N-CRD)-Linker-(C-CRD),
wherein the N-CRD (N-terminal Carbohydrate Recognition Domain) is
(a) a polypeptide having the amino acid sequence of SEQ ID NO: 3,
(b) a variant thereof differing from the amino acid sequence of SEQ ID NO: 3 by a deletion, substitution or addition of 1 to 8 amino acid residues and maintaining a carbohydrate recognition activity of N-CRD of natural galectin 9, or
(c) a variant thereof having an amino acid sequence at least 70% homologous to SEQ ID NO: 3 and maintaining a carbohydrate recognition activity of N-CRD of natural galectin 9;
wherein the C-CRD (C-terminal Carbohydrate Recognition Domain) is
(a) a polypeptide having the amino acid sequence of SEQ ID NO: 4,
(b) a variant thereof differing from the amino acid sequence of SEQ ID: 4 by a deletion, substitution or addition of 1 to 21 amino acid residues and maintaining a carbohydrate recognition activity of C-CRD of natural galectin 9, or
(c) a variant thereof having an amino acid sequence at least 70% homologous to SEQ ID NO: 4, and maintaining a carbohydrate recognition activity of C-CRD of natural galectin 9; and wherein the Linker is
(a) an amino acid sequence consisting of 2 arbitrary natural amino acid residues, or
(b) the amino acid sequence Arg Ile Pro, and
wherein the pharmaceutical drug is an immunoregulator or immunomodulator capable of treating refractory autoimmune disease, pain disorder, asthmatic disease, rheumatism, rheumatoid arthritis, allergic disease, inflammatory disease, or a disorder related to bone metabolism.

2. A pharmaceutical drug according to claim 1, wherein
the refractory autoimmune disease is autoimmune hemolytic anemia,
the pain disorder is neuropathic pain, inflammatory pain, chronic pain or acute pain,
the allergic disease is allergic asthma or urticaria,
the inflammatory disease is pleurisy, dermatitis, arthritis, angiitis, acute respiratory distress syndrome (ARDS), interstitial pneumonia, chronic inflammatory disease or acute inflammatory disease, and
the disorder related to bone metabolism is osteoporosis, loss of bone mass or bone fracture.

3. A pharmaceutical drug comprising:
an effective amount of a protein, or a salt thereof,
wherein the protein, or a salt thereof, comprises a mutant galectin 9 protein having β-galactoside binding activity and having the structure (N-CRD)-Linker-(C-CRD),
wherein the N-CRD (N-terminal Carbohydrate Recognition Domain) is
(a) a polypeptide having the amino acid sequence of SEQ ID NO: 3, (b) a variant thereof differing from the amino acid sequence of SEQ ID NO: 3 by a deletion, substitution or addition of 1 to 8 amino acid residues and maintaining a carbohydrate recognition activity of N-CRD of natural galectin 9, or
(c) a variant thereof having an amino acid sequence at least 70% homologous to SEQ ID NO: 3 and maintaining a carbohydrate recognition activity of N-CRD of natural galectin 9;
wherein the C-CRD (C-terminal Carbohydrate Recognition Domain) is
(a) a polypeptide having the amino acid sequence of SEQ ID NO: 4,
(b) a variant thereof differing from the amino acid sequence of SEQ ID: 4 by a deletion, substitution or addition of 1 to 21 amino acid residues and maintaining a carbohydrate recognition activity of C-CRD of natural galectin 9, or
(c) a variant thereof having an amino acid sequence at least 70% homologous to SEQ ID NO: 4, and maintaining a carbohydrate recognition activity of C-CRD of natural galectin 9; and
wherein the Linker is
(a) an amino acid sequence consisting of 2 arbitrary natural amino acid residues, or
(b) the amino acid sequence Arg Ile Pro, and
wherein the pharmaceutical drug is an antineoplastic or antitumor agent capable of treating a blood cell tumor, non-epithelial neoplasm or epithelial neoplasm.

4. A pharmaceutical drug according to claim 3, wherein the blood cell tumor is leukemia, the non-epithelial neoplasm is malignant melanoma, malignant lymphoma, Hodgkin's disease, plasmacytoma, glioma, myelofibrosis associated with agnogenic myeloid metaplasia, or others or sarcoma, and the epithelial neoplasm is brain tumor (glioblastoma multiforme, etc.), spinal tumor, maxillary sinus carcinoma, pancreatic ductal adenocarcinoma, gingival cancer, tongue cancer, lip cancer, nasopharyngeal cancer, oropharyngeal cancer, hypopharyngeal cancer, laryngeal cancer, thyroid cancer, parathyroid cancer, lung cancer, pleural tumor, carcinomatous peritonitis, carcinomatous pleurisy, esophageal cancer, stomach cancer, colon cancer, bile duct cancer, gall bladder cancer, pancreatic cancer, liver cancer, renal cancer, urinary bladder cancer, prostatic cancer, penile cancer, testicular tumor, adrenal cancer, cervical cancer, endometrial cancer, vaginal cancer, vulvar cancer, ovarian cancer, chorioepithelioma, malignant bone tumor, soft part sarcoma, breast cancer, skin cancer, or basal cell tumor.

5. A method for treating refractory autoimmune disease, rheumatoid arthritis, allergic disease, inflammatory disease, or a disorder related to bone metabolism, which comprises administering to a subject in need thereof a therapeutically effective amount of the pharmaceutical drug according to claim 1 or 2.

6. A method for treating blood cell tumor, non-epithelial neoplasm or epithelial neoplasm, which comprises administering to a subject in need thereof a therapeutically effective amount of the pharmaceutical drug according to claim 3 or 4.

* * * * *